(12) United States Patent
Anderson et al.

(10) Patent No.: US 8,541,003 B2
(45) Date of Patent: Sep. 24, 2013

(54) VECTORS EXPRESSING SARS IMMUNOGENS, COMPOSITIONS CONTAINING SUCH VECTORS OR EXPRESSION PRODUCTS THEREOF, METHODS AND ASSAYS FOR MAKING AND USING

(75) Inventors: D. Karl Anderson, Meriden, CT (US); Kathleen M. Holtz-Corris, Cheshire, CT (US); Rick Chubet, Middletown, CT (US); Daniel Adams, East Haven, CT (US); Manon Cox, East Haven, CT (US)

(73) Assignee: Protein Sciences Corporation, Meriden, CT (US)

( * ) Notice: Subject to any disclaimer, the term of this patent is extended or adjusted under 35 U.S.C. 154(b) by 713 days.

(21) Appl. No.: 10/873,424

(22) Filed: Jun. 21, 2004

(65) Prior Publication Data

US 2013/0216566 A1 Aug. 22, 2013

Related U.S. Application Data

(60) Provisional application No. 60/554,742, filed on Mar. 19, 2004, provisional application No. 60/480,118, filed on Jun. 20, 2003.

(51) Int. Cl.
*A61K 39/12* (2006.01)
*A61K 39/215* (2006.01)
*C12P 19/34* (2006.01)
*C12P 21/04* (2006.01)
*C12P 21/06* (2006.01)
*C12N 15/09* (2006.01)
*C12N 15/63* (2006.01)
*C12N 15/64* (2006.01)
*C12N 15/66* (2006.01)

(52) U.S. Cl.
USPC ............... 424/221.1; 424/199.1; 424/204.1; 435/69.1; 435/69.3; 435/69.7; 435/70.1; 435/91.1; 435/91.4; 435/91.41; 435/91.5; 435/91.51

(58) Field of Classification Search
None
See application file for complete search history.

(56) References Cited

U.S. PATENT DOCUMENTS

| | | |
|---|---|---|
| 2,909,462 A | 10/1959 | Warfield et al. |
| 4,196,265 A | 4/1980 | Koprowski et al. |
| 4,376,110 A | 3/1983 | David et al. |
| 4,745,051 A | 5/1988 | Smith et al. |
| 4,879,236 A | 11/1989 | Smith et al. |
| 4,999,291 A | 3/1991 | Souza |
| 5,334,379 A | 8/1994 | Pillai et al. |
| 5,476,929 A | 12/1995 | Briles et al. |
| 5,602,007 A | 2/1997 | Dunn et al. |
| 5,753,463 A | 5/1998 | Briles et al. |
| 5,762,939 A | 6/1998 | Smith et al. |
| 5,804,193 A | 9/1998 | Briles et al. |
| 5,811,104 A | 9/1998 | Dale et al. |
| 5,849,303 A | 12/1998 | Wasmoen et al. |
| 5,856,170 A | 1/1999 | Briles et al. |
| 5,858,368 A | 1/1999 | Smith et al. |
| 5,858,369 A | 1/1999 | Matsuo et al. |
| 5,858,373 A | 1/1999 | Paoletti et al. |
| 5,871,943 A | 2/1999 | Briles et al. |
| 5,910,306 A | 6/1999 | Alving et al. |
| 5,955,089 A | 9/1999 | Briles et al. |
| 5,965,141 A | 10/1999 | Briles et al. |
| 5,965,400 A | 10/1999 | Briles et al. |
| 5,980,909 A | 11/1999 | Briles et al. |
| 5,997,882 A | 12/1999 | Briles et al. |
| 6,004,802 A | 12/1999 | Briles et al. |
| 6,027,734 A | 2/2000 | Briles et al. |
| 6,042,838 A | 3/2000 | Briles et al. |
| 6,103,526 A | 8/2000 | Smith et al. |
| 6,143,872 A | 11/2000 | Barbour et al. |
| 6,159,477 A | 12/2000 | Audonnet et al. |
| 6,224,882 B1 | 5/2001 | Smith et al. |
| 6,228,846 B1 | 5/2001 | Audonnet et al. |
| 6,231,870 B1 | 5/2001 | Briles et al. |
| 6,232,116 B1 | 5/2001 | Briles et al. |
| 6,245,532 B1 | 6/2001 | Smith et al. |
| 6,348,540 B1 | 2/2002 | Sugioka et al. |
| 6,372,224 B1 | 4/2002 | Miller et al. |
| 6,387,376 B1 | 5/2002 | Audonnet et al. |
| 6,485,729 B1 | 11/2002 | Smith et al. |
| 6,500,613 B1 | 12/2002 | Briles et al. |
| 7,220,852 B1* | 5/2007 | Rota et al. .............. 536/23.72 |
| 2003/0104008 A1 | 6/2003 | Loosmore et al. |
| 2005/0249742 A1* | 11/2005 | Ruprecht et al. .......... 424/185.1 |
| 2006/0257852 A1* | 11/2006 | Rappuoli et al. .............. 435/5 |

FOREIGN PATENT DOCUMENTS

WO    WO 00/46354    8/2000

OTHER PUBLICATIONS

Jiang et al. SARS Vaccine Development. Emerging Infectious Diseases Jul. 2005, vol. 11, No. 7, p. 1016-1020.*

(Continued)

*Primary Examiner* — Louise Humphrey
(74) *Attorney, Agent, or Firm* — Vedder Price P.C.; Thomas J. Kowalski; Deborah L. Lu

(57) ABSTRACT

SARS (severe acute respiratory syndrome virus, a coronavirus) immunogens, antigens, or epitopes, nucleic acid molecules encoding such immunogens, antigens, or epitopes; vectors containing such nucleic acid molecules, e.g., viral vectors such as baculovirus vectors, DNA vectors, such as DNA plasmid vectors, e.g., DNA plasmids that express a nucleic acid molecule in a mammalian cell, uses for such immunogens, antigens or epitopes and vectors, e.g., as an active component immunogenic, immunological or vaccine compositions, or to generate antibodies, such as monoclonal antibodies, and methods for making, and using such immunogens, antigens or epitopes, vectors, antibodies, including in methods for eliciting an immunological or immunogenic or vaccine response, as well as in assays or diagnostic kits or methods, are discussed, as well as a seamless fusion of sequences in a plasmid or vector, e.g., a sequence encoding a leader sequence and a sequence encoding a protein, epitope or immunogen or antigen.

20 Claims, 56 Drawing Sheets

(56) References Cited

OTHER PUBLICATIONS

Zhi et al. SARS Vaccine: Progress and Challenge. Cellular & Molecular Immunology 2005, vol. 2(2), p. 101-105.*

Navas-Martin et al. Coronavirus replication and pathogenesis: Implications for the recent outbreak of severe acute respiratory syndrome (SARS), and the challenge for vaccine development. Journal of NeuroVirology 2004, vol. 10, p. 75-85.*

Xu et al. Genetic Variation of SARS Coronavirus in Beijing Hospital. Emerging Infectious Diseases, May 2004, vol. 10, No. 5, pp. 789-794.*

Bonavia et al. Identification of a Receptor-Binding Domain of the Spike Glycoprotein of Human Coronavirus HCoV-229E. Journal of Virology, Feb. 2003, vol. 77, No. 4, p. 2530-2538.*

Bonavia, A., B. D. Zelus, et al. (2003). "Identification of a receptor-binding domain of the spike glycoprotein of human coronavirus HCoV-229E." J Virol 77(4): 2530-8.

Brown, E. G. and J. A. Tetro (2003). "Comparative analysis of the SARS coronavirus genome: a good start to a long journey." Lancet 361(9371): 1756-7.

Corapi, W. V., R. J. Darteil, et al. (1995). "Localization of antigenic sites of the S glycoprotein of feline infectious peritonitis virus involved in neutralization and antibody-dependent enhancement." J Virol 69(5): 2858- 62.

Drosten, C., S. Gunther, et al. (2003). "Identification of a novel coronavirus in patients with severe acute respiratory syndrome." N Engl J Med 348(20): 1967-76.

Eldridge, J. H., J. K. Staas, et al. (1991). "Biodegradable microspheres as a vaccine delivery system." Mol Immunol 28(3): 287-94.

Fouchier, R. A., T. Kuiken, et al. (2003). "Aetiology: Koch's postulates fulfilled for SARS virus." Nature 423(6937): 240.

Holmes, K. V. (2003). "SARS-associated coronavirus." N Engl J Med 348(20): 1948-51.

Holmes Kathryn V et al: "Virology. The SARS coronavirus: a postgenomic era." Science (New York, N.Y.) May 30, 2003, vol. 300, No. 5624, pp. 1377-1378.

Jones, T., F. Allard, et al. (2003). "A nasal Proteosome influenza vaccine containing baculovirus-derived hemagglutinin induces protective mucosal and systemic immunity." Vaccine 21(25-26): 3706-12.

Klepfer, S., A. P. Reed, et al. (1995). "Cloning and expression of FECV spike gene in vaccinia virus. Immunization with FECV S causes early death after FIPV challenge." Adv Exp Med Biol 380: 235-41.

Kontoyiannis, D. P., R. Pasqualini, et al. (2003). "Aminopeptidase N inhibitors and SARS." Lancet 361(9368): 1558.

Ksiazek, T. G., D. Erdman, et al. (2003). "A novel coronavirus associated with severe acute respiratory syndrome." N Engl J Med 348(20): 1953-66.

Marra, M. A., S. J. Jones, et al. (2003). "The Genome sequence of the SARS-associated coronavirus." Science 300(5624): 1399-404.

Rosen (1968). Hemagglutination with Animal Viruses in Fundamental Techniques in Virology. New York, Academic Press.

Rota, P. A., M. S. Oberste, et al. (2003). "Characterization of a novel coronavirus associated with severe acute respiratory syndrome." Science 300(5624): 1394-9.

Ruan, Y. J., C. L. Wei, et al. (2003). "Comparative full-length genome sequence analysis of 14 SARS coronavirus isolates and common mutations associated with putative origins of infection." Lancet 361(9371): 1779-85.

Saelens Xavier et al: "Protection of mice 1-12, against a lethal influenza virus challenge 22-56 after immunization with yeast-derived secreted influenza virus hemagglutinin" European Journal of Biochemistry, Berlin; DE, vol. 260, No. 1, Feb. 1, 1999, pp. 166-175.

Saif, L. J. (1993). "Coronavirus immunogens." Vet Microbiol 37(3-4): 285-97.

Schultze, B., H. J. Gross, et al. (1991). "The S protein of bovine coronavirus is a hemagglutinin recognizing 9-O-acetylated sialic acid as a receptor determinant." J Virol 65(11): 6232-7.

Scott, F. W. (1987). "Immunization against feline coronaviruses." Adv Exp Med Biol 218: 569-76.

Song C S et al: "Induction of protective 1-12, immunity in chickens vaccinated with 22-56 infectious bronchitis virus S1 glycoprotein expressed by a recombinant baculovirus." The Journal of General Virology, vol. 79 ( Pt 4), Apr. 1998, pp. 719-723.

Tuboly, T., E. Nagy, et al. (1994). "Immunogenicity of the S protein of transmissible gastroenteritis virus expressed in baculovirus." Arch Virol 137(1-2): 55-67.

Xiao Xet Al: "The SARS-CoV S glycoprotein: expression and functional characterization" Biochemical and Biophysical Research Communications, Academic Press Inc. Orlando, FL, US, vol. 312, No. 4, Dec. 26, 2003, pp. 1159-1164.

Zhou Z et al: "A recombinant baculovirus-expressed S glycoprotein vaccine elicits high titers of SARS-associated coronavirus (SARS-CoV) neutralizing antibodies in mice" Vaccine, Butterworth Scientific. Guildford, GB, vol. 24, No. 17, Apr. 24, 2006, pp. 3624-3631.

Goes et al., Bovine Papillomavirus Type 4 L1 Gene Transfection in a *Drosophila* S2 Cell Expression System: Absence of L1 Protein Expression, Brazilian Journal of Microbiology (2008) 39:1-4.

Toepfer, Heterologous expression of a functional domain of the nicotinic acetylcholine receptor, FU Berlin digitale dissertation, Oct. 2, 2002.

* cited by examiner

```
                    2179                  2166
   1 - ATGTTTATTTTCTTATTATTTCTTACTCTCACTAGTGGTAGTGACCTTGACCGGTGCACC - 60
     - M  F  I  F  L  L  F  L  T  L  T  S  G  S  D  L  D  R  C  T
  61 - ACTTTTGATGATGTTCAAGCTCCTAATTACACTCAACATACTTCATCTATGAGGGGGGTT - 120
     - T  F  D  D  V  Q  A  P  N  Y  T  Q  H  T  S  S  M  R  G  V
 121 - TACTATCCTGATGAAATTTTTAGATCAGACACTCTTTATTTAACTCAGGATTTATTTCTT - 180
     - Y  Y  P  D  E  I  F  R  S  D  T  L  Y  L  T  Q  D  L  F  L
 181 - CCATTTTATTCTAATGTTACAGGGTTTCATACTATTAATCATACGTTTGGCAACCCTGTC - 240
     - P  F  Y  S  N  V  T  G  F  H  T  I  N  H  T  F  G  N  P  V
 241 - ATACCTTTTAAGGATGGTATTTATTTTGCTGCCACAGAGAAATCAAATGTTGTCCGTGGT - 300
     - I  P  F  K  D  G  I  Y  F  A  A  T  E  K  S  N  V  V  R  G
 301 - TGGGTTTTTGGTTCTACCATGAACAACAAGTCACAGTCGGTGATTATTATTAACAATTCT - 360
     - W  V  F  G  S  T  M  N  N  K  S  Q  S  V  I  I  I  N  N  S
 361 - ACTAATGTTGTTATACGAGCATGTAACTTTGAATTGTGTGACAACCCTTTCTTTGCTGTT - 420  2172
     - T  N  V  V  I  R  A  C  N  F  E  L  C  D  N  P  F  F  A  V
 421 - TCTAAACCCATGGGTACACAGACACATACTATGATATTCGATAATGCATTTAATTGCACT - 480
     - S  K  P  M  G  T  Q  T  H  T  M  I  F  D  N  A  F  N  C  T
 481 - TTCGAGTACATATCTGATGCCTTTTCGCTTGATGTTTCAGAAAAGTCAGGTAATTTTAAA - 540
     - F  E  Y  I  S  D  A  F  S  L  D  V  S  E  K  S  G  N  F  K
 541 - CACTTACGAGAGTTTGTGTTTAAAAATAAAGATGGGTTTCTCTATGTTTATAAGGGCTAT - 600
     - H  L  R  E  F  V  F  K  N  K  D  G  F  L  Y  V  Y  K  G  Y
 601 - CAACCTATAGATGTAGTTCGTGATCTACCTTCTGGTTTTAACACTTTGAAACCTATTTTT - 660
     - Q  P  I  D  V  V  R  D  L  P  S  G  F  N  T  L  K  P  I  F
 661 - AAGTTGCCTCTTGGTATTAACATTACAAATTTTAGAGCCATTCTTACAGCCTTTTCACCT - 720
     - K  L  P  L  G  I  N  I  T  N  F  R  A  I  L  T  A  F  S  P
 721 - GCTCAAGACATTTGGGGCACGTCAGCTGCAGCCTATTTTGTTGGCTATTTAAAGCCAACT - 780  2168
     - A  Q  D  I  W  G  T  S  A  A  A  Y  F  V  G  Y  L  K  P  T        2167
 781 - ACATTTATGCTCAAGTATGATGAAAATGGTACAATCACAGATGCTGTTGATTGTTCTCAA - 840  2173
     - T  F  M  L  K  Y  D  E  N  G  T  I  T  D  A  V  D  C  S  Q
 841 - AATCCACTTGCTGAACTCAAATGCTCTGTTAAGAGCTTTGAGATTGACAAAGGAATTTAC - 900
     - N  P  L  A  E  L  K  C  S  V  K  S  F  E  I  D  K  G  I  Y
 901 - CAGACCTCTAATTTCAGGGTTGTTCCCTCAGGAGATGTTGTGAGATTCCCTAATATTCA - 960
     - Q  T  S  N  F  R  V  V  P  S  G  D  V  V  R  F  P  N  I  T
 961 - AACTTGTGTCCTTTTCGAGAGGTTTTTAATGCTACTAAATTCCCTTCTGTCTATGCATGG - 1020
     - N  L  C  P  F  G  E  V  F  N  A  T  K  F  P  S  V  Y  A  W
1021 - GAGAGAAAAAAATTTCTAATTGTGTTGCTGATTACTCTGTGCTCTACAACTCAACATTT - 1080
     - E  R  K  K  I  S  N  C  V  A  D  Y  S  V  L  Y  N  S  T  F
1081 - TTTTCAACCTTTAAGTGCTATGGCGTTTCTGCCACTAAGTTGAATGATCTTTGCTTCTCC - 1140
     - F  S  T  F  K  C  Y  G  V  S  A  T  K  L  N  D  L  C  F  S
1141 - AATGTCTATGCAGATTCTTTTGTAGTCAAGGGAGATGATGTAAGACAAATAGCGCCAGGA - 1200
     - N  V  Y  A  D  S  F  V  V  K  G  D  D  V  R  Q  I  A  P  G
1201 - CAAACTGGTGTTATTGCTGATTATAATTATAAATTGCCAGATGATTTCATGGGTTGTGTC - 1260  2174
     - Q  T  G  V  I  A  D  Y  N  Y  K  L  P  D  D  F  M  G  C  V
1261 - CTTGCTTGGAATACTAGGAACATTGATGCTACTTCAACTGGTAATTATAATTATAAATAT - 1320
     - L  A  W  N  T  R  N  I  D  A  T  S  T  G  N  Y  N  Y  K  Y
1321 - AGGTATCTTAGACATGGCAAGCTTAGGCCCTTTGAGAGAGACATATCTAATGTGCCTTTC - 1380
     - R  Y  L  R  H  G  K  L  R  P  F  E  R  D  I  S  N  V  P  F
1381 - TCCCCTGATGGCAAACCTTGCACCCCACCTGCTCTTAATTGTTATTGGCCATTAAATGAT - 1440
     - S  P  D  G  K  P  C  T  P  P  A  L  N  C  Y  W  P  L  N  D
1441 - TATGGTTTTTACACCACTACTGGCATTGGCTACCAACCTTACAGAGTTGTAGTACTTTCT - 1500
     - Y  G  F  Y  T  T  T  G  I  G  Y  Q  P  Y  R  V  V  L  S
1501 - TTTGAACTTTTAAATGCACCGGCCACGGTTTGTGGACCAAAATTATCCACTGACCTTATT - 1560
     - F  E  L  L  N  A  P  A  T  V  C  G  P  K  L  S  T  D  L  I
1561 - AAGAACCAGTGTGTCAATTTTAATTTTAATGGACTCACTGGTACTGGTGTGTTAACTCCT - 1620
     - K  N  Q  C  V  N  F  N  F  N  G  L  T  G  T  G  V  L  T  P
1621 - TCTTCAAAGAGATTTCAACCATTTCAACAATTTGGCCGTGATGTTTCTGATTTCACTGAT - 1680  2175
     - S  S  K  R  F  Q  P  F  Q  Q  F  G  R  D  V  S  D  F  T  D
1681 - TCCGTTCGAGATCCTAAAACATCTGAAATATTAGACATTTCACCTTGCGCTTTTGGGGGT - 1740
     - S  V  R  D  P  K  T  S  E  I  L  D  I  S  P  C  A  F  G  G
1741 - GTAAGTGTAATTACACCTGGAACAAATGCTTCATCTGAAGTTGCTGTTCTATATCAAGAT - 1800
     - V  S  V  I  T  P  G  T  N  A  S  S  E  V  A  V  L  Y  Q  D
1801 - GTTAACTGCACTGATGTTTCTACAGCAATTCATGCAGATCAACTCACACCAGCTTGGCGC - 1860
     - V  N  C  T  D  V  S  T  A  I  H  A  D  Q  L  T  P  A  W  R
1861 - ATATATTCTACTGGAAACAATGTATTCCAGACTCAAGCAGGCTGTCTTATAGGAGCTGAG - 1920
```

FIGURE 1A

```
              - I  Y  S  T  G  N  N  V  F  Q  T  Q  A  G  C  L  I  G  A  E
1921 - CATGTCGACACTTCTTATGAGTGCGACATTCCTATTGGAGCTGGCATTTGTGCTAGTTAC - 1980
              - H  V  D  T  S  Y  E  C  D  I  P  I  G  A  G  I  C  A  S  Y
1981 - CATACAGTTTCTTTATTACGTAGTACTAGCCAAAAATCTATTGTGGCTTATACTATGTCT - 2040
              - H  T  V  S  L  L  R  S  T  S  Q  K  S  I  V  A  Y  T  M  S
2041 - TTAGGTGCTGATAGTTCAATTGCTTACTCTAATAACACCATTGCTATACCTACTAACTTT - 2100   2176
              - L  G  A  D  S  S  I  A  Y  S  N  N  T  I  A  I  P  T  N  F
2101 - TCAATTAGCATTACTACAGAAGTAATGCCTGTTTCTATGGCTAAAACCTCCGTAGATTGT - 2160
              - S  I  S  I  T  T  E  V  M  P  V  S  M  A  K  T  S  V  D  C
2161 - AATATGTACATCTGCGGAGATTCTACTGAATGTGCTAATTTGCTTCTCCAATATGGTAGC - 2220
              - N  M  Y  I  C  G  D  S  T  E  C  A  N  L  L  L  Q  Y  G  S
2221 - TTTTGCACACAACTAAATCGTGCACTCTCAGGTATTGCTGCTGAACAGGATCGCAACACA - 2280
              - F  C  T  Q  L  N  R  A  L  S  G  I  A  A  E  Q  D  R  N  T
2281 - CGTGAAGTGTTCGCTCAAGTCAAACAAATGTACAAAACCCCAACTTTGAAATATTTTGGT - 2340
              - R  E  V  F  A  Q  V  K  Q  M  Y  K  T  P  T  L  K  Y  F  G
2341 - GGTTTTAATTTTTCACAAATATTACCTGACCCTCTAAAGCCAACTAAGAGGTCTTTTATT - 2400
              - G  F  N  F  S  Q  I  L  P  D  P  L  K  P  T  K  R  S  F  I
2401 - GAGGACTTGCTCTTTAATAAGGTGACACTCGCTGATGCTGGCTTCATGAAGCAATATGGC - 2460
              - E  D  L  L  F  N  K  V  T  L  A  D  A  G  F  M  K  Q  Y  G
2461 - GAATGCCTAGGTGATATTAATGCTAGAGATCTCATTTGTGCGCAGAAGTTCAATGGACTT - 2520   2170
              - E  C  L  G  D  I  N  A  R  D  L  I  C  A  Q  K  F  N  G  L          2169
2521 - ACAGTGTTGCCACCTCTGCTCACTGATGATATGATTGCTGCCTACACTGCTGCTCTAGTT - 2580
              - T  V  L  P  P  L  L  T  D  D  M  I  A  A  Y  T  A  A  L  V
2581 - AGTGGTACTGCCACTGCTGGATGGACATTTGGTGCTGGCGCTGCTCTTCAAATACCTTTT - 2640   SapI
              - S  G  T  A  T  A  G  W  T  F  G  A  G  A  A  L  Q  I  P  F
2641 - GCTATGCAAATGGCATATAGGTTCAATGGCATTGGAGTTACCCAAAATGTTCTCTATGAG - 2700
              - A  M  Q  M  A  Y  R  F  N  G  I  G  V  T  Q  N  V  L  Y  E
2701 - AACCAAAAACAAATCGCCAACCAATTTAACAAGGCGATTAGTCAAATTCAAGAATCACTT - 2760
              - N  Q  K  Q  I  A  N  Q  F  N  K  A  I  S  Q  I  Q  E  S  L
2761 - ACAACAACATCAACTGCATTGGGCAAGCTGCAAGACGTTGTTAACCAGAATGCTCAAGCA - 2820
              - T  T  T  S  T  A  L  G  K  L  Q  D  V  V  N  Q  N  A  Q  A
2821 - TTAAACACACTTGTTAAACAACTTAGCTCTAATTTTGGTGCAATTTCAAGTGTGCTAAAT - 2880
              - L  N  T  L  V  K  Q  L  S  S  N  F  G  A  I  S  S  V  L  N
2881 - GATATCCTTTCGCGACTTGATAAAGTCGAGGCGGAGGTACAAATTGACAGGTTAATTACA - 2940   2177
              - D  I  L  S  R  L  D  K  V  E  A  E  V  Q  I  D  R  L  I  T
2941 - GGCAGACTTCAAAGCCTTCAAACCTATGTAACAACAACTAATCAGGGCTGCTGAAATC - 3000
              - G  R  L  Q  S  L  Q  T  Y  V  T  Q  Q  L  I  R  A  A  E  I
3001 - AGGGCTTCTGCTAATCTTGCTGCTACTAAAATGTCTGAGTGTGTTCTTGGACAATCAAAA - 3060
              - R  A  S  A  N  L  A  A  T  K  M  S  E  C  V  L  G  Q  S  K
3061 - AGAGTTGACTTTTGTGGAAAGGGCTACCACCCTTATGTCCTTCCCACAAGCAGCCCCGCAT - 3120
              - R  V  D  F  C  G  K  G  Y  H  L  M  S  F  P  Q  A  A  P  H
3121 - GGTGTTGTCTTCCTACATGTCACGTATGTGCCATCCCAGGAGAGGAACTTCACCACAGCG - 3180
              - G  V  V  F  L  H  V  T  Y  V  P  S  Q  E  R  N  F  T  T  A
3181 - CCAGCAATTTGTCATGAAGGCAAAGCATACTTCCCTCGTGAAGGTGTTTTTGTGTTTAAT - 3240
              - P  A  I  C  H  E  G  K  A  Y  F  P  R  E  G  V  F  V  F  N
3241 - GGCACTTCTTGGTTTATTACACAGAGGAACTTCTTTTCTCCACAAATAATTACTACAGAC - 3300
              - G  T  S  W  F  I  T  Q  R  N  F  F  S  P  Q  I  I  T  T  D
3301 - AATACATTTGTCTCAGGAAATTGTGATGTCGTTATTGGCATCATTAACAACACAGTTTAT - 3360   Seq #7
              - N  T  F  V  S  G  N  C  D  V  I  G  I  I  N  N  T  V  Y          SapI
3361 - GATCCTCTGCAACCTGAGCTTGACTCATTCAAAGAAGAGCTGGACAAGTACTTCAAAAAT - 3420
              - D  P  L  Q  P  E  L  D  S  F  K  E  E  L  D  K  Y  F  K  N
3421 - CATACATCACCAGATGTTGATCTTGGCGACATTTCAGGCATTAACGCTTCTGTCGTCAAC - 3480
              - H  T  S  P  D  V  D  L  G  D  I  S  G  I  N  A  S  V  V  N
3481 - ATTCAAAAGAAATTGACCGCCTCAATGAGGTCGCTAAAAATTTAAATGAATCACTCATT - 3540
              - I  Q  K  E  I  D  R  L  N  E  V  A  K  N  L  N  E  S  L  I
3541 - GACCTTCAAGAATTGGGAAAATATGAGCAATATATTAAATGGCCTTGGTATGTTTGGCTC - 3600
              - D  L  Q  E  L  G  K  Y  E  Q  Y  I  K  W  P  W  Y  V  W  L
3601 - GGCTTCATTGCTGGACTAATTGCCATCGTCATGGTTACAATCTTGCTTTGTTGCATGACT - 3660
              - G  F  I  A  G  L  I  A  I  V  M  V  T  I  L  L  C  C  M  T
3661 - AGTTGTTGCAGTTGCCTCAAGGGTGCATGCTCTTGTGGTTCTTGCTGCAAGTTTGATGAG - 3720
              - S  C  C  S  C  L  K  G  A  C  S  C  G  S  C  C  K  F  D  E
3721 - GATGACTCTGAGCCAGTTCTCAAGGGTGTCAAATTACATTACACATAA - 3768
              - D  D  S  E  P  V  L  K  G  V  K  L  H  Y  T  *                     2171
```

Figure 1B

```
ATGtttattttcttattatttcttactctcactagtggtAGTgaccttgaccggtgcaccacttt
tgatgatgttcaagctcctaattacactcaacatacttcatctatgaggggggtttactatcctg
atgaaattttagatcagacactctttatttaactcaggatttatttcttccatttattctaat
gttacagggtttcatactattaatcatacgtttggcaaccctgtcatacctttaaggatggtat
ttattttgctgccacagagaaatcaaatgttgtccgtggtgggttttggttctaccatgaaca
acaagtcacagtcggtgattattattaacaattctactaatgttgttatacgagcatgtaacttt
gaattgtgtgacaacccttctttgctgtttctaaacccatgggtacacagacacatactatgat
attcgataatgcatttaattgcactttcgagtacatatctgatgccttttcgcttgatgtttcag
aaaagtcaggtaattttaaacacttacgagagtttgtgtttaaaaataaagatgggtttctctat
gtttataagggctatcaacctatagatgtagttcgtgatctaccttctggttttaacactttgaa
acctattttaagttgcctcttggtattaacattacaaattttagagccattcttacagcctttt
cacctgctcaagacatttggggcacgtcagctgcagcctattttgttggctatttaaagccaact
acatttatgctcaagtatgatgaaaatggtacaatcacagatgctgttgattgttctcaaaatcc
acttgctgaactcaaatgctctgttaagagctttgagattgacaaaggaatttaccagacctcta
atttcagggttgttccctcaggagatgttgtgagattccctaatattacaaacttgtgtcctttt
ggagaggtttttaatgctactaaattcccttctgtctatgcatgggagagaaaaaaaatttctaa
ttgtgttgctgattactctgtgctctacaactcaacatttttttcaaccttaagtgctatggcg
tttctgccactaagttgaatgatctttgcttctccaatgtctatgcagattcttttgtagtcaag
ggagatgatgtaagacaaatagcgccaggacaaactggtgttattgctgattataattataaatt
gccagatgatttcatgggttgtgtccttgcttgaatactaggaacattgatgctacttcaactg
gtaattataattataaatataggtatcttagacatggcaagcttaggccctttgagagagacata
tctaatgtgcctttctccctgatggcaaaccttgcacccacctgctcttaattgttattggcc
attaaatgattatggttttacaccactactggcattggctaccaaccttacagagttgtagtac
tttcttttgaacttttaaatgcaccggccacggtttgtggaccaaaattatccactgaccttatt
aagaaccagtgtgtcaattttaattttaatggactcactggtactggtgtgttaactccttcttc
aaagagatttcaaccatttcaacaatttggccgtgatgtttctgatttcactgattccgttcgag
atcctaaaacatctgaaatattagacatttccccttgcgcttttggggtgtaagtgtaattaca
cctggaacaaatgcttcatctgaagttgctgttctatatcaagatgttaactgcactgatgtttc
tacagcaattcatgcagatcaactcacaccagcttggcgcatatattctactggaaacaatgtat
tccagactcaagcaggctgtcttataggagctgagcatgtcgacacttcttatgagtgcgacatt
cctattggagctggcatttgtgctagttaccatacagtttctttattacgtagtactagccaaaa
atctattgtggcttatactatgtctttaggtgctgatagttcaattgcttactctaataacacca
ttgctatacctactaacttttcaattagcattactacagaagtaatgcctgtttctatggctaaa
acctccgtagattgtaatatgtacatctgcggagattctactgaatgtgctaatttgcttctcca
atatggtagcttttgcacacaactaaatcgtgcactctcaggtattgctgctgaacaggatcgca
acacacgtgaagtgttcgctcaagtcaaacaaatgtacaaaaccccaacttgaaatatttggt
ggttttaattttttcacaaatattacctgaccctctaaagccaactaagaggtcttttattgagga
cttgctctttaataaggtgacactcgctgatgctggcttcatgaagcaatatggcgaatgcctag
gtgatattaatgctagagatctcatttgtgcgcagaagttcaatggacttacagtgttgccacct
ctgctcactgatgatatgattgctgcctacactgctgctctagttagtggtactgccactgctgg
atggacatttggtgctggcgctgctcttcaaatacctttgctatgcaaatggcatataggttca
atggcattggagttacccaaaatgttctctatgagaaccaaaaacaaatcgccaaccaatttaac
aaggcgattagtcaaattcaagaatcacttacaacaacatcaa
```

FIGURE 2A ctgcattgggcaagctgcaagacgttgttaaccagaatgctcaagcattaaaca
cacttgttaaacaacttagctctaattttggtgcaatttcaagtgtgctaaatg
atatcctttcgcgacttgataaagtcgaggcggaggtacaaattgacaggttaa
ttacaggcagacttcaaagccttcaaacctatgtaacacaacaactaatcaggg
ctgctgaaatcagggcttctgctaatcttgctgctactaaaatgtctgagtgtg
ttcttggacaatcaaaaagagttgacttttgtggaaagggctaccaccttatgt
ccttcccacaagcagccccgcatggtgttgtcttcctacatgtcacgtatgtgc
catcccaggagaggaacttcaccacagcgccagcaatttgtcatgaaggcaaag
catacttccctcgtgaaggtgttttttgtgtttaatggcacttcttggtttatta
cacagaggaacttcttttctccacaaataattactacagacaatacatttgtct
caggaaattgtgatgtcgttattggcatcattaacaacacagtttatgatcctc
tgcaacctgagcttgactcattcaaagaagagctggacaagtacttcaaaaatc
atacatcaccagatgttgatcttggcgacatttcaggcattaacgcttctgtcg
tcaacattcaaaaagaaattgaccgcctcaatgaggtcgctaaaaatttaaatg
aatcactcattgaccttcaagaattgggaaaatatgagcaatatattaaatggc
cttggtatgtttggctcggcttcattgctggactaattgccatcgtcatggtta
caatcttgctttgttgcatgactagttgttgcagttgcctcaagggtgcatgct
cttgtggttcttgctgcaagtttgatgaggatgactctgagccagttctcaagg
gtgtcaaattacattacacaTAA

Figure 2B

E PROTEIN DNA SEQUENCE

ATGTACTCATTCGTTTCGGAAGAAACAGGTACGTTAATAGTTAATAGCGTACT
TCTTTTTCTTGCTTTCGTGGTATTCTTGCTAGTCACACTAGCCATCCTTACTGC
GCTTCGATTGTGTGCGTACTGCTGCAATATTGTTAACGTGAGTTTAGTAAAAC
CAACGGTTTACGTCTACTCGCGTGTTAAAAATCTGAACTCTTCTGAAGGAGTT
CCTGATCTTCTGGTCTAA

FIGURE 3

E PROTEIN AMINO ACID SEQUENCE

MYSFVSEETGTLIVNSVLLFLAFVVFLLVTLAILTALRLCAYCCNIVNVSLVKPTVYVYS
RVKNLNSSEGVPDLLV

FIGURE 4

M PROTEIN DNA SEQUENCE

ATGGCAGACAACGGTACTATTACCGTTGAGGAGCTTAAACAACTCCTGGAAC
AATGGAACCTAGTAATAGGTTTCCTATTCCTAGCCTGGATTATGTTACTACAA
TTTGCCTATTCTAATCGGAACAGGTTTTTGTACATAATAAAGCTTGTTTTCCTC
TGGCTCTTGTGGCCAGTAACACTTGCTTGTTTTGTGCTTGCTGCTGTCTACAGA
ATTAATTGGGTGACTGGCGGGATTGCGATTGCAATGGCTTGTATTGTAGGCTT
GATGTGGCTTAGCTACTTCGTTGCTTCCTTCAGGCTGTTTGCTCGTACCCGCTC
AATGTGGTCATTCAACCCAGAAACAAACATTCTTCTCAATGTGCCTCTCCGGG
GGACAATTGTGACCAGACCGCTCATGGAAAGTGAACTTGTCATTGGTGCTGT
GATCATTCGTGGTCACTTGCGAATGGCCGGACACTCCCTAGGGCGCTGTGAC
ATTAAGGACCTGCCAAAAGAGATCACTGTGGCTACATCACGAACGCTTTCTT
ATTACAAATTAGGAGCGTCGCAGCGTGTAGGCACTGATTCAGGTTTTGCTGC
ATACAACCGCTACCGTATTGGAAACTATAAATTAAATACAGACCACGCCGGT
AGCAACGACAATATTGCTTTGCTAGTACAGTAA

FIGURE 5

M PROTEIN AMINO ACID SEQUENCE

MADNGTITVEELKQLLEQWNLVIGFLFLAWIMLLQFAYSNRNRFLYIIKLVFLWLLWPVT
LACFVLAAVYRINWVTGGIAIAMACIVGLMWLSYFVASFRLFARTRSMWSFNPETNILLN
VPLRGTIVTRPLMESELVIGAVIIRGHLRMAGHSLGRCDIKDLPKEITVATSRTLSYYKL
GASQRVGTDSGFAAYNRYRIGNYKLNTDHAGSNDNIALLVQ

FIGURE 6A

N Protein DNA sequence atggaccccaatcaaaccaacgtagtgcccccgcattacatttggtggacccacagattcaactgacaata
accagaatggaggacgcaatggggcaaggccaaaacagcgccgaccccaaggtttacccaataatactgcgt
cttggttcacagctctcactcagcatggcaaggaggaacttagattccctcgaggccagggcgttccaatca
acaccaatagtggtccagatgaccaaattggctactaccgaagagctacccgacgagttcgtggtggtgacg
gcaaaatgaaagagctcagcccagatggtacttctattacctaggaactggcccagaagcttcacttccct
acggcgctaacaaagaaggcatcgtatggggttgcaactgagggagccttgaatacacccaaagaccacattg
gcacccgcaatcctaataacaatgctgccaccgtgctacaacttcctcaaggaacaacattgccaaaaggct
tctacgcagagggaagcagaggcggcagtcaagcctcttctcgctcctcatcacgtagtcgcggtaattcaa
gaaattcaactcctggcagcagtaggggaaattctcctgctcgaatggctagcggaggtggtgaaactgccc
tcgcgctattgctgctagacagattgaaccagcttgagagcaaagtttctggtaaaggccaacaacaacaag
gccaaactgtcactaagaaatctgctgctgaggcatctaaaaagcctcgccaaaaacgtactgccacaaaac
agtacaacgtcactcaagcatttgggagacgtggtccagaacaaacccaaggaaatttcggggaccaagacc
taatcagacaaggaactgattacaaacattggccgcaaattgcacaatttgctccaagtgcctctgcattct
ttggaatgtcacgcattggcatggaagtcacaccttcgggaacatggctgacttatcatggagccattaaat
tggatgacaaagatccacaattcaaagacaacgtcatactgctgaacaagcacattgacgcatacaaaacat
tcccaccaacagagcctaaaaaggacaaaaagaaaaagactgatgaagctcagccttgccgcagagacaaa
agaagcagcccactgtgactcttcttcctgcggctgacatggatgatttctccagacaacttcaaaattcca
tgagtggagcttctgctgattcaactcaggcataa

FIGURE 6B

N Protein Amino Acid sequence

MSDNGPQSNQRSAPRITFGGPTDSTDNNQNGGRNGARPKQRRPQGLPNNTASWFTALTQH
GKEELRFPRGQGVPINTNSGPDDQIGYYRRATRRVRGGDGKMKELSPRWYFYYLGTGPEA
SLPYGANKEGIVWVATEGALNTPKDHIGTRNPNNNAATVLQLPQGTTLPKGFYAEGSRGG
SQASSRSSSRSRGNSRNSTPGSSRGNSPARMASGGGETALALLLLDRLNQLESKVSGKGQ
QQQGQTVTKKSAAEASKKPRQKRTATKQYNVTQAFGRRGPEQTQGNFGDQDLIRQGTDYK
HWPQIAQFAPSASAFFGMSRIGMEVTPSGTWLTYHGAIKLDDKDPQFKDNVILLNKHIDA
YKTFPPTEPKKDKKKKTDEAQPLPQRQKKQPTVTLLPAADMDDFSRQLQNSMSGASADST
QA

FIGURE 6C

| 2165 (5') | AGGTTC GCTCTTC A ATG TTTATTTTCTTATTATTTCTTACTCTC<br>Start |
|---|---|
| 2166 (5') | AGGTTC GCTCTTC A GCG GGTAGTGACCTTGACCGGTGC<br>Mature |
| 2167 (3') | AGGTTCGCTCTTCATTAGGTACCAATAGCCAACAAAATAGGCTGCAGCTGAC<br>Sap  Kpn  Pst |
| 2168 (5') | CGTCAGCTGCAGCCTATTTTGTTGGC<br>PstI |
| 2169 (3') | AGGTTCGCTCTTCATTAGGTACCCAAATGAGATCTCTAGCATTAATATCACC<br>Sap  Kpn  Bcl |
| 2170 | AGGTTCGGATCCAGATCTCATTTGTGCGCAG<br>Bam  Bcl II |
| 2171 | AGGTTCGGTACCTTATGTGTAATGTAATTTGACACC<br>KpnI<br>Stop |

FIGURE 7

Restriction Map of the S-ORF

**SARS S Protein ORF
3768nt**

```
         PstI                                BglII
├─────────┼───────┼──────────┼──────────┼────┼──┼────────┤
├─ Front ─┤                                SapI    SapI
   761nt  ├──────── Middle ──────────┤
                    1737nt           ├──────── Back ────────┤
                                              1270nt
```

FIGURE 8

Transfer plasmid

Full length cDNA

Polyhedrin promoter

*Processing Signals

*PCR-direct cloning

Full length cDNA

*Linearized BV DNA

↓ Recombination

Full length cDNA

BV expression vector

FIGURE 9

PROCESS FLOW DIAGRAM SARS ΔTM S PROTEIN

| | |
|---|---|
| FERMENTATION D3252 IN SF+ CELLS<br>in serum-free media | |
| Centrifugation<br>Cells harvested by low speed centrifugation (6000xg 15 minutes)<br>ΔTM S protein recovered in supernatant | Pellet discarded<br>Cellular material removed |
| pH supernatant adjusted to 8 followed by centrifugation<br>Supernatant clarified by low speed centrifugation (6000xg 15 minutes)<br>ΔTM S protein recovered in supernatant | Pellet discarded<br>DNA and other contaminants removed |
| Supernatant concentration by TFF<br>Hold at -20°C | QC study ongoing to confirm stability |
| Cation Exchange Chromatography (UnosphereS)<br>Concentrated material is applied to the column.<br>Equilibration Buffer:<br>ΔTM S protein flows through the Unosphere S column | Contaminants discarded<br>Additional viral clearance<br>DNA and protein impurities removed |
| Anon Exchange Chromatography (Q)<br>FT is applied to the column.<br>Equilibration Buffer:<br>Elution Buffer:<br>ΔTM S protein flows binds to the Q column and is eluted with 150 mM NaCl | Contaminants discarded<br>Additional viral clearance<br>DNA and protein impurities removed |
| Lentil Lectin Chromatography<br>ΔTM S protein eluate from Q is applied to a lentil lectin chromatography column<br>Equilibration Buffer / Wash buffer<br>Elution buffer: 0.5M N- Methyl-α-D-mannopyranoside, 20mM Tris, 0.1% Triton X-100, 0.01% β-mercaptoethanol, pH=7.4<br>ΔTM S protein binds to the lentil lectin column. The column is washed with Equilibration / Wash buffer, then ΔTM S protein is eluted with Elution buffer. | Contaminants are discarded<br>Final purity is achieved with this column<br>Protein impurities removed |
| Size chromatography SEC<br>Necessary ?<br>Lentil lectin column eluate is applied to column.<br>Equilibration buffer:<br>Wash buffer:<br>Elution buffer: | Detergent exchange and protein concentration is achieved with this column<br>Lentil lectin is removed from the protein |

FIGURE 12C

Process Flow Diagram SARS ΔTM S protein

| | |
|---|---|
| FERMENTATION D3252 IN SF+ CELLS<br><br>in serum-free media | |
| Centrifugation<br>Cells harvested by low speed centrifugation (6000xg 15 minutes)<br>ΔTM S protein recovered in supernatant | Pellet discarded<br><br>Cellular material removed |
| Cation Exchange Chromatography (UnosphereS)<br>Material is applied to the column.<br><br>*Equilibration Buffer:* 20 mM Tris pH 7.4<br><br>ΔTM S protein flows through the Unosphere S column | Contaminants discarded<br><br>Additional viral clearance<br><br>DNA and protein impurities removed |
| Anon Exchange Chromatography (Q)<br>FT is applied to the column.<br><br>*Equilibration Buffer:* 20 mM Tris pH 7.4<br><br>*Elution Buffer:* 0.15 M NaCl, 20 mM Tris pH 7.4<br><br>ΔTM S protein flows through the Q column | Contaminants discarded<br><br>Protein impurities removed |
| Lentil Lectin Chromatography<br>ΔTM S protein eluate from Q is applied to a lentil lectin chromatography column<br><br>*Equilibration Buffer / Wash buffer:* 20 mM Tris pH 7.4<br><br>*Elution buffer:* 0.5M N-Methyl-α-D-mannopyranoside, 20mM Tris, 0.1% Triton X-100, 0.01% β-mercaptoethanol, pH=7.4<br><br>ΔTM S protein binds to the lentil lectin column. The column is washed with Equilibration / Wash buffer, then ΔTM S protein is eluted with Elution buffer. | Protein impurities removed |
| Q column chromatography<br>Lentil lectin column eluate is applied to column.<br><br>Protein binds to the column | Protein is concentrated on this column and can be eluted in PBS |

FIGURE 12E

CLUSTAL W (1.82) Multiple Sequence Alignments

```
Sequence format is Pearson
Sequence 1: PSC                         1255 aa  Coronavirus SARS S protein
Sequence 2: sp|P15423|VGL2_CVH22        1173 aa  Human coronavirus 229E S protein
Sequence 3: tr|Q66928                   1454 aa  Feline coronavirus S protein
Sequence 4: sp|P36300|VGL2_CVCAI        1451 aa  canine enteric coronavirus
Sequence 5: sp|P18450|VGL2_CVPFS        1449 aa  Porcine transmissible gastro coronav
Sequence 6: tr|Q65984                   1453 aa  Canine coronavirus S protein
Sequence 7: sp|P24413|VGL2_CVPRM        1225 aa  Porcine respiratory coronavirus
Sequence 8: tr|Q84712                   1383 aa  Porcine epidemic diarrhea virus
Sequence 9: sp|P10033|VGL2_FIPV         1452 aa  Feline infectious peritonitis virus
Sequence 10: tr|O12031                   544 aa  Avian infectious bronchitis virus
Sequence 11: sp|P25192|VGL2_CVBLY       1363 aa  Bovine coronavirus
Start of Pairwise alignments
Aligning...
Sequences (1:2) Aligned. Score:  22
Sequences (1:3) Aligned. Score:  20
Sequences (1:4) Aligned. Score:  21
Sequences (1:5) Aligned. Score:  21
Sequences (1:6) Aligned. Score:  22
Sequences (1:7) Aligned. Score:  19
Sequences (1:8) Aligned. Score:  21
Sequences (1:9) Aligned. Score:  21
Sequences (1:10) Aligned. Score:  12
Sequences (1:11) Aligned. Score:  30
Sequences (2:3) Aligned. Score:  47
Sequences (2:4) Aligned. Score:  46
Sequences (2:5) Aligned. Score:  47
Sequences (2:6) Aligned. Score:  47
Sequences (2:7) Aligned. Score:  47
Sequences (2:8) Aligned. Score:  48
Sequences (2:9) Aligned. Score:  47
Sequences (2:10) Aligned. Score:  12
Sequences (2:11) Aligned. Score:  24
Sequences (3:4) Aligned. Score:  92
Sequences (3:5) Aligned. Score:  80
Sequences (3:6) Aligned. Score:  92
Sequences (3:7) Aligned. Score:  89
Sequences (3:8) Aligned. Score:  43
Sequences (3:9) Aligned. Score:  95
Sequences (3:10) Aligned. Score:  11
Sequences (3:11) Aligned. Score:  22
Sequences (4:5) Aligned. Score:  78
Sequences (4:6) Aligned. Score:  93
Sequences (4:7) Aligned. Score:  88
Sequences (4:8) Aligned. Score:  43
Sequences (4:9) Aligned. Score:  91
Sequences (4:10) Aligned. Score:  14
Sequences (4:11) Aligned. Score:  22
Sequences (5:6) Aligned. Score:  79
Sequences (5:7) Aligned. Score:  96
Sequences (5:8) Aligned. Score:  44
Sequences (5:9) Aligned. Score:  79
Sequences (5:10) Aligned. Score:  13
Sequences (5:11) Aligned. Score:  22
Sequences (6:7) Aligned. Score:  89
Sequences (6:8) Aligned. Score:  43
Sequences (6:9) Aligned. Score:  92
Sequences (6:10) Aligned. Score:  11
Sequences (6:11) Aligned. Score:  22
Sequences (7:8) Aligned. Score:  47
Sequences (7:9) Aligned. Score:  89
Sequences (7:10) Aligned. Score:  11
Sequences (7:11) Aligned. Score:  23
Sequences (8:9) Aligned. Score:  44
Sequences (8:10) Aligned. Score:  16
Sequences (8:11) Aligned. Score:  18
Sequences (9:10) Aligned. Score:  14
Sequences (9:11) Aligned. Score:  22
Sequences (10:11) Aligned. Score:  13
Guide tree       file created:    [/ebi/extserv/old-work/clustalw-20030619-29750057.dnd]
Start of Multiple Alignment
There are 10 groups
Aligning...
Group 1:                        Delayed
Group 2: Sequences:     2       Score:30679
Group 3: Sequences:     2       Score:31002
Group 4: Sequences:     4       Score:30462
```

Figure 13A

```
Group 5: Sequences:   2        Score:26225
Group 6: Sequences:   6        Score:27200
Group 7: Sequences:   2        Score:18754
Group 8: Sequences:   8        Score:18554
Group 9:                       Delayed
Group 10:                      Delayed
Sequence:11      Score:10123
Sequence:1       Score:9693
Sequence:10      Score:3778
Alignment Score 171702
CLUSTAL-Alignment file created   [/ebi/extserv/old-work/clustalw-20030619-29750057.aln]
```

Your Multiple Sequence Alignment clustalw-20030619-29750057.aln

CLUSTAL W (1.82) multiple sequence alignment

```
sp|P36300|VGL2_CVCAI    MIVLTLCLFLFL-YSSVSCTSNNDCVQVNVTQLPGNENIIKDFLFQN---FKEEGSLVVG 56
tr|Q65984               MIVLILCLLLFS-YNSVICTSNNDCVQGNVTQLPGNENIIKDFLFHT---FKEEPSVVVG 56
tr|Q66928               MIVLVTCILLLCSYHTVSSTSNNDCRQVNVTQLAGNENLIRDFLFQS---FKEEGIVVVG 57
sp|P10033|VGL2_FIPV     MIVLVTCLLLLCSYHTVLSTTNNECIQVNVTQLAGNENLIRDFLFSN---FKEEGSVVVG 57
sp|P18450|VGL2_CVPFS    MKKLFVVLVVMP----LIYGDNFPCSKLTNRTIGNHWNLIETFLLNYSSRLSPNSDVVLG 56
sp|P24413|VGL2_CVPRM    MKKLFVVLVVMP----LIYGDKFP------------------------------------ 20
sp|P15423|VGL2_CVH22    ------MFVLLVAYALLHIAG----CQTTN------------------------------ 20
tr|Q84712               MRSLIYFWLLLPVLPTLSLPQDVTRCQSTTNFRRFFSKFNVQAPAVV---------VLG 50
sp|P25192|VGL2_CVBLY    ----MFLILLISLPMALAVIGDLKCTTVSINDVDTGVPSVSTDTVDVTN---------- 45
PSC                     -------MFIFLLFLTLTSGSDLDRCTTFDDVQAPNYTQHTSSMR-------------- 38
tr|O12031               ------------------------------------------------------------ sp|P36300|VGL2_CVCAI    GYYPT-EVWYNCSTTQQTTAYKYFSNIHAFYFDMEAMENSTGNARGKPLLVHVHGNPVSI 115
tr|Q65984               GYYPT-EVWYNCSRSATTTAYKDFSNIHAFYFDMEAMENSTGNARGKPLLVHVHGDPVSI 115
tr|Q66928               GYYPT-EVWYNCSRTATTTAYEYFNNIHAFYFDMEAMENSTGNARGKPLLVHVHGEPVSI 116
sp|P10033|VGL2_FIPV     GYYPT-EVWYNCSRTARTTAFQYFNNIHAFYFVMEAMENSTGNARGKPLLFHVHGEPVSV 116
sp|P18450|VGL2_CVPFS    DYFPTVQPWFNCIHNNSNDLYVTLENLKALYWDY-ATENSTWNHKQR-LNVVVNGYPYSI 114
sp|P24413|VGL2_CVPRM    ------------------------------------------------------------
sp|P15423|VGL2_CVH22    ----GLNTS--------------------------------------------------- 25
tr|Q84712               GYLPSMNSSSWYCGTGIETASGVHGIFLSYIDSGQGFEIGISQEPFDPSGYQLYLHKATN 110
sp|P25192|VGL2_CVBLY    ----GLGTYYVLDRVYLNTTLLLNGYYPTSGSTYRNMALKGTLLLSTLWFKPPFLSDFIN 101
PSC                     ------GVYYPDEIFRSDTLYLTQDLFLPFYSNVTGFHTIN------------------- 73
tr|O12031               ------------------------------------------------------------ sp|P36300|VGL2_CVCAI    IVYISAYRDDVQFRPLLKHGLLCITKND---TVDYNSFTINQWRDICLGDDRKIPFSVVP 172
tr|Q65984               IIYISAYRDDVQPRPLLKHGLLCITKNK---IIDYNTFTSAQWSAICLGDDRKIPFSVIP 172
tr|Q66928               IIYISAYGDDVQQRPLLKHGLLCITKNR---NIDYNTFTSNQWDSICTGNDRKIPFSVIP 173
sp|P10033|VGL2_FIPV     II--SAYRDDVQQRPLLKHGLVCITKNR---HINYEQFTSNQWNSTCTGADRKIPFSVIP 171
sp|P18450|VGL2_CVPFS    TVTTTRNFNSAE------GAIICICKGSPPTTTTESSLTCNWGSECRLNHKFPICPSNSE 168
sp|P24413|VGL2_CVPRM    ------------------------------------------------------------
sp|P15423|VGL2_CVH22    ------------------------------------------------------------
tr|Q84712               GNTNATARLRICQFPDNKTLGPTVNDVT---------------TGRNCLFNKAIPAYM 153
sp|P25192|VGL2_CVBLY    GIFAKVKNTKVIKNGVMYSEFPAITIGS----------------TFVNTSYSVVVQPHT 144
PSC                     ------------------------------------------------------------
tr|O12031               ------------------------------------------------------------ sp|P36300|VGL2_CVCAI    TDNGTKLFGLEWNDDYVTAYISDESHRLNINNNWFNNVTLLYSRSTST--ATWQHSAAYVY 230
tr|Q65984               TDNGTKIFGLEWNDDYVTAYISDRSHHLNINNNWFNNVTILYSRSSS---ATWQKSAAYVY 230
tr|Q66928               RDNGTKIYGLEWNDEFVTAYISGRSYNWNINNNWFNNVTLLYSRSST---ATWHHSAAYVY 231
sp|P10033|VGL2_FIPV     TDNGTKIYGLEWNDDFVTAYISGRSYHLNINTNWFNNVTLLYSRSST---ATWEYSAAYAY 229
sp|P18450|VGL2_CVPFS    ANCGNMLYGLQWFADAVVAYLHGASYRISFENQWSGTVTLGDMRATTLETAGTLVDLWWF 228
sp|P24413|VGL2_CVPRM    ------------------------------------------------------------
sp|P15423|VGL2_CVH22    ------------------------------------------------------------
tr|Q84712               RDGKDIVVGITWDNDRVTVF-ADKIYHFYLKNDWSRVATRCYNRRSC---------AMQYV 204
sp|P25192|VGL2_CVBLY    TNLDNKLQGLLEIS---------------------------------------VCQYT 163  polymorphic
PSC                     ------------------------------------------------------------
tr|O12031               ------------------------------------------------------------
```

Figure 13B

```
sp|P36300|VGL2_CVCAI    QGVSNFTYYKLNKTAGLKSYELCEDYEYCTGYATNVFAPTSGGYIPDGFSFN--NWFMLT 288
tr|Q65984               QGVSNFTYYKLNNTNGLKSYELCEDYEYCTGYATNVFAPTVGGYIPHGFSFN--NWFMRT 288
tr|Q66928               QGVSNFTYYKLNNTNGLKTYEFCEDYEYCTGYATNVFAPTVGGYIPDGFSFN--NWFLLT 289
sp|P10033|VGL2_FIPV     QGVSNFTYYKLNNTNGLKTYELCEDYEHCTGYATNVFAPTSGGYIPDGFSFN--NWFLLT 287
sp|P18450|VGL2_CVPFS    NPVYDVSYYRVNNKNGTTVVSNCTD--QCASYVANVFTTQPGGFIPSDFSFN--NWFLLT 284
sp|P24413|VGL2_CVPRM    ----------------TSVVSNCTD--QCASYVANVFTILPGGFIPSDFSFN--NWPLLT 60
sp|P15423|VGL2_CVH22    ------------------YSVCNG---CVGYSENVFAVESGGYIPSDFAPN--NWPLLT 61
tr|Q84712               YTPTYYMLNVTSAGEDGIYYEPCTAN--CTGYAANVFATDSNGHIPEGFSFN--NWFLLS 260
sp|P25192|VGL2_CVBLY    MCEYPHTICHPNLGNRRIELWHWDTGVVSCLYKRNFTYDVNADYLYFHPYQEGGTFYAYF 223
PSC                     ---------------HTFGNPVIPFKDGIYFAATEKSNVVRGWVFGSTMNNKSQSVIII 117
tr|O12031               ------------------------------------------------------------ sp|P36300|VGL2_CVCAI    NSSTFVSGRFVTNQPLLVNCLWPVPSFGVAAQEFCFEGAQFSQCNGVSLNNTVDVIRFNL 348
tr|Q65984               NSSTFVSGRFVTNQPLLVNCLWPVPSFGVAAQQFCFEGAQFSQCNGVSLNNTVDVIRFNL 348
tr|Q66928               NSSTFVSGRFVTNQPLLVNCLWPVPSFGVAAQEFCFEGAQFSQCSGVSLNNTVDVIRFNL 349
sp|P10033|VGL2_FIPV     NSSTFVSGRFVTNQPLLINCLWPVPSFGVAAQEFCFEGAQFSQCNGVSLNNTVDVIRFNL 347
sp|P18450|VGL2_CVPFS    NSSTLVSGKLVTKQPLLVNCLWPVPSFEEAASTFCFEGAGFDQCNGAVLNNTVDVIRFNL 344
sp|P24413|VGL2_CVPRM    NSSTLVNGKLVTKQPLLVNCLWPVPSFEEVASTFCFEGADFDQCNGAVLNNTVDVIRFNL 120
sp|P15423|VGL2_CVH22    NTSSVVDGVVRSFQPLLLNCLWSVSGLRFTTGFVYFNGTGRGDCKGFSSDVLSDVIRYNL 121
tr|Q84712               NDSTLLHGKVVSNQPLLVNCLLAIPKIYGLGQFFSFNHTMDGVCNGAAVDRAPEALRFNI 320
sp|P25192|VGL2_CVBLY    TDTGVVTKFLFNVYLGTVLSHYYVMPLTCNSAMTLEYWVTPLTSKQYLLAFNQDGVIFNA 283
PSC                     NNSTNVVIRACNFELCDNPFFAVSKPMGTQTHTMIFDNAFNCTFEYISDAFSLDVSEKSG 177
tr|O12031               ------------------------------------------------------------ sp|P36300|VGL2_CVCAI    N-FTTDVQSGMGATVFSLNTTGGVILEISCYNDTVSESSFYSYGEIPFGVTDGPRYCYV- 406
tr|Q65984               N-FTALVQSGMGATVFSLNTTGGVILEISCYNDTVSESSFYSYGEISFGVTDGPRYCFA- 406
tr|Q66928               N-FTADVQSGMGATVFSLNTTGGVILEISCYNDTVSESSFYSYGEIPFGITDGPRYCYV- 407
sp|P10033|VGL2_FIPV     N-FTADVQSGMGATVFSLNTTGGVILEISCYSDTVSESSSYSYGEIPPGITDGPRYCYV- 405
sp|P18450|VGL2_CVPFS    N-FTTNVQSGKGATVFSLNTTGGVILEISCYNDTVSDSSFSSYGEISFGVTDGPRYCYV- 402
sp|P24413|VGL2_CVPRM    N-FTTNVQSGKGATVFSLNTTGGVTLEISCYNDTVSDSSFSSYGEIPFGVTNGPRYCYV- 178
sp|P15423|VGL2_CVH22    N-FEENLRRG----TILFKTSYG-VVVFYCTNN-TLVSG---DAHIPFGTVLGNFYCFVN 171
tr|Q84712               NDTSVILAEG----SIVLHTALGTNLSFVCSNSSDPHLA---IFAIPLGATEVPYYCFLK 373
sp|P25192|VGL2_CVBLY    VDCKSDFMSEIKCCKTLSIAPSTG-VYELNGYTVQPIADVYRRIPNLPDCNIEAWLNDKSV 342
PSC                     N-FKHLREFVFKNKDGFLYVYKGYQPIDVVRDLPSGFNTLKPIFKLPLGINITNFRAILT 236
tr|O12031               ------------------------------------------------------------ sp|P36300|VGL2_CVCAI    --------LYNGTALKYLGTLPPSVKEIAISKWGHFYINGYNFFSTFPIDCIAFNLT--- 455
tr|Q65984               --------LYNGTALKYLGTLPPSVKEIAISKWGHFYINGYNFFSTFPIDCISFNLT--- 455
tr|Q66928               --------LYNGTALKYLGTLPPSVKEIAISKWGHFYINGYNFFSTFPIDCISFNLT--- 456
sp|P10033|VGL2_FIPV     ---------LYNGTALKYLGTLPPSVKEIAISKWGHFYINGYNFFSTFPIGCISFNLT--- 454
sp|P18450|VGL2_CVPFS    --------LYNGTALKYLGTLPPSVKEIAISKWGHFYINGYNFFSTFPIDCISFNLT--- 451
sp|P24413|VGL2_CVPRM    --------LYNGTALKYLGTLPPSVKEIAISKWGHFYINGYNFFSTFPIDCISFNLT--- 227
sp|P15423|VGL2_CVH22    TT------IGNETTSAFVGALPKTVREFVISRTGHFYINGYRYFTLGNVEAVNFNVT--- 222
tr|Q84712               VD------TYNSTVYKFLAVLPSTVREIVITKYGDVYVNGFGYLHLGLLDAVTIYFTGHG 427
sp|P25192|VGL2_CVBLY    PS------PLNWERKTFSNCNFNMSSLMSFIQADSFTCNNIDAAKIYGMCFSSITIDKFA 396
PSC                     AFSPAQDIWGTSAAAYFVGYLKPTTFMLKYDENGTITDAVDCSQNPLAELKCSVKSFEID 296
tr|O12031               ------------------------------------------------------------ sp|P36300|VGL2_CVCAI    -TGASGAFWTIAYTSYTEAL-VQVENTAIKKVTYCNSHINNIKCSQLTANLQNGFYPVAS 513
tr|Q65984               -TGDSGAFWTIAYTSYTDAL-VQVENTAIKKVTYCNSHINNIKCSQLTANLQNGFYPVAS 513
tr|Q66928               -TGDSGAFWTIAYTSYTEAL-VQVENTAIKKVTYCNSHINNIKCSQLTANLNNGFYPVAS 514
sp|P10033|VGL2_FIPV     -TGVSGAFWTIAYTSYTEAL-VQVENTAIKNVTYCNSHINNIKCSQLTANLNNGFYPVAS 512
sp|P18450|VGL2_CVPFS    -TGDSDVFWTIAYTSYTEAL-VQVENTAITKVTYCNSYVNNIKCSQLTANLNNGFYPVSS 509
sp|P24413|VGL2_CVPRM    -TGDSDVFWTIAYTSYTEAL-VQVENTAITNVTYVNNIKCSQLTANLNNGFYPVSS 285
sp|P15423|VGL2_CVH22    -TAETTDFCTVALASYADVL-VNVSQTSIANIIYCNSVINRLRCDQLSFDVPDGFYSTSP 280
tr|Q84712               TDDDVSGFWTIASTNFVDAL-IEVQGTSIQRILYCDDPVSQLKCSQVAFDLDDGFYPISS 486
sp|P25192|VGL2_CVBLY    IPNGRKVDLQLGNLGYLQSFNYRIDTTATSCQLYYNLPAANVSVSRFNPSTWNRRFGFTE 456
PSC                     KGIYQTSNFRVVPSGDVVRFPNITNLCPFGEVFNATKFPSVYAWERKKISNCVADYSVLY 356
tr|O12031               ------------------------------------------------------MLV 3 sp|P36300|VGL2_CVCAI    SEVGLVNK--SVVLLPSFYSHTSVNITIDLGMKRS-VTVTIASPLS-NITLPMQDNNIDV 569
tr|Q65984               SEVGLVNK--SVVLLPSFYSHTSVNITIDLGMKRSGYGQPIASTLS-NITLPMQDNNTDV 570
tr|Q66928               SEVGLVNK--SVVLLPIFFAHTAINITIDLGMKRSGYGQPIASTLS-NITLPMQDNNTDV 571
sp|P10033|VGL2_FIPV     SEVGFVNK--SVVLLPSFFTYTAVNITIDLGMKLSGYGQPIASTLS-NITLPMQDNNTDV 569  A1 antigen
sp|P18450|VGL2_CVPFS    SEVGFVNK--SVVLLPTFYTHTIVNITIGLGMKRSGYGQPIASTLS-NITLPMQDNNIDV 566
sp|P24413|VGL2_CVPRM    SEVGSVNK--SVVLLPFLTHTIVNITIGLGMKRSGYGQPIASTLS-NITLPMQDNNNDV 342
sp|P15423|VGL2_CVH22    --IQSVELPVSIVSLPVYHKHTFIVLYVDFKPQSGGGKCFNCYPAGVNITLANFNETKGP 338
tr|Q84712               RNLLSHEQPISFVTLPSFNDHSFVNITVS--AAFGGLSSANLVAS--DTTINGFSS---- 538
sp|P25192|VGL2_CVBLY    QSVFKPQPVGVFTDHDVVYAQHCFKAPTNFCPCKLDGSLCVGSGSG--IDAGYKNSGIGT 514
PSC                     NSTFFSTFKCYGVSATKLNDLCFSNVYADSFVVKGDDVRQIAPGQTGVIADYNYKLPDDF 416
tr|O12031               KSLFLVTILFALCSANLYDNESFVYYQSAFRPGHGWHLHGGAYAVVNVSSENNNAGTAP 63
```

Figure 13C

```
sp|P36300|VGL2_CVCAI    YCIRSNQFSVYVHSTCKSSLWDNNFNSACTDVLDATAVIKTGTCPFSFDKLNNYLTFNKF 629
tr|Q65984               YCIRSNRFSVYFHSTCKSSLWDDVFNSDCTDVLYATAVIKTGTCPFSFDKLNNYLTFNKF 630
tr|Q66928               YCIRSNQFSVYVHSICKSSLWDNIFNQECTDVLDATAVIKTGTCPFSFDKLNNYLTFNKF 631
sp|P10033|VGL2_FIPV     YCIRSNQFSVYVHSTCKSSLWDNIFNQDCTDVLEATAVIKTGTCPFSFDKLNNYLTFNKF 629  A1
sp|P18450|VGL2_CVPFS    YCIRSDQFSVYVHSTCKSALWDNVFKRNCTDVLDATAVIKTGTCPFSFDKLNNYLTFNKF 626
sp|P24413|VGL2_CVPRM    YCVRSDQFSVYVHSTCKSVLWDNVFKRNCTDVLDATAVIKTGTCPFSFDKLNNYLTFNKF 402
sp|P15423|VGL2_CVH22    LCVDTSHFTTKYVAVYAN-----------VGRWSASINTGNCPFSFGKVNNFVKFGSV  385
tr|Q84712               FCVDTRQFTITLFYNVTN-----------SYGYVSKSQDSNCPFTLQSVNDYLSFSKF  585
sp|P25192|VGL2_CVBLY    CPAGTNYLTCHNAAQCDC-----------LCTPDPITSKSTGPYKCPQTKYLVGIGEH  561  N_parvus(534-983)
PSC                     MGCVLAWNTRNIDATSTG----------NYNYKYRYLRHGKLRPFERDISNVPFSPDGK  465
tr|O12031               SCTAG-----------------------AIGYSKNLSAASVAMTAPLSGMSWSANSF   97 sp|P36300|VGL2_CVCAI    CLSLNPVG-----ANCKLDVAAR-TRTNEQVFG----SLYVIYEEGDNIVGVPSDNSGLH 679
tr|Q65984               CLSLNPVG-----ANCKFDVAAR-TRTNEQVVR----SLYVIYEEGDNIVGVPSDNSGLH 680
tr|Q66928               CLSLSPVG-----ANCKFDVAAR-TRTNEQVVR----SLYVIYEEGDNIVGVPSDNSGLH 681
sp|P10033|VGL2_FIPV     CLSLSPVG-----ANCKFDVAAR-TRTNEQVVR----SLYVIYEEGDNIVGVPSDNSGLH 679  A2
sp|P18450|VGL2_CVPFS    CLSLSPVG-----ANCKFDVAAR-TRANDQVVR----SLYVIYEEGDNIVGVPSDNSGLH 676
sp|P24413|VGL2_CVPRM    CLSLSPVG-----ANCKFDVAAR-TRTNDQVVR----SLYVIYEEGDSIVGVPSDNSGLH 452
sp|P15423|VGL2_CVH22    CFSLKDIP-----GGCAMPIVANWAYSKYYTIG----SLYVSWSDGDGITGVPQPVEGVS 436  RB 417-547
tr|Q84712               CVSTSLLA-----GACTIDLFGYPAFGSGVKLT----SLYFQFTKGELITGTPKPLEGIT 636
sp|P25192|VGL2_CVBLY    CSGLAIKSDYCGGNPCTCQPQAFLGWSVDSCLQGDRCNIFANFILHDVNSGTTCSTDLQK 621  N_parvus(534-983)
PSC                     PCTPPALN-------CYWPLNDYGFYTTTGIGY----QPYRVVVLSFELLNAPATVCGPK 514
tr|O12031               CTAHCNPT----------------------------SYIVFVTHCYKSGS--------- 119 sp|P36300|VGL2_CVCAI    DLSVLHLDSCTDYNIYGRTGVGIIRKTNSTLLS---GLYYTSLSGDLLGFKNVSDGVVYS 736
tr|Q65984               DLSVLHLDSCTDYNIYGITGVGIIRQTNSTLLS---GLYYTSLSGDLLGFKNVSDGVIYS 737
tr|Q66928               DLSVLHLDSCTEYNIYGRTGVGIIRQTNSTLLS---GLYYTSLSGDLLGFKNVSDGVIYS 738
sp|P10033|VGL2_FIPV     DLSVLHLDSCTDYNIYGRTGVGIIRRTNSTLLS---GLYYTSLSGDLLGFKNVSDGVIYS 736
sp|P18450|VGL2_CVPFS    DLSVLHLDSCTDYNIYGRSGVGIIRQTNRTLLS---GLYYTSLSGDLLGFKNVSDGVIYS 733
sp|P24413|VGL2_CVPRM    DLSVLHLDSCTDYNIYGRGVGIIRNRTILS-----GLYYTSLSGDLLGFKNVSDGVIYS 509
sp|P15423|VGL2_CVH22    SFMNVTLDKCTKYNIYDVSGVGVIRVSNDTFLN---GITYTSTSGNLLGFKDVTKGTIYS 493  RB 417-547
tr|Q84712               DVSFMTLDVCTKYTIYGFKGEGIITLTNSSILA---GVYYTSDSGQLLAFKNVTSGAVYS 693
sp|P25192|VGL2_CVBLY    SNTDIILGVCVNYDLYGITGQGIFVEVNATYYNSWQNLLYDS-NGNLYGFRDYLTNRTFM 680
PSC                     LSTDLIKNQCVNFNFNGLTGTGVLTPSSKRFQP--FQQFGRDVSDFTDSVRDPKTSEILD 572
tr|O12031               -------NSCPLTGLIPSGYIRIAAMKHGSAMP---GHLFYNLTVSVTKYPKFRS----- 164 sp|P36300|VGL2_CVCAI    VTPCDVSAQAAVIDGAIVGAMTSINSELLGLTHWTTTP---------NFYYYSIYNYTNV 787
tr|Q65984               VTPCDVSAHAAVIDGAIVGAMTSINSELLGLTHWTTTP---------NFYYYSIYNYTNE 788
tr|Q66928               VTPCDVSAQAAVIDGAIVGAMTSINSELLGLKHWTTTP---------NFYYYSIYNYTNE 789
sp|P10033|VGL2_FIPV     VTPCDVSAQAAVIDGAIVGAMTSINSELLGLTHWTTTP---------NFYYYSIYNYTSE 787
sp|P18450|VGL2_CVPFS    VTPCDVSAQAAVIDGTIVGAITSINSELLGLTHWTTTP---------NFYYYSIYNYTND 784
sp|P24413|VGL2_CVPRM    VTPCDVSAQAAIDGTIVGAITSINSELLGLTHWTTTP---------NFYYYSIYNYTND 560
sp|P15423|VGL2_CVH22    ITPCNPPDQLVVYQQAVVGAMLSENFTSYGFSNVVELP---------KFFYASNGTYN-- 542  RB 417-547
tr|Q84712               VTPCSFSEQAAYVNDDIVGVIS--SLSNSTFNNTRELP---------GFFYHSNDGSN-- 740
sp|P25192|VGL2_CVBLY    IRSCYSGRVSAAFHANSSEPALLWFRNIKCNYVFNNTLSRQLQPINYFDSYLGCVVNADNS 740
PSC                     ISPCAFGGVSVITPGTNASSEVAVLYQDVNCTDVSTAIHADQLTPAWRIYSTGNNVFQTQ 632
tr|O12031               -LQCVNNYTSVYLNGDLVFTSNYTEDVVAAGVHFKSGG-------------------- 201 sp|P36300|VGL2_CVCAI    M-------NRGTAID-NDIDCEPIITYSNIGVCKNGALVFINVTHS-DGDVQPISTG-- 835
tr|Q65984               R-------TRGTAIDSNDVDCEPIITYSNIGVCKNGALVFINVTHS-DGDVQPISTG-- 837
tr|Q66928               R-------TRGTAIDSNDVDCEPIITYSNIGVCKNGALVFINVTHS-DGDVQPISTG-- 838
sp|P10033|VGL2_FIPV     R-------TRGTAIDSNDVDCEPVITYSNIGVCKNGALVFINVTHS-DGDVQPISTG-- 836
sp|P18450|VGL2_CVPFS    M-------TRGTAIDSNDVDCEPVITYSNIGVCKNGALVFINVTHS-DGDVQPISTG-- 833
sp|P24413|VGL2_CVPRM    K-------TRGTPIGSNDVDCEPVITYSNIGVCKNGALVFINVTHS-DGDVQPISTG-- 609
sp|P15423|VGL2_CVH22    -------------------CTDAVLTYSSFGVCADGSIIAVQPRNVSYDSVSAIVTA-- 580  S1 aa560end
tr|Q84712               --------------------CTEPVLVYSNIGVCKSGSIGYV-PSQYGQVKIAPTVTG- 777
sp|P25192|VGL2_CVBLY    T--------SSAVQTCDLTVGSGYCVDYSTKRRSRAITTGYRFTNFEPFTVNSVNDSLE 792  S1/S2 cleavage
PSC                     AGCLIGAEHVDTSYECDIPIGAGICASYHTVSLLRSTSQKSIVAYTMSLGADSSIAYSNN 692
tr|O12031               ---------------------PITYKVMR------------------------------ 209 sp|P36300|VGL2_CVCAI    ------NVTIPTNFTISVQVEYIQVYTTPVSIDCARYVCNGNPRCNKLLTQYVSACQTIE 889
tr|Q65984               ------NVTIPTNFTISVQVEYIQVYTTPVSIDCSRYVCNGNPRCNKLLTQYVSACQTIE 891
tr|Q66928               ------TVTIPTNFTISVQVEYLQVYTTPVSIDCARYVCNGNPRCNKLLTQYVSACQTIE 892
sp|P10033|VGL2_FIPV     ------NVTIPTNFTISVQVEYMQVYTTPVSIDCARYVCNGNPRCNKLLTQYVSACQTIE 890
sp|P18450|VGL2_CVPFS    ------NVTIPTNFTISVQVEYIQVYTTPVSIDCSRYVCNGNPRCNKLLTQYVSACQTIE 887
sp|P24413|VGL2_CVPRM    ------NVTIPTNFTISVQVEYIQVYTTPVSIDCSRYVCNGNPRCNKLLTQYVSACQTIE 663
sp|P15423|VGL2_CVH22    ------NLSIPSNWTTSVQVEYLQITSTPIVVDCSTYVCNGNVRCVELLKQYTSACKTIE 634
tr|Q84712               ------NISIPTNFSMSIRTEYLQLYNTPVSVDCATYVCNGNSRCKQLLTQYTAACKTIE 831
sp|P25192|VGL2_CVBLY    PVGGLYEIQIPSEFTIGNMEEFIQISSPKVTIDCSAFVCGDYAACKSQLVEYGSFCDNIN 852
PSC                     ------TIAIPTNFSISITTEVMPVSMAKTSVDCNMYICGDSTECANLLLQYGSFCTQLN 746
tr|O12031               ------EVKALAYFVNGTAHDVILCDDTPRGLLACQYNTGNFS--------DGFYPFTN 254
```

Figure 13D

```
sp|P36300|VGL2_CVCAI    QALAMGARLENMEIDSMLFVSENALKLASVEAFNSTENLDPIYKEWPNIGGSWLGGLKDI  949
tr|Q65984               QALAMGARLENMEIDSMLFVSENALKLASVEAFNSTETLDPIYKEWPNIGGSWLGGLKDI  951
tr|Q66928               QALAMGARLENMEVDSMLFVSENALKLASVEAFNSTENLDPIYKEWPNIGGSWLGGLKDI  952
sp|P10033|VGL2_FIPV     QALAMGARLENMEVDSMLFVSENALKLASVEAFNSTENLDPIYKEWPSIGGSWLGGLKDI  950
sp|P18450|VGL2_CVPFS    QALAVGARLENMEVDSMLFVSENALKLASVEAFNSSETLDPIYKEWPNIGGSWLEGLKYI  947
sp|P24413|VGL2_CVPRM    QALAMGARLENMEVDSMLFVSENALKLASVEAFNSSETLDPIYKEWPNIGGFWLEGLKYI  723
sp|P15423|VGL2_CVH22    DALRNSARLESADVSEMLTFDKKAFTLANVSSFG------------DYNLSSVIPS---  678
tr|Q84712               SALQLSARLESVEVNSMLTISEEALQLATISSFNGD----------GYNFTNVLGASVY  880
sp|P25192|VGL2_CVBLY    AILTEVNELLDTTQLQVANSLMNGVTLSTKLKDGVN----------FNVDDINFSPVLGC  902
PSC                    RALSGIAAEQDRNTREVFAQVKQMYKTPTLKYFG------------------GFNFSQ   786
tr|O12031               TSIVKDKFIVYRESSVNTTLTLTNFTFS-------------------------------  282
                                           :         .

sp|P36300|VGL2_CVCAI    LPSHNSKRKYRSAIEDLLFDKVVTSGLGTVDEDYKRSAGGYD-IADLVCARYYNGIMVLP 1008
tr|Q65984               LPSHNSKRKYRSAIEDLLFDKVVTSGLGTVDEDYKRCTGGYD-IADLVCAQYYNGIMVLP 1010
tr|Q66928               LPSHNSKRKYRSAIEDLLFDKAVTSGLGTVDEDYKRCTGGYD-IADLVCAQYYNGIMVLP 1011
sp|P10033|VGL2_FIPV     LPSHNSKRKYGSAIEDLLFDKVVTSGLGTVDEDYKRCTGGYD-IADLVCAQYYNGIMVLP 1009
sp|P18450|VGL2_CVPFS    LPSDNSKRKYRSAIEDLLFSKVVTSGLGTVDEDYKRCTGGYD-IADLVCAQYYNGIMVLP 1006
sp|P24413|VGL2_CVPRM    LPSDNSKRKYRSAIEDLLFSKVVTSGLGTVDEDYKRCTGGYD-IADLVCAQYYNGIMVLP  782
sp|P15423|VGL2_CVH22    LPTSGSRVAGRSAIEDILFSKLVTSGLGTVDADYKKCTKGLS-IADLACAQYYNGIMVLP  737
tr|Q84712               DPASGRVVQKRSVIEDLLFNKVVTNGLGTVDEDYKRCSNGRS-VADLVCAQYYSGVMVLP  939
sp|P25192|VGL2_CVBLY    LGSDCNKVSSRSAIEDLLFSKVKLSDVG-FVEAYNNCTGGAE-IRDLICVQSYNGIKVLP  960
PSC                    ILPDPLKPTKRSFIEDLLFNKVTLADAG-FMKQYGECLGDIN-ARDLICAQKFNGLTVLP  844
tr|O12031               --NESGAPPNTGGVDSFILYQTQTAQSGYYNFNFSFLSSFVYRESNYMYGSYHPRCSFRP  340
                          .  ::.:::    :         *          :             * sp|P36300|VGL2_CVCAI    GVANDDKMTMYTASLTGGITLGALSG----GAVAIPFAVAVQARLNYVALQTDVLNKNQQ 1064
tr|Q65984               GVANDDKMAMYTASLAGGITLGSLGG----GAVSIPFAIAVQARLNYVALQTDVLNKNQQ 1066
tr|Q66928               GVANDDKMTMYTASLAGGITLGALGG----GAVAIPFAVAVQARLNYVALQTDVLNKNQQ 1067
sp|P10033|VGL2_FIPV     GVANADKMTMYTASLAGGITLGALGG----GAVAIPFAVAVQARLNYVALQTDVLNKNQQ 1065
sp|P18450|VGL2_CVPFS    GVANADKMTMYTASLAGGITLGALGG----GAVAIPFAVAVQARLNYVALQTDVLNKNQQ 1062
sp|P24413|VGL2_CVPRM    GVANADKMTMYTASLAGGITLGALGG----GAVAIPFAVAVQARLNYVALQTDVLNKNQQ  838
sp|P15423|VGL2_CVH22    GVADAERMAMYTGSLIGGIALGGLT-----SAVSIPFSLAIQARLNYVALQTDVLQENQK  792
tr|Q84712               GVVDAEKLHMYSASLIGGMALGGIT-----AAAALPFSYAVQARLNYLALQTDVLQRNQQ  994
sp|P25192|VGL2_CVBLY    PLLSENQISGYTLAATSASLPPPWS-----AAAGVPFYLNVQYRINGIGVTMDVLSQNQK 1015
PSC                    PLLTDDMIAAYTAALVSGTATAGWTFGAG-AALQIPFAMQMAYRFNGIGVTQNVLYENQK  903
tr|O12031               ETLNGLWFNSLSVSLTYGPIQGGCKQSVFNGKATCCYAYSYGGPRGCKGVYRGELTQHFE  400
                                                              .          *  .:  .

sp|P36300|VGL2_CVCAI    ILANAFNQAIGNITQAFGKVNDAIHQTSKGLATVAKALAKVQDVVNTQGQALSHLTVQLQ 1124
tr|Q65984               ILANAFNQAIGNITQAFGKVNDAIHQTSQGLATVAKVLAKVQDVVNTQGQALSHLTLQLQ 1126
tr|Q66928               ILANAFNQAIGNITQAFGKVNDAIHQTSKGLATVAKALAKVQDVVNTQGQALSHLTLQLQ 1127
sp|P10033|VGL2_FIPV     ILANAFNQAIGNITQAFGKVNDAIHQTSQGLATVAKALAKVQDVVNTQGQALSHLTLQLQ 1125
sp|P18450|VGL2_CVPFS    ILASAFNQAIGNITQSFGKVNDAIHQTSRGLATVAKALAKVQDVVNTQGQALSHLTVQLQ 1122
sp|P24413|VGL2_CVPRM    ILASAFNQAIGNITQSFGKVNDAIHQTSRGLTTVAKALAKVQDVVNTQGQALRHLTVQLQ  898
sp|P15423|VGL2_CVH22    ILAASFNKAMTNIVDAFTGVNDAITQTSQALQTVATALNKIQDVVNQQGNSLNHLTSQLR  852
tr|Q84712               LLAESFNSAIGNITSAPESVKEAISQTSKGLNTVAHALTKVQEVVNSQGSALNQLTVQLQ 1054
sp|P25192|VGL2_CVBLY    LIANANFNNALDAIQEGFDATN-----------SALVKIQAVVNANAEALNNLLQQLS  1061
PSC                    QIANQFNKAISQIQESLTTTS---------------TALGKLQDVVNQNAQALNTLVKQLS  949
tr|O12031               CGLLVY---------------------------VTKSDGSRIQTATQPPVLTQNFY  429
                                :                    :  *  :     .    *  ::

sp|P36300|VGL2_CVCAI    NNFQAISSSISDIYNRLDELSADAQVDRLITGRLTALNAFVSQTLTRQAEVRASRQLAKD 1184
tr|Q65984               NNFQAISSSISDIYNRLDELSADAQVDRLITGRLTALNAFVSQTLTRQAEVRASRQLAKD 1186
tr|Q66928               NNFQAISSSISDIYNRLDELSADAQVDRLITGRLTALNAFVSQTLTRQAEVRASRQLAKD 1187
sp|P10033|VGL2_FIPV     NNFQAISSSISDIYNRLDELSADAQVDRLITGRLTALNAFVSQTLTRQAEVRASRQLAKD 1185
sp|P18450|VGL2_CVPFS    NNFQAISSSISDIYNRLDELSADAHVDRLITGRLTALNAFVSQTLTRQAEVRASRQLAKD 1182
sp|P24413|VGL2_CVPRM    NNFQAISSSISDIYNRLDELSADAQVDRLITGRLTALNAFVSQTLTRQAEVRASRQLAKD  958
sp|P15423|VGL2_CVH22    QNFQAISSSIQAIYDRLDTIQADQQVDRLITGRLAALNVFVSHTLTKYTEVRASRQLAQQ  912
tr|Q84712               HNFQAISSSIDDIYSRLDILLADVQVDRLITGRLSALNAFVAQTLTKYTEVQASRKLAQQ 1114
sp|P25192|VGL2_CVBLY    NRFGAISSSLQEILSRLDALEAQAQIDRLINGRLTALNAVVSQQLSDSTLVKFSAAQAME 1121
PSC                    SNFPGAISSVLNDILSRLDKVEAEVQIDRLITGRLQSLQTYVTQQLIRAAEIRASANLAAT 1009
tr|O12031               NNINLGKCVDYNIYGRIGQGLITNVTDLAVSYNYLSDAGLAILDTSGAIDIFVVQGEYGP  489
                       .:   ..   * .*:.       *  :.. :                   :

sp|P36300|VGL2_CVCAI    KVNECVRSQSQRFGFCG-NGTHLFSLANAAPNGMIFFHTVLLPTAYETVTAWSGICASDG 1243
tr|Q65984               KVNECVRSQSQRFGFCG-NGTHLFSLANAAPNGMIFFHTVLLPTAYETVTAWSGICASDG 1245
tr|Q66928               KVNECVRSQSQRFGFCG-NGTHLFSLANAAPNGMIFFHTVLLPTAYETVTAWPGICASDG 1246
sp|P10033|VGL2_FIPV     KVNECVRSQSQRFGFCG-NGTHLFSLANAAPNGMIFFHTVLLPTAYETVTAWSGICASDG 1244
sp|P18450|VGL2_CVPFS    KVNECVRSQSQRFGFCG-NGTHLFSLANAAPNGMIFFHAVLLPTAYETVTAWAGICALDG 1241
sp|P24413|VGL2_CVPRM    KVNECVRSQSQRFGFCG-NGTHLFSLANAAPNGMIFFHTVLLPTAYETVTAWSGICALDV 1017
sp|P15423|VGL2_CVH22    KVNECVKSQSKRYGFCG-NGTHIFSIVNAAPEGLVFLHTVLLPTQYKDVEAWSGLCVDG-  970
tr|Q84712               KVNECVKSQSQRYGFCGGDGEHIFSLVQAAPQGLLFLHTVLVPGDFVNVLAIAGLCVNG- 1173
sp|P25192|VGL2_CVBLY    KVNECVKSQSSRINFCG-NGNHIISLVQNAPYGLYFIHFSYVPTKYVTAKVSPGLCIAG- 1179
PSC                    KMSECVLGQSKRVDFCG-KGYHLMSFPQAAPHGVVPLHVTYVPSQERNFTTAPAICHEG- 1067
tr|O12031               NYYKVNPGEDVNQQFVVSGGKLVGILTSRNETGSQLLENQFYIKITNGTRRSRRS-----  544
                           :     :.  ... *    *  . :    *  :.   ::.
```

Figure 13E

```
sp|P36300|VGL2_CVCAI    SRTFGLVVEDVQLTLFRN-----LDEKFYLTPRTMYQPRVATSSDFVQIEGCDVLFVNGT  1298
tr|Q65984               DRTFGLVVKDVQLTLFRN-----LDDKFYLTPRTMYQPIVATSSDFVQIEGCDVLFVNAT  1300
tr|Q66928               DRTFGLVVKDVQLTLFRN-----LDDKFYLTPRTMYQPRAATSSDFVQIEGCDVLFVNAT  1301
sp|P10033|VGL2_FIPV     DRTFGLVVKDVQLTLFRN-----LDDKFYLTPRTMYQPRVATSSDFVQIEGCDVLFVNAT  1299
sp|P18450|VGL2_CVPFS    DRTFGLVVKDVQLTLFRN-----LDDKFYLTPRTMYQPRVATSSDFVQIEGCDVLFVNAT  1296
sp|P24413|VGL2_CVPRM    DRTFGLVVKDVQLTLFRN-----LDDKFYLTPRTMYQPRVATSSDFVQIEGCDVLFVNTT  1072
sp|P15423|VGL2_CVH22    --TNGYVLRQPNLALYK------EGNYYRITSRIMFEPRIPTMADFVQIENCNVTFVNIS  1022
tr|Q84712               --EIALTLREPGLVLFTHELQTYTATEYFVSSRRMFEPRKPTVSDFVQIESCVVTYVNLT  1231
sp|P25192|VGL2_CVBLY    --DRGIAPKSGYFVNVNN--------TWMFTGSGYYYPEPITGNNVVVMSTCAVNYTKAP  1229
PSC                     ---KAYPPREGVFVFNGT--------SWFITQRNFFSPQIITTDNTFVSGNCDVVIGIIN  1116
tr|O12031               ------------------------------------------------------------ sp|P36300|VGL2_CVCAI    VIELPSIIPDYIDINQTVQDILENFRPNWTVPELPLDIFHATYLNLTGEINDLEFRSEKL  1358
tr|Q65984               VIDLPSIIPDYIDINQTVQDILENFRPNWTVPELPLDIFNATYLNLTGEINDLEFRSEKL  1360
tr|Q66928               VIDLPSIIPDYIDINQTVQDILENYRPNWTVPELTLDIFNATYLNLTGEIDDLEFRSEKL  1361
sp|P10033|VGL2_FIPV     VIDLPSIIPDYIDINQTVQDILENYRPNWTVPEFTLDIFNATYLNLTGEIDDLEFRSEKL  1359
sp|P18450|VGL2_CVPFS    LSDLPSIIPDYIDINQTVQDILENFRPNWTVPELTFDIFNATYLNLTGEIDDLEFRSEKL  1356
sp|P24413|VGL2_CVPRM    VSDLPSIIPDYIDINQTVQDILENFRPNWTVPELTLDVFNATYLNLTGEIDDLEFRSEKL  1132
sp|P15423|VGL2_CVH22    RSELQTIVPEYIDVNKTLQELSYKL-PNYTVPDLVVEQYNQTILNLTSEISTLENKSAEL  1081
tr|Q84712               SDQLPDVIPDYIDVNKTLDEILASL-PNRTGPSLPLDVFNATYLNLTGEIADLEQRSESL  1290
sp|P25192|VGL2_CVBLY    DVMLNISTPNLPDFKEELDQWFKNQ--TSVAPDLSLDYINVTFLDLQDEMN---------  1278
PSC                     NTVYDPLQPELDSFKEELDKYFKNHTSPDVDLG-DISGINASVVNIQKEID---------  1166
tr|O12031               ------------------------------------------------------------ sp|P36300|VGL2_CVCAI    HNTTVELAILIDNINNTLVNLEWLNRIETYVKWPWYVWLLIGLVVIFCIPILLFCCCSTG  1418
tr|Q65984               HNTTVELAILIDNINNTLVNLEWLNRIETYVKWPWYVWLLIGLVVIFCIPILLFCCCSTG  1420
tr|Q66928               HNTTVELAILIDNINNTLVNLEWLNRIETYVKWPWYVWLLIGLVVIFCIPLLLFCCCSTG  1421
sp|P10033|VGL2_FIPV     HNTTVELAILIDNINNTLVNLEWLNRIETYVKWPWYVWLLIGLVVVFCIPLLLFCCFSTG  1419
sp|P18450|VGL2_CVPFS    HNTTVELAILIDNINNTLVNLEWLNRIETYVKWPWYVWLLIGLVVIFCIPLLLFCCCSTG  1416
sp|P24413|VGL2_CVPRM    HNTTVELAILIDNINNTVVNLEWLNRIETYVKWPWYVWLLIGLVVIFCIPLLLFCCCSTG  1192
sp|P15423|VGL2_CVH22    NYTVQKLQTLIDNINSTLVDLKWLNRVETYIKWPWWVWLCISVVLIFVVSMLLLCCCSTG  1141
tr|Q84712               RNTTEELRSLINNINNTLVDLEWLNRVETYIKWPWWVWLIIVIVLIFVVSLLVFCCISTG  1350
sp|P25192|VGL2_CVBLY    -----RLQEAIKVLNQSYINLKDIGTYEYYVKWPWYVWLLIGLAGVAMLVLLFFICCCTG  1333   membrane anchor
PSC                     -----RLNEVAKNLNESLIDLQELGKYEQYIKWPWYVWLGFIAGLIAIVMVTILLCCMTS  1221
tr|O12031               ------------------------------------------------------------ sp|P36300|VGL2_CVCAI    CCG-CIGCLGSCCHSICSRGQFESYEPIEKVHVH--  1451
tr|Q65984               CCG-CIGCLGSCCHSICSRRQFESYEPIEKVHVH--  1453
tr|Q66928               CCG-CIGCLGSCCHSMCSRRQFENYEPIEKVHVH--  1454
sp|P10033|VGL2_FIPV     CCG-CIGCLGSCCHSICSRRQFENYEPIEKVHVH--  1452
sp|P18450|VGL2_CVPFS    CCG-CIGCLGSCCHSICSRRQFENYEPIEKVHIH--  1449
sp|P24413|VGL2_CVPRM    CCG-CIGCLGSCCHSIFSRRQFENYEPIEKVHVH--  1225
sp|P15423|VGL2_CVH22    CCG-FFSCFASSIRGCCESTKLP-YYDVEKIHIQ--  1173
tr|Q84712               CCG-CCGCCGACFSGCCRGPRLQPYEAFEKVHVQ--  1383
sp|P25192|VGL2_CVBLY    CGTSCFKKCGGCCDDYTGHQELVIKTSHDD------  1363
PSC                     CCS--CLKGACSCGSCCKFDEDDSEPVLKGVKLHYT 1255
tr|O12031               ------------------------------------
```

Figure 13F

Schematic Presentation of the Three Constructs that Were Generated

S PROTEIN

Gel # 070303_d3 SARS P2

| Lane # | Lane description |
|---|---|
| 1 | Protein marker (NMW1) |
| 2 | P2, F2B1, D3217, pellets (07/03/03) |
| 3 | P2, F2B1, D3217, S/N (07/03/03) |
| 4 | P2, F2B2, D3217, pellets (07/03/03) |
| 5 | P2, F2B2, D3217, S/N (07/03/03) |
| 6 | Control. None-infected cells |
| 7 | Control, S/N of none-infected cells |

Gel # 070703_d5 SARS P3

| Lane # | Lane description |
|---|---|
| 1 | Protein marker (NMW1) |
| 2 | P3, F2B1, D3217, pellets (07/03/03) |
| 3 | P3, F2B1, D3217, S/N (07/03/03) |
| 4 | P3, F2B2, D3217, pellets (07/03/03) |
| 5 | P3, F2B2, D3217, S/N (07/03/03) |
| 6 | Control. None-infected cells |
| 7 | Control, S/N of none-infected cells |

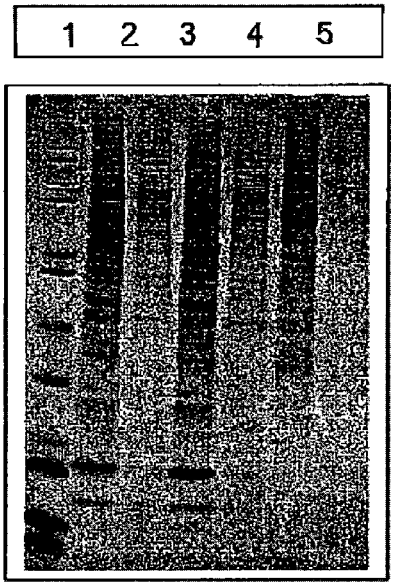

FIGURE 16

Coomassie Blue gel

Protein Marker
188
62
49
38
28
18
14
6
3

1: NMW2 (protein marker)
2: D3217.1a, 48 hpi, pellets (8/2/03)
3: D3217.1a, 48 hpi, S/N (8/2/03)
4: D3217.1a, 72 hpi, pellets (8/2/03)
5: D3217.1a, 72 hpi, S/N (8/2/03)
6: D3217.1a, 96 hpi, pellets (8/2/03)
7: D3217.1a, 96 hpi, S/N (8/2/03)
8: D3217.1a, 120 hpi, pellets (8/2/03)
9: D3217.1a, 120 hpi, S/N (8/2/03)
10: 10L, D3217.1a, total (7/21/03), 72hpi
11: 10L, D3217.1a, pellet, (7/21/03), 72hpi
12: D3217.1a, 72hpi (7/21/03), P solubilization
13: Fast track, 5841b LL, conc.
14: 10L, D3217.1a, total (8/02/03), 96 hpi
15: 10L, D3217.1a, pellets, (8/02/03), 96 hpi

FIGURE 17

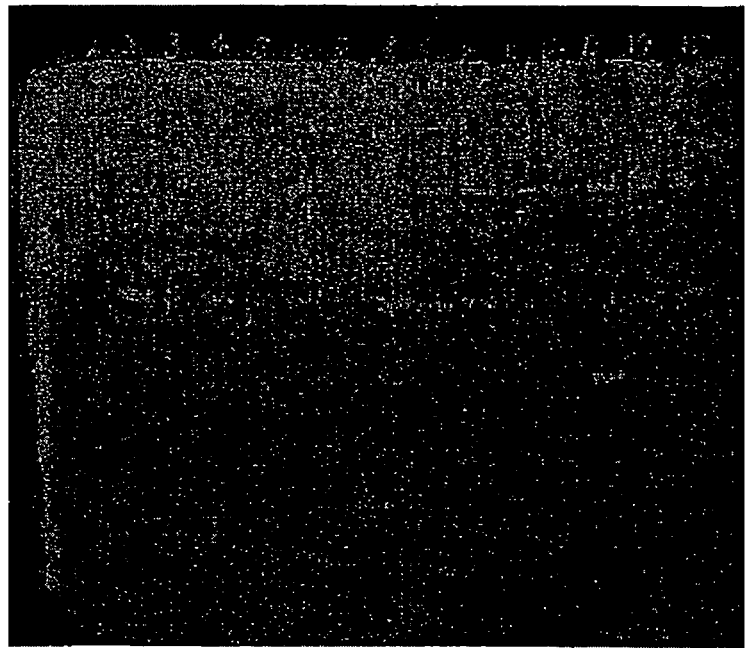
Primary Ab: Acute Serum
Primary Ab: Convalescent Serum
FIGURE 18

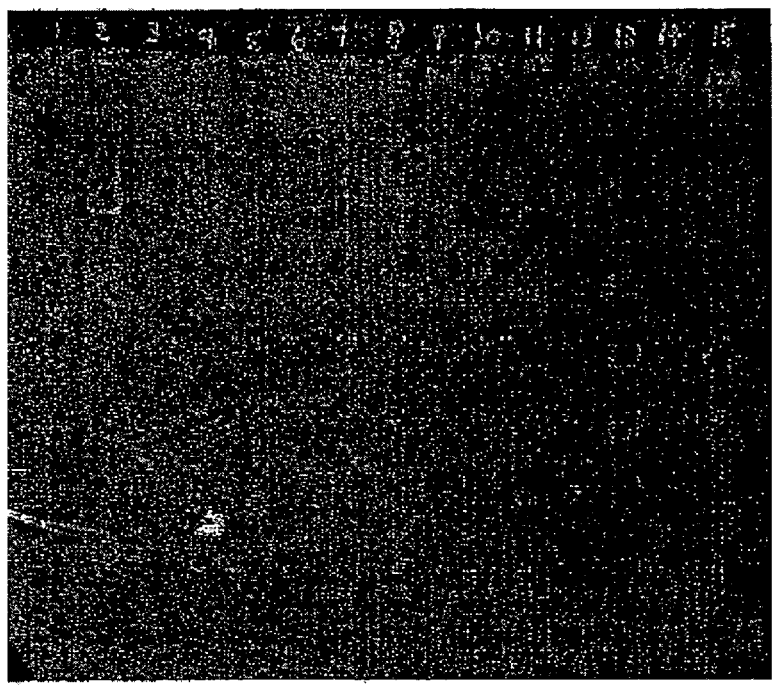
acute serum
convalescent serum
FIGURE 19

1: Marker. The indicated marker in the picture is not correct (Correct marker sizes are 188, 62, 49, 38, 28, 18, 14)
2: Negative control TN4 67/68 10x conc.
3: S protein 67/68 10x conc.
4: Negative control TN4 before conc.
5: S protein 67/68 before conc.
6: 10L D3217.1a T 7/21/03
7: 10L D3217.1a P 7/21/03
8: 10L D3217.1a S 7/21/03

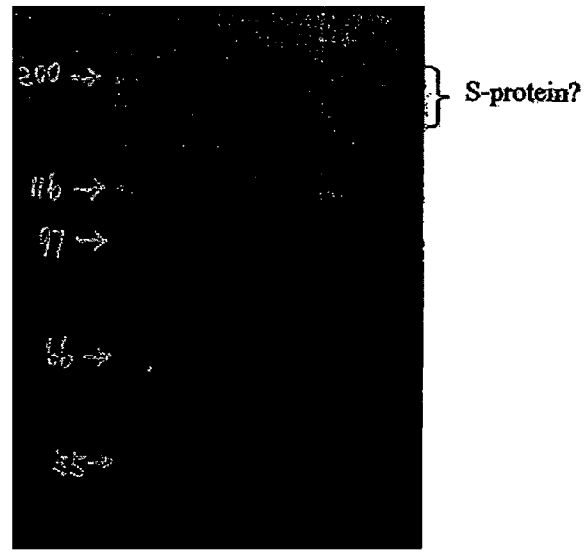

FIGURE 20

| Lane | Description |
|---|---|
| 1 | Protein marker (188, 62, 49, 38, 28, 18 & 14) |
| 2 | S-17 st, reducing |
| 3 | 10 L, D3217.1a, @ 23°C, 96 hpi, total |
| 4 | 10 L, D3217.1a, @ 23°C, 96 hpi, pellets |
| 5 | 10 L, D3217.1a, @ 23°C, 96 hpi, S/N |
| 6 | 10 L, D3217.1a, @ 23°C, 120 hpi, total |
| 7 | 10 L, D3217.1a, @ 23°C, 120 hpi, pellets |
| 8 | 10 L, D3217.1a, @ 23°C, 120 hpi, S/N |
| 9 | 10 L, D3217.1a, @ 23°C, 144 hpi, total |
| 10 | 10 L, D3217.1a, @ 23°C, 144 hpi, pellets |
| 11 | 10 L, D3217.1a, @ 23°C, 144 hpi, S/N |
| 12 | 10 L, D3217.1a, @ 23°C, 168 hpi, total |
| 13 | 10 L, D3217.1a, @ 23°C, 168 hpi, pellets |
| 14 | 10 L, D3217.1a, @ 23°C, 168 hpi, S/N |
| 15 | Control, uninfected cells |

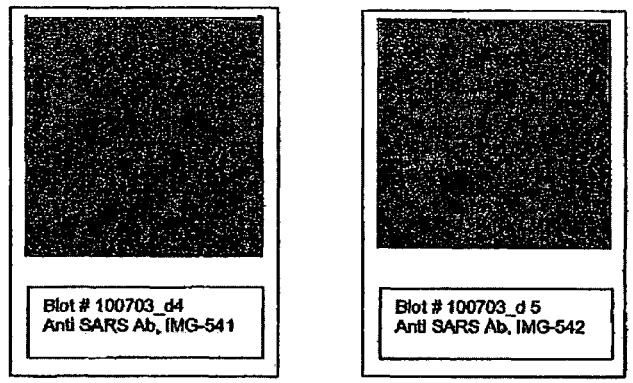

Blot # 100703_d4
Anti SARS Ab, IMG-541

Blot # 100703_d 5
Anti SARS Ab, IMG-542

FIGURE 21

| Lane | Description |
|---|---|
| 1. | Protein marker, Seeblue |
| 2 | S-17, std, reducing |
| 3 | P3, D3217.1a, # 100203, pellets |
| 4 | P3, D3217.1a, # 100203, S/N |
| 5 | P3, D3217.1a, # 100303, pellets |
| 6 | P3, D3217.1a, # 100303, S/N |
| 7 | P3, D3227.1a, # 100603, pellets |
| 8 | P3, D3227.1a, # 100603, S/N |
| 9 | P3, D3252.2a, # 100603, pellets |
| 10 | P3, D3252.2a, # 100603, S/N |

Blot # 100703_d6

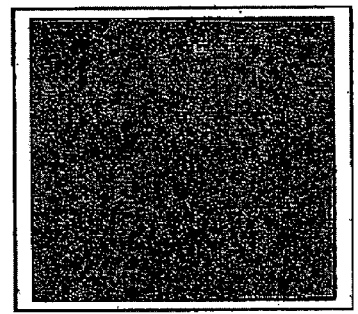

Blot # 100703_d7

FIGURE 22

| Lane | Description |
|---|---|
| 1 | Protein marker |
| 2 | S-17 st, reducing |
| 3 | 10 L, D3217.1a, 72 hpi, total (#072103) |
| 4 | 10 L, D3217.1a, 72 hpi, pellets (#072103) |
| 5 | 10 L, D3217.1a, 72 hpi, S/N (#072103) |
| 6 | 10 L, D2217.1a, 96 hpi, total (# 080203) |
| 7 | 10 L, D3217.1a, 96 hpi, pellets (# 080203) |
| 8 | 10 L, D3217.1a, 96 hpi, S/N ( # 080203) |
| 9 | 2 L, D3217.1a, 120 hpi, total, (#081703) |
| 10 | 2 L, D3217.1a, 120 hpi, , pellets (# 081703) |
| 11 | 12L, D3217.1a, 120 hpi, S/N (# 081703) |
| 12 | 10 L, D3217.1a, 72hpi, total(#082603) |
| 13 | 10 L, D3217.1a, 72 hpi, pellets (#082603) |
| 14 | 10 L, D3217.1a, 72 hpi, S/N (#082603) |
| 15 | Control, (-ve) uninfected cells |

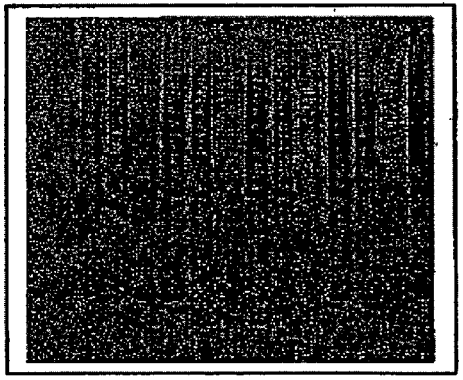

Gel # 101003_d3

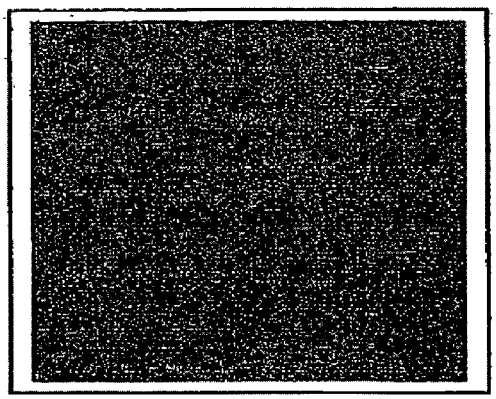

Blot # 101003_d3

FIGURE 23

Lane 1 mw
Lane 2 LL conc to 6 ml
Lanes 3-12 SEC fractions 6-24 (2 ml each)
Lane 13 2l pellet after 1st solubilization
Lane 14 2nd solubilization spun
Lane 15 Teal N4 negative control

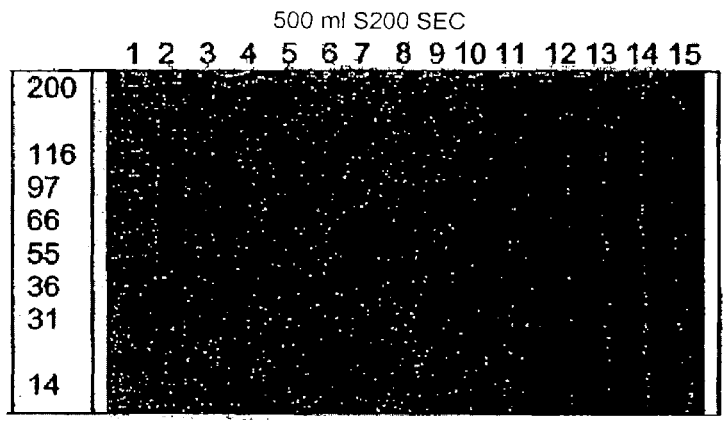

FIGURE 28

Lentil Lectin

Lane 1 mw 200, 116, 97, 66, 55, 36, 31, 21
Lane 2 Positive Blot standard
Lane 3 Applied sample
Lane 4 Flow through
Lane 5 Column wash
Lanes 6-14 Elution fractions Fractions from lanes 6-10 were pooled to yield 100 ml.

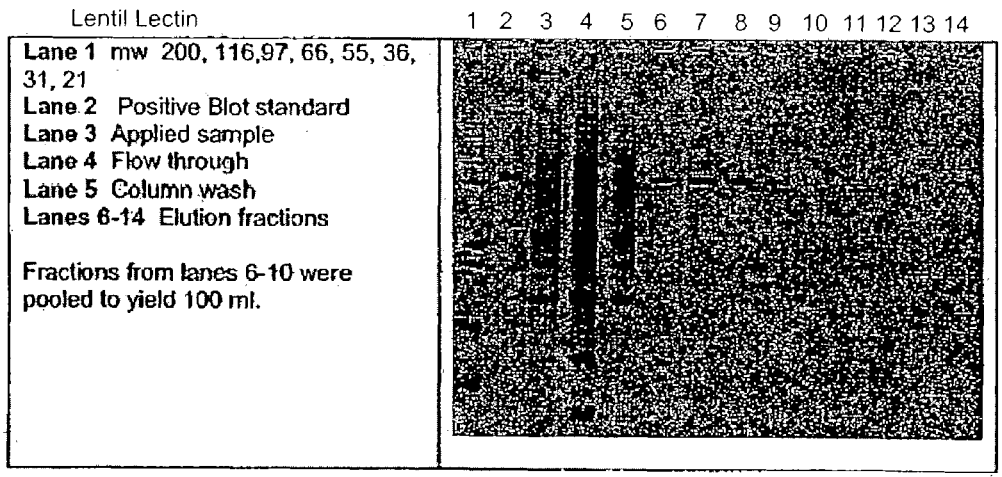

FIGURE 29

Lentil Lectin using 2M urea

Lane 1 mw
Lane 2,11,12 stnd
Lane 3 8M UREA
Lane 4 8M diluted to 2M
Lane 5 LL FT
Lane 6,7,8,9,10 LL elutions
Lane 13 lane 7,8 concentrated
Lane 14 lane 9,10 concentrated

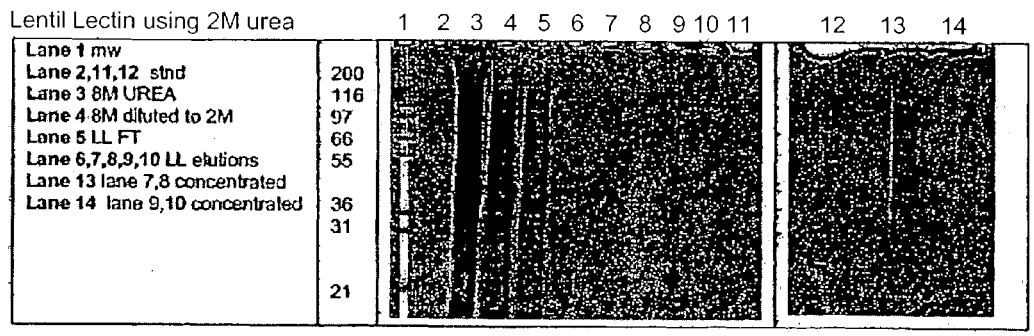

FIGURE 30

SDS-PAGE

BLOT with 541

SDS-PAGE

Blot 541

Lane 1 S 17 reducing
Lane 2 Hy ap reducing (separate exp.)
Lane 3 SEC pool 1 reducing
Lane 4 SEC pool 2 reducing
Lane 5 S 17 reducing
Lane 6 Hy ap non-reducing (separate exp.)
Lane 7 SEC pool 1 non-reducing
Lane 8 SEC pool 2 non-reducing
Lane 9 MW
Lane 10 Hy ap reducing (separate exp.)
Lane 11 SEC pool 1 reducing
Lane 12 SEC pool 2 reducing
Lane 13 Hy ap non-reducing (separate exp.)
Lane 14 SEC pool 1 non-reducing
Lane 15 SEC pool 2 non-reducing Blot done with 541 antibody

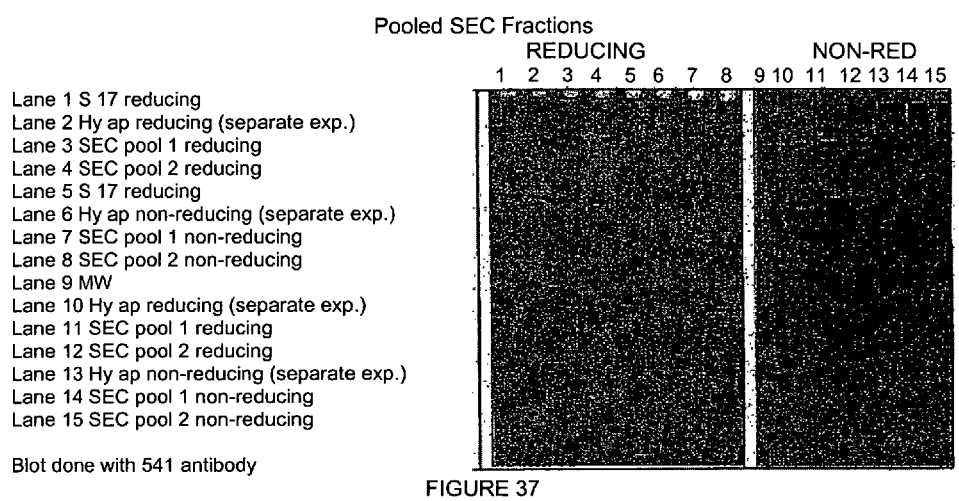

FIGURE 37

| Lane # | Lane Description |
|---|---|
| 1 | Protein marker |
| 2 | S-16, std, reducing |
| 3 | P3, D3217.1a, pellets |
| 4 | P3, D3217.1a, S/N |

Blot 102703_d7 Ab IMG-541

| Lane # | lane description |
|---|---|
| 1 | Protein marker |
| 2 | S-16, st, reducing |
| 3 | 2L, D3217.1a, 48hpi, pellets |
| 4 | 2L, D3217.1a, 48 hpi, S/N |
| 5 | 2L, D3217.1a, 72hpi, Pellets |
| 6 | 2L, D3217.1a, 72hpi, S/N |
| 7 | Control, (-ve), none-infected cells |
| 8 | Control, (-ve), infected cells |

Blot 111103_d3 Ab IMG-542

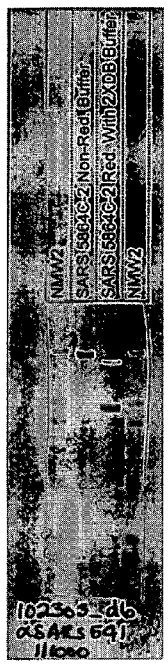 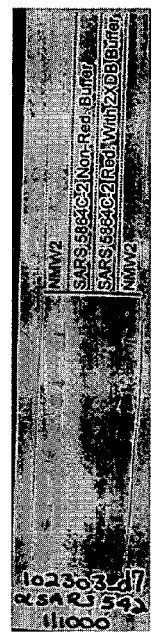
Figure 41 Blot 102303-D6 Anti-SARS 541
Figure 42 Blot 102303-D7 Anti-SARS 542

Figure 43 Blot 102303-D8 Anti-SARS CDC
Figure 44 Gel Number 102303_d6, lanes 1-4
Lane 1=NMW2    Lane 2=SARS 5864C-2 Non-red.
Lane 3=SARS 5864C-2 Red.    Lane 4=NMW2

| Lane # | Lane Description |
|---|---|
| 1 | Protein marker |
| 2 | 10L D3252.2a,, total, 72 hpi |
| 3 | 10L D3252.2a, pellets, 72hpi |
| 4 | 10L d3252.2a, supernatant, 72hpi |
| 5 | Control, (-ve), non-infected |
| 6 | Control, (-ve), infected cells |

Blot 102103_d6 Ab IMG-541

| Lane # | Lane Discription |
|---|---|
| 1 | Protein marker |
| 2 | S-16, st, reducing |
| 3 | P3, D3540.1a, pellets |
| 4 | P3, D3540.1a, S/N |
| 5 | 10L, D3540.1a, pellets, 72 hpi |
| 6 | 10L, D3540.1a, S/N , 72 hpi |
| 7 | Control, (-ve), none-infected cells |
| 8 | Control, (-ve), infected cells |

Blot 111103_d2, Ab IMG-542

Lentil Lectin

SDS-PAGE          BLOT

Lane 1, 22 MW
Lane 2, 13, 21 Standard
Lane 3, 20 Applied sample at pH 7; 0,1% tergitol
Lane 4, 19 LL flow through
Lane 5 high salt wash
Lane 6 elution 1
Lane 7, 18 elution 2
Lane 8, 17 elution 3
Lane 9, 16 elution 4
Lane 14 elution 2 blotted with CDC sera
Lane 15 elution 2 blotted with IMG-541

SDS-PAGE                BLOT with IMG-542

Lane 1,7 mw
Lane 2,6 fraction 20
Lane 3,5 fraction 21
Lane 4  fraction 22

SDS-PAGE gel of full length his-tagged S-protein in 20 mM Tris buffer, 0.1% Tergitol
0.1% BME 100 mM a-D-methyl-mannopyroside SEC column FPLC 5890 (010904_d2)

| Lane 1 | Molecular Weight Marker |
| Lane 2 | SARS S ΔTM 3µg @ 0.5µg/10µl |
| Lane 3 | SARS S

| Sample time (hpi) | Viability (%) |
|---|---|
| 48 | 75 |
| 54 | 68 |
| 60 | 50 |
| 72 | 41 |
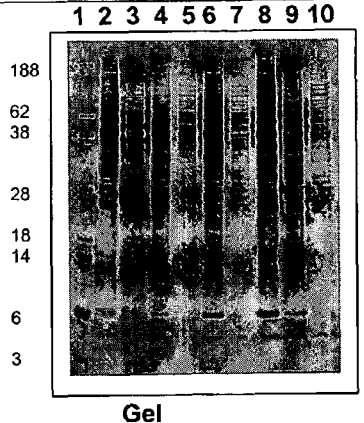
Gel
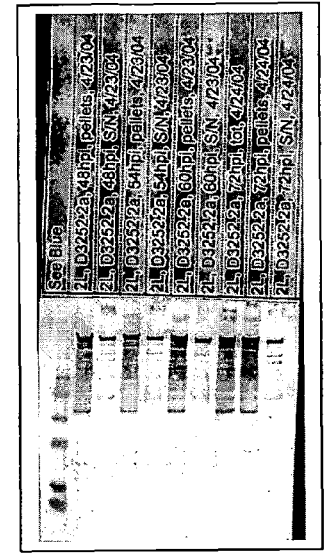
Western Blot (042604_d3)
PSC Antibody 1:5000
FIGURE 63
SDS-PAGE and Western Blot
2L process w/o pH and conc.
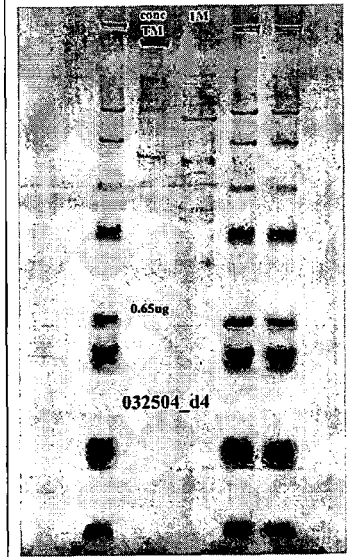
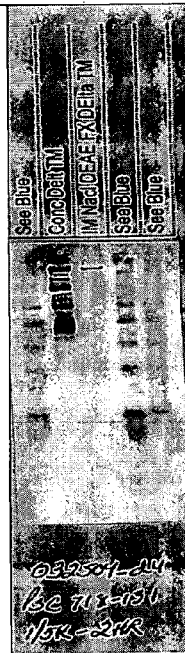
FIGURE 64

VECTORS EXPRESSING SARS IMMUNOGENS, COMPOSITIONS CONTAINING SUCH VECTORS OR EXPRESSION PRODUCTS THEREOF, METHODS AND ASSAYS FOR MAKING AND USING

RELATED APPLICATIONS/INCORPORATION BY REFERENCE

This application claims priority from U.S. Provisional Application Nos. 60/480,118 filed Jun. 20, 2003 and 60/554,742 filed Mar. 19, 2004. Each of the above applications, together with each document cited therein, and each of the documents referenced or cited in documents cited therein, are hereby incorporated herein by reference. Additionally, each document cited in this text ("application cited documents") and each document cited or referenced in each of the application cited documents, and any manufacturer's specifications, data sheets, descriptions, product literature, instructions and the like for any products mentioned herein or in herein cited documents or in documents cited in herein cited documents, is hereby incorporated herein by reference. None of the documents incorporated by reference into this text is admitted to be prior art with respect to the present invention, but, documents incorporated by reference into this text may be employed in the practice of the invention.

SEQUENCE LISTING

The instant application contains a Sequence Listing which has been submitted in ASCII format via EFS-Web and is hereby incorporated by reference in its entirety. Said ASCII copy, created on Nov. 16, 2011, is named 43122238.txt and is 156,110 bytes in size.

FIELD OF THE INVENTION

The invention relates to SARS (severe acute respiratory syndrome virus, a coronavirus) immunogens, antigens, or epitopes, nucleic acid molecules encoding such immunogens, antigens, or epitopes, vectors containing such nucleic acid molecules, e.g., viral vectors such as baculovirus vectors, DNA vectors, such as DNA plasmid vectors, e.g., DNA plasmids that express a nucleic acid molecule in a mammalian cell, uses for such immunogens, antigens or epitopes and vectors, e.g., as an active component immunogenic, immunological or vaccine compositions, or to generate antibodies, such as monoclonal antibodies, and methods for making, and using such immunogens, antigens or epitopes, vectors, antibodies, including in methods for eliciting an immunological or immunogenic or vaccine response, as well as in assays or diagnostic kits or methods. The invention also involves the seamless fusion of sequences in a plasmid or vector, e.g., a sequence encoding a leader sequence and a sequence encoding a protein, epitope or immunogen or antigen.

BACKGROUND

SARS—or severe acute respiratory syndrome—is a respiratory disease. Main symptoms include fever, dry cough, headache, shortness of breath and difficulty of breathing. Many of those infected develop viral pneumonia resulting in infection of the lower respiratory tract. SARS is highly contagious, and is spread by droplets caused by coughing or sneezing or through other methods such as fecal contamination. WHO estimates that SARS is fatal in around 10-15% of all cases. As of May 28, 2003, 8,240 cases were identified worldwide and 745 people died (Source: World Health Organization). Among the elderly, specifically those patients 60 years or older, there is a 43% fatality rate. (Stohr, 2003). Currently, there is no specific treatment for SARS, nor is there a reliable diagnostic test to date.

Recently Koch's postulates were fulfilled for associating the SARS coronavirus with the SARS disease (Fouchier, Kuiken et al. 2003). Fouchier et al. described proof from experimental infection of cynomolgus macaques, that the SARS-associated virus (SCV) is indeed the aetiological agent of the disease. Earlier, other groups had already described the isolation of SCV from diseased hosts and cultivation of the SCV in host cells (Drosten, Gunther et al. 2003; Ksiazek, Erdman et al. 2003).

Coronaviruses infect a variety of livestock, poultry and companion animals. Coronaviruses are spherical, enveloped viruses, ranging from 160-180 nm in diameter and containing a positive-stranded RNA genome. With their genome of approximately 30,000 bases, they are considered the largest of the known RNA viruses. Like influenza viruses they have the ability to genetically recombine with other members of the coronavirus family. Coronavirus is infamous for being a cause of the common cold.

The morphology of the Coronavirus is shown in FIG. 10 and a schematic picture is shown in FIG. 11.

SARS, caused by a coronavirus, has become a problem. This is evidenced by the following: SARS has been demonstrated to grow in VERO (green African monkey kidney) cells and has been found in mammalian species, e.g., civet cat and racoon-dog, and such factors indicate that the virus will remain active for the indefinite future and may increase in virulence.

SARS immunogens, antigens, or epitopes, nucleic acid molecules encoding such immunogens, antigens, or epitopes, vectors containing such nucleic acid molecules, uses for such immunogens, antigens or epitopes and vectors, e.g., as an active component immunogenic, immunological or vaccine compositions, or to generate antibodies, such as monoclonal antibodies, and methods for making, and using such immunogens, antigens or epitopes, vectors, antibodies, including in methods for eliciting an immunological or immunogenic or vaccine response, as well as in assays or diagnostic kits or methods, would be useful in addressing SARS.

OBJECTS/SUMMARY OF THE INVENTION

An object of the invention can be to clone and express, purify, scale-up, characterize and produce coronavirus, e.g., SARS, proteins, such as the S-protein, e.g., SARS S protein, for instance, using the baculovirus expression vector system; advantageously, the proteins, such as SARS S protein, are useful in immunogenic, immunological or vaccine compositions, or to generate monoclonal antibodies that are useful in kits, tests, methods or assays (e.g., diagnostics). The S protein can be full length or truncated or a fusion. And, the invention also can have as an object providing seamless joining of nucleic acid molecules. Furthermore, the invention provides combination compositions, e.g., compositions that contain and/or express one or more SARS antigens, epitopes or immunogens, and one or more antigens, epitopes or immunogens of another pathogen, such as influenza, e.g., influenza HA and/or NA. The invention further envisions compositions that contain and/or express one or more SARS antigens, epitopes or immunogens from more than one isolate, e.g., at least two isolates, such as three or more isolates, advantageously three isolates. On this point, as an influenza vaccine contains and/or expresses one or more HA and/or NA antigens, epitopes or immunogens, such as three HA and/or NA antigens, epitopes or immunogens, e.g., from different strains, such as those chosen by the WHO, in a combination composition, it is advantageous to likewise contain and/or express one or more HA and/or NA antigens, epitopes or immunogens; and, even further, it may be advantageous for the composition to contain and/or express a SARS protein from more than one isolate, such as at least two isolates, e.g., three or more isolates, for instance three isolates. And as to SARS antigens, epitopes or immunogens, while any or all of S, S1, S2, M, N and E or portions(s) thereof are envisioned by the invention, S, such as full length S is considered advantageous.

It is noted that in this disclosure, terms such as "comprises", "comprised", "comprising", "contains", "containing" and the like can have the meaning attributed to them in U.S. Patent law; e.g., they can mean "includes", "included", "including" and the like. Terms such as "consisting essentially of" and "consists essentially of" have the meaning attributed to them in U.S. Patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. Patent law; namely, that these terms are closed ended.

Other aspects of the invention are described in or are obvious from (and within the ambit of the invention) the following disclosure.

BRIEF DESCRIPTION OF THE DRAWINGS

The following Detailed Description, given by way of example, but not intended to limit the invention to any specific embodiments described, may be understood in conjunction with the accompanying drawings, incorporated herein by reference, in which:

FIGS. 1A, 1B show an amino acid sequence for the SARS S protein and a nucleotide sequences encoding a SARS S protein with restriction sites and primers for cloning indicated (SEQ ID Nos: 1 and 2) (see also FIG. 7);

FIGS. 2A, 2B show a nucleotide sequence encoding the SARS S ORF; ATG, AGT and TAA in bold (SEQ ID NO: 3);

FIG. 3 shows a nucleotide sequence encoding SARS E protein (SEQ ID NO: 4);

FIG. 4 shows a SARS E protein amino acid sequence (SEQ ID NO: 5);

FIG. 5 shows a nucleotide sequence encoding SARS M protein (SEQ ID NO: 6);

FIG. 6A shows a SARS M protein amino acid sequence (SEQ ID NO: 7);

FIG. 6B shows a nucleic acid sequence encoding SARS N protein (SEQ ID NO: 8);

FIG. 6C shows an amino acid sequence for SARS N protein (SEQ ID NO: 9);

FIG. 7 shows primers for cloning of SARS S ORF: primer 2165 (SEQ ID NO: 10); primer 2166 (SEQ ID NO: 11); primer 2167 (SEQ ID NO: 12); primer 2168 (SEQ ID NO: 13); primer 2169 (SEQ ID NO: 14); primer 2170 (SEQ ID NO: 15); primer 2171 (SEQ ID NO: 16) (see also FIG. 1);

FIG. 8 shows a restriction map of the SARS S ORF;

FIG. 9 shows a schematic strategy for preparing a baculovirus (BEVS or BV) expression vector;

FIGS. 13A-F show sequence alignments of canine enteric coronavirus (SEQ ID NO: 17), canine coronavirus (SEQ ID NO: 18), feline coronavirus (SEQ ID NO: 19), feline infectious peritonitis virus (SEQ ID NO: 20), porcine transmissible gastro coronavirus (SEQ ID NO: 21), porcine respiratory coronavirus (SEQ ID NO: 22), human coronavirus (SEQ ID NO: 23), porcine epidemic diarrhea virus (SEQ ID NO: 24), bovine coronavirus (SEQ ID NO: 25), SARS coronavirus (SEQ ID NO: 26), and avian infectious bronchitis virus (SEQ ID NO: 27).

FIG. 16 is a picture of a gel.
FIG. 17 is a picture of a gel.
FIG. 18 is a picture of a Western Blot.
FIG. 19 is picture of a Western Blot.
FIG. 20 is a picture of a Western Blot.
FIG. 21 is a picture of two Western Blots.
FIG. 22 is a picture of two Western Blots.
FIG. 23 is picture of a gel and a Western Blot.
FIG. 28 is a picture of a gel.
FIG. 29 is a picture of a gel.
FIG. 30 is a picture of a gel.
FIG. 37 is a picture of a gel and Western Blot.
FIG. 41 is a picture of a Western Blot.
FIG. 42 is a picture of a Western Blot.

FIG. 43 is a picture of a Western Blot.
FIG. 44 is a picture of a gel.
FIG. 63 is a picture of a gel and a Western Blot.
FIG. 64 is a picture of a gel and a Western Blot.
FIG. 70 is a picture of a gel.
FIG. 71 is a bar graph.

DETAILED DESCRIPTION

As discussed above, this invention relates to SARS (severe acute respiratory syndrome virus, a coronavirus) immunogens, antigens, or epitopes, nucleic acid molecules encoding such immunogens, antigens, or epitopes, vectors containing such nucleic acid molecules, e.g., viral vectors such as baculovirus vectors, DNA vectors, such as DNA plasmid vectors, e.g., DNA plasmids that express a nucleic acid molecule in a mammalian cell, uses for such immunogens, antigens or epitopes and vectors, e.g., as an active component immunogenic, immunological or vaccine compositions, or to generate antibodies, such as monoclonal antibodies, and methods for making, and using such immunogens, antigens or epitopes, vectors, antibodies, including in methods for eliciting an immunological or immunogenic or vaccine response, as well as in assays or diagnostic kits or methods.

Figure 10:
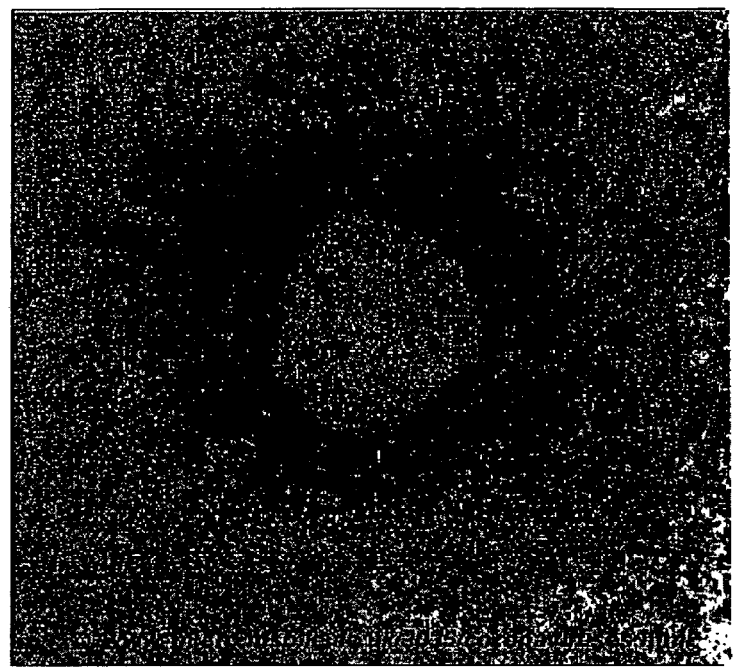
FIG. 10 shows coronavirus particles; the coronavirus particles are irregularly-shaped, ~60-220 nm in diameter, with an outer envelope bearing distinctive, 'club-shaped' peplomers (~20 nm long×10 nm at wide distal end); this 'crown-like' appearance (Latin, corona) gives the family its name; the center of the particle appears amorphous in negatively stained EM preps, the nucleocapsid being in a loosely wound rather disordered state.
Figure 11:
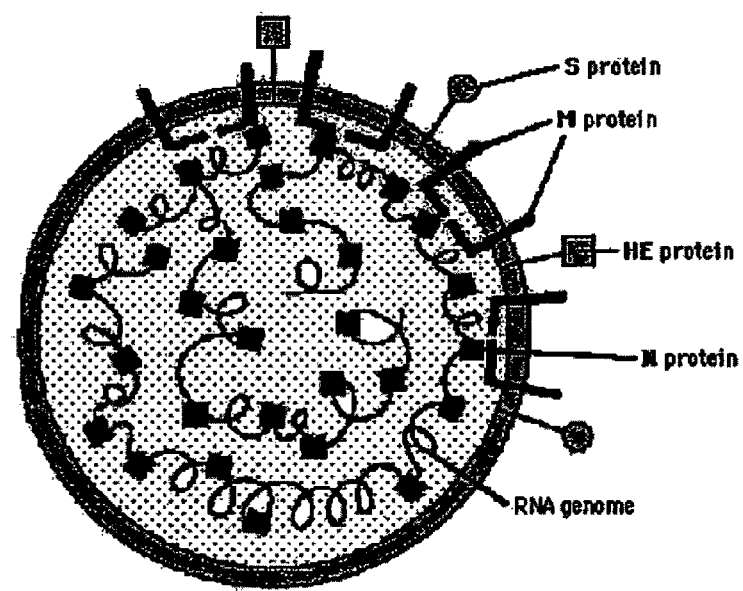
FIG. 11 shows a schematic representation of the SARS coronavirus; the envelope carries two glycoproteins: S—Spike glycoprotein: receptor binding, cell fusion, major antigen (180-200 kDa) and M—Membrane glycoprotein: transmembrane—budding and envelope formation (30-35 kDa); in a few types, there is a third glycoprotein: HE—Haemagglutinin-esterase (65-70 kDa), this protein has not been identified in the coronavirus associated with SARS (Ruan et al., 2003); the genome is associated with a basic phosphoprotein, N.
Figure 12A:
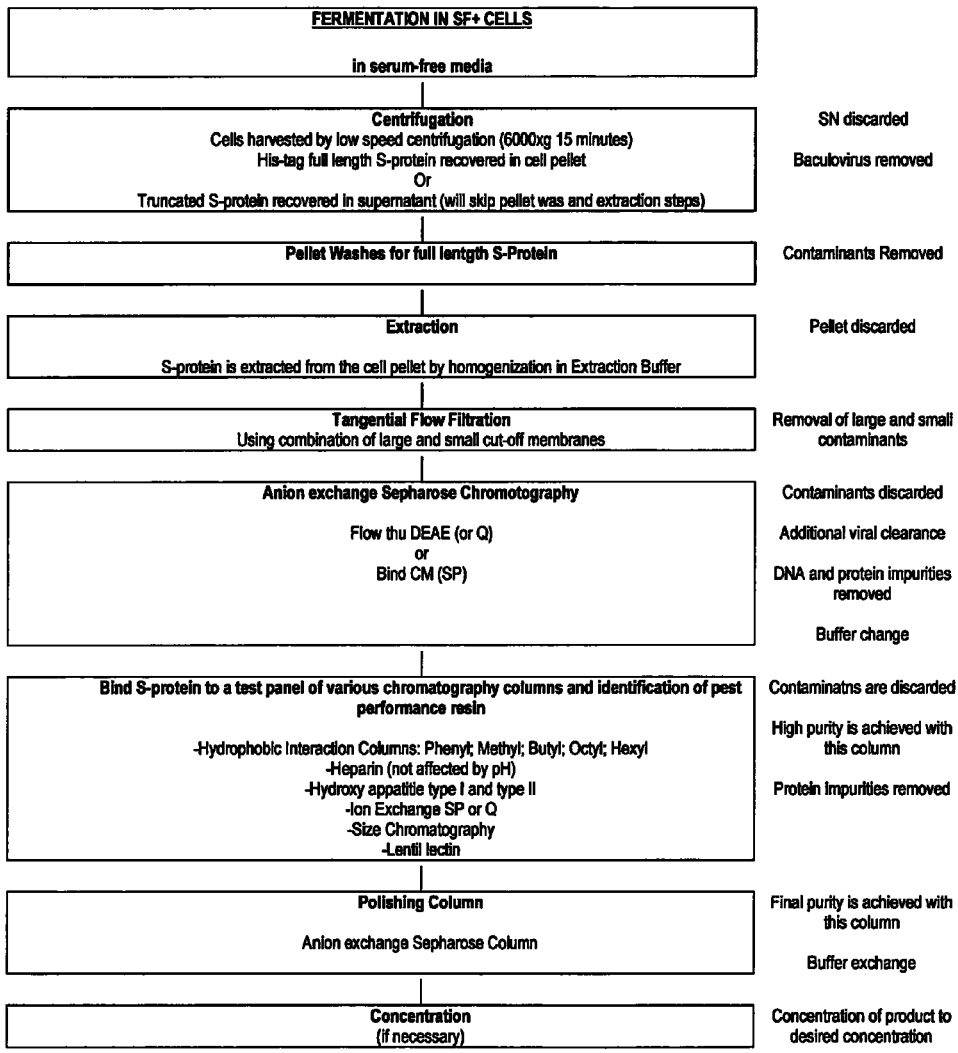
FIGS. 12A, B, C, D and E show schematic overviews of S-protein production processes.
Figure 12B:
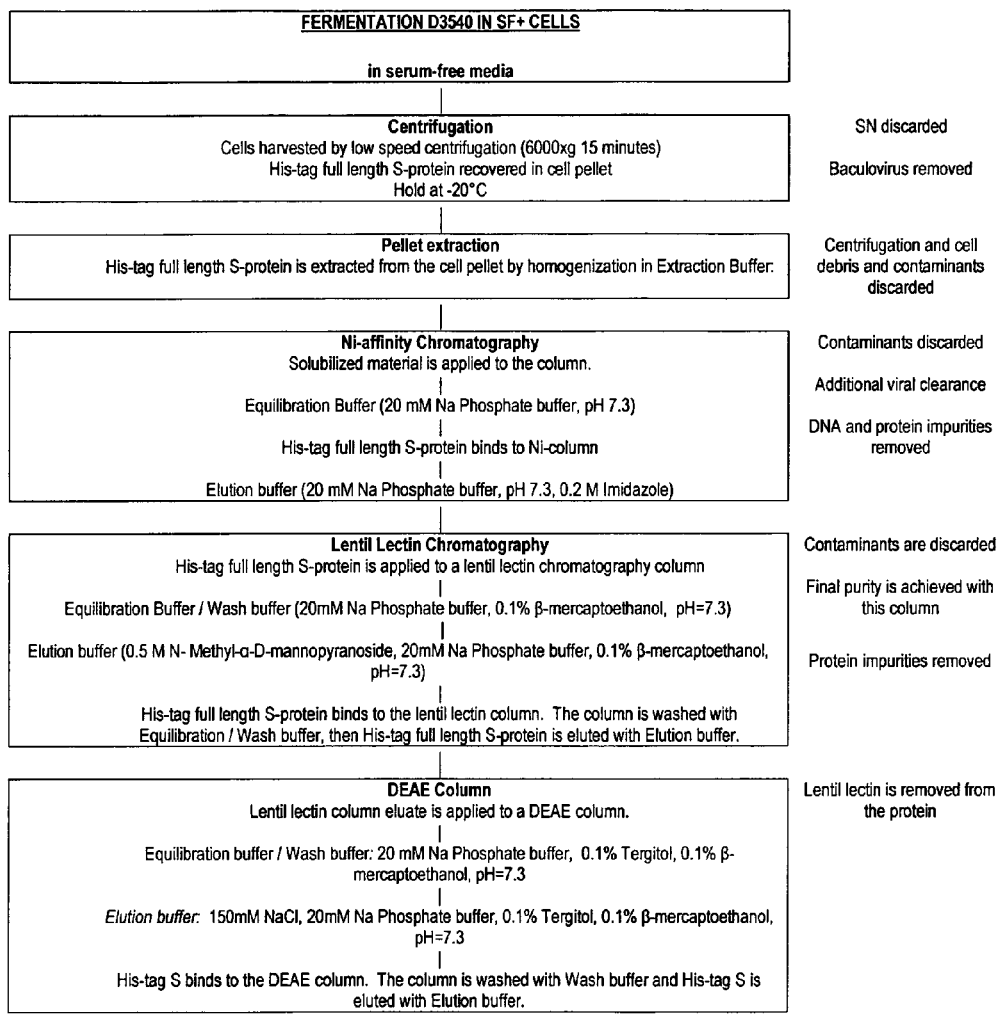

FIGS. 1A, 1B, 2A, 2B, 3-6C (SEQ ID Nos: 1-9) provide nucleic acid sequences encoding SARS immunogens, antigens or epitopes, and amino acid sequences for such immunogens, antigens or epitopes. FIGS. 7 and 8 (SEQ ID Nos: 10-16) provide primers for cloning SARS S ORF, as well as a restriction map for the SARS S ORF. FIGS. 10 and 11 provide information on the SARS coronavirus. FIG. 9 provides a schematic for preparing a BEVS expression vector that can contain one or more of the nucleic acid molecules encoding SARS immunogens, antigens or epitopes, FIG. 12 provides a protein purification strategy, e.g., as to SARS S; and, FIG. 13 (SEQ ID Nos: 17-27) provides a sequence alignment. Thus, through the figures, the description provides that to which the invention relates, and the reader is invited to view the figures in conjunction with the herein discussion.

Applicants received passage #3 of SARS CoV 3200300841 in Trizol LS Reagent from the CDC (Dr Erdman, Acting Chief, Respiratory Virus Section, CDC/NCID/DVRD/REVB). This virus was prepared from culture batch 809940 that had a titer of 4 log on plaque assay. Lysate from this culture was added to TRIzol reagent and 1 ml was received by Applicants. The Applicants used this lysate to isolate RNA and produce cDNA. This cDNA was then used to prepare a recombinant expression vectors, e.g., viral expression vectors, DNA plasmid expression vectors, advantageously a baculovirus expression vector for the gene construct by co-transfection of insect cells with the baculovirus transfer plasmid and a baculovirus Autographa californica Nuclear Polyhedrosis Virus (AcNPV) parent vector. During this process, the gene was transferred into the baculovirus genome via homologous recombination such that the S-protein is under the control of the highly expressed AcNPV polyhedrin promoter. Recombinant viruses are identified by plaque assay, isolated and purified. Cloning is being done in such a way as to preserve the exact S-protein amino-acid sequence. The protein can be expressed with a baculovirus signal peptide (see, e.g., U.S. Pat. No. 6,245,532, as well as for general methods involving expression in recombinant baculovirus).

A recombinant AcNPV-S-protein baculovirus virus bank is prepared by infection of serum-free insect cells (see, e.g., U.S. Pat. No. 6,103,526) and harvest of the supernatant media containing high titers of infectious baculoviruses. See, e.g., PCT Publication WO 00/46354 regarding apparatus and methods for high density growth of cells, including cells infected with recombinant virus such as baculovirus.

The expression of the recombinant S-protein is analyzed by SDS-PAGE/Coomassie Blue staining and Western blot analyses.

The titer of the virus stock is determined and this virus stock is used to produce a 10 L cell pellet. This pellet can be used for purification.

Full-length S-protein can be secreted from insect cells and be attached to the surface of the cell membrane. Using mild detergent conditions the S-protein is solubilized. The protein is then purified to eliminate contaminating proteins and nucleic acids by using column chromatography.

N-terminal sequencing confirms that it is an authentic, full-length antigen. In addition, biological activity of the S-protein may be assessed based on its ability to agglutinate mice red blood cells. As described above, recombinant virus from a single viral plaque is propagated through several passages at a low multiplicity of infection to generate a large quantity of inoculum and stored in aliquots in liquid nitrogen as the working virus bank (WVB). The WVB is tested for freedom from bacteria, fungi and other adventitious agents, including contaminating wild type or other recombinant baculoviruses. Identity is confirmed by Southern blot analysis of the insert from purified baculovirus DNA and by Western blot analysis of the recombinant protein produced in infected insect cells.

As to truncated S-protein, Applicants' truncated forms of the S-protein can lack the cytoplasmic and trans-membrane portion of the S-protein, e.g., comprise, consist essentially of or consist of, the S1 or S2 region. Applicants' constructs include a construct encoding an S-protein that contains a his-tag to facilitate purification development. It appears the S protein may be expressed as a trimer. Moreover, M and/or N and/or E proteins, or portions thereof, are expressed in accordance with the invention.

Identity tests include SDS-PAGE and Western blot analysis and, amino acid analysis and N-terminal sequencing. These confirm an authentic, full-length antigen. A test of sterility can be done in accordance with 21 CFR 610.12. A test for purity can be done in accordance with 21 CFR 610.13 and this measures the purity of the S-protein antigen and measure for the presence of pyrogenic substances. A measure of the amount of S-protein antigen present in the bulk material is done using a standard chemical assay for protein and used to calculate the dilution required for the final container fill.

The S protein is a candidate antigen for coronavirus vaccines since it induces virus neutralizing (VN) antibodies. The S protein (spike glycoprotein, a surface protein) appears to be a major antigen of SARS and is key to infection through ACE2 receptor binding. In addition the haemagglutinin-esterase (HE) protein has been described to stimulate the production of VN and HE inhibiting antibodies (Saif 1993), however this protein is not present in SCV. Also, the M protein was described to induce antibodies that neutralize virus in the presence of complement (Saif 1993). Antigenic specificity of the virion can be determined by neutralization tests (S and HE), or complement fixation tests (M). Protective immunity is induced in the form of complement independent neutralizing antibodies.

The full length gene encoding the S-protein including various fragments from the transmissible gastroenteritis virus (TGEV) were cloned and expressed in baculovirus vectors. Piglets were immunized with cells infected with the recombinant viruses and it was shown that the amino terminal half of the S protein, containing all four major antigenic sites (A, B, C and D), induced VN antibody titers (Tuboly, Nagy et al. 1994). Soluble truncated S-proteins from human coronavirus HCoV-229E by using baculovirus expression vectors can be produced and the receptor-binding domain of the spike glycoprotein in the N-terminal 547 amino acids of the full length gene can be identified and located (Bonavia, Zelus et al. 2003).

In the case of feline infectious peritonitis virus (FIPV) vaccination with the S-protein cloned and expressed in vaccinia virus vectors has been implicated in antibody-mediated enhancement of the virus infection (Vennema, de Groot et al. 1990; Vennema, de Groot et al. 1990; Klepfer, Reed et al. 1995). In addition, similar phenomena was reported after immunization of cats against FIV with inactivated or live FIP virus (Scott 1987). Specific antigenic sites of the S-protein were reported to be involved in this antibody-dependent enhancement (Corapi, Darteil et al. 1995).

However, Paoletti in U.S. Pat. No. 5,858,373 reports the utility of attenuated vectors, e.g., NYVAC, ALVAC, expressing FIPV antigens, e.g., S, S1, S2, S3, M, N, M+N. Accordingly, it is believed that the alleged issue of enhancement of virus infection may be due to the nature of the vector employed in previous studies or may be unique to cats. Thus, the present invention envisions an attenuated or non-replicating vector (in mammalian cells), such as a DNA plasmid, MVA, ALVAC, NYVAC, or a baculovirus that employs a mammalian promoter such as a CMV promoter or an SV40 promoter, for expressing one or more SARS proteins, such as S and/or S1 and/or S2 and/or E and/or M and/or N in vivo. Documents cited herein may be consulted for the construction and use of such a vector. But generally, the teachings in the Paoletti 373 patent may be employed in constructing and using poxvirus, e.g., MVA ALVAC and NYVAC SARS vectors; and the teachings in Audonnet U.S. Pat. Nos. 6,228,846 and 6,159,477 may be relied upon for DNA plasmid teachings that can be employed in constructing and using DNA plasmids that contain and express in vivo SARS proteins. Generally, a plasmid for a vaccine or immunological composition can comprise DNA encoding an antigen (e.g., SARS S, S1, S2, E, M, N or combinations thereof) operatively linked to regulatory sequences which control expression or expression and secretion of the antigen from a host cell, e.g., a mammalian cell; for instance, from upstream to downstream, DNA for a promoter, such as a mammalian virus promoter (e.g., a CMV promoter such as an hCMV or mCMV promoter, e.g., an early-intermediate promoter, or an SV40 promoter—see documents cited or incorporated herein for useful promoters), DNA for a eukaryotic leader peptide for secretion (e.g., for tissue plasminogen activator—see documents cited or incorporated herein for useful leader peptides), DNA for the antigen (SARS S and/or S1 and/or S2 and/or E and/or M), and DNA encoding a terminator (e.g., the 3' UTR transcriptional terminator from the gene encoding Bovine Growth Hormone or bGH polyA—see documents cited or incorporated herein). A composition can contain more than one plasmid or vector, whereby each vector contains and expresses a different SARS protein or antigen or epitope. Mention is also made of Wasmoen U.S. Pat. No. 5,849,303, and Dale U.S. Pat. No. 5,811,104, whose text may be useful. There may be no cleavage of the SARS S-protein contrary to the coronaviruses that belong to group 1, such that full length S may be more advantageous than S1 and S2—either expressed by plasmid, vector or recombinant virus preparations or in subunit preparations.

Furthermore, the invention envisions compositions, e.g., immunogenic, immunological or vaccine compositions, containing, consisting essentially of or consisting of one or more isolated SARS antigens, immunogens or epitopes, e.g., one or more of S, S1, S2, E, M, N, such as N1 such as combinations thereof, S or S1 and/or S+E and/or M and/or N such as N1.

Even further still, the invention envisions compositions that contain SARS proteins and/or vectors and/or plasmids expressing SARS proteins from more than one isolate, e.g., from two or more isolates, such as from three different isolates. Advantageously, compositions contain S proteins or portions thereof, e.g., S1 or S2, from three different isolates, or vectors or plasmids that express such S proteins or portions thereof from three different isolates. Isolates should be selected so as to maximize the immunogenic response to the composition.

Compositions in forms for various administration routes are envisioned by the invention. The effective dosage and route of administration are determined by known factors, such as age, sex, weight of the patient or subject and other screening procedures which are known and do not require undue experimentation. Dosages of each active agent (antigen, immunogen or epitope) can be as in herein cited or incorporated by reference documents and/or can range from one or a few to a few hundred or thousand micrograms, e.g., 1 µg to 1 mg. Recombinants or vectors can be administered in a suitable amount to obtain in vivo expression corresponding to the dosages described herein and/or in herein cited documents. For instance, suitable ranges for viral suspensions can be determined empirically. The viral vector or recombinant in the invention can be administered to a subject or patient or infected or transfected into cells in an amount of about at least $10^3$ pfu; more preferably about $10^4$ pfu to about $10^{10}$ pfu, e.g., about $10^5$ pfu to about $10^9$ pfu, for instance about $10^6$ pfu to about $10^8$ pfu, per dose, e.g. of about 2 ml. And, if more than one gene product is expressed by more than one recombinant, each recombinant can be administered in these amounts; or, each recombinant can be administered such that there is, in combination, a sum of recombinants comprising these amounts. In plasmid compositions employed in the invention, dosages can be as described in documents cited herein or as described herein. For instance, suitable quantities of each plasmid DNA in plasmid compositions can be 1 µg to 2 mg, preferably 50 µg to 1 mg. Documents cited herein regarding DNA plasmid vectors may be consulted by the skilled artisan to ascertain other suitable dosages for DNA plasmid vector compositions of the invention, without undue experimentation. However, the dosage of the composition(s), concentration of components therein and timing of administering the composition(s), which elicit a suitable immunologenic response, can be determined by methods such as by antibody titrations of sera, e.g., by ELISA and/or seroneutralization assay analysis and/or by vaccination challenge evaluation in test animals. Such determinations do not require undue experimentation from the knowledge of the skilled artisan, this disclosure and the documents cited herein. And, the time for sequential administrations (as sequential administrations of compositions of the invention are envisioned by this disclosure, e.g., wherein the same or different compositions are administered sequentially, such as in a prime-boost regimen; for instance, a vector can be administered and thereafter an isolated protein composition or vice versa) can be likewise ascertained with methods ascertainable from this disclosure, and the knowledge in the art, without undue experimentation. Indeed, as to subunit preparations, it is advantageous to administer two doses, each averaging about 50 micrograms of the SARS protein.

In addition, the invention envisions combination or cocktail compositions; that is, compositions that contain antigens or epitopes or immunogens of other pathogens, such as influenza, e.g., influenza HA, NA or M2 or portions thereof and/or contain vectors or plasmids or recombinants that express additional antigens or epitopes or immunogens of other pathogens, such as influenza, e.g., influenza HA or NA or M2. An advantageous composition can contain one or more SARS proteins, for instance, S proteins or portions thereof, e.g., S1, S2 or an epitope thereof, e.g., from different isolates, such as three different isolates, as discussed above, and influenza HA and/or NA or epitopic portions thereof, e.g., influenza HA or portions thereof from one or more strains such as from three strains and/or NA or portions thereof from one or more strains such as from three strains (e.g., influenza strains selected by WHO as they do annually for the annual trivalent influenza vaccine). The amount of HA and NA in such a combination composition can be as in herein cited documents, as well as in available influenza vaccine preparations. Likewise, a vector or plasmid or recombinant virus composition can express in vivo such SARS and influenza proteins. In this fashion, SARS and influenza may be addressed in the same preparation, especially as SARS may, like influenza, call for annual administration or immunization or vaccination. And, of course, inventive compositions can contain all of M, S, N and E of SARS, e.g., from different isolates, such as from three or four different isolates, alone, or in further combination with other antigens, epitopes, or immunogens of other pathogens, such as influenza HA and/or NA and/or M2 as herein discussed, and/or vector(s), plasmid(s) and/or recombinant virus(es) that express such SARS and/or other antigens, epitopes or immunogens, e.g., influenza HA and/or NA and/or M2 (such as from one or two or three or four or more different strains), in vivo. Further, proteosomes may be utilized in the vaccines of the present invention, including through methods described by Jones et al. (Jones, Allard et al. 2003).

Such combination compositions can be administered in forms employed for anti-influenza preparations, e.g., by injection, intranasally (mucosally), etc. and as herein described for herein compositions and as in documents cited and incorporated herein by reference.

Additionally or alternatively, the additional antigen, epitope or immunogen—either present in the composition and/or expressed by a vector in a composition of the invention can be from Pneumonia, e.g., *Streptococcus pneumonia*, such as PspA, PspC or any of the 23 antigens or epitopes typically used in an anti-pneumonia preparation; see, e.g., U.S. Pat. Nos. 6,500,613, 6,232,116, 6,231,870, 6,042,838, 6,027,734, 6,004,802, 5,997,882, 5,980,909, 5,965,400, 5,965,141, 5,955,089, 5,871,943, 5,856,170, 5,804,193, 5,753,463, 5,476,929 and documents cited therein. The pneumococcal antigen, epitope or immunogen can be present or expressed as in documents cited herein or incorporated herein by reference or as in known preparations; and, such combination compositions can be administered in forms employed for anti-pneumonia preparations, e.g., by injection, intranasally (mucosally), orally, etc. and as herein described for herein compositions and as in document cited and incorporated herein by reference. Compositions of the invention may be used for parenteral or mucosal administration, preferably by intradermal or intramuscular routes. When mucosal administration is used, it is possible to use oral, nasal, or ocular routes. Topical administration is also envisioned by the invention; see, e.g., Tang U.S. Pat. No. 6,348,540 and U.S. PATENT APPLICATION NO. 20030045492, and U.S. Pat. Nos. 5,910,306 and 5,980,898, whose text may be consulted for the topical administration of vector or plasmid compositions, as well as for compositions containing immunogen(s), antigen(s) or epitope(s).

In such compositions the immunogen(s), antigen(s) or epitope(s), or the vector or plasmid may be in a mixture with a suitable carrier, diluent, or excipient such as sterile water, physiological saline, glucose or the like, and/or with an adjuvant. The compositions can also be lyophilized or frozen. The compositions can contain auxiliary substances such as pH buffering agents, adjuvants, preservatives, polymer excipients used for mucosal routes, and the like, depending upon the route of administration and the preparation desired. Standard texts, such as "REMINGTON'S PHARMACEUTICAL SCIENCE" (Gennaro 1985), "HAND BOOK OF PHARMACEUTICAL EXCIPIENTS" (Rowe, Sheskey et al. 2003), incorporated herein by reference, may be consulted to prepare suitable preparations, without undue experimentation. Suitable dosages can also be based upon the text herein and documents cited herein.

Adjuvants are substances that enhance the immune response to immunogens.

Insect cells or fractions thereof may be an adjuvant; see, e.g., U.S. Pat. No. 6,224,882. Thus, while a purity of 90% or greater than 90% such as 95% or greater than 95% is desired, a "self-adjuvanting" composition that contains insect cells or fractions thereof may also be employed.

Adjuvants, can include aluminum hydroxide and aluminum phosphate, saponins e.g., Quil A, water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di(caprylate/caprate), glyceryl tri(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycerol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic® products, especially L121 (Hunter. 1995). For example, it is possible to use the SPT emulsion described on page 147 of (Powell, Newman et al. 1995), and the emulsion MF59 described on page 183 of this same book. For instance, the adjuvant-containing composition is prepared in the following way: 67% v/v of aqueous phase comprising the immunogen are emulsified in 2.3% w/v of anhydromannitol oleate, 2.6% w/v of oleic acid ethoxylated with 11 EO (ethylene oxide) and 28.1% v/v of light liquid paraffin oil (European Pharmacopea type) with the aid of an emulsifying turbomixer. An alternative method for preparing the emulsion consists in emulsifying, by passages through a high-pressure homogenizer, a mixture of 5% w/v squalane, 2.5% w/v Pluronic® L121, 0.2% w/v of an ester of oleic acid and of anhydrosorbitol ethoxylated with 20 EO, 92.3% v/v of the aqueous phase comprising the immunogen.

It is also possible to formulate with synthetic polymers (e.g., homo- and copolymers of lactic and glycolic acid, which have been used to produce microspheres that encapsulate immunogens (Eldridge, Staas et al. 1991), e.g., biodegradable microspheres), with cytokines such as IL-2 and IL-12 (see, e.g., U.S. Pat. No. 5,334,379), and GMCSF (granulocyte macrophage-colony stimulating factor; see, generally, U.S. Pat. Nos. 5,602,007, 4,999,291 and 5,641, 663, see also Clark and Grant (Clark and Kamen 1987; Grant and Heel 1992), inter alia. Certain adjuvants can be expressed in vivo with immunogen(s) and/or epitope(s); e.g., cytokines, GMCSF.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Pharmeuropa 1996). Persons skilled in the art can also refer to U.S. Pat. No. 2,909,462 (incorporated herein by reference) which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol (BF Goodrich, Ohio, USA) are particularly appropriate. They are cross-linked with an allyl sucrose or with allyl pentaerythritol. Among then, there may be mentioned Carbopol 974P, 934P and 971P. Among the copolymers of maleic anhydride and alkenyl derivative, the copolymers EMA (Monsanto) which are copolymers of maleic anhydride and ethylene, linear or cross-linked, for example cross-linked with divinyl ether, are preferred. Reference may be made to (Regelson, Kuhar et al. 1960), incorporated herein by reference. The dissolution of these polymers in water leads to an acid solution that is neutralized, preferably to physiological pH, in order to give the adjuvant solution into which the immunogenic, immunological or vaccine composition itself is incorporated. The carboxyl groups of the polymer are then partly in COO$^-$ form. Preferably, a solution of adjuvant according to the invention, especially of carbomer, is prepared in distilled water, preferably in the presence of sodium chloride, the solution obtained being at acidic pH. This stock solution is diluted by adding it to the desired quantity (for obtaining the desired final concentration), or a substantial part thereof, of water charged with NaCl, preferably physiological saline (NaCl 9 g/l) all at once in several portions with concomitant or subsequent neutralization (pH 7.3 to 7.4), preferably with NaOH. This solution at physiological pH is used as it is for mixing with the vaccine, which may be especially stored in freeze-dried, liquid or frozen form. The polymer concentration in the final vaccine composition can be 0.01% to 2% w/v, e.g., 0.06 to 1% w/v, such as 0.1 to 0.6% w/v.

DNA or DNA plasmid formulations can be formulated with or inside cationic lipids; and, as to cationic lipids, as well as adjuvants, mention is also made of Loosmore U.S. Patent Application 2003/0104008.

In addition, as previously mentioned, insect cells or fractions thereof may be an adjuvant; see, e.g., U.S. Pat. No. 6,224,882. Thus, while a purity of 90% or greater than 90% such as 95% or greater than 95% is desired, a "self-adjuvanting" composition that contains insect cells or fractions thereof may also be employed.

From this disclosure and the knowledge in the art, the skilled artisan can select a suitable adjuvant, if desired, and the amount thereof to employ in an immunological, immunogenic or vaccine composition according to the invention, without undue experimentation.

Oral or mucosal administration of SARS proteins or epitopes or vectors containing and/or expressing or compositions containing SARS proteins or vectors expressing them (either alone or also containing or expressing antigens, epitopes or immunogens of other antigens) are also envisioned by the instant invention. Such compositions can be formulated as in U.S. Pat. Nos. 6,500,613, 6,232,116, 6,231, 870, 6,042,838, 6,027,734, 6,004,802 and documents cited therein. Generally, oral administration compositions may containing a flavor, such as a pharmaceutically acceptable flavor, or may be in food or bait, e.g., if for use in the wild or with animals, or small children. The mucosal administration preferably is effected intranasally, e.g., to the olfactory mucosa; and thus the composition may be administered via an aerosol, e.g., via an aerosolizer. The intranasal administration also may provide protection to the host against pulmonary infection as well as protection to the host against an infection starting as a pulmonary infection. However, the mucosal administration can also involve respiratory mucosa, gingival mucosa or alveolar mucosa. Thus, the administration can be perlingual or sublingual or into the mouth or respiratory tract; but intranasal administration is preferred. Compositions of the invention, especially for nasal administration, are conveniently provided as isotonic aqueous solutions, suspensions or viscous compositions which may be buffered to a selected pH. The viscous compositions may be in the form of gels, lotions, ointments, creams and the like and will typically contain a sufficient amount of a thickening agent so that the viscosity is from about 2,500 to 6,500 cps, although more viscous compositions, even up to 10,000 cps may be employed. Viscous compositions have a viscosity preferably of 2,500 to 5,000 cps, since above that range they become more difficult to administer. Liquid sprays and drops are normally easier to prepare than gels and other viscous compositions. Additionally, they are somewhat more convenient to administer, especially in multi-dose situations. Viscous compositions, on the other hand can be formulated within the appropriate viscosity range to provide longer contact periods with mucosa, such as the nasal mucosa. Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropl cellulose, carbomer, and the like. The preferred concentration of the thickener will depend upon the agent selected. The important point is to use an amount which will achieve the selected viscosity. Viscous compositions are normally prepared from solutions by the addition of such thickening agents. Compositions within the scope of this invention can contain a humectant to inhibit drying of the mucous membrane and to prevent irritation. Any of a variety of pharmaceutically acceptable humectants can be employed including, for example sorbitol, propylene glycol or glycerol. As with the thickeners, the concentration will vary with the selected agent, although the presence or absence of these agents, or their concentration, is not an essential feature of the invention. Enhanced absorption across the mucosal and especially nasal membrane can be accomplished employing a pharmaceutically acceptable surfactant. Typically useful surfactants for compositions include polyoxyethylene derivatives of fatty acid partial esters of sorbitol anhydrides such as Tween 80, Polyoxyl 40 Stearate, Polyoxyethylene 50 Stearate and Octoxynol. The usual concentration is from 1% to 10% based on the total weight. A pharmaceutically acceptable preservative can be employed to increase the shelf-life of the compositions. Benzyl alcohol may be suitable, although a variety of preservatives including, for example, Parabens, thimerosal, chlorobutanol, or bezalkonium chloride may also be employed. A suitable concentration of the preservative will be from 0.02% to 2% based on the total weight although there may be appreciable variation depending upon the agent selected immunogenic compositions including vaccines may be prepared as inhalables, sprays and the like (e.g., nasal spray, aerosol spray or pump spray and the like), e.g., as liquid solutions or emulsions, etc. Aerosol spray preparations can be in a pressurized container with a suitable propellant such as a hydrocarbon propellant. Pump spray dispensers can dispense a metered dose or a dose having a particular particle or droplet size. Pump spray dispensers are commercially available, e.g., from Valois of America, Inc., Connecticut. Nasal spray dispensers are commonly fabricated from a flexible material such as plastic and cause a spray to dispense in response to being squeezed. Anti-inflammatories, such as "Vanceril" are commercially available in oral and nasal aerosol form for mucosal administration; the anti-inflammatory "Vancerase" is commercially available in a pump-spray dispenser for nasal administration; cold remedies such as "Dristan" are commercially available in nasal spray (squeeze) dispensers (so that the reader is aware that aerosol, pump and squeeze dispensers are known and available); and, even anti-influenza vaccines are provided in forms for nasal administration, e.g., via an aerosol or aerosolizer (by MedImume), and the compositions of the instant invention may be analogous dispensed.

With respect to the invention involving truncated SARS proteins or epitopes of SARS proteins, one can determine a suitable truncated SARS protein or epitope from the herein disclosure and knowledge in the art, without undue experimentation, with the following additionally provided: An immune response is generated, in general, as follows: T cells recognize proteins only when the protein has been cleaved into smaller peptides and is presented in a complex called the "major histocompatibility complex" (MHC) located on another cell's surface. There are two classes of MHC complexes—class I and class II, and each class is made up of many different alleles. Different patients have different types of MHC complex alleles; they are said to have a "different HLA type".

Class I MHC complexes are found on virtually every cell and present peptides from proteins produced inside the cell. Thus, Class I MHC complexes are useful for killing cells that have been infected by viruses or which have become cancerous as the result of expression of an oncogene. T cells that have a protein called CD4 on their surface bind to the MHC class I cells and secrete lymphokines. The lymphokines stimulate a response; cells arrive and kill the viral infected cell.

Class II MHC complexes are found only on antigen-presenting cells and are used to present peptides from circulating pathogens which have been endocytosed by the antigen-presenting cells. T cells which have a protein called CD8 bind to the MHC class II cells and kill the cell by exocytosis of lytic granules.

Some guidelines in determining whether a protein contains epitopes of interest which stimulate a T cell response include: Peptide length—the peptide should be at least 8 or 9 amino acids long to fit into the MHC class I complex and at least 13-25 amino acids long to fit into a class II MCH complex. This length is a minimum for the peptide to bind to the MHC complex. It is preferred for the peptides to be longer than these lengths because cells may cut the expressed peptides. The peptide should contain an appropriate anchor motif which enables it to bind to the various class I or class II molecules with high enough specificity to generate an immune response (Engelhard 1994; Bocchia, Wentworth et al. 1995). This can be done, without undue experimentation, by comparing the sequence of the protein of interest with published structures of peptides associated with the MHC molecules. Protein epitopes recognized by T cell receptors are peptides generated by enzymatic degradation of the protein molecule and are presented on the cell surface in association with class I or class II MHC molecules.

Further, the skilled artisan can ascertain an epitope of interest by comparing the protein sequence with sequences listed in the protein data base. Regions of the protein which share little or no homology are better choices for being an epitope of that protein and are therefore useful in a vaccine or immunological composition. Regions which share great homology with widely found sequences present in vital cells should be avoided. Thus, as to S, S1, S2, E, N and M of SARS, the skilled artisan can compare these proteins with similar proteins of other coronaviruses and employ regions of dissimilarity in the SARS proteins as epitopic regions. In this regard, as an Example, attached is FIG. 13 showing an alignment.

Even further, another method is simply to generate or express portions of a protein of interest, generate monoclonal antibodies to those portions of the protein of interest, and then ascertain whether those antibodies inhibit growth in vitro of the pathogen from which the protein was derived. The skilled artisan can use the other guidelines set forth in this disclosure and in the art for generating or expressing portions of a protein of interest for analysis as to whether antibodies thereto inhibit growth in vitro.

For example, the skilled artisan can generate portions of a protein of interest by: selecting 8 to 9 or 13 to 25 amino acid length portions of the protein, selecting hydrophilic regions, selecting portions shown to bind from X-ray data of the antigen (full length)-antibody complex, selecting regions which differ in sequence from other proteins, selecting potential HLA anchor binding motifs, or any combination of these methods or other methods known in the art.

Epitopes recognized by antibodies are expressed on the surface of a protein. To determine the regions of a protein most likely to stimulate an antibody response one skilled in the art can preferably perform an epitope map, using the general methods described above, or other mapping methods known in the art.

Accordingly, no undue experimentation is needed to determine an epitope of a SARS protein.

Full length SARS proteins, or truncated portions of SARS proteins, such as epitopes, may be expressed as fusion proteins. Typically the fusion partner (portion of the fusion protein that is fused with the epitope or truncated or full length SARS protein) enhances secretion and/or immunogenicity. As mentioned, the baculovirus signal sequence may be fused with a SARS protein to enhance secretion. There are also several methods described for chemical or enzymatic cleavage of the fusion protein that provide efficient strategies to obtain the desired peptide (see, e.g., U.S. Pat. Nos. 6,143,872, 6,451,769. Frequently employed fusion systems are the Staphylococcal protein A fusion system and the synthetic ZZ variant which have IgG affinity and have been used for the generation of antibodies against short peptides, the glutathione S-transferase fusion system, the Beta-galactosidase fusion system, and the trpE fusion system. Several of these systems are commercially available as kits, including vectors, purification components and detailed instructions. In brief, the method to obtain short defined epitopes involves the synthesis of the corresponding oligodeoxynucleotide with appropriate termini to facilitate introduction, in translational frame with the fusion partner, into the desired expression vector. One can employ the lipidation *B. burgdorferi* OspA in fusion with a SARS protein or truncated portion thereof or epitope thereof to enhance immunogenicity. Likewise, a T-cell epitope can be fused to a SARS protein or truncated portion thereof or epitope thereof to enhance immunogenicity. Fusion proteins can have all or a portion of a SARS protein, such as S or S1 or S2 or an epitopic region of S protein, or M or E or a portion thereof, and all or a portion of influenza hemagglutinin or neuraminidase, or M2 or an epitopic portion thereof as a fusion partner or a fusion partner as recited in U.S. Pat. No. 5,858,369 or other patents cited herein.

Compositions of the invention can elicit an immunological, immunogenic or protective immune response. An immunogenic (or immunological) composition elicits an immunological response—local or systemic. A vaccine composition elicits a local or systemic protective response. The terms "immunological composition" and "immunogenic composition" include a "vaccine composition" (as the two former terms can be protective compositions). The immune response can be used to obtain antibodies, including monoclonal antibodies. Monoclonal antibodies are immunoglobulin produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., U.S. Pat. No. 4,196,265, incorporated herein by reference. Uses of monoclonal antibodies are known. One such use is in diagnostic methods, e.g., U.S. Pat. No. 4,376,110, incorporated herein by reference. Monoclonal antibodies have also been used to recover materials by immunoadsorption chromatography, e.g. (Milstein 1980), incorporated herein by reference. Monoclonal antibodies against a SARS protein, e.g., S, S1, or S2, are useful in kits, tests, methods or assays for diagnosis or determining the presence of SARS or its causative agent in a sample such as sera or body fluid or secretion or excretion.

Monoclonal antibodies can be prepared using hybridoma technology (Kohler and Milstein 1975; Kohler, Howe et al. 1976; Kohler and Milstein 1976; Hammerling 1981). In general, such procedures involve immunizing an animal (preferably a mouse) with, a SARS antigen, epitope or immunogen, for example SARS M, N, E, S, such as S protein, or, more preferably, with a cell that expresses such an antigen, epitope or immunogen. Suitable cells can be recognized by their capacity to bind to an antibody against a SARS protein. Such cells may be cultured in any suitable tissue culture medium; however, it is preferable to culture cells in Earle's modified Eagle's medium supplemented with 10% fetal bovine serum (inactivated at about 56° C.), and supplemented with about 10 μg/l of nonessential amino acids, about 1,000 U/ml of penicillin, and about 100 μg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP2O), available from the American Type Culture Collection, Manassas, Va. After fusion, the resulting hybridoma cells are selectively maintained in HAT medium, and then cloned by limiting dilution as described by Wands and colleagues (Wands and Zurawski 1981). The hybridoma cells obtained through such a selection are then assayed to identify clones which secrete antibodies capable of binding the antigen of interest.

Alternatively, additional antibodies capable of binding to the SARS antigen, epitope or immunogen, for example, SARS S protein, can be produced in a two-step procedure through the use of anti-idiotypic antibodies. Such a method makes use of the fact that antibodies are themselves antigens, and that, therefore, it is possible to obtain an antibody which binds to a second antibody. In accordance with this method, protein-specific antibodies are used to immunize an animal, preferably a mouse. The splenocytes of such an animal are then used to produce hybridoma cells, and the hybridoma cells are screened to identify clones, which produce an antibody, whose ability to bind to the protein-specific antibody can be blocked by the protein antigen. Such antibodies comprise anti-idiotypic antibodies to the specific antibody and can be used to immunize an animal to induce formation of further protein-specific antibodies.

It will be appreciated that Fab and F(ab')2 and other fragments of the antibodies of the present invention may be used in the manner of antibodies of the invention.

Thus, the invention involves a method for determining the presence of SARS in a sample comprising contacting that sample with a monoclonal antibody specific to a SARS protein, such as SARS S, S1, S2, E, N, or M, advantageously S, S1 or S2, more advantageously S, and detecting the presence of binding to the monoclonal antibody. The monoclonal can be labeled for detecting the binding.

In the practice of the invention, the full length S-protein is considered advantageous as it induces VN antibodies, but also it is noted that that truncated forms of the S-protein may be employed as they have similar capabilities. The baculovirus expression vector system (BEVS) is advantageous for the production of the S-protein (Tuboly, Nagy et al. 1994; Bonavia, Zelus et al. 2003).

Baculoviruses can be used as highly efficient eukaryotic expression vectors for the production of recombinant proteins in cultured insect cells (Summers and Smith 1987). Baculoviruses are DNA viruses in the family Baculoviridae and have a narrow host-range limited primarily to Lepidopteran species of insects (butterflies and moths). The *Autographa* californica Nuclear Polyhedrosis Virus (AcNPV), the prototype strain of baculovirus, replicates efficiently in susceptible cultured insect cells. AcNPV has a double-stranded closed circular DNA genome of about 130,000 base pairs and is well characterized with regard to host range, molecular biology, and genetics.

Baculoviruses form large protein crystalline occlusions within the nucleus of infected cells. A single polypeptide termed polyhedrin accounts for approximately 95% of the protein mass of these occlusion bodies. The gene for polyhedrin is present as a single copy in the AcNPV viral genome. Because the polyhedrin gene is not essential for virus replication in cultured cells, it can be readily modified to express foreign genes (Smith 1983). Recombinant baculoviruses that express foreign genes are constructed by way of homologous recombination between baculovirus genomic DNA and chimeric plasmids containing the gene sequence of interest. Recombinant viruses can be detected by virtue of their distinct plaque morphology; plaques derived from viruses containing the polyhedrin gene have a cloudy appearance, and plaques derived from recombinant viruses in which the polyhedrin gene has been replaced by a foreign gene are clear.

The general scheme for construction of a recombinant baculovirus for expression of a foreign protein is shown in FIG. 9. Coding sequences from a foreign gene are inserted into a plasmid known as a baculovirus transfer plasmid using standard cloning techniques. The transfer plasmid contains the polyhedrin promoter upstream of a multiple cloning site, bounded by sequences naturally flanking the polyhedrin locus in AcNPV. The transfer plasmid is co-transfected with baculovirus genomic DNA that has been linearized with an enzyme that removes the polyhedrin gene and removes part of an essential gene downstream of the polyhedrin locus, rendering the genomic DNA non-infectious.

The transfer plasmid contains the portion of the essential gene removed by linearization of the genomic DNA; thus, homologous recombination between the transfer plasmid and the linearized genomic DNA rescues the virus. The efficiency of recovery of recombinant viruses versus non-recombinants is nearly 100%. This process results in plaques that are nearly homogeneous, eliminating the need for multiple rounds of plaque purification. Because the original baculovirus genomic DNA before linearization contains the polyhedrin gene, non-recombinant virus plaques (which are cloudy) can be distinguished from plaques due to recombinant viruses (clear plaques).

The baculovirus expression vector system (BEVS) provides an excellent method for the development of the ideal subunit vaccine, immunogenic or immunological composition for a variety of reasons. Baculovirus expression of recombinant proteins is produced in approximately eight weeks. This is especially critical during when there is a pandemic threat. Baculoviruses are safe by virtue of their narrow host range, which is restricted to a few taxonomically related insect species. They have not been observed to replicate in mammalian cells (Hartig, Chapman et al. 1989; Hartig, Cardon et al. 1991). Additionally, very few organisms are known to be able to replicate in both insect cells and mammalian cells, reducing the possibility of adventitious agent contamination in batches of vaccine prepared from proteins purified from insect cell cultures. Finally, because the insects infected by baculoviruses are non-biting, humans generally do not have pre-existing immunity to insect cell proteins which could cause an allergic reaction to trace amounts of insect cell proteins in the vaccine preparation.

Baculovirus-expressed proteins appear to be correctly folded and processed in virtually all of cases, even when the protein is fairly large. This is not the case with proteins expressed in prokaryotic and lower eukaryotic systems. Additionally, insect cells are capable of many of the post-translational modifications that occur in mammalian cells, such as glycosylation, phosphorylation, acylation, and amidation. Glycosylation in insect cells appears to employ similar mechanisms as those used in mammalian cells in that the same residues of a particular protein are modified in each. Although the carbohydrate moieties added to proteins in insect cells appear to be less complex than those on their mammalian cell-expressed counterparts, the immunogenicity of insect cell-expressed and mammalian cell-expressed glycoproteins appear to be equivalent. Finally, baculovirus-expressed proteins usually self-assemble into the higher-order structures normally assumed by the natural proteins.

An element of the BEVS system is the extremely high activity of the polyhedrin promoter, which drives the expression of a foreign gene inserted downstream. (Although for expression in mammalian cells, this promoter can be substituted with a promoter from a mammalian virus, such as an SV40 promoter or a CMV promoter, e.g., CMV-EI, such as hCMV-EI or mCMV-EI; see also U.S. Pat. No. 6,156,567 with respect to truncated CMV promoters.) The highest levels reported using baculovirus expression vectors is 25%-50% of the total cellular protein, corresponding to approximately 11 grams of protein per liter of insect cells. Yields of foreign proteins in the BEVS system, however, are typically 10 mg-500 mg per liter. In the cases where different eukaryotic expression systems have been compared, the BEVS system has usually outperformed the other expression systems in overall protein production. Although proteins normally expressed in mammalian cells are predicted to be produced, but not completely, more authentically in mammalian systems, the expression levels in these systems is typically far lower than in baculovirus systems. Thus, proteins can be produced with the BEVS system at significantly lower cost while maintaining the key elements of authentic structure.

In particularly advantageous embodiments, restriction enzymes that cut at a distance from the recognized restriction site are used to prepare a vector, e.g., the transfer vector for producing a recombinant virus, such as a recombinant poxvirus or baculovirus; and, this technique is general to vector preparation methods and the general use of this technique is considered an additional aspect of the invention. For instance, in the technique of homologous recombination, a vector, e.g., plasmid, is prepared. This vector can contain exogenous nucleic acid molecule(s) to be within the recombinant virus to be produced and is typically used to transfect a cell which is also infected or transfected with suitable virus, such that within the cell a recombination or crossing-over event occurs to produce the virus containing exogenous nucleic acid molecule(s). The invention envisions preparing a vector, e.g., plasmid, with a restriction site; cutting the vector at a distance from the restriction site by an enzyme that so cuts (a cut at a distance enzyme), whereby the restriction site is excised from the vector and the vector has a unique sticky end; in a separate reaction, performing a polymerase chain reaction or other amplification reaction whereby the restriction site is part of the amplification product of the reaction; digesting the amplification product with a distance cutting restriction enzyme (type II), whereby the amplification product has a unique sticky end; and, ligating the vector having the unique sticky end and the amplification product having the unique sticky end. In this fashion, extraneous intervening nucleic acid molecules may be avoided. For instance, this technique is useful for joining a nucleic acid molecule encoding a leader sequence, such as the coding sequence for the aforementioned baculovirus leader sequence, to a nucleic acid molecule encoding an antigen, epitope or immunogen, e.g., SARS S, S1, S2, E, M, N, combinations thereof, or epitopes thereof. The use of such a distance cutter enzyme in this fashion is not believed to have been heretofore disclosed or suggested. Such an enzyme is known as SapI and is commercially available. In the case of the SARS S protein coding sequences, Applicants used both PCR amplification and unique and non-obvious solutions to specific problems. For instance, as to the SARS S it was useful to employ the SapI type II restriction enzyme. This allowed the cloning of the desired sequences into the vector of choice (e.g., pPSC12—a baculovirus transfer vector available from Protein Sciences Corporation) without the addition of a single nucleotide. Most cloning strategies involve the addition of restriction sites, and the consequent nucleotides making up the restriction site at the 5' and 3' ends of the desired sequences. Use of SapI avoids this. In addition, the desired SARS S DNA sequences contain two naturally occurring SapI recognition sites within them. Thus, in order to use SapI on the extreme ends, the DNA sequences were divided into sub-fragments that either contained the SapI sites (in the middle) or did not (near the ends) and later assembled into the complete desired sequence. Thus, the use of this "seamless" procedure on the SARS S protein was especially inventive.

The invention is further described by, and a better understanding of the present invention and of its many advantages will be had from, the following examples, given by way of illustration.

EXAMPLES

Example 1

Cloning of SARS S-Protein Encoding Sequences into Baculovirus Transfer Plasmids

Applicants obtained passage #3 of SARS CoV 3200300841 in Trizol LS Reagent from Dr Erdman, Acting Chief, Respiratory Virus Section, CDC/NCID/DVRD/REVB. This virus was prepared from culture batch 809940 that had a titer of 4 $\log_{10}$ on plaque assay. Lysate from this culture was added to TRIzol reagent and 1 ml was received. RNA was isolated from the lysate obtained from CDC according to TRIzol instruction provided by CDC. This RNA preparation was used to produce cDNA using a Titan kit (Roche) following manufacturers instructions. The sequence for the S-gene was obtained from Genbank Accession number AY274119 nt 21493-25259. Because of the large size of the S-gene and the presence of certain internal restriction sites, Applicants decided to clone the S-protein in three pieces. The front end cloned directly into the Baculovirus transfer vector pPSC12 (available from Protein Sciences Corporation) using primers 2179 and 2167 (Front: nt 40-750); see, FIGS. 1 and 7. The MiddleBack part (nt 750-3768) is cloned using primers 2168 and 2171 in an *E. coli* pUC18 vector; see FIGS. 1 and 7. Specifically, the 5' portion of the S ORF was PCR amplified using primers O-2179 and O-2167 and cloned into pPSC12 to give construct D3215. The longer 3' portion of the S OFR (MiddleBack) was PCR amplified using primers O-2168 and O-2171 and cloned into pUC18 to give D3157. After sequencing to confirm their identities, the MiddleBack portion of the S ORF in D3157 was subcloned behind the Front portion in D3215 using the PstI restriction site within the ORF and the KpnI site of the polylinker to yield D3217. In addition the complete S-gene is cloned into a baculovirus transfer vector. As to the tripartite cloning strategy, various parts are thereafter assembled to form the complete S ORF. A restriction map of the S-ORF is shown in FIG. 8 and the primers used for cloning purposes are listed in FIG. 7. Various clones that were correct based on restriction enzyme patterns were submitted for sequence analyses and clone D3215 was identified to contain the correct 5' end of the S-ORF. Clone D3157 was identified to have correct middle and back sequence of the S-ORF.

Assembly of Front and MiddleBack part: Clone D3215 was digested with KpnI and PstI and used as a vector. Clone 3157 was also digested with KpnI and PstI and used as an insert. Using the full-length clone with the established correct DNA sequence, the truncated versions are produced, wherein the cytoplasmic and transmembrane portions of the S-protein are deleted. The transmembrane domain is located at the 3' end of the ORF. In one construct there is a precise deletion of the transmembrane and cytoplasmic domain using site-directed mutagenesis. The other truncated construct is produced by deleting the BglI 3' end of the S-ORF. In addition, using this clone, a his-tagged version of the S-protein is produced to facilitate purification development.

The immunogenic epitopes and receptor binding domains of other coronavirus S-proteins have been shown to be contained in the first 600 amino acids, all of which is encoded by both truncated constructs. Both truncated constructs are secreted and may be expressed at higher levels than the non-secreted full length version of the S-protein. Truncated molecules may fold correctly.

The resulting chimeric plasmids consist of the polyhedrin promoter followed by ATG start signal, 61 kDa signal sequence and the complete S-protein or truncated coding sequences, a polyadenylation site, and flanking baculovirus sequences.

Figure 14:
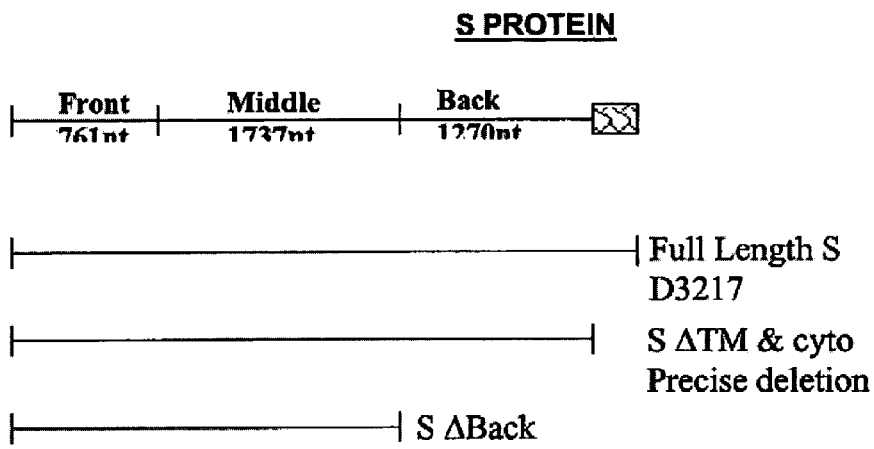
FIG. 14 is a schematic presentation of the three generated constructs.

Resulting clones D3216 and D3217 were submitted for sequence analysis. Both sequences were confirmed to have the correct complete S-protein coding sequence. Clone D3217 was selected for further processing (cell culture and site directed mutagenesis to generate the deletion constructs, shown in FIG. 14.)

Site-directed mutagenesis was used to create both the S Δ transmembrane & cytoplasmic (S ΔTM & cyto) construct and the more truncated version of the S-protein (S Δ Back) in PSC12. Two isolates of the S Δ Back and one isolate of the S ΔTM & cyto clones were submitted for sequence analysis.

The cloning and sequences of all three SARS constructs has been completed. To facilitate the purification of the S-protein pPSC12 vector was constructed using site directed mutagenesis to allow His6 tagging of insert.

All three constructs (full length, Δ TM/cyto and Δ A Back) of the S-variants were also cloned into the into pBAD/H is B vector (*E. coli* expression vector) for expression of N-terminal His6 tagged versions of these proteins in *E. coli*. The purified tagged protein was used for raising polyclonal antibodies to SARS S-protein.

The arabinose promoter system was selected because it is reported to have very little leakage when uninduced. This is important because of the potential toxicity of SARS S-protein. Another advantage of this vector is that SARS S gene is fused downstream of a His6 tag and an enterokinase cleavage site for later removal of the tag. Clones containing all 3 versions were identified and their identity was confirmed by sequencing.

Example 2

Protein Expression

The techniques used for generating, isolating and scaling up recombinant baculoviruses have been refined over the past fifteen years at Protein Sciences Corporation, and have been used to produce over 1,000 recombinant viruses; see, e.g., patents assigned to Protein Sciences Corporation cited herein. Linearized parental *Augotgraphica californica* Nuclear Polyhedrosis vaccine (AcNPV) DNA and transfer plasmid containing the S-protein encoding gene are mixed, co-precipitated with calcium chloride, and Sf9 insect cells are transfected as described (Summers and Smith, 1987). Recombinant viruses are identified by their plaque morphology and several are plaque-purified and used to infect 5-ml cultures of Sf9 cells in T-flasks. The infected cells are screened for expression of recombinant protein using SDS-polyacrylamide gels and Western blotting. Passage 1 recombinant viruses are scaled up in the serum-free expresSF+® cells (insect cells that can grow in serum free media available from Protein Sciences Corporation) and all subsequent scale-up and production are done in this serum-free cell line.

Figure 15:
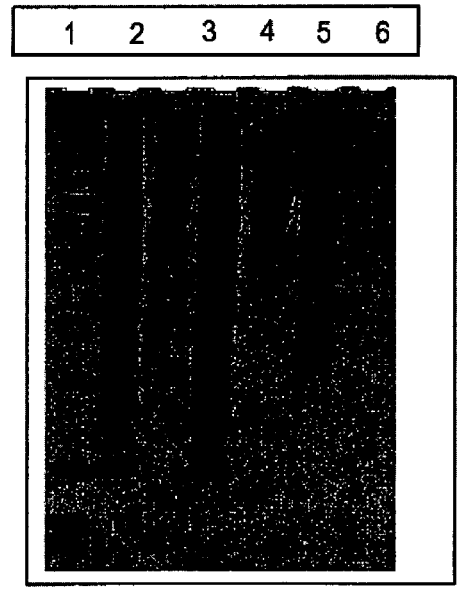
FIG. 15 is a picture of a gel.

Cell culture material for purification was developed using one of two approaches: fast track, which omits the plaque purification; or standard, which includes the plaque purification. Using the fast track approach, a P3 virus stock was generated using the full length S-gene containing transfer vector, D3217. The insect cells from this P3 stock were generally considered well infected (based on microscopic observation and SDS-PAGE, see FIG. 16). A separate P2 was also generated from D3217 using the standard method. Analysis of the P2 showed a clear P10 baculovirus-protein band indicating that the cells were well infected (FIG. 15).

Example 3

Fermentation: A Series of Expression Time Courses were Performed Using Medium Scale Fermentations SDS gels and Western blots from these fermentations are used to determine the harvest time which maximizes production of high-quality the S-protein. Very late in infection, cellular lysis can lead to accumulation of cellular and viral proteases. This can result in proteolytic degradation of susceptible proteins. In addition, the multiplicity of infection (MOI) can affect the kinetics of expression. In general, use of a minimal MOI to avoid the production of defective and mutant baculoviruses is advantageous. All of these factors are taken into account in defining optimal infection and harvest conditions.

An optimization experiment was performed using 50 ml spinners at 28° C. to test two different MOI (1 and 3) and to evaluate the optimum harvesting time (from 48 to 120 hpi). The Coomassie blue gel results, as shown in FIG. 17, suggest that the infection was good, as confirmed by P10 or lower bands (see lanes 2-9). Two Western blots were prepared and shipped to Hong Kong for incubation with acute and convalescent serum. The Western blot (FIG. 18—convalescent serum) did not show any band near 188 KD for the 48 hpi sample, however, it showed a typical band around 28 KD. Lanes 4 and 8 (72 and 120 hpi samples, respectively) showed faint double bands at ~160 in addition to the other bands above 62 and at 28 KD. These lower bands appeared not to be specific, since they are also present in the negative control lane (see blot, FIG. 19, lane 15). Similar results were obtained with the 72 hpi-harvested 10 L and the solubilized pellets' samples (see lanes 11 and 12). These samples were also positive using convalescent serum on the first blot, see FIG. 20. It appears that the proteins that react with the acute serum represent a non-specific signal see blot, FIG. 19, lane 15.

The virus stock (purified virus) recombinant D3217.1a full length S-protein was used to run an additional fermentation using a regular procedure (harvested 72 hours post infections (hpi)). Pellets of this fermentation were used for further purification development.

The purified recombinant viruses of the two deletion constructs D3227 (=SARS S ΔBack) and D3252 (=SARS S ΔTM/cyto) were scaled up to P1, P2 and P3, using the presence of the viral p10 band as an indication for good infection. Two 0.5 L fermentations were performed in the presence of leupeptin (1 ug/ml) and harvested at 72 hpi.

His-tagged truncated S-protein D3519 (ΔTM/cyto) and his-tagged truncated S-protein D3527 (Aback) were both scaled up to P2 and will be scaled to P3 later if we decide to proceed with these his-tag deletion constructs.

Figure 45:
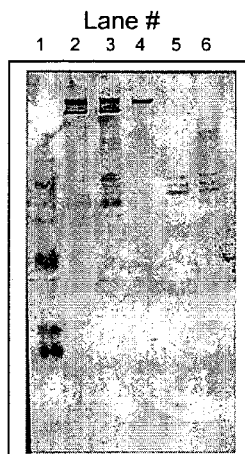
FIG. 45 is a picture of a Western Blot.

Construct D3252 (truncated clone of S-protein, ΔTM/Cyto) showed promising expression, and was secreted, therefore a 10 L fermentation at 28° C. was performed. Leupeptin was added at 48 hpi. The fermentation was harvested 72 hpi (see FIG. 45).

Figure 46:
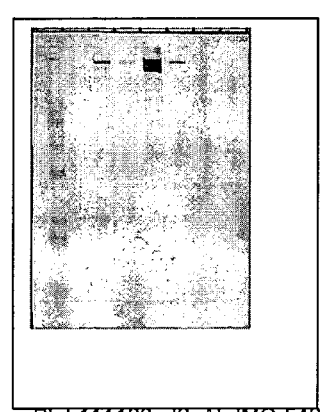
FIG. 46 is a picture of a Western Blot.
Figure 47:
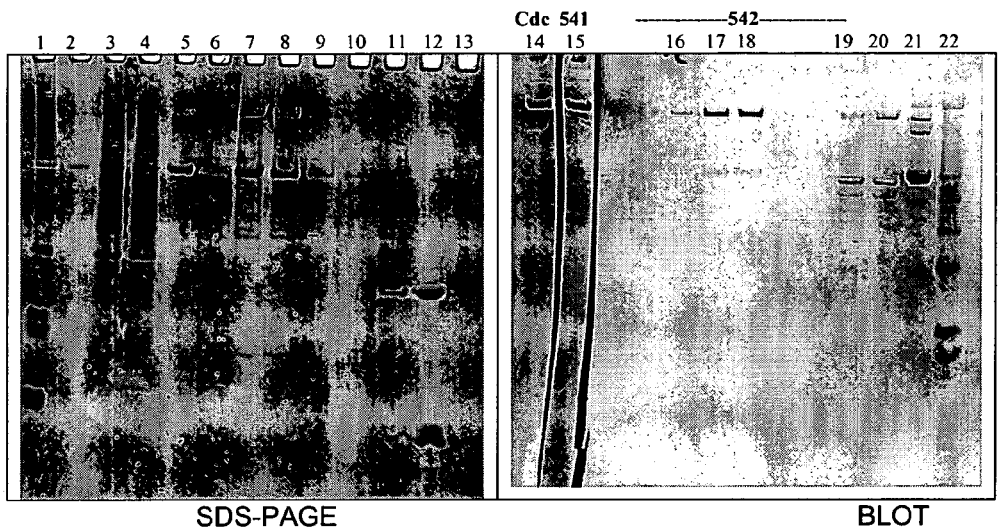
FIG. 47 is a picture of a gel and a Western Blot.
Figure 48:
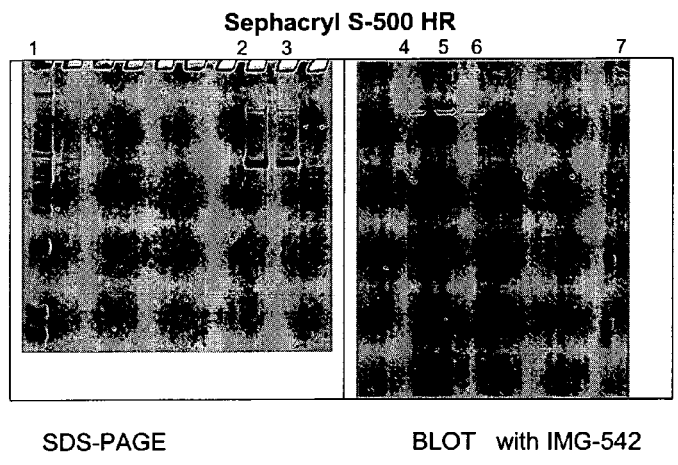
FIG. 48 is a picture of a gel and a Western Blot.
Figure 49:
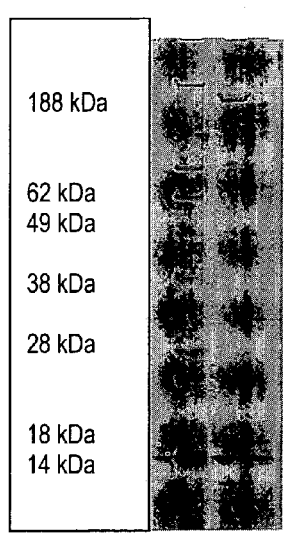
FIG. 49 is a picture of a gel.

The sequenced constructed clone for C-terminal his-tagged S protein (full length) D3540 was scaled up to P3, after it was shown that the DNA sequence was indeed correct. This P3 was used to infect a 10 L fermenter, incubated at 28° C. and harvested 72 hpi. The cell viability was 50% and morphological features of complete infection were observed at time of harvest. Both pellet and supernatant were saved for purification. Protease inhibitor and leupeptin were added to the infected culture at 2 μg/ml at 48 hpi (see FIG. 46)

A 45 L fermentation was performed for construct D3252 (truncated clone of S-protein, ΔTM/Cyto). Leupeptin was added 48 hpi and the bioreactor was harvested 72 hpi.

A 500 mL culture was co-infected with the full-length S containing recombinant baculovirus and the M gene containing baculovirus. Another 500 mL culture was co-infected with the full-length S containing recombinant baculovirus and the E gene containing baculovirus. A third 500 mL culture was co-infected with the full-length S containing recombinant baculovirus, the M gene containing baculovirus and the E gene containing baculovirus.

The constructed clones for C-terminal his-tagged S-protein (full length) D3445, S-protein (ΔTM/cyto) D3456, D3457 and D3461 and truncated S-protein (ΔBack) D3468, D3477 and D3481 were transfected and all purified recombinant viruses were scaled up after receiving sequence analysis results.

In order to avoid formation of aggregated expressed protein, the temperature of the fermentation was lowered to room temperature (~23° C.) after infection of the insect cell culture with the purified virus stock of full length S-protein D3217.1a. The progress of the infection and the viability of the infected cells were observed over the total time of fermentation. Ninety six hours post infection, microscopic observation confirmed that cells were infected; however the infection was not complete (viability measurement was ~90%). Two liters were harvested and stored for purification development. At the end of the 7$^{th}$ day (168 hpi), the culture was harvested and pellets of this fermentation were used for further purification. Infection and viability of the culture did not progress much further than when harvested at 96 hpi. Results are shown in FIG. 21 (using IMG-541 and 542 SARS spike antibody, respectively). It was concluded that the full length S-protein is indeed produced at 23° C. The optimum harvest time and temperature were selected based on purification results.

The correctly sequenced constructed clones for C-terminal his-tagged S-protein (full length) D3540, S-protein (Δ TM/cyto) D3519 and truncated S-protein (Δ back) D3527 were all transfected. Purified recombinant viruses for both truncated constructs and the full S-protein, his-tagged construct D3540, were scaled up to P1.

A Western Blot for the P3 master virus bank of the two deletion constructs D3227.1a (SARS S Δ Back) and D3252.2a (SARS Δ TM/cyto), harvested after 72 hpi and ran at 28° C., was performed using antibody IMG-541 and 542 (see lanes 7, 8, 9 and 10 in FIG. 22, blot #100703_d6 and 100703_d7 respectively). A 0.5 L fermentation was performed for each clone and supernatants of this fermentation were used for further purification development. Lanes 3-6 contained samples from full length S-protein virus stocks (D3217.1a) prepared under various conditions. Both deletion constructs showed expression. In both cases the protein appears to be partly secreted.

Samples from all the full length S-protein baculovirus construct (D3217.1a) were used in 10 and 2 L fermentations performed at 28° C., performed at various times. The results were examined in gel/blot #101003_d3 (FIG. 23). It was concluded that the expression levels appear to be comparable at various time points, and expression at 120 hpi appears to be the best.

A further time course study was performed with ΔTM D3252.2A. The experiment was performed in 2 L fermenter with a starting cell density of $2.5 \times 10^{\wedge}6$ cell/ml and viability of 98%. The cell culture was infected with the recombinant virus at MOI of 1.0. Protease inhibitor (Leupeptin) was added at 48 hpi. Samples were taken at different time points, 48, 54, 60 and 72 hpi. Viability of the withdrawn samples are shown in the table in FIG. 63. SDS-Page and western blots were performed for all samples, as also shown in FIG. 63.

It was determined that degradation products were present through out the fermentation. A more quantitative method was needed to determine what the most optimal harvest time would be. Current tests indicate that harvesting the cultures at 60 hours post infection may be more optimal.

Example 4

Purification: The Schematics Presented in FIGS. 12A-E Show the Purification Development Approach SARS Full Length S Protein
Schematic Overview of S-Protein Production Process:

Upstream processing. This work is initiated as soon as cell pellets or culture supernatants are available from larger-scale (0.5-10 L) fermentations. Since the S-protein contains a trans-membrane domain, it is anticipated that the full length protein is associated to the cells. That is, the S-protein forms particles. The cell pellets are washed to remove undesired contaminants and mild detergent conditions are employed to solubilize the S-protein. The truncated S-proteins are secreted and therefore pellet wash and solubilization steps are omitted in their purification processes. Tangential flow filtration is then used to remove both large and small contaminants.

Initial Column Chromatography. The purpose of this step is to remove DNA and partially purify the soluble S-protein. This is accomplished by either binding the protein to a CM column or flowing it thru a DEAE column. Applicants advantageously make use of the relatively low pI of the S-protein (theoretical pI=5.56) in this step, for example the protein is likely to bind to DEAE when buffer of neutral pH are used. Ideally, the recombinant S-protein is present in a buffer compatible with the next step in the process.

Purification. The S-protein contains a trans-membrane domain, and based on this characteristic, hydrophobic interaction column chromatography leads to purification. The S-protein is a large protein (130-140 kDa) and therefore size chromatography may be employed to obtain purity beyond 95%. Finally, the S-protein contains many glycosylation sites and therefore lentil lectin can be used to obtain significant purification (95% or 95+%) as well.

The S-protein of SARS is secreted in the baculovirus expression vector system (BEVS). The molecular weight of the soluble secreted S-protein is 140,000 and this is exploited by the use of a dual filtration system that effectively eliminates all proteins below 100,000 and greater than 300,000. A 75% purification of contaminating proteins is obtained before any chromatography is done.

Final chromatographic step. If the elution buffer necessary to obtain required purity levels on the previous column is not compatible with formulation and/or parenteral use, a final polishing column is employed. This step removes any undesirable reagents and transfers the protein into a neutral buffered saline solution suitable for reagent formulation.

The pI of the S-protein is 5.56, so at neutral pH an anion exchange column is used to bind and elute the S-protein. A final polishing hydrophobic interaction column that exploits the highly hydrophobic C-terminus of the S-protein is used to achieve final purity.

The S-protein is dialyzed into PBS and has a final purity of >95%. Importantly, the highly pure S-protein retains its immunogenicity and hence its utility.

Figure 24:
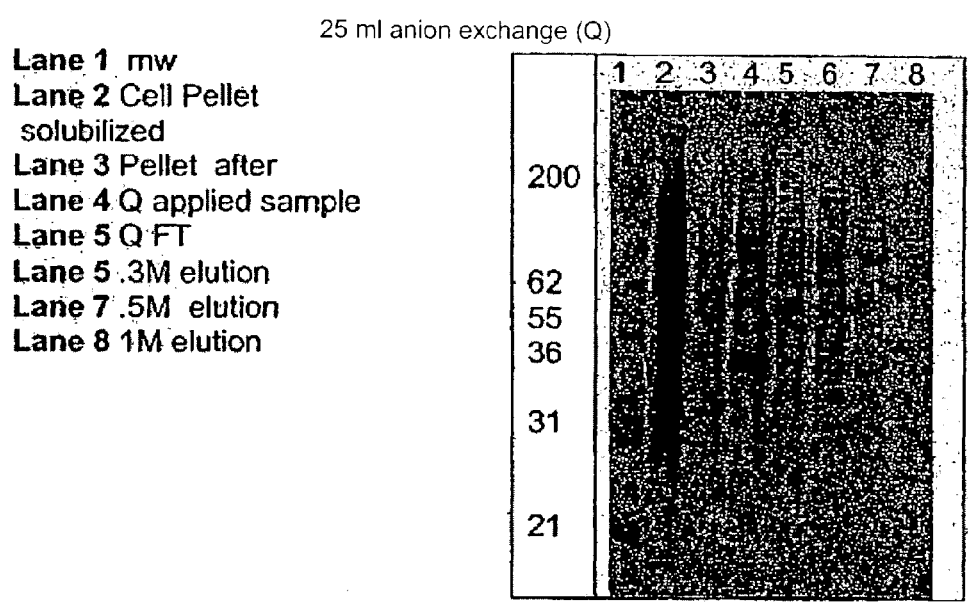
FIG. 24 is a picture of a gel.

Purification by Lentil Lectin Column:

Concurrent purifications using negative control pellets (derived from a fermentation of a different recombinant Baculovirus) were performed. Based on the pI and the hydrophobic C terminus, it was anticipated that at neutral pH and 1% detergent the protein could be extracted and bound to an anion exchange column. The gel in FIG. 24 represents this initial extraction of a 1 L 72 hpi pellet in 20 mM PO4 pH 7.0 with 1% Tergitol and applied to a 25 ml Q column.

Figure 25:
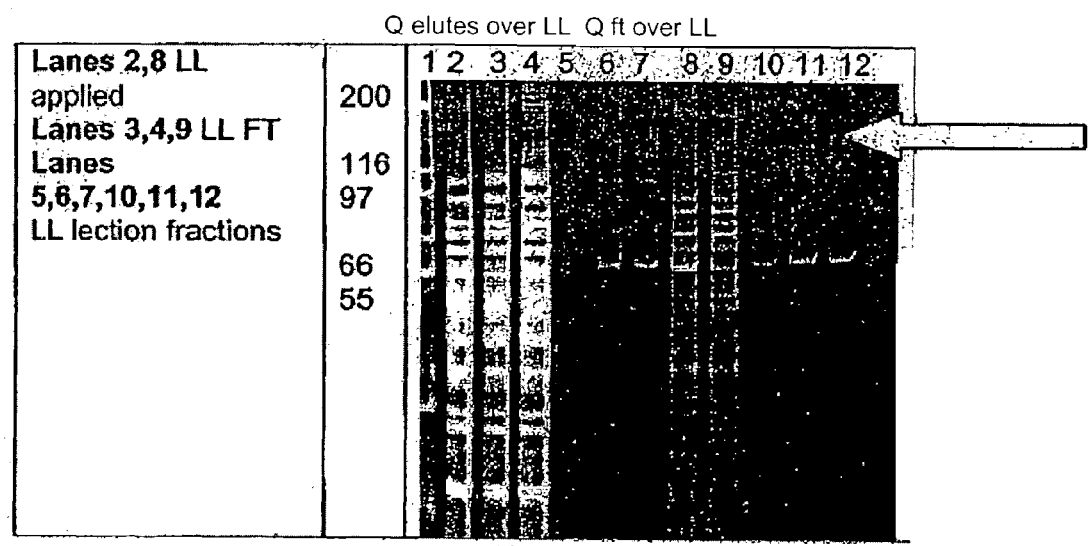
FIG. 25 is a picture of a gel.
Figure 26:
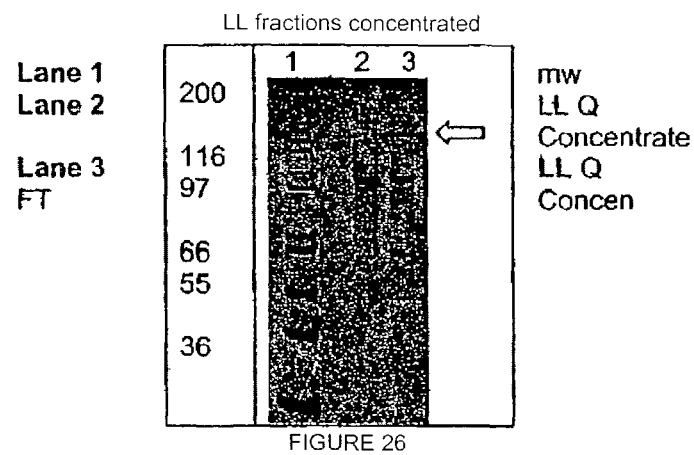
FIG. 26 is a picture of a gel.

The 0.3, 0.5 and 1 M elutions were pooled and applied to a 10 ml Lentil Lectin column. S-protein was expected to bind because of the 18 putative glycosolation sites. Additionally, the flow through (ft) from the Q column was also loaded on the same LL column after the Q column elutions. The column was eluted with 0.5M methylpyranoside in 20 mM PO4 (FIG. 25). The eluted fractions 5, 6, 7 and 10, 11, 12 were concentrated separately in an Amicon centricon spin concentrator from 6 ml to 200 ul (FIG. 26).

These higher protein bands were not observed in the negative control sample, and were therefore thought to comprise the full length S-protein. The product shown in lane 2 was included on a blot to be probed with human anti-SARS sera. However, this protein did not appear to be the S-protein since it did not react with the convalescent serum (see FIG. 20).

It was therefore decided to utilize the size of the protein and the characteristic that the protein is thought to be heavily glycosylated in order to purify the protein. Additionally, the solubilization strategy was changed. The addition of BME and 0.5M NaCl was intended to reduce ionic interactions and break aggregation between between cysteines. Also, the use of BME should increase the solubility of the S-protein, while the use of TFF (Tangential Flow Filtration) from Millipore decreased the total protein loaded on the first column.

Figure 27:
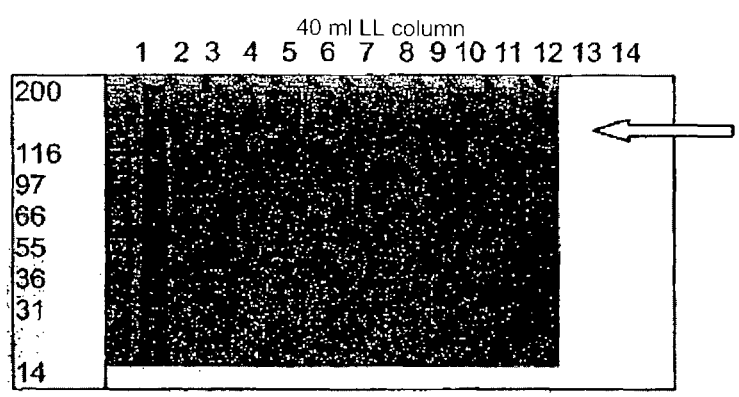
FIG. 27 is a picture of a gel.
Figure 31:
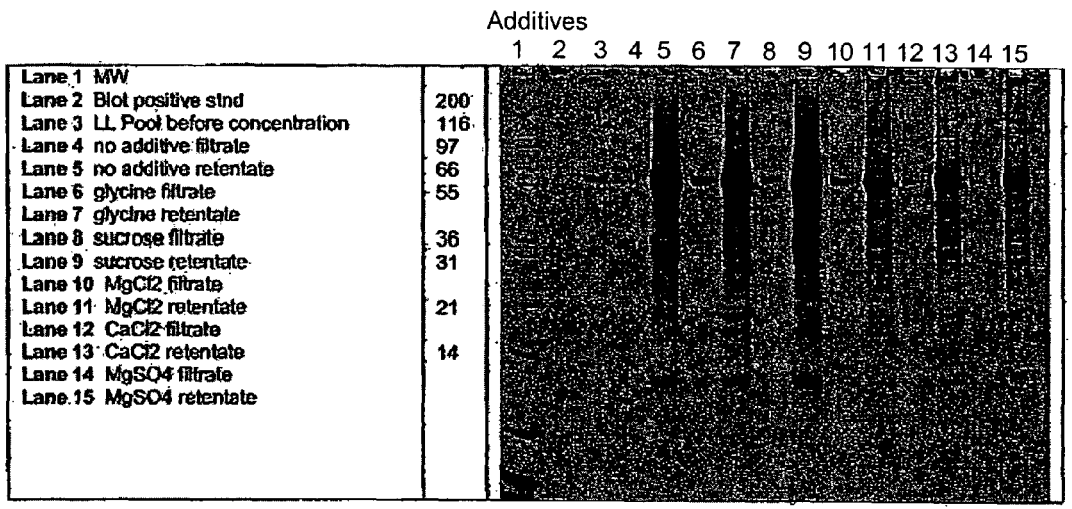
FIG. 31 is a picture of a gel.
Figure 32:
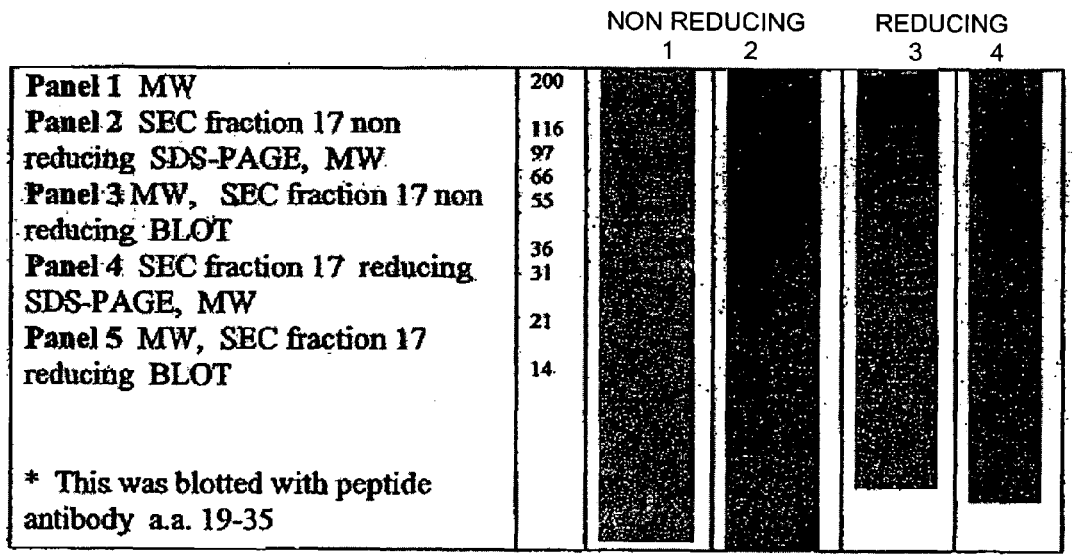
FIG. 32 are pictures of gels and Western Blots.
Figure 33:
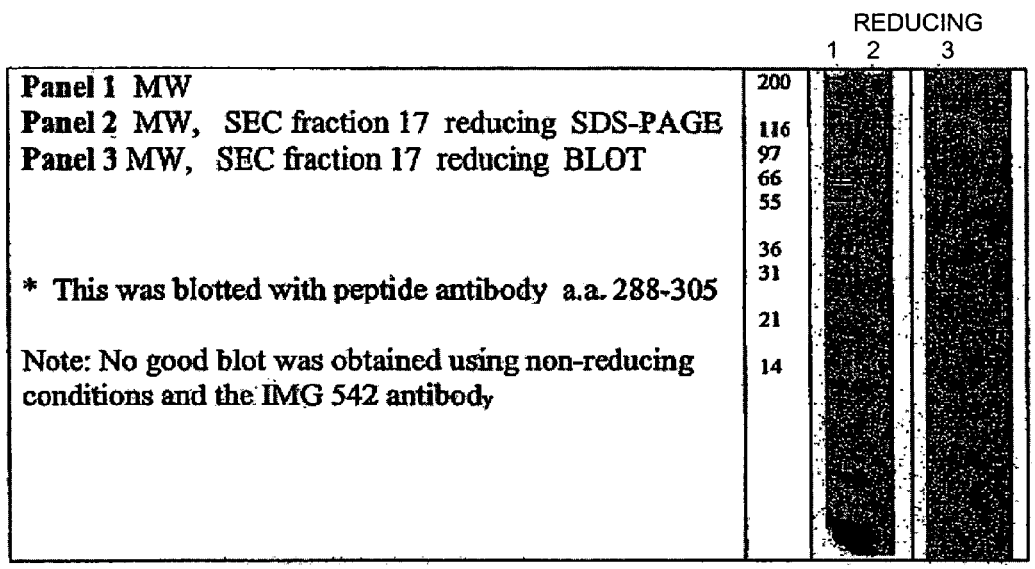
FIG. 33 is a picture of a gel and Western Blot showing SEC fraction 17 blotted with Imgenex peptide antibody corresponding to a.a. #288-305 (542).
Figure 34:
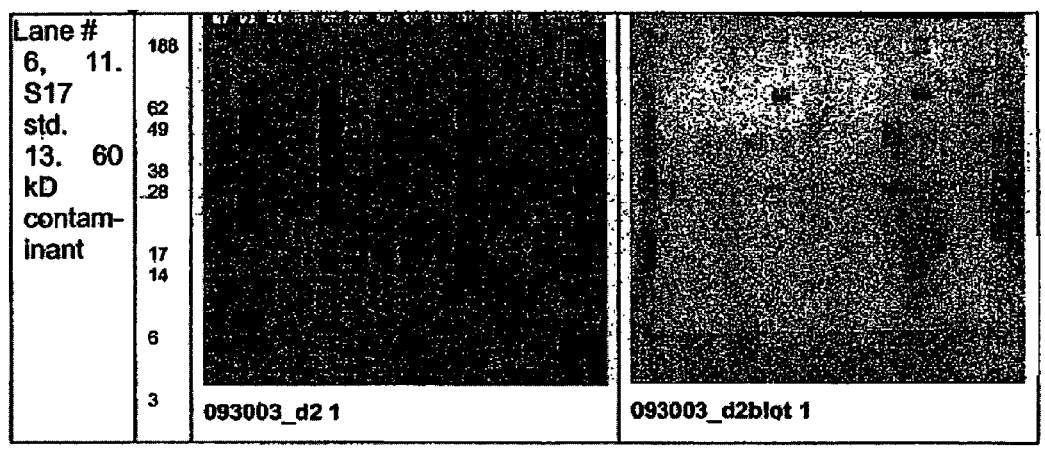
FIG. 34 is a picture of a gel and Western Blot.

2 L of a 72 HPI cell pellet was solubilized in 2 L of 20 mM PO4 pH 7.0, 1% Tergitol, 0.5M NaCl and 0.1% B-ME. This was polytroned and spun. The 2 L supernatant was reduced using a 100 kDa molecular weight cutoff TFF filter and diafiltered using the same buffer minus the tergitol in order to reduce detergent buildup. A final 400 ml retentate was applied to a 40 ml LL column equilibrated with 20 mM PO4 pH 7.0 0.5M NaCl. The column was eluted with the same buffer and 1M methyl-pyranoside (FIG. 27).

The LL fractions were pooled and concentrated to 6 ml and loaded on to a 500 ml S200 SEC. The column was equilibrated with PBS (20 mM PO4 pH 7.4, 0.15M NaCl) and the 6 ml fraction was loaded.

This gel was blotted and tested with anti-SARS sera from Hong Kong (FIG. 28) using reducing conditions. Included on this blot was the pellet of the solubilization (Lane 13) and a re-extraction of the initial pellet (Lane 14) in order to determine if the S-protein is soluble using these conditions. A negative control was also included to determine the extent of baculovirus infected insect cells background (Lane 15). The column was run in PBS as opposed to 20 mM PO4+1M NaCl as previously.

Lanes 8, 9 and 10 of the Western Blot (FIG. 19) show a positive signal at the expected size when reacted with the convalescent serum. Although the protein does not react with the acute serum, it appears that the protein is solubilized using the above-described conditions.

The purity of this product was estimated to be 20% with a major contaminant co-eluting with the S-protein from the Lentil Lectin column. Size exclusion chromatography under reducing conditions and high ionic strength were tried to separate these two proteins, however resolution was not achieved. The S-protein and the major contaminant behaved as an aggregate.

An upstream purification method (solubilization of material using 1% tergitol followed by elution from a LL column) was initially used at scale to purify the protein of interest and to generate sufficient material for anion, cation and hic (hydrophobic interaction column) chromatography. Using various column chromatography methods at different pHs could possibly reveal a way to separate the S-protein from its aggregated partners. FIG. 29 represents the processing of a 1 L cell pellet.

The cell pellets from the Tergitol extracted material were also re-extracted with 8M urea to potentially increase recovery yields, since the S-protein was still partly present after the Tergitol extraction.

The pellet was dissolved in 50 mM Tris pH 8.5, 8M urea. After all material was dissolved, the extract was diluted 4× to a final urea concentration of 2M. This material was applied to a LL column (see FIG. 30). The 62 kDa contaminant band seems to be less prevalent in the eluted fractions when the pellet is re-extracted. It was interesting to note that lectin was also eluting from this column (see protein band at 21 kDa).

Various additives, derived from Bondos and Bicknell (Bondos and Bicknell 2003) were used to break up the aggregation between the S-protein and the 62 kDa contaminant, which was believed to be gp64, the major baculovirus envelope protein. A representative agent from each category was tested. Each of the following components: 0.2M MgSO4, 0.1M CaCl2, 0.1M MgCl2, 1% glycine and 1M sucrose, was added to a LL pool and concentrated to a minimum volume using a 100 kDa molecular weight cutoff centricon column from Millipore. Both the retentate (retained on the membrane) and the filtrate were subjected to SDS-PAGE. The presence of the 62 kDa protein in the filtrate was used to determine a possible anti-aggregation effect. The negative control (no additive) is shown in Lanes 4 and 5 of FIG. 31. All additives displayed some anti aggregation effects when compared to the negative control, with glycine being the best. Consequently, in subsequent development 0.1M glycine was incorporated in buffers.

As shown in FIG. 47, the full length S protein is present along with gp64. It shows strong response with the CDC and IMG-542 antibody.

Another attempt was made to disrupt the aggregation using 50 mM DTT and 6 M urea. Fraction 2 from above was centriconed and diafiltered into buffer containing 6M urea. A Sephacryl S-500 high resolution column was packed and loaded (gel and blot in FIG. 48). FIG. 48 shows that the aggregation between the 2 molecules is still intact even under high Urea and DTT concentrations.

An alternative purification process was also utilized wherein the cell pellet was solubilized using 1% Triton-X-100. The solubilized material was subsequently loaded onto a Ni-column. The eluted material, which had a purity of approximately 70%, was then loaded onto a lentil lectin column and the eluted material has a purity of greater than 90%. The estimated yield is approximately 2 mg/l. As an alternative to the lentil lectil column, we are currently testing the DEAE IEX column, which has shown promise in the deltaTM S protein purification. FIG. 49 depicts a gel of the full length his-tagged S-protein.

Recently two peptide antibodies became available from Imgenex. The 542 antibody was raised against amino acids 288-303 and the 541 antibody against amino acids 19-35. The SEC fraction 17 (S17) which blotted positive using the convalescent sera from Hong Kong was used to test these sera. The S17 was run and blotted in a reduced and nonreduced format (FIGS. 32 and 35). The non reduced SDS-PAGE shows no evidence of the 62 kDa contaminant. The 542 antibody reacts weakly, if at all, with non-reduced S17.

Further analysis was done to compare the response of antibodies IMG541, IMG542 and CDC using a protein sample (5864C), which was prepared as follows: the pellet was solubilized using 1% tergitol in the absence of BME, followed by lentil lectin chromatography and stringent column washes prior to column elution. Subsequently this material was bound to hydroxyl-apatite and eluted. Samples were loaded using non-reducing buffer and regular sample loading buffer. Three blots were prepared and each blot was incubated with an antibody. Results are shown in FIGS. 41-44:

The unglycosylated SARS full-length S-protein has a predicted molecular weight of approximately 139 kDa. The predicted molecular weight of the glycosylated full length S-protein is expected to be around 160 KDa. None of the bands that were present using the CDC antibody raised against SARS in humans were located in that molecular weight range described above. The most abundant bands represent the gp64 baculovirus protein, this runs at around 180 kDa under non-reduced conditions, and at around 60 kDa under reducing conditions. The IMG antibody 541 cross reacts very strongly with the gp64 protein and will therefore not be used for further Western Blot analysis.

Two protein samples were submitted to the Keck Facility at Yale University for N-terminal analysis. The S17 protein sample initially found to be immunoreactive with anitsera in Hong Kong and later with antibody from Imgenex was submitted (see lanes 6 and 11 in gel/blot 090303_d2, FIG. 34). When analyzed under non-reducing conditions, the two characteristic bands disappear and a new higher molecular weight band is formed (see FIG. 34) suggesting that the S-protein is composed of two fragments joined by a disulfide bridge. The second sample submitted for N-terminal analysis consisted primarily of a 60 kD band on a reducing page gel (see lane 13 in gel/blot 090303_d2, FIG. 34) that is not immunoreactive with the Imgenex antibody (IMG-542). This protein species is a suspected co-migrating contaminant of baculovirus or insect cell origin that also binds to Lentil Lectin resin. This sample also contained a minor gel band that is highly reactive with the antibody. The complete separation of the S-protein and its degradation products from the proposed 60 kDa contaminant using lentil lectin chromatography was not possible. Both samples were submitted as acetone washed precipitates with expected analysis to give results on the majority contributors.

Following the discovery that the full length S-protein breaks down under reducing conditions into two different size fragments of 60 and 150 kDa an experiment was performed to identify what would happen if β-ME was excluded from the process.

Figure 35:
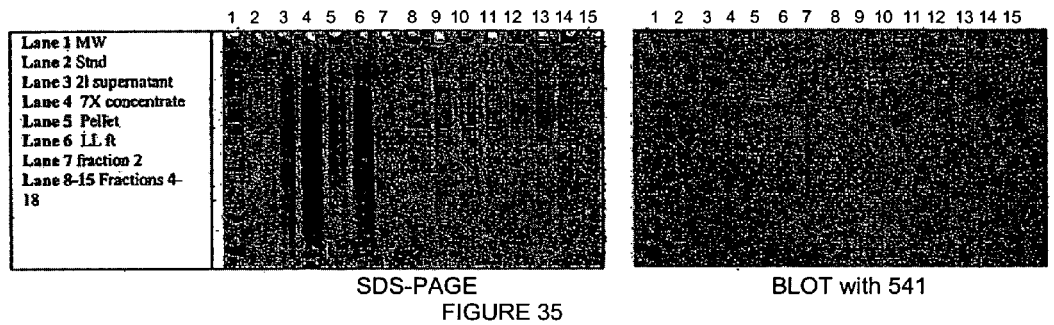
FIG. 35 is a picture of a gel and Western Blot.

2 L of the fermentation performed at 23° C. and harvested at 168 HPI was solubilized in 20 mM $PO_4$ and 1% Tergitol. The sample was polytroned for 2 minutes and centrifuged at 4.5 k for 30 minutes. The supernatant was concentrated using TFF with a 100 kDa molecular weight cut-off filter and dia-filtered with 20 mM PO4 buffer. A final volume of 350 ml was loaded on a pre-equilibrated 40 ml LL column and eluted with 10 mM PO4, 50% ethylene glycol, and 0.5 M methylpyranoside (see FIG. 35).

The yield increased when compared to the LL column that was extracted using reducing conditions. The band at 180 also reacted with the 541 antibody along with higher molecular weight forms.

Figure 36:
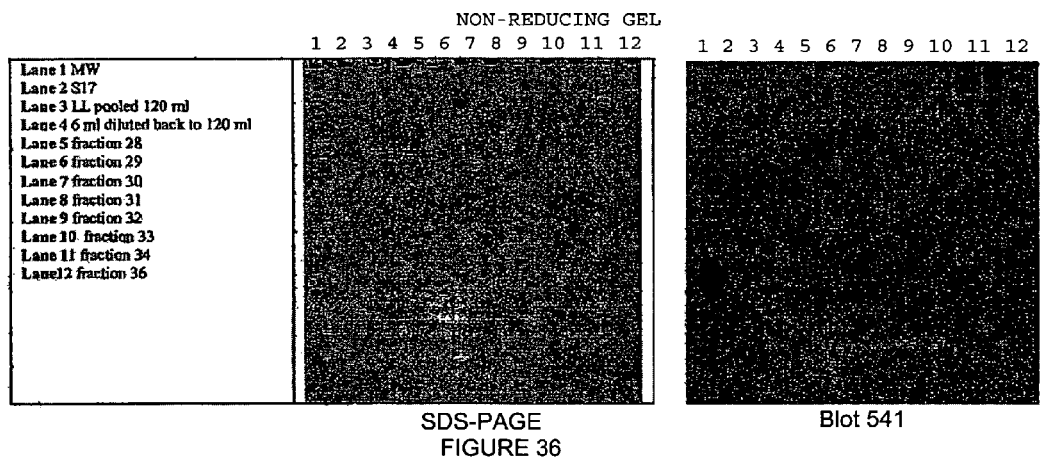
FIG. 36 is a picture of a gel and Western Blot.

Fractions 4-14 were concentrated to 6 ml from 120 ml and loaded to a 600 ml S200 SEC column (see FIG. 36).

The full length S-protein was present in the first peak off the SEC column. The protein eluted with lower molecular weight products. It appeared that some of these were reacting in the blot and may represent S breakdown products. The other major band that appeared in the applied sample at 60-62 kDa (Lanes 3, 4) eluted 15 tubes away from the main peak. Again, this may represent a mixture of S breakdown and viral protein that are the same weight. An interesting note was the increase in Lane 4 of the blot when compared to lane 3; apparently the concentration led to an increase of reactive 62 kDa protein.

The experiments were repeated with the exact same results. The main S fractions were pooled and analyzed in reducing and non-reducing formats (FIG. 37). The final process yield appears greater when (β-ME was omitted from the extraction.

SARS ΔTM S Protein Purification

N-Terminal Sequencing of Partially Purified SARS ΔTM S Protein.

Figure 50:
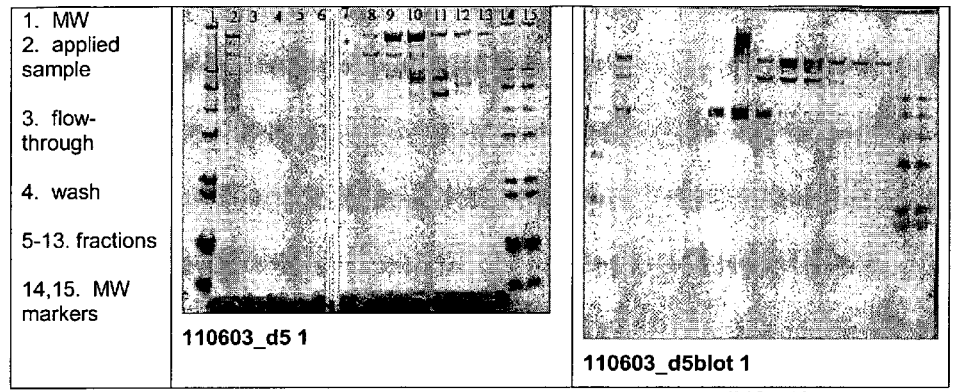
FIG. 50 is a picture of a gel and a Western Blot.

The ΔTM S protein sample was prepared as follows. One liter supernatant from a 10 L fermentation (102103, 72 hpi, 28° C.) was directly applied to a lentil lectin column at pH 7.4. The ΔTM S protein was eluted from the lentil lectin then flowed through a cation exchange column (CM) at pH 7.4. The CM flow-through was processed over a DEAE anion exchange column at pH 7.4. The ΔTM S bound to the column and eluted midway through a linear 20 CV gradient up to 250 mM NaCl. An ~150 kD band in the Q fractions is reactive with CDC antibody and IMG 542 antibody (see lanes 9-13 in gel/blot of FIG. 50). The Q fraction #12 (see lane 9 in gel/blot of FIG. 50) was transferred to a PVDF membrane for N-terminal analysis.

The N-terminal sequencing permitted the tentative assignment as follows: X1-D-L-D-R-X2-X3-T-X4-D where X1 was probably S, X2 was probably either a silent residue (e.g. Cys or glycosylated/phosphorylated S/T) or L, X3 was probably T and X4 may have been F. The assignments from the more intense signals as well as the more uncertain assignments match the expected N-terminus of mature S protein cleaved after the PSC chitinase signal sequence (SDLDRCT-TFDDV).

Purification of ΔTM S Protein from Fermentation Supernatant (D3252.2a, 72 hpi, 28° C.)

Figure 51:
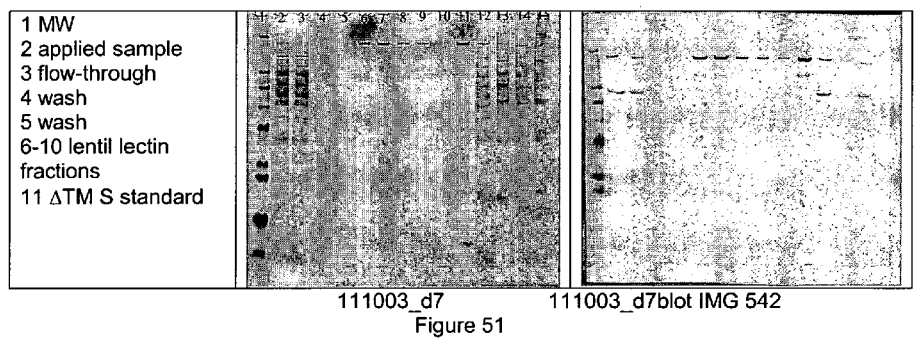
FIG. 51 is a picture of a gel and a Western Blot.

Supernatant was directly loaded onto lentil lectin column (1 liter/40 mL column) equilibrated in 20 mM Tris/0.5 M NaCl pH 7.7. The 0.5 M NaCl is used to remove non-specific binding contaminants. After washing to baseline with the same buffer, the column was washed with 20 mM Tris pH 7.5 to lower conductivity and then eluted with 1 M N-methyl-α-D mannopyrannoside in 20 mM Tris pH 7.5. Some S protein flows-through the column (see lane 3 in gel/blot of FIG. 51). Flow-through was not observed using this same column for identical 1 L material and processing under similar conditions. Sample flow-through may be attributed to including the NaCl wash which was not initially performed by TEK or it may be due to the repeated use of this particular column. At least half of the material was bound and eluted into 6-25 mL fractions (see lanes 6-10 in gel/blot of FIG. 51). The fractions were pooled and processed over an anion exchange Q column.

Figure 52:
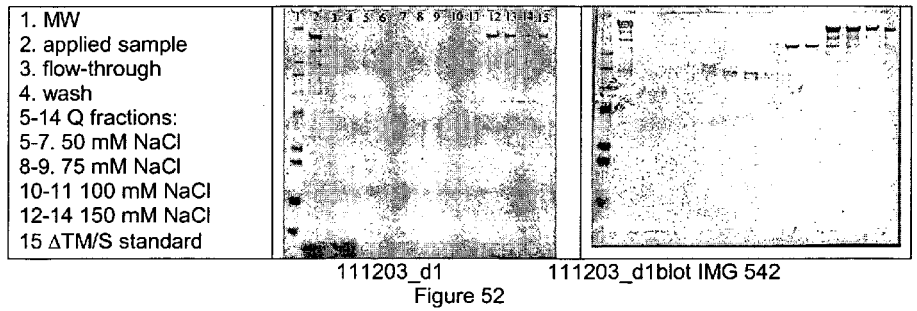
FIG. 52 is a picture of a gel and a Western Blot.
Figure 53:
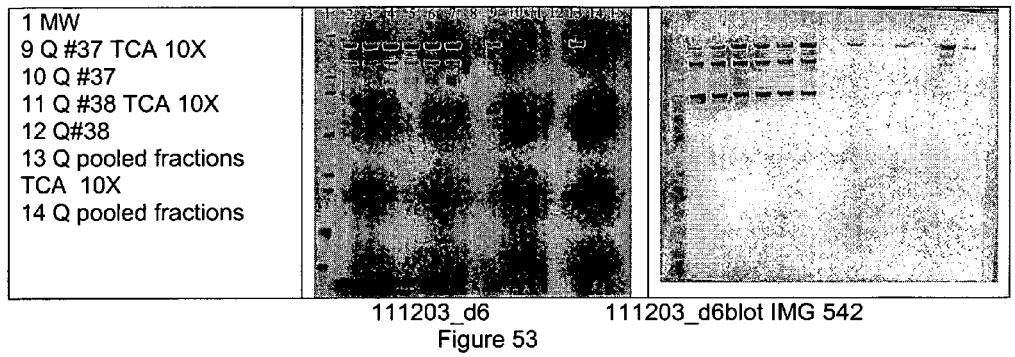
FIG. 53 is a picture of a gel and a Western Blot.

A 30 mL Q column equilibrated in 20 mM Tris pH 7.5 was loaded with the pooled lentil lectin eluate and was step eluted with 50 mM, 75 mM, 100 mM, 150 mM, 200 mM, 250 mM, 300 mM, 500 mM NaCl. The material bound to the column with no evidence of ΔTM/S protein in the flow-through or wash (see lanes 2-4 gel/blot of FIG. 52). Degradation products of S are removed with 75 mM NaCl (lanes 8-9) and 100 mM NaCl (lanes 10-11). The bulk of the ΔTM S protein elutes with 150 mM NaCl (see lanes 12-14 of gel in FIG. 52). Additional ΔTM S protein and a lower MW protein elute with 500 mM NaCl (see lanes 9 and 11 gel in FIG. 53). The bulk elution at 150 mM NaCl was pooled (see lane 13 gel of FIG. 53) and dialyzed into 10 mM Na phosphate pH 7.4. The material will be combined with product from additional runs. Concentration of the dilute protein samples will be attempted using a small Q column followed by size exclusion chromatography to remove lower molecular weight contaminants. The estimated yield from BCA assay is 0.5 mgs/L. Yields around 1 mg/L are expected if the flow-through loss on the lentil lectin column is avoided.

Figure 54:
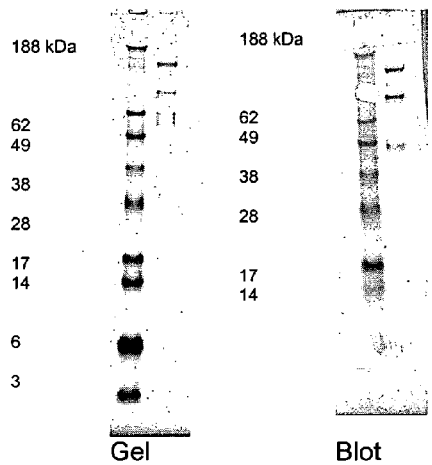
FIG. 54 is a picture of a gel and a Western Blot.

In an alternative purification scheme, the ΔTM S protein was purified from a 10 L fermentation. A schematic overview of this process is shown in FIG. 12C. The resulting purified protein is shown in FIG. 54. The resulting product was provided for mice immunogenicity studies.

Purification of the ΔTM S protein from 45 L fermentation has been performed. Briefly the material was centrifuged and the supernatant was pH-adjusted to a pH of 8, followed by another centrifugation (this step removes non-protein material and certain protein contaminants). Subsequently the material was concentrated 8 times prior to storage at −20° C. Three liters of the concentrated material were then applied to a 750 mL Cation (UnosphereS) column. The ΔTM S protein flows through this column (FT). The FT was applied to a 250 mL anion (Q) column and eluted using 150 mM NaCl. The DEAF column was too small, since approx. 65% of the material flows through this column.

The total amount of protein purified from the 45 L fermentation was approximately 10 mg. The product showed degradation following concentration and contained high levels of endotoxin. A technique was used as described by Liu et al. (Liu, Tobias et al. 1997) based on TX-114 phase separation and ion-exchange chromatography to remove endotoxin, however this resulted in major losses.

Figure 12D:
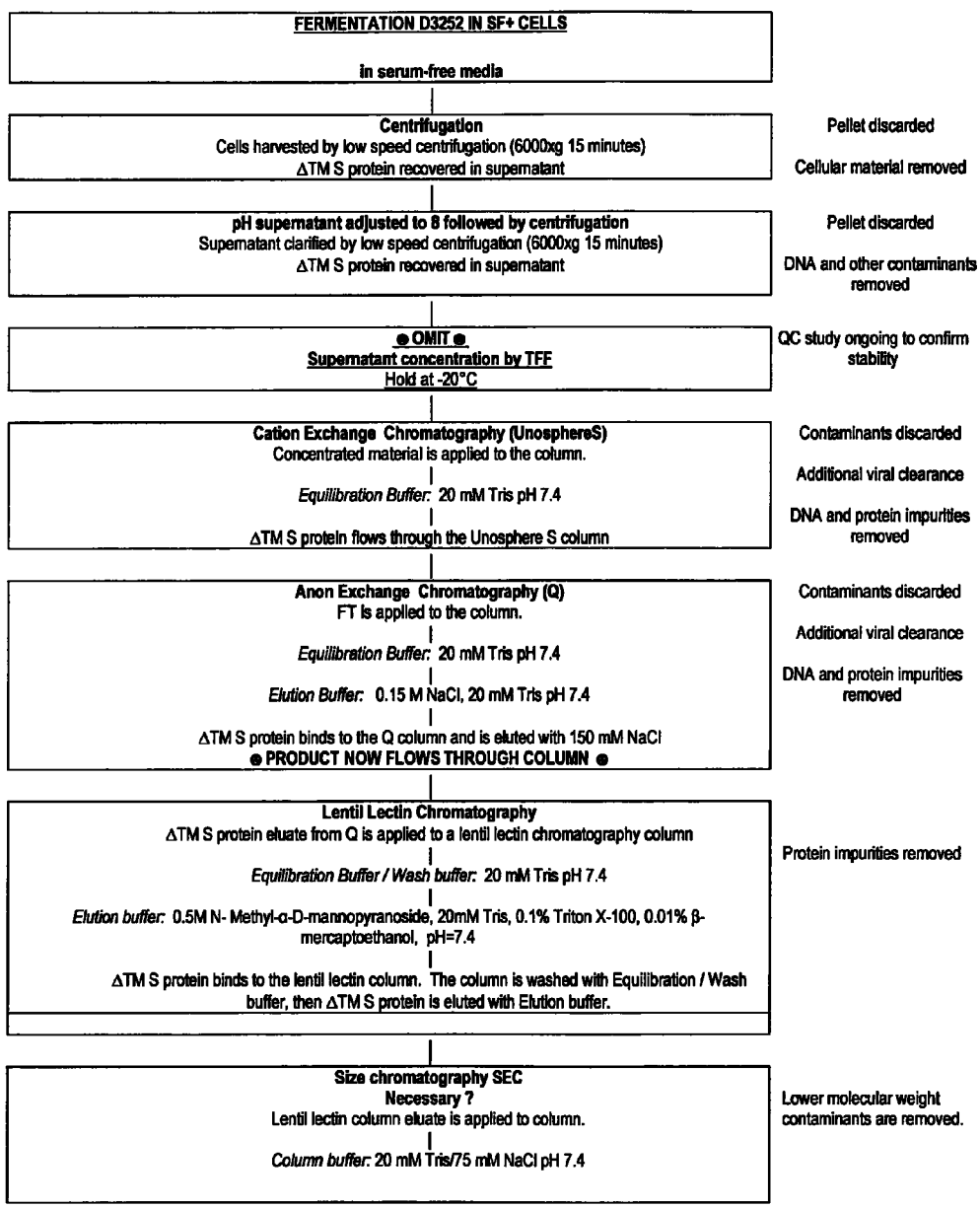

The TFF concentration step resulted in major losses and therefore was omitted this step in the subsequent 10 L purification. As a result of this process change the protein did not bind to the Q column anymore. A schematic overview of the changed process is shown in FIG. 12D.

The delta TM harvested was pH adjusted to 7.4 using 1M Tris, pH=8.0. The supernatant was then centrifuged at 4500 rpm for 30 min. Subsequently the supernatant was loaded on a 500 ml S-column, linked to 500 ml Q-column. Most of the delta-TM protein unexpectedly flowed thru both columns.

The flow thru was loaded to 50 ml LL column. The LL elution fractions looked good and were stirred cell concentrated to 100 mls. During concentration precipitation problems occurred and the product was dialyzed 100 mls into PBS.

The product yield from the FT was approx. 10-12 mgs from this 10 L fermentation. The endotoxin content in end product was high. Endotoxins were removed using Triton-X treatment.

The 2-3 mgs delta TM that did bind to bind to the Q column was eluted in 100 mM NaCl and processed over LL also contained high endotoxins.

A later preparation of delta TM was harvested and was pH adjusted to 7.4 using 1M Tris, pH=8.0. The supernatant was then centrifuged @ 4500 rpm for 30 min. Subsequently the supernatant was loaded on a 500 ml S-column, linked to 500 ml DEAE column. Again most delta-TM protein flowed thru both columns.

The flow thru was loaded to 50 ml LL column. The LL elution fractions looked good and were dialyzed into PBS prior to stirred cell concentration to 100 mls.

The product yield from the FT was now 15-20 mgs and no delta TM in was found in the 100 mM or 150 mM elution from the DEAE column. Endotoxin content was still high but lower than the previous purification run. This material was used to formulate the product for the mouse immunogenicity study (see Example 10).

Process Optimization

Figure 55:
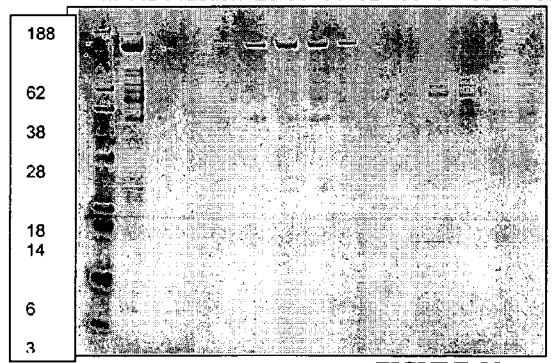
FIG. 55 is a picture of a gel.

The above process was further optimized using material from the initial 3 L concentrate. Part of the ΔTM S protein did not bind to the Q column as anticipated. Therefore, this flow thru (referred to as 1&2) were processed over a larger Q, using similar elution conditions (fplc 5888), the eluate was then further processed on LL, again using similar elution conditions (fplc 5889). The fractions containing the ΔTM S protein were pooled, concentrated and processed over the SEC column (fplc 5890). The results are shown in FIG. 55 below:

Fractions 31-35 gave a purity of approximately 70-80%.

Subsequently, flow thru 3 was processed using the same Q column (fplc 5891, however now the column elution was changed using a step elution from 0.15M NaCl to 50 mM NaCl, 100 mM NaCl and then 150 mM NaCl (one column volume of each molarity). The results are shown in FIG. 56.

Figure 56:
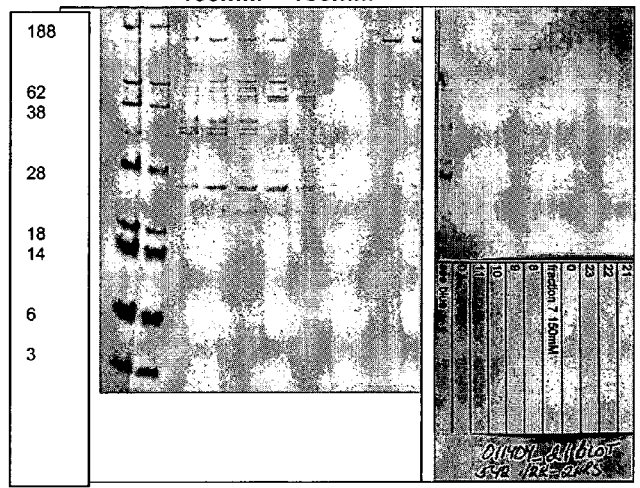
FIG. 56 is a picture of a gel and a Western Blot.
Figure 57:
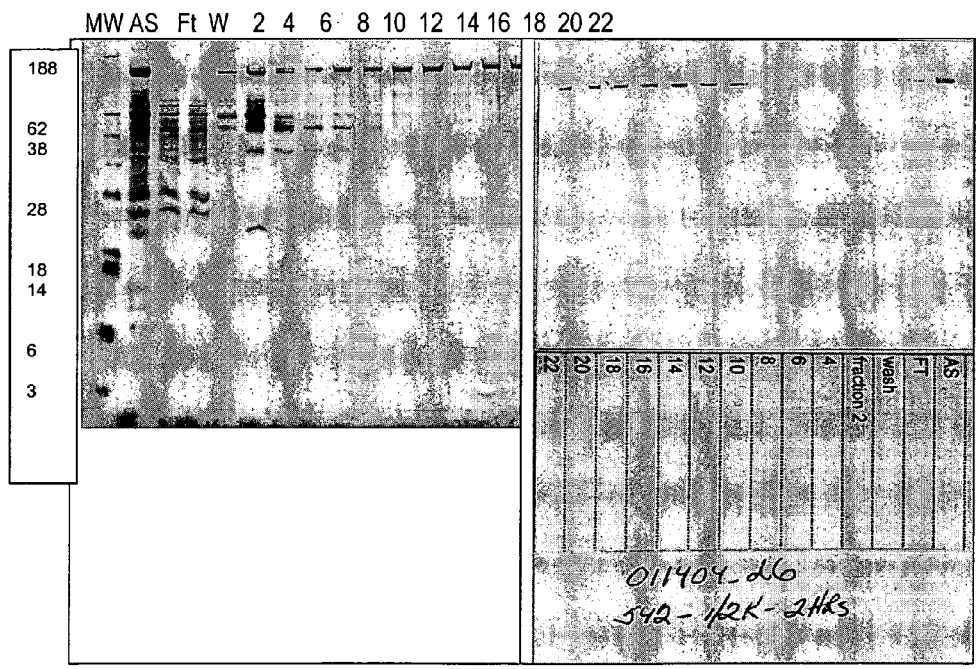
FIG. 57 is a picture of a gel and a Western Blot.

The 100 mM eluate fractions do not react with the Sars Ab, whereas the 150 mM fractions do react with the antibody (In FIG. 56, note the blot is reverse to the gel). The 150 mM fractions were then pooled and loaded to the same LL (fplc run 5892). The elution was now changed from 0.5M sugar to 0.1M (fractions 1-5), 0.2M (fractions 6-10), 0.3M (fractions 11-15), 0.4M (fractions 16-20), 0.5M (fraction 21-24) sugar using two column volumes of each molarity. The results are shown in FIG. 57.

Figure 58:
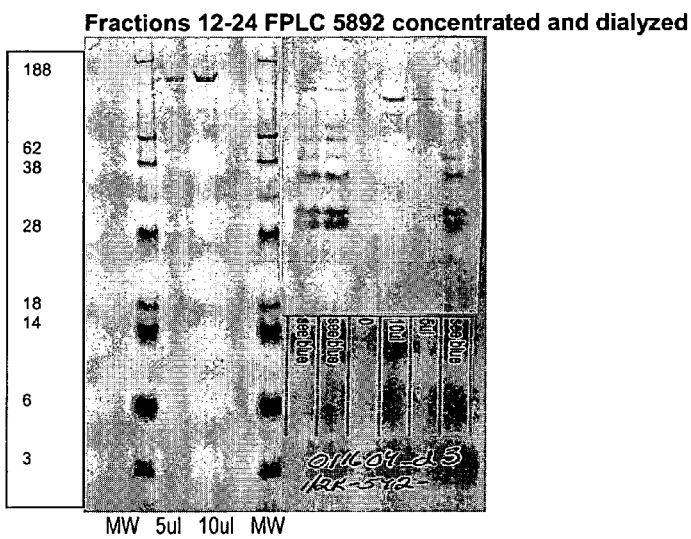
FIG. 58 is a picture of a gel and a Western Blot.

Fractions 10-24 reacted with the Sars Ab, whereas fractions 1-9 did not (011404-d5blot). Fractions 12-24 were pooled, concentrated and dialyzed using an amicon system to a volume of 8 mls. A gel/blot of this material is shown in FIG. 58. This material has a purity of greater than 90% and all visible bands in the gel react with the Sars Ab, suggesting that the SEC step can be removed from the process.

Figure 38:
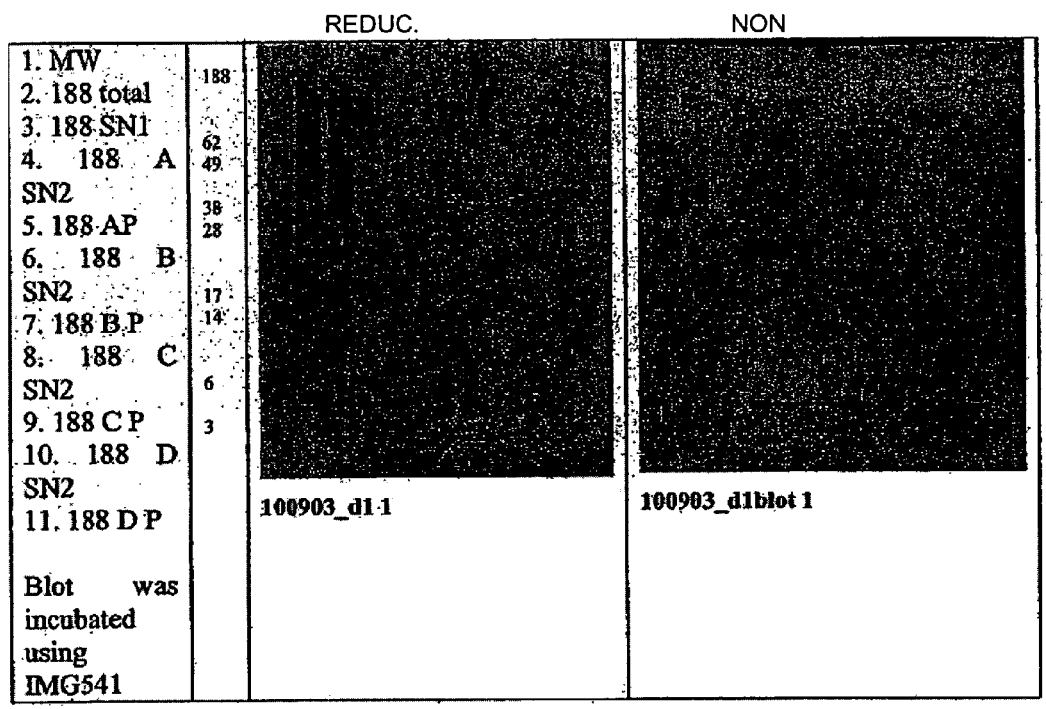
FIG. 38 is a picture of a gel and Western Blot.

Optimization studies were continued by introducing a filtration step with or without pH adjustment to the purification. 2 L of fresh supernatant was filtered thru a 0.2 um filter. The pH was not adjusted, and the supernatant was loaded to linked UNO-S and DEAE columns. The flow thru from 5907 was loaded on a 50 ml new LL column. LL eluted the same as in past experiments. Fractions were pooled and dialyzed into PBS overnight. The material was then concentrated by stirred celled to 30 mls. The material contained more fragments than that which was used for the mouse study because certain side fractions were included in the pool. See FIG. 64. All bands were recognized by the Ab. Loading 0.5 ug protein results in 70% intact with the remaining portion comprising fragments.

The total protein concentration yielded by this purification was 271 ug/ml, with a yield per liter of approximately 4 mg. The material had an endotoxin level of 80 EU/ml.

The study showed that the introduction of the filtration step and use of fresh resin improved endotoxin content. Omitting the pH adjustment and concentration step led to better overall process yields.

The experiment was repeated, with the second run providing material that was identical to that used in the mouse study as far as intact to fragment ratio (results are shown in FIG. 65). The second run had a protein concentration of 494 ug/ml and a yield per liter of approximately 3.5 mg/L. Low endotoxin levels were observed in this sample. The similar results between the two runs demonstrate that the results are reproducible.

The third run of the non-PH adjusted supernatant proceeded as expected. The purity and yield results were about the same as the previous two runs. Final yield numbers were difficult o compare as this pool was split and run over a Q Sepharose column. A gel and blot of the resulting material is in FIG. 66. Endotoxin numbers were less than 40 for the preconcentrate and less than 320 for the concentrate. These results show that the Q column appears to be an alternative for stirred cell concentration.

Further optimization studies were performed by altering the purification technique by using reduced column sizes in order to prepare the process for large scale manufacturing and to determine required column sizes. UNO S and DEAF columns were scaled down from 500 mls to 100 mls. LL columns were reduced from 50 mls to 7.5 mls and instead of stirred cell concentration a 5 ml Q Sepharose column was used. The gel and blot of the resulting material is shown in FIG. 67. The results showed that it is feasible to reduce the column sizes while maintaining the purity of final product. The results show that there appear to be fewer fragments when using the Q Sepharose columns in place of stirred cell concentration. A flow chart that represents this process is shown in FIG. 12E.

Further analysis will include repeating this modified process with 1 L of the original concentrate. The procedure will include the use of a larger S/Q column using step elution (100 mM/150 mM elution). The eluate would be applied to LL using various (0.1, 0.2, 0.3, 0.4, 0.5M) sugar elutions.

Extraction Study

Experiments were performed to improve the extraction of the S-protein from insect cells. Previous experiments have shown that 0.1% tergitol removed significant levels of contaminating proteins leaving the S-protein associated with the cell pellet. In addition, additives such as betaine and glycerol may increase the extraction efficiency of tergitol at 0.1-1.0%. Using the fermentation culture grown at 23° C., 168 hpi harvest (lot #100303), a series of extraction experiments were performed. The pellet was initially washed with 20 mM Tris, 0.1% Tergitol pH 8.47 and then divided into equally aliquots. The aliquots were centrifuged and the 0.1% Tergitol supernatants were pooled. The resulting aliquots/pellets were re-extracted with 1.0% Tergitol with and without additives (10% glycerol, 0.4 M Betaine, 0.5 M NaCl). Based on the gel and blot (see FIG. 38), complete protein extraction of the pellets was achieved with the initial wash step using 0.1% tergitol (lane 1, 188 SN1). This result may be attributed to the different conditions of this recent fermentation (lower temperature, late harvest). The high ratio of the cell pellet weight to the re-suspension volume (50×) may also have improved extraction efficiency when using with lower amounts of detergent.

Example 5

Assay Development

The S-protein has been described to possess hemagglutinating activity (Schultze, Gross et al. 1991). Protein Sciences has developed a hemagglutination assay for its influenza program and Applicants modified this method to measure the bio-activity of the S-protein because appropriate biological activity indicates correct folding.

It has been previously described that the S-protein from various Coronaviruses can agglutinate red blood cells by the interaction of the S-protein on the virus with sialic acid on the surface of the cells. Hemagglutination assays are done essentially as described by Rosen (Rosen 1968). Fresh chicken RBCs are washed with phosphate buffered saline (PBS) and suspended as a 0.5% solution in PBS. 50 p. 1 of washed RBCs are added to each well in U-bottom 96-well microtiter plates. Sample is serially diluted in PBS and 50 µl of each dilution is added to each well. The plates are covered and incubated at room temperature for 30 minutes and then scored for agglutination. One HA unit is defined as the dilution at which 50% of the cells agglutinate. The assay is being performed using both chicken and mouse red blood cells.

Example 6

Manufacturing

Preparation of Working Virus Bank (WVB). The virus inoculum used in S-protein production is derived from separate Working Virus Banks (WVB). As described above, recombinant virus from a single viral plaque is propagated through several passages at a low multiplicity of infection to generate a large quantity of inoculum and stored in aliquots in liquid nitrogen as the WVB.

The Working Virus Bank is tested for freedom from bacteria, fungi and other adventitious agents, including contaminating wild type or other recombinant baculoviruses. Identity is confirmed by Southern blot analysis of the insert from purified baculovirus DNA, and by Western blot analysis of the recombinant protein produced in infected insect cells. To maintain the genetic stability of the recombinant baculovirus used for protein production, the Working Virus Bank (WVB) is prepared by thawing out one aliquot and propagating it for a limited number of passages at a low multiplicity of infection (equal or less than 1 plaque-forming-unit (pfu)/cell).

Figure 39:
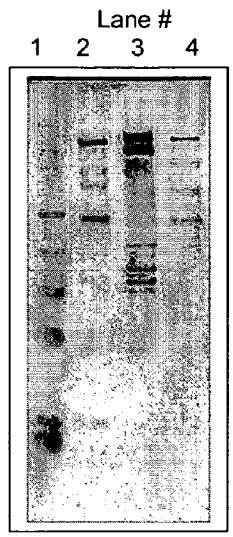
FIG. 39 is a picture of a Western Blot.

In order to prepare a MVB a culture was infected with a low MOI (usually of 0.1) and the culture is harvested 72 hpi. The WVB P3 was frozen and stored in the manufacturing area and will be used for future process development and manufacturing use. The blot for the FL S-protein (D3217.1a) unexpectedly showed the presence of full length S-protein in the supernatant (FIG. 39).

Figure 40:
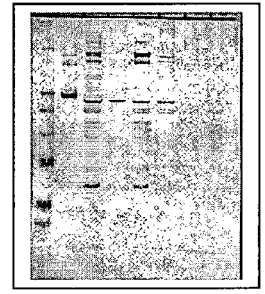
FIG. 40 is a picture of a Western Blot.

Because of the presence of the full length S protein in the supernatant of the virus bank, an additional 2 L fermentation was performed. The progress of the infection, viability of the infected cells, protein expression of FL S-protein D3217.1a and stability of the produced protein (as a result of adding leupeptin more than one time and at higher concentration) was monitored and measured over total time of fermentation of 72 hpi. The fermentation was performed in 2 L bioreactor. Twenty-four hours after infection, leupeptin was added to the culture in concentration of 2 µg/ml (=double the previously used concentration). At 48 hpi, samples were taken, viability was measured (82%) and 0.5 L was harvested and both pellets and supernatant were stored @ −20° C. for purification. Protease inhibitor, leupeptin was added again @ 48 hpi at 2 µg/ml. Seventy hours post infection (hpi), the culture was harvested. The cell viability at time of harvest was 55%. Microscopic observation confirmed that cells were well infected. FIG. 40 describes the expression progress.

Qualify Working Virus Banks.

The WVB is qualified by testing for titer and sterility. The cell line used for fermentation is checked for sterility on a continuous basis. In addition the fermentation is checked for sterility at the time of infection and harvest, and the crude sample (either infected cells or spent culture media, for intracellular and secreted proteins, respectively). Intermediate in-process samples from the various steps of the purification process and a sample of the bulk product are analyzed on SDS-polyacrylamide gels and Western blots to ensure that the recovery process performed as expected.

Final Bulk Lot Testing.

Tests are performed on each bulk antigen batch including assays for total protein, identity, purity, DNA contamination, process contaminants, and freedom from mycoplasma and adventitious agents. The methods and release specifications for all tests are provided in the following table. Bulk Lot Sterility testing is performed in accordance with the methods described in 21 C.F.R. §610.12 and the USP sections listed therein.

Release Testing and Specifications for Bulk Protein

| Tests | Method | Acceptance Criteria |
|---|---|---|
| Bulk sterility | CFR 610.12 | No growth observed |
| Mycoplasma | Indicator cell/DNA stain | No mycoplasma detected |
| Viruses | Co-cultivation, 3 cell types | No viruses detected |
| Identity | SDS-PAGE | 130 kDa mol. Wt. |
| | Western Blot | Positive against specific anti-antisera |
| Purity | Scanning densitometry | >90% advantageously >95% |
| Endotoxins | Limulus Amebocyte Lysate Assay | Less than 10 EU/ml |
| Protein concentration | Modified Lowry (BCA; Pierce) | Test and report |
| Protein activity | Agglutination assay | Activity observed |

Example 7

Quality Control

Tests are being performed using a study protocol to establish the stability of the concentrated and non-concentrated material at two different temperatures (−20° C. and 2-8° C.).

The results of the study to date show that the concentrated material appears to be more stable when stored at −20° C. The non-concentrated material appears to be similar independent of storage temperature.

A further stability study was performed to establish the optimal storage time of SARS ΔTM culture supernatant. Samples of SARS ΔTM culture supernatant were stored as either TFF concentrated or unconcentrated at either 4° C. or −20° C. The culture was harvested and samples were tested. The data is currently under evaluation with a densitometer.

Figure 68:
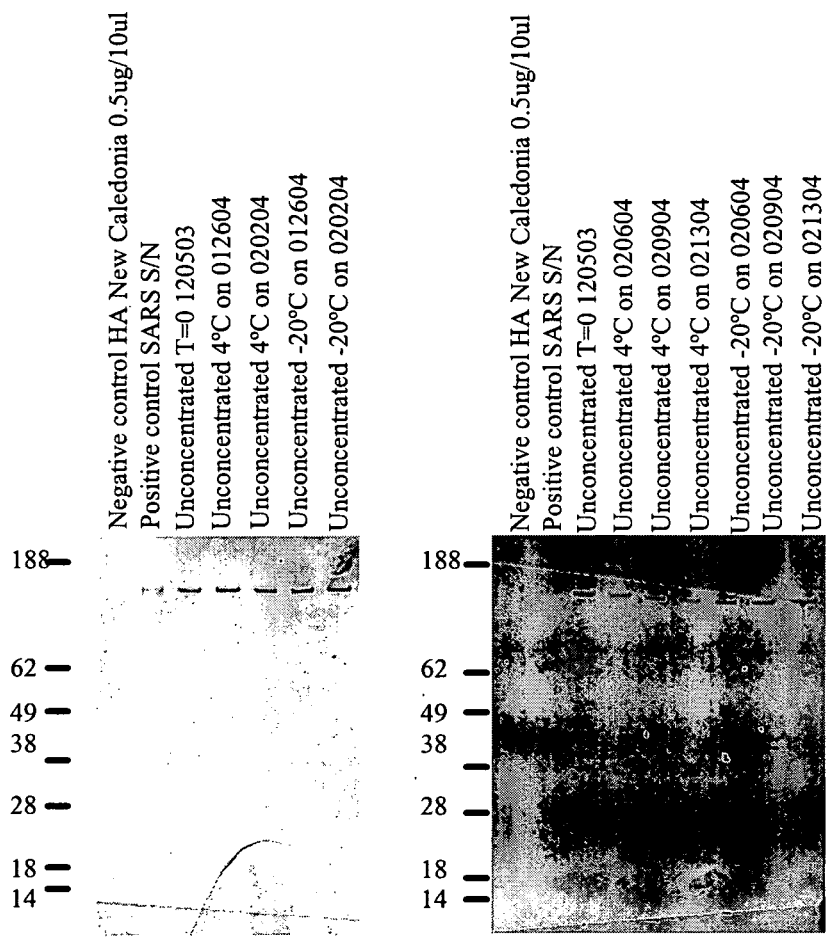
FIG. 68 is a picture of two gels.

All blots were processed using the same antibody (IMG 542). Qualitatively, it can be concluded that the unconcentrated SARS ΔTM culture supernatant is stable at either 4° C. or −20° C. for up to two months (see FIG. 68). FIG. 68 shows time points of unconcentrated SARS ΔTM culture supernatant stored at 4° C. versus −20° C. Western blots were also performed of unconcentrated SARS ΔTM culture supernatant stored at 4° C. versus −20° C. Qualitatively, no change in degradation or band signal was detected within 2 months of storage when compared to the T=0 sample. A decrease in intensity of the protein band beyond two months of storage was observed.

Figure 69:
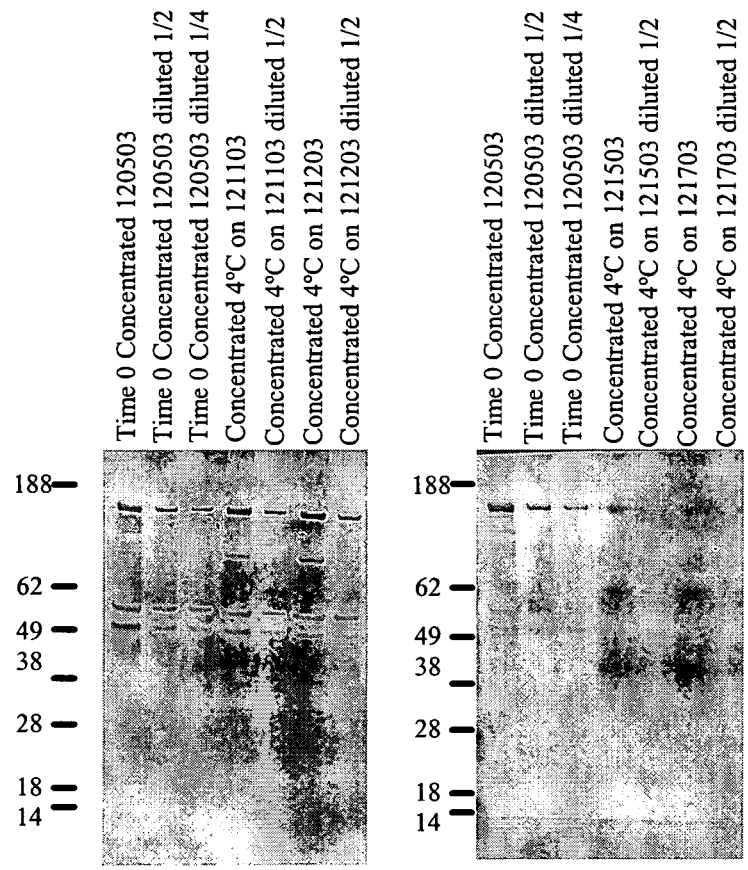
FIG. 69 is a picture of two gels.

The concentrated SARS ΔTM culture supernatant was stable at 4° C. for up to 1 week (see FIG. 69), although an additional band appears on the blot at approximately 100 kD at the first time point tested (see band in FIG. 69). It should be noted, however, that the concentrated culture supernatant stored at 4° C. became contaminated during the study. It is possible that the contamination led to the rapid degradation at 4° C. FIG. 69 shows time points of concentrated SARS ΔTM culture supernatant stored at 4° C. Western blots were also performed of concentrated SARS ΔTM culture supernatant stored at 4° C. Qualitatively, the protein was fairly stable in the concentrated culture supernatant when stored at 4° C. for up to 1 week, with the exception of the appearance of an additional ~100 kD band. The protein was almost completely degraded beyond this time.

Figures 70, 71:
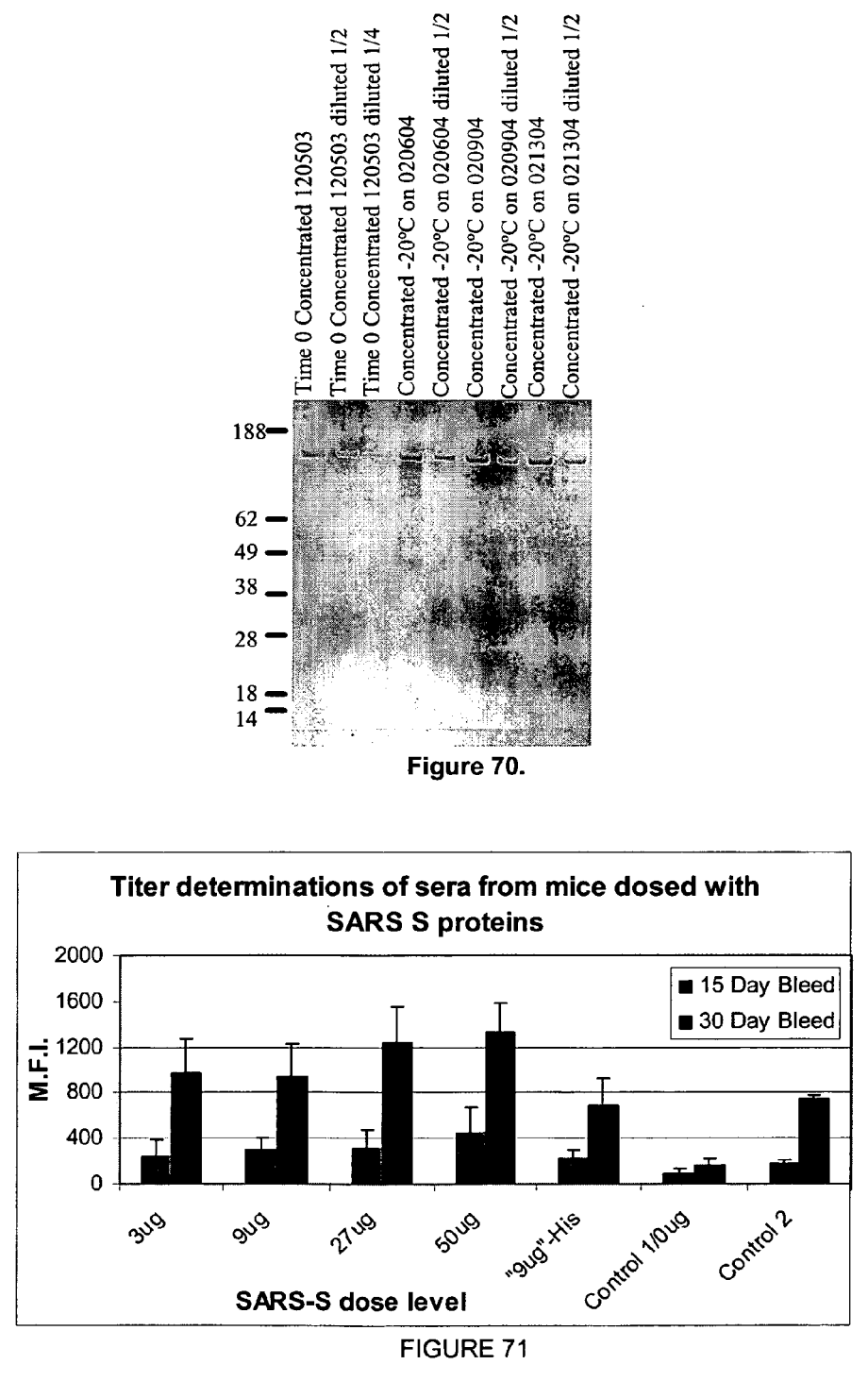

The concentrated SARS ΔTM culture supernatant was stable at −20° C. for up to 2 months (see FIG. 70). FIG. 70 shows time points of concentrated SARS ΔTM culture supernatant stored at −20° C. A Western blot was also performed of concentrated SARS ΔTM culture supernatant stored at −20° C. Qualitatively, no change in degradation or band signal was detected within 2 months of storage when compared to the T=0 sample. A band at approximately 100 kD may have started to appear or could be varying on the blot from an inconsistent transfer.

Example 8

Production of Polyclonal Sera for the SARS S Protein

The ΔTM S protein was produced using the bacterial expression system pBAD/H is (Invitrogen) and the *E. coli* strain LMG194. The target protein was extracted from the cell pellet and purified over a Ni-chelating column. A significant level of protein degradation was reported. In addition, significant losses were encountered in the concentration of the final product using the Centriprep concentrators.

The polyclonal antibody service included the purchase of 1 specific pathogen-free rabbit (animal #V610) for antibody production. A pre-immunization bleed was performed. Thus far two immunizations have been performed and two post-immunization small volume bleeds have been received at PSC (see Table below). Four additional immunizations are scheduled. Two more small volume bleeds and a final terminal bleed pool (40-70 mLs) are expected.

Figure 59:
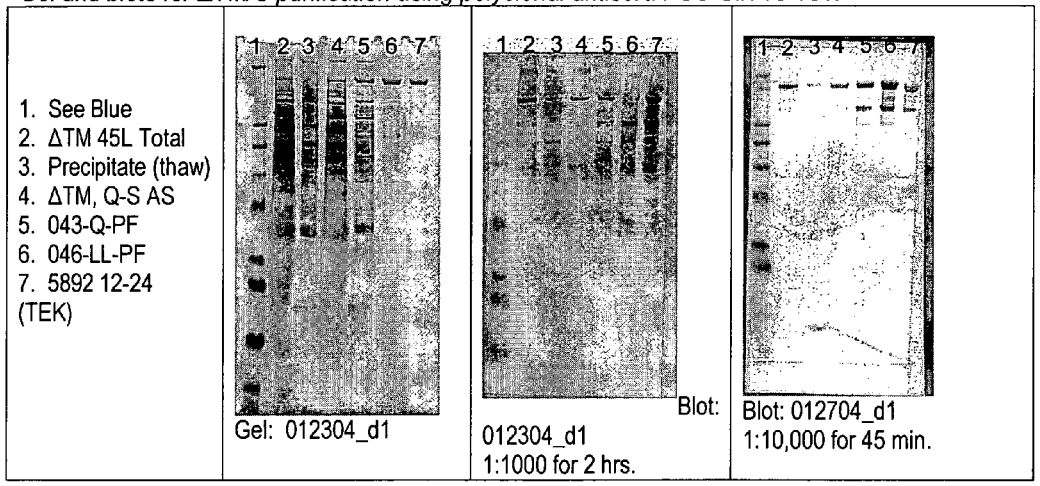
FIG. 59 is a picture of a gel and Western Blots.

The $2^{nd}$ immunization bleed has been used to probe western blots of the 45 L ΔTM S protein purification process. Western blots have been performed at 1:1000 and 1:10,000 dilutions for 2 hours and 45 minutes, respectively, using the primary antibody. The secondary antibody (rabbit IgG) is used at 1:1000 for 1 hour (see gel and blots in FIG. 59). The 1:10,000 dilution of the $2^{nd}$ immunization bleed provides a reasonable blot signal. The blot incubation time may be extended to 1-2 hours for improved signal. Using the 1:10,000 dilution, the $2^{nd}$ immunization bleed should provide sufficient material for at least 1,000 more blots.

Three mg of the ΔTM S protein was provided for mouse immunogenicity studies. Preliminary data reported indicate that good serum ELISA titers and virus neutralization titers were obtained when immunizing mice by IM route with Alum. Two doses were used in this study.

Example 9

Animal Testing

This study was blinded by the Center for Disease Control.

The test materials for this study were truncated S protein (Delta TM) and full length his-tagged S protein (histag). Routine safety precautions were followed, and additional routine safety precautions were followed as needed.

The test materials were stored frozen (20° C.). All materials were stored as specified by the supplier and documented.

All quantities of test materials that were dispensed were documented. The test material dose formulations were prepared and shipped in separate vials—one vial per dose level per immunization time point. On each dosing day, the prepared dose vials were thawed prior to dosing.

Male and female (nulliparous, non-pregnant) CD1, VAF/Plus, mice were purchased from Charles River Laboratories for this study. Animals weighed approximately 16-18 grams (specified purchase weight range) and were approximately four weeks of age upon arrival. Mice are frequently used in immunological studies; in particular for hypersensitivity reactions and a large amount of background data are available, rendering the mouse a suitable candidate for this study. The mice were housed up to six per cage in plastic solid-bottom cages with hardwood chip bedding. Animal rooms and cages were cleaned and sanitized prior to the study start and cages were changed as needed thereafter. This was done in accordance with accepted animal care practice.

Animal rooms were lighted with fluorescent lights and maintained on a 12-hr light/dark cycle. To the maximum extent possible, room temperature was maintained at approximately 18-26° C. and relative humidity at approximately 30-70% in accordance with the National Research Council's, "Guide for the Care and Use of Laboratory Animals", 1996. Room temperature and relative humidity values were recorded daily.

Certified Rodent Diet [e.g., Purina Rodent Diet 5002 (PMI Nutrition International, Brentwood, Mo.)] was available ad libitum. An analysis of each feed lot was provided by the manufacturer and maintained with facility records. No known contaminants were present in the diet that would have adversely impacted the integrity of the study. City of Chicago tap water was provided ad libitum via an automatic drinking water distribution system or in water bottles. Fresh water (bottles) was provided at least twice weekly. Water analytical reports were maintained.

Animals selected for the study received a permanent identification number by ear mark or ear punch. Individual cage cards also identified the test animals by animal number and study group. The identifying numbers assigned were unique within the study.

The test material was administered to mice by IM injection according to the study design shown below. The animals were weighed and assigned to treatment groups using a constrained random process such that all groups tested were comparable in pretest body weight, and the weight variation of each animal used did not exceed ±20% of the mean weight. The animals received 50 μl of the dose formulation containing graded doses of test material. On the days specified, animals were euthanized and sera was collected. Sera was shipped for analysis by ELISA and serum neutralization assay.

| | | Day 1 | | Day 15 | | Day 30 | | Day 45 | | Day 60 | Day 75 |
|---|---|---|---|---|---|---|---|---|---|---|---|
| Group | Dose Level | Dose 1 | S | Dose 2 | S | Dose 3 | S | Dose 4 | S | S | S |
| 1 | 3 μg | 40 | — | 32 | 8 | 24 | 8 | 16 | 8 | 8 | 8 |
| 2 | 9 μg | 40 | — | 32 | 8 | 24 | 8 | 16 | 8 | 8 | 8 |
| 3 | 9 μg-histag | 40 | — | 32 | 8 | 24 | 8 | 16 | 8 | 8 | 8 |
| 4 | 27 μg | 40 | — | 32 | 8 | 24 | 8 | 16 | 8 | 8 | 8 |
| 5 | 50 μg | 40 | — | 32 | 8 | 24 | 8 | 16 | 8 | 8 | 8 |
| Control | — | NA | 8 | NA | — | NA | 4 | NA | — | 4 | 4 |

Dose = number of mice dosed IM (50 μl) - half males, half females
S = sacrificed for bleed - half males, half females
NA = not applicable The animals purchased for use in this study were held in quarantine for at least one week. During quarantine, the animals were observed at least once daily. At the conclusion of quarantine, the health status of the animals was reviewed by the Staff Veterinarian prior to release for testing.

Animals were weighed weekly and were observed daily for signs of toxicity and survival. All signs of altered behavior, changes in coat condition, unusual discharge of body fluid, lesions, or other relevant observations were recorded. Animals found dead were noted and disposed of without gross necropsy. Necropsy was not be performed on animals found dead or sacrificed in moribund condition. No tissues were preserved at animal termination.

Animals received a total of one, two, three or four 50 μl IM injections containing test material. Animals were immunized on study Days 1, 15, 30 and 45. A 0.5 cc plastic disposable sterile syringe and 27 g×½ inch needle were used to inject the dose formulations. Control animals were not dosed.

Mice were heavily anesthetized prior to bleeding and whole blood collected from the retro-orbital sinus, abdominal aorta or via cardiac puncture. Serum samples were collected by allowing the blood to clot, centrifugation at 1300×g for 20 minutes and removing the serum to appropriately labeled tubes. The sera was stored at approximately −20° C. until shipped following the Day 30 and Day 75 bleeds. The study animals were euthanized by exsanguination from the abdominal aorta following anesthetization with sodium pentobarbital or by $CO_2$ asphyxiation.

Body weights and weekly body weight gains were presented as mean and standard deviations of exposure groups at each time point. The log-transformed data was statistically analyzed for differences between treatment groups by analysis of variance (ANOVA) and, if appropriate, Dunnett's test or Tukey's HSD test. A P value of $\leqq 0.05$ was considered to be a significant difference. Clinical observations were summarized by incidence.

Example 10

ELISA Assay for Measurement of Antibody Levels in Mouse Sera

In order to measure the antibody levels in the mouse sera, an ELISA was developed using purified −TM as the source antigen on the plate, the polyclonal rabbit antibody, hrp conjugated secondary, and the Pico CLW ELISA detection kit from Pierce. A Perkin Elmer fluorimeter is used with the excitation lamp off.

Figure 60:
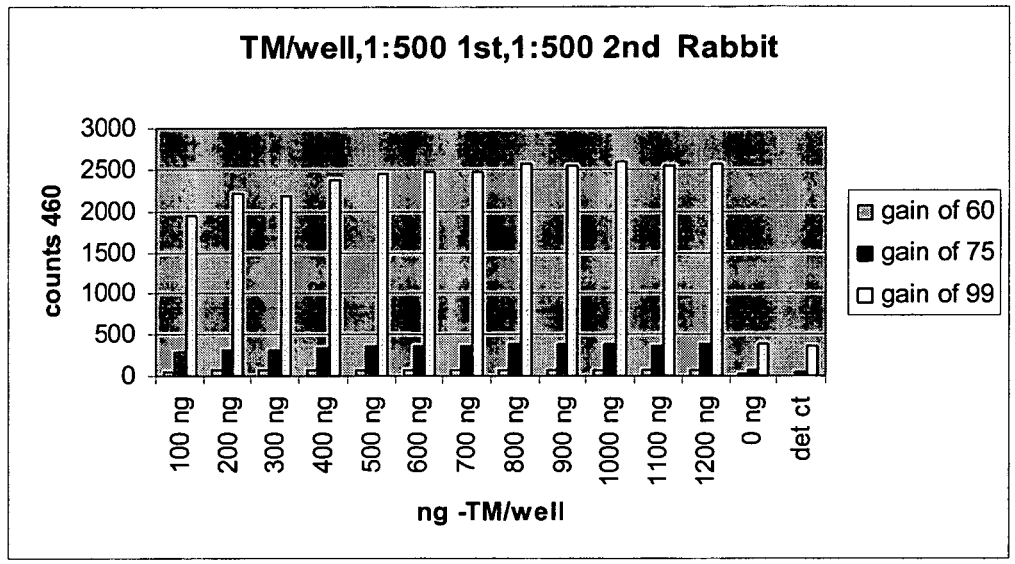
FIG. 60 is a bar graph.
Figure 61:
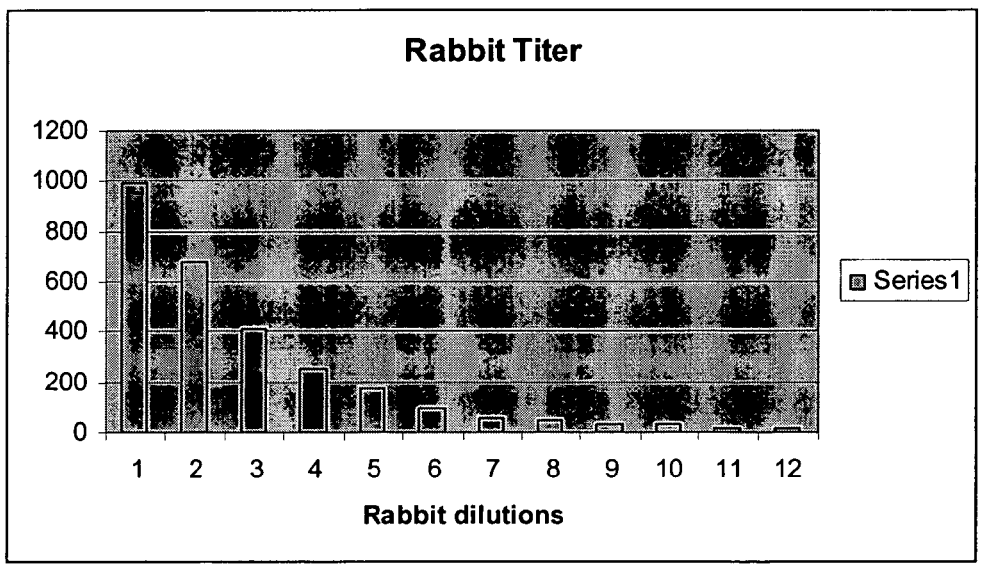
FIG. 61 is a bar graph.
Figure 62:
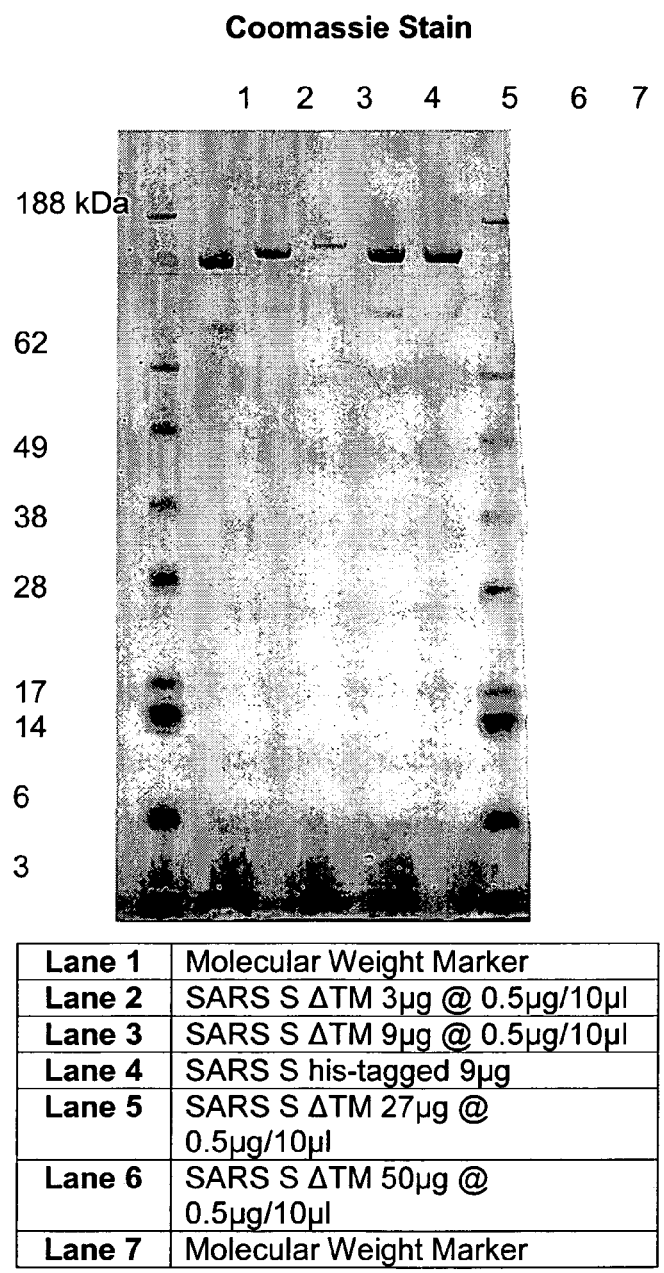
FIG. 62 is a picture of a gel.
Figure 65:
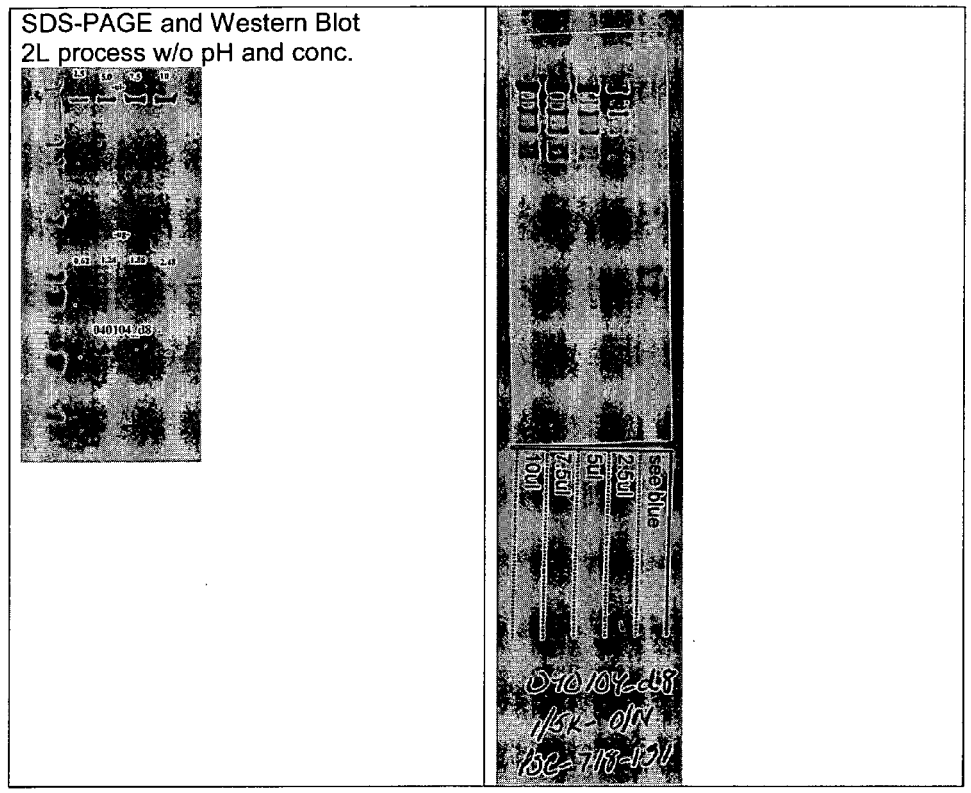
FIG. 65 is a picture of a gel and a Western Blot.
Figure 66:
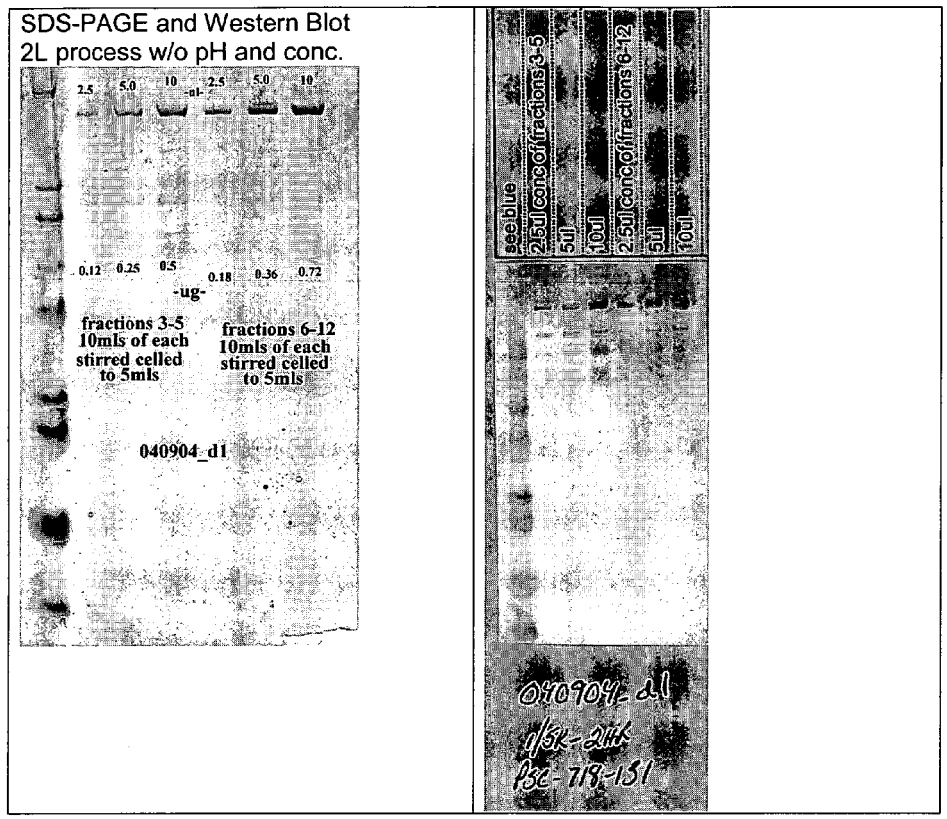
FIG. 66 is a picture of a gel and a Western Blot.
Figure 67:
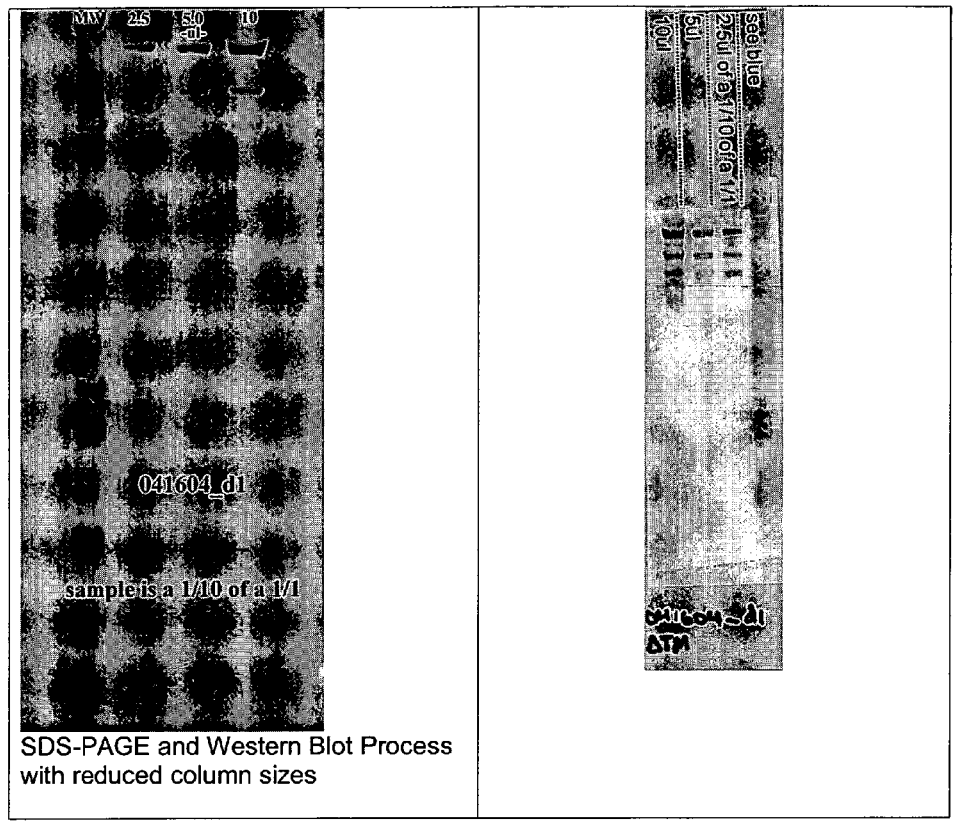
FIG. 67 is a picture of a gel and a Western Blot.

FIGS. 60 and 61 are Excel graphs demonstrating that the system worked with the polyclonal rabbit sera. In FIG. 60, varying amounts of antigen are plated using a constant concentration of primary and secondary antibody (dilution 1:500). FIG. 61 shows a titration of the rabbit polyclonal using 100 ng of −TM per well and 1:1000 dilution of secondary. The dilutions are 2 fold starting at 1:1000.

Figure 72:
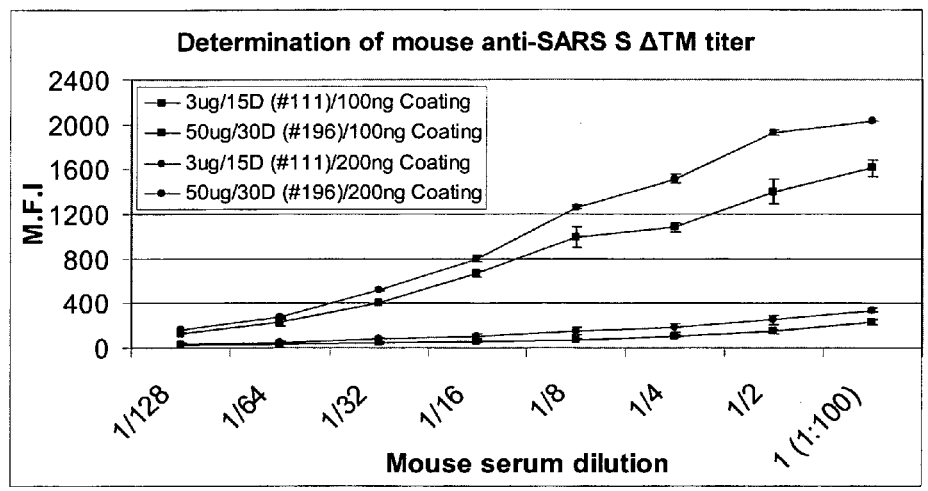
FIG. 72 is a line chart.

In a double-blind study, six groups of mice (five experimental groups, one control group) were immunized with varying doses of SARS S delta TM and the His-tagged full length S protein, as described in the table below. Mice were bled on days 1, 15, 30, 45, 60 and 75.

The working serum dilution was determined to be a 1:100 dilution based on pre-run experiments. Anti-S ΔTM antibody titer was determined for each sample with capture immunoassay, where 100 ng of S ΔTM was coated in each well of 96-well plate. After anti-S ΔTM antibodies were bound to S ΔTM, HRP-conjugated sheep anti-mouse antibody was used to produce specific signals (ECL). Results reported in FIG. 71 are averages of both male and female subjects. Control 1 includes sera from $1^{st}$ (red) and $30^{th}$ (blue) bleed days, and control 2 are assay controls, including negative (PBS, red) and positive (rabbit anti-S ΔTM). All assays were run in duplicate on two plates. The study was not unblended until after all assays were completed and data was collected.

The graph in FIG. 71 clearly showed that anti-SARS S, ΔTM or His-tagged full length, antibodies could be induced in a dose-dependent and boost-effective fashion. The results were producible on the duplicate plate. Further, the graph of FIG. 75 also clearly depicts the elevation of antibody titer over time.

The His-tagged S protein used in the study (9 ug dose level) was re-measured for its concentration. The 9 ug was overestimated due to interferences in the protein preparation, and the actual dose was more accurately reflected as approximately 2 ug. This new estimation is in line with the current study. Values from mice dosed with His-tagged full length S protein are less than those from mice with the 3 ug dose level, indicating that actual dose may be less than 3 ug.

Additional experiments were performed to validate the capture immunoassay used in the mouse study.

The optimal coating condition in the first part of SARS S immunogenicity study in mice (above), 100 ul of 1 ug/ml SARS S ΔTM, was determined with rabbit anti-His-tagged SARS ΔTM. The primary Ab (mouse sera) working dilution, 1:100, was based on a previous pilot experiment, where selected mouse sera were serially diluted and tested for SARS ΔTM binding. Two serum samples were selected for the current study. One was #111 (3 ug dose, 15$^{th}$ day bleed), representing the lower end of specific signal. The other was #196 (50 ug dose, 30$^{th}$ day bleed, the strongest signal in the mouse study), the higher end. Sera were serially diluted, starting with 1:100 dilution, and assays were run in duplicates on a plate with two coating conditions, 1 ug/ml and 2 ug/ml SARS S ΔTM. Results are shown in FIG. 72.

For #111, the signal was weak but detectable. Signals from dilutions were linear but at the lower end of the assay linear range. A 1:100 dilution apparently was the best choice for this sample and further dilution will jeopardize the quality of the assay. On the other hand, #196 showed a linear decrease of specific signals along with serial dilutions. A 1:100 dilution instead was at higher end of the titration. This dilution compromises both weak and strong specific signals. Therefore, the current study validated the assay conditions used in the immunogenicity study in mice.

Increasing coating concentration to 2 ug/ml improved the detection of the lower titer, but sera with higher titer must be further diluted in order to stay in the linear detection range.

Figure 73:
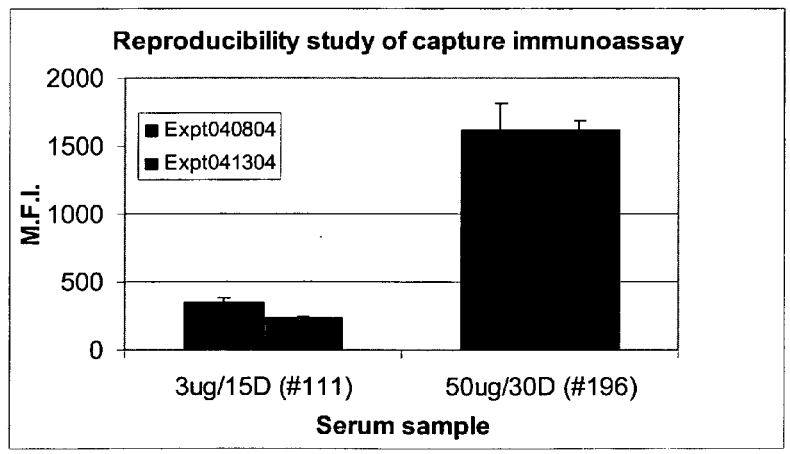
FIG. 73 is a bar graph.

Since two identical serum samples were tested on two different days, it allowed for the evaluation of the reproducibility of the capture immunoassay (see FIG. 73). Results from two assays were reproducible. CV (StDev/Average) is about 10% for Day 1 due to the averaged result from two plates (also called inter-plate CV), while CV from Day 2 is less than 10%, benefiting from the average from the same plate (intra-plate CV). #111 had weak signals and was positioned in the lower end of the assay range.

Part II of the study included bleeds on days 45$^{th}$, 60$^{th}$, and 75$^{th}$. The total serum samples obtained including those from the bleeds on days 45, 60 and 75 are shown in the below table.

| | | | Bleed Day | | | | | |
|---|---|---|---|---|---|---|---|---|
| Group | Dose Level | Sex | 1st | 15th | 30th | 45th | 60th | 75th |
| Group 1 | 3 μg S ΔTM | Male | 0 | 5 | 3 | 4 | 4 | 4 |
| | | Female | 0 | 4 | 4 | 4 | 4 | 4 |
| Group 2 | 9 μg S ÄTM | Male | 0 | 4 | 4 | 4 | 4 | 4 |
| | | Female | 0 | 4 | 4 | 4 | 4 | 4 |
| Group 3 | 3 μg His-S FL | Male | 0 | 4 | 4 | 4 | 4 | 4 |
| | | Female | 0 | 4 | 4 | 4 | 4 | 4 |
| Group 4 | 27 μg S ÄTM | Male | 0 | 4 | 4 | 4 | 4 | 4 |
| | | Female | 0 | 4 | 4 | 4 | 4 | 4 |
| Group 5 | 50 μg S ÄTM | Male | 0 | 4 | 4 | 4 | 4 | 4 |
| | | Female | 0 | 4 | 4 | 4 | 4 | 4 |
| Control | Naïve | Male | 4 | 0 | 2 | 0 | 2 | 2 |
| | | Female | 4 | 0 | 2 | 0 | 2 | 2 |

All mice anti-SARS S protein sera were sent to CDC in Canada for virus neutralization studies. Virus neutralization tests of mice sera were performed following SOP. Sera were 2-fold serially diluted. For each dilution, 100 infectious units of virus were added. Virus neutralization occurred during incubation. The mixtures were used to inoculate Vero-E6 cells and cytopathic effect (CPE) was monitored. Results of unheated (Titre 1) and heated (56° C. for 30 minutes, Titre 2) sera are summarized in the following table.

| | | | | Bleed | | | | | |
|---|---|---|---|---|---|---|---|---|---|
| | | | | Day 15th | | | Day 30th | | |
| | | | | Immuno- | Virus neutralization | | Immuno- | Virus neutralization | |
| | Dose level | Sex | ID | genicity Titer | Titre-1 | Titre-2 (56 C.) | ID | genicity Titer | Titre-1 | Titre-2 (56 C.) |
| Group 1 | 3 ug S ΔTM | Male | #1 | 2,000 | <10 | <10 | #5 | 16,000 | 20 | 20 |
| | | | #2 | 4,000 | <10 | 10 | | | | |
| | | | #3 | 2,000 | <10 | <10 | #7 | 32,000 | 80 | 80 |
| | | | #4 | 1,000 | <10 | <10 | #8 | 32,000 | 40 | 10 |
| | | | #6 | 8,000 | <10 | <10 | | | | |
| | | Female | #111 | 16,000 | 20 | 40 | #115 | 128,000 | 320 | 640 |
| | | | #112 | 8,000 | <10 | <10 | #116 | 64,000 | 80 | 80 |
| | | | #113 | 2,000 | <10 | <10 | #117 | 32,000 | 80 | 20 |
| | | | #114 | 32,000 | 20 | <10 | #118 | 64,000 | 320 | 160 |
| | Average | | | | | | | | | |
| Group 2 | 9 ug S ΔTM | Male | #21 | 2,000 | 10 | <10 | #25 | 32,000 | 320 | 80 |
| | | | #22 | 4,000 | <10 | <10 | #26 | 32,000 | 160 | 80 |
| | | | #23 | 4,000 | 20 | 10 | #27 | 8,000 | 20 | 10 |
| | | | #24 | 4,000 | <10 | 10 | #28 | 32,000 | 160 | 40 |
| | | Female | #131 | 32,000 | 40 | 20 | #135 | 128,000 | 320 | 80 |
| | | | #132 | 32,000 | 10 | <10 | #136 | 128,000 | 320 | 160 |
| | | | #133 | 16,000 | 10 | 20 | #137 | 64,000 | 160 | 160 |
| | | | #134 | 2,000 | <10 | <10 | #138 | 64,000 | 160 | 80 |
| | Average | | | | | | | | | |
| Group 3 | "9" ug His-S FL | Male | #41 | <1000 | <10 | <10 | #45 | 2000 | 10 | <10 |
| | | | #42 | 1000 | <10 | <10 | #46 | 64000 | 160 | 160 |
| | | | #43 | 1000 | <10 | <10 | #47 | 16000 | 10 | 10 |
| | | | #44 | <1000 | <10 | <10 | #48 | 32000 | 80 | 80 |
| | | Female | #151 | | 40 | 20 | #155 | | 40 | 20 |
| | | | #152 | | 10 | <10 | #156 | | 10 | <10 |

-continued

|  |  |  |  |  |  |  | #153 | <10 | 10 | #157 | 40 | 20 |
|  |  |  |  |  |  |  | #154 | <10 | <10 | #158 | 80 | 80 |
|  |  | Average |  |  |  |  |  |  |  |  |  |  |
| Group 4 | 27 ug S ΔTM | Male | #61 | 10 | <10 | #65 | 160 | 40 |
|  |  |  | #62 | <10 | <10 | #66 | 160 | 40 |
|  |  |  | #63 | <10 | <10 | #67 | 160 | 40 |
|  |  |  | #64 | <10 | <10 | #68 | 160 | 160 |
|  |  | Female | #171 | <10 | <10 | #175 | 320 | 160 |
|  |  |  | #172 | <10 | <10 | #176 | 320 | 160 |
|  |  |  | #173 |  |  | #177 | 160 | 160 |
|  |  |  | #174 | 20 | 10 | #178 | 40 | 80 |
|  |  | Average |  |  |  |  |  |  |
| Group 5 | 50 ug S ΔTM | Male | #81 | 10 | <10 | #85 | 320 | 80 |
|  |  |  | #82 | 40 | 10 | #86 | 80 | 40 |
|  |  |  | #83 | 10 | 10 | #87 | 320 | 640 |
|  |  |  | #84 | 20 | <10 | #88 | 320 | 320 |
|  |  | Female | #191 | <10 | <10 | #195 | 320 | 320 |
|  |  |  | #192 | 40 | 10 | #196 | 2560 | 320 |
|  |  |  | #193 | 20 | 20 | #197 | 80 | 80 |
|  |  |  | #194 | 10 | 20 | #198 | 80 | 320 |
|  |  | Average |  |  |  |  |  |  |
| Control | naive | Male |  |  |  | #105 | <10 | <10 |
|  |  |  |  |  |  | #106 | <10 | <10 |
|  |  | Female |  |  |  | #215 | <10 | <10 |
|  |  |  |  |  |  | #216 | <10 | <10 |
|  |  | Average |  |  |  |  |  |  |

|  |  |  | Day 45th |  | Day 60th |  | Day 75th |  |
|---|---|---|---|---|---|---|---|---|
| Dose level | Sex | ID | Immunogenicity Titer | ID | Immunogenicity Titer | ID | Immunogenicity Titer |
| Group 1 | 3 ug S ΔTM | Male | #9 | 64,000 | #13 | 32,000 | #17 | 32,000 |
|  |  |  | #10 | 64,000 | #14 | 128,000 | #18 | 16,000 |
|  |  |  | #11 | 32,000 | #15 | 128,000 | #19 | 256,000 |
|  |  |  | #12 | 256,000 | #16 | 64,000 | #20 | 64,000 |
|  |  | Female | #119 | 256,000 | #123 | 128,000 | #127 | 128,000 |
|  |  |  | #120 | 128,000 | #124 | 128,000 | #128 | 256,000 |
|  |  |  | #121 | 512,000 | #125 | 128,000 | #129 | 128,000 |
|  |  |  | #122 | 512,000 | #126 | 128,000 | #130 | 128,000 |
|  | Average |  |  | 228,000 |  | 108,000 |  | 126,000 |
| Group 2 | 9 ug S ΔTM | Male | #29 | 64,000 | #33 | 64,000 | #37 | 64,000 |
|  |  |  | #30 | 128,000 | #34 | 64,000 | #38 | 128,000 |
|  |  |  | #31 | 64,000 | #35 | 128,000 | #39 | 128,000 |
|  |  |  | #32 | 128,000 | #36 | 128,000 | #40 | 32,000 |
|  |  | Female | #139 | 512,000 | #143 | 64,000 | #147 | 128,000 |
|  |  |  | #140 | 512,000 | #144 | 128,000 | #148 | 256,000 |
|  |  |  | #141 | 128,000 | #145 | 256,000 | #149 | 256,000 |
|  |  |  | #142 | 256,000 | #146 | 64,000 | #150 | 256,000 |
|  | Average |  |  | 224,444 |  | 111,556 |  | 152,667 |
| Group 3 | "9" ug His-S FL | Male | #49 | 256,000 | #53 | 512,000 | #57 | 512,000 |
|  |  |  | #50 | 64,000 | #54 | 512,000 | #58 | 128,000 |
|  |  |  | #51 | 64,000 | #55 | 256,000 | #59 | 32,000 |
|  |  |  | #52 | 128,000 | #56 | 64,000 | #60 | 1,032,000 |
|  |  | Female | #159 | 1,032,000 | #163 | 1,032,000 | #167 | 256,000 |
|  |  |  | #160 | 32,000 | #164 | 256,000 | #168 | 32,000 |
|  |  |  | #161 | 64,000 | #165 | 64,000 | #169 | 1,032,000 |
|  |  |  | #162 | 1,032,000 | #166 | 512,000 | #170 | 256,000 |
|  | Average |  |  | 321,827 |  | 368,840 |  | 381,407 |
| Group 4 | 27 ug S ΔTM | Male | #69 | 16,000 | #73 | 128,000 | #77 | 64,000 |
|  |  |  | #70 | 128,000 | #74 | 64,000 | #78 | 512,000 |
|  |  |  | #71 | 256,000 | #75 | 256,000 | #79 | 64,000 |
|  |  |  | #72 | 32,000 | #76 | 512,000 | #80 | 512,000 |
|  |  | Female | #179 | 256,000 | #183 | 256,000 | #187 | 512,000 |
|  |  |  | #180 | 512,000 | #184 | 512,000 | #188 | 256,000 |
|  |  |  | #181 | 256,000 | #185 | 512,000 | #189 | 256,000 |
|  |  |  | #182 | 512,000 | #186 | 512,000 | #190 | 128,000 |
|  | Average |  |  | 246,000 |  | 344,000 |  | 288,000 |
| Group 5 | 50 ug S ΔTM | Male | #89 | 256,000 | #93 | 32,000 | #97 | 512,000 |
|  |  |  | #90 | 512,000 | #94 | 512,000 | #98 | 64,000 |
|  |  |  | #91 | 128,000 | #95 | 512,000 | #99 | 64,000 |
|  |  |  | #92 | 16,000 | #96 | 64,000 | #100 | 512,000 |
|  |  | Female | #199 | 2,048,000 | #203 | 256,000 | #207 | 512,000 |
|  |  |  | #200 | 128,000 | #204 | 1,024,000 | #208 | 128,000 |
|  |  |  | #201 | 1,024,000 | #205 | 128,000 | #209 | 256,000 |
|  |  |  | #202 | 1,024,000 | #206 | 512,000 | #210 | 512,000 |
|  | Average |  |  | 642,000 |  | 380,000 |  | 320,000 |

Note: for virus neutralization tests, red and black numbers are from tests 042104 and 051104, respectively Results from this study showed that all the mice that received two doses had sera that neutralized SARS-CoV, while most of those that received one dose produced neutralization sera. This neutralization ability was clearly boost-effective. Results also demonstrated the general trend of dose dependency, though at dose levels beyond 9 ug a plateau was reached.

Figure 74:
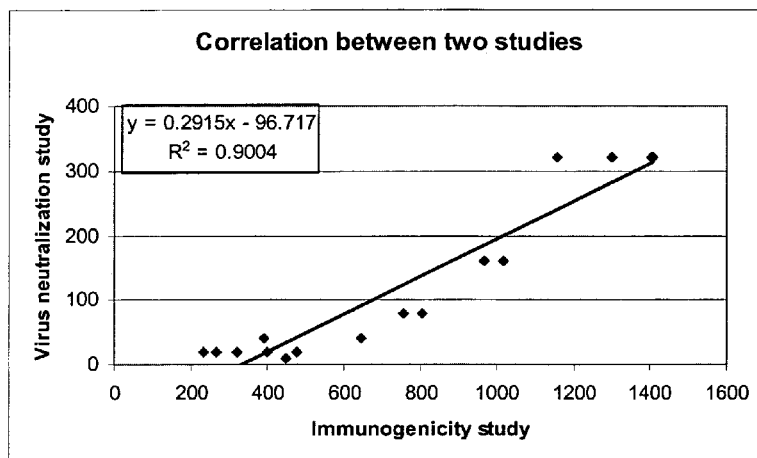
FIG. 74 is a line chart.
Figure 75:
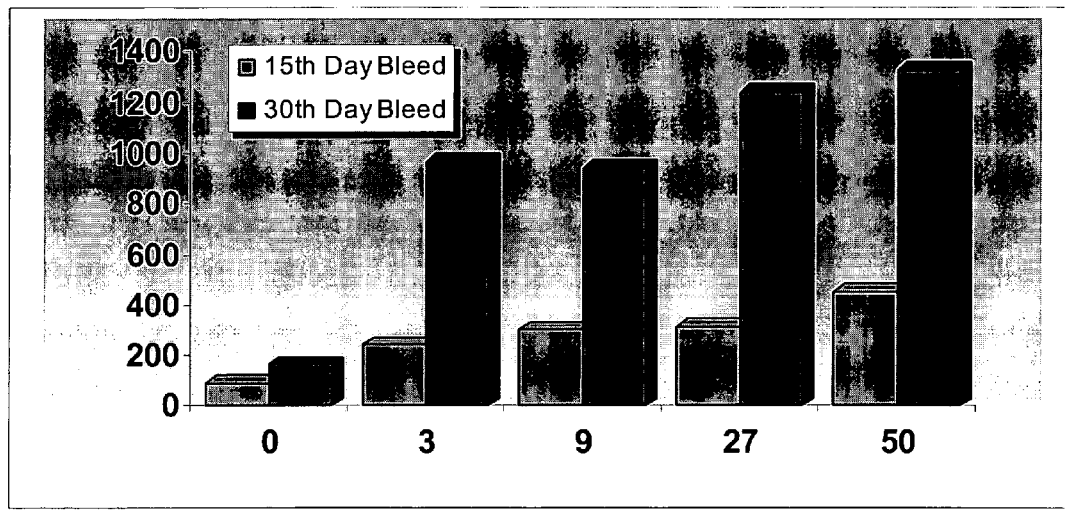
FIG. 75 is a bar graph.

A subset of data was further analyzed for correlation. Since MFI values were obtained at 100-fold dilution for all the mice sera from their immunogenicity studies (see Example 11), both sets of data could be plotted in the same graph to look at their correlation. In FIG. 74, Y-axis represents Titre 1 of virus neutralization, while X-axis showed the MFI values of the same sera. All negatives (Titre 1<10) and one outliner (Animal ID#25) were excluded.

With a sample size of 16, the graph showed a R2 value of 0.90, indicating a good correlation between two studies (see FIG. 74).

Example 12

Biological Activity of SARS S Delta TM

Figure 76:
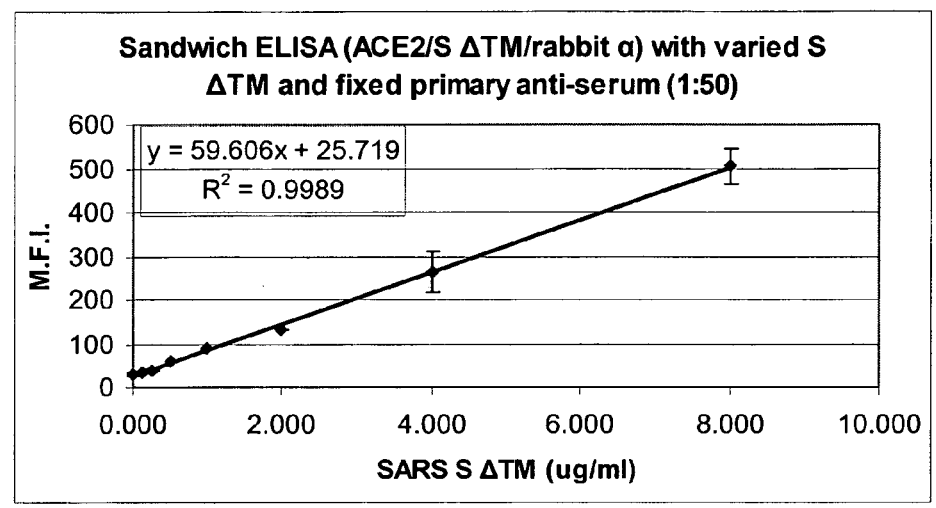
FIG. 76 is a line chart.

MFI values were obtained with ACE2/S delta TM/rabbit α for varied SARS S delta TM concentrations with fixed primary anti-serum in a 1:50 dilution. Results are shown in FIG. 76, and indicate that the MFI values correlate well with the concentration of the sample, with a R2 value of 0.99. This result represents functional activity of the SARS S delta TM, and shows that the purified recombinant folded correctly. This also indicates that the SARS S delta TM is an appropriate antigen for a vaccine.

In summary, these studies have demonstrated recombinant SARS S proteins can elicit mice SARS-CoV-neutralizing sera in a dose dependent and boost-effective fashion. Furthermore, the vaccine appeared to be well tolerated during the studies.

Example 12

Formulation of SARS S ΔTM with Alhydrogel

SARS S delta TM was tested for binding with an adjuvant, Alhydrogel. A fixed amount of purified SARS S delta TM (after four columns), was mixed with varied amounts of Alhydrogel to make final $Al(OH)_3$ concentrations of 0.05%, 0.1%, 0.15%, and 0.2%. The mixtures were let sit on bench for one hour before being spun at 10,000 RPM, RT, for 10 minutes. The resulting supernatants were analyzed for SARS S delta TM concentrations.

Based on the protein concentrations in the supernatants, the amounts of SARS S delta TM in the pellets (presumably bound to Alhydrogel) were calculated. At 0.05%, 0.1%, 0.15%, and 0.2% of $Al(OH)_3$, 96 ug, 61 ug, 46 ug, and 38 ug of SARS S delta TM bound for every mg of $Al(OH)_3$.

It is known that divalent anions, such as phosphate group, particulate with $Al(OH)_3$. Extensive studies have been performed to analyze how buffers interfere with particulation. By visual observation, the order of interference from strong to weak is as follows:

PBS>TBS/Tris>MES>1% Acetic Acid=$H_2O$

PBS kept its effect even diluted 20-fold. At this level, however, Tris/HCl was seen less effect.

These observations were further investigated with BSA dissolved $H_2O$, PBS, TBS, 100 mM, 50 mM, 20 mM, and 10 mM Tris-HCl, pH7.3. Due to interference with BCA, effects from BSA in 100 mM and 50 mM Tris couldn't be evaluated (BSA standards weren't prepared in either 100 mM or 50 mM Tris). At 0.1% Alhydrogel (equals 0.15% $Al(OH)_3$), 156 ug, 325 ug, 323 ug, and 326 ug BSA bound per mg $Al(OH)_3$ when diluted with PBS, 20 mM Tris, 10 mM Tris, and $H_2O$, respectively. Except for BSA/PBS, nearly all the BSA (maxi-out) was bound with $Al(OH)_3$ in Tris or $H_2O$. The actual binding capacity for BSA may be higher. In a separate experiment where $Al(OH)_3$ was maxed-out, as high as 500 ug BSA when diluted with $H_2O$ was bound per mg $Al(OH)_3$.

These results indicate that SARS S delta TM in PBS could be particulated with $Al(OH)_3$, but in a less efficient fashion, due to the interference of phosphate anion. If it is desired that SARS S delta TM particulate with $Al(OH)_3$, it would likely be better for the SARS S delta TM to be in $H_2O$ or 10/20 mM Tris.

The invention is further described by the following numbered paragraphs:

1. An isolated SARS protein, or a vector, e.g., plasmid, recombinant virus, such as a recombinant baculovirus, that expresses such a protein in vivo and/or in vitro.

2. The isolated SARS protein of paragraph 1 that is expressed recombinantly expressed.

3. The isolated SARS protein of paragraph 2 that is expressed by a recombinant virus, or the vector of paragraph 1 that is a recombinant virus.

4. The isolated SARS protein of paragraph 2 that is expressed by a DNA plasmid or the vector of paragraph 1 that is a DNA plasmid.

5. The isolated SARS protein of paragraph 3 that is expressed by a recombinant baculovirus, or the virus of paragraph 3 that is a recombinant baculovirus.

6. The isolated SARS protein or vector expressing it of any of the preceding paragraphs wherein the protein is S, M, E or N, or an epitopic fragment thereof or combination thereof.

7. The isolated SARS protein or vector expressing it of paragraph 6 which is an S protein.

8. The isolated SARS protein or vector expressing it of paragraph 6 which is S1.

9. The isolated SARS protein or vector expressing it of paragraph 6 which is S2.

10. The isolated SARS protein or vector expressing it of paragraph 6 which is an immunogenic fragment of S.

11. The isolated SARS protein or vector expressing it of paragraph 10 which is an epitope of S.

12. The isolated SARS protein or vector expressing it of paragraph 6 which is an M protein.

13. The isolated SARS protein or vector expressing it of paragraph 6 which is an immunogenic fragment of M.

14. The isolated SARS protein or vector expressing it of paragraph 13 which is an epitope of M.

15. The isolated SARS protein or vector expressing it of paragraph 6 which is an N protein.

16. The isolated SARS protein or vector expressing it of paragraph 6 which is an immunogenic fragment of N.

17. The isolated SARS protein or vector expressing it of paragraph 10 which is an epitope of N.

18. The isolated SARS protein or vector expressing it of paragraph 6 which is an E protein.

19. The isolated SARS protein or vector expressing it of paragraph 6 which is an immunogenic fragment of E.

20. The isolated SARS protein or vector expressing it of paragraph 10 which is an epitope of E.

21. The isolated SARS protein or vector that expresses the protein of any of the preceding paragraphs produced by expression from a first vector, such a baculovirus prepared via a method of homologous recombination involving a second transfer vector, e.g., plasmid, which contains exogenous nucleic acid molecule(s) to be within the first vector, wherein the transfer vector, e.g., plasmid, is prepared having a restriction site; and the preparation of the transfer vector involves cutting the transfer vector at a distance from the restriction site by an enzyme that so cuts (a cut at a distance enzyme), whereby the restriction site is excised from the transfer vector and the transfer vector has a unique sticky end; in a separate reaction, performing a polymerase chain reaction or other amplification reaction whereby the restriction site is part of amplification product of the reaction; cutting the amplification product with the cut at a distance enzyme, whereby the amplification product has a unique sticky end; and, ligating the transfer vector having the unique sticky end and the amplification product having the unique sticky end, so that intervening nucleic acid molecules are avoided.

21. The SARS protein of any of the preceding paragraphs purified to at least 90% or greater than 90% or at least 95% or greater than 95%.

22. An immunogenic, immunological or vaccine composition containing, consisting essentially or consisting of a SARS protein or vector that expresses the SARS protein as in any of the preceding paragraphs.

23. The composition of paragraph 22 wherein the SARS protein is purified to at least 90% or greater than 90% or at least 95% or greater than 95%.

24. The composition of paragraph 22 or 23 including a carrier or diluent and/or adjuvant.

25. A method for eliciting an immunological response against SARS in a host susceptible to infection thereby comprising administering the composition of paragraph 22 or the protein or vector of any of the preceding paragraphs to the host.

26. The method of paragraph 25 wherein the administering is by injection, or orally, or mucosally, or topically.

27. An anti-SARS protein antibody elicited by the protein or vector of any of the preceding paragraphs.

28. The antibody of paragraph 27 which is specific to the S protein.

29. The antibody of paragraphs 27 or 28 which is a monoclonal antibody.

30. A diagnostic kit or assay comprising the monoclonal antibody of paragraph 29 or a protein of any of the preceding paragraphs.

31. A method for detecting SARS comprising detecting in a sample binding by an antigen to a monoclonal antibody of paragraph 29, or detecting binding of an antibody in the sample to a protein of any of the preceding paragraphs.

32. In an anti-influenza vaccine wherein the improvement comprises it containing or expressing a SARS protein as in any of the preceding paragraphs, or a vector as in any of the preceding paragraphs.

33. In an anti-pneumonia vaccine wherein the improvement comprises it containing or expressing a SARS protein as in any of the preceding paragraphs, or a vector as in any of the preceding paragraphs.

34. In an anti-influenza vaccine wherein the improvement comprises it containing or expressing a SARS protein as in any of the preceding paragraphs, or a vector as in any of the preceding paragraphs, and it containing or expressing a pneumoccocal protein.

35. In an anti-pneumococcal vaccine wherein the improvement comprises it containing or expressing a SARS protein as in any of the preceding paragraphs, or a vector as in any of the preceding paragraphs, and it containing or expressing an influenza protein.

36. A composition of any of the preceding paragraphs in an aerosolizer, or aerosol form or a pump spray dispenser, those aerosolizers, aerosol forms or pump spray dispenser intended for intranasal administration.

37. A composition of any of the preceding paragraphs wherein the SARS protein, present or expressed, is from more than one isolate, e.g., at least two or three isolates, such as three isolates.

38. A composition as in any of the preceding paragraphs wherein the influenza protein, expressed or present, is HA and/or NA and/or M2.

39. A composition as in any of the preceding paragraphs wherein the influenza protein, expressed or present, is from one or more, such as two or more, e.g., three, different influenza strains.

40. A kit for preparing a composition of any of the preceding paragraphs comprising (a) SARS protein(s) or vector(s) expressing SARS protein(s) in one or more containers, and/or (b) influenza protein(s) or vectors(s) expressing influenza protein(s) in one or more containers, and/or (c) pneumonia protein(s) or vector(s) expressing pneumonia protein(s) in one or more containers, wherein the kit optionally contains instructions for administration of the compositions and/or admixture of ingredients, and the containers are optionally in the same packaging.

41. A method for preparing a first vector, such a baculovirus, prepared via a method of homologous recombination involving a second transfer vector, e.g., plasmid, which contains exogenous nucleic acid molecule(s) to be within the first vector, wherein the transfer vector, e.g., plasmid, is prepared having a restriction site; and the preparation of the transfer vector involves cutting the transfer vector at a distance from the restriction site by an enzyme that so cuts (a cut at a distance enzyme), whereby the restriction site is excised from the transfer vector and the transfer vector has a unique sticky end; in a separate reaction, performing a polymerase chain reaction or other amplification reaction whereby the restriction site is part of amplification product of the reaction; cutting the amplification product with the cut at a distance enzyme, whereby the amplification product has a unique sticky end; and, ligating the transfer vector having the unique sticky end and the amplification product having the unique sticky end, so that intervening nucleic acid molecules are avoided.

42. The method of paragraph 41 wherein the method is for joining a nucleic acid molecule for a leader sequence to a nucleic acid molecule encoding a protein of interest.

43. The method of any of paragraphs wherein the enzyme is SapI.

44. An isolated protein or vector that expresses the protein produced by expression from a first vector, such a baculovirus prepared via a method of homologous recombination involving a second transfer vector, e.g., plasmid, which contains exogenous nucleic acid molecule(s) to be within the first vector, wherein the transfer vector, e.g., plasmid, is prepared having a restriction site; and the preparation of the transfer vector involves cutting the transfer vector at a distance from the restriction site by an enzyme that so cuts (a cut at a distance enzyme), whereby the restriction site is excised from the transfer vector and the transfer vector has a unique sticky end; in a separate reaction, performing a polymerase chain reaction or other amplification reaction whereby the restriction site is part of amplification product of the reaction; cutting the amplification product with the cut at a distance enzyme, whereby the amplification product has a unique sticky end; and, ligating the transfer vector having the unique sticky end and the amplification product having the unique sticky end, so that intervening nucleic acid molecules are avoided.

Having thus described in detail preferred embodiments of the present invention, it is to be understood that the invention defined by the appended claims is not to be limited by particular details set forth in the above description as many apparent variations thereof are possible without departing from the spirit or scope thereof.

REFERENCES

Alving, C. R. and G. M. Glenn. U.S. Pat. No. 5,910,306 Jun. 8, 1999
Audonnet, J.-C. and P. Baudu. U.S. Pat. No. 6,159,477 Dec. 12, 2000
Audonnet, J.-C., A. Bouchardon, et al. U.S. Pat. No. 6,228,846 May 8, 2001
Audonnet, J.-C. F., P. G. N. Baudu, et al. U.S. Pat. No. 6,387,376 May 14, 2002
Barbour, A. G., S. Bergstrom, et al. U.S. Pat. No. 6,143,872 Nov. 7, 2000
Bocchia, M., P. A. Wentworth, et al. (1995). "Specific binding of leukemia oncogene fusion protein peptides to HLA class I molecules." Blood 85(10): 2680-4.
Bonavia, A., B. D. Zelus, et al. (2003). "Identification of a receptor-binding domain of the spike glycoprotein of human coronavirus HCoV-229E." J Virol 77(4): 2530-8.
Bondos, S. E. and A. Bicknell (2003). "Detection and prevention of protein aggregation before, during, and after purification." Anal Biochem 316(2): 223-31.
Briles, D. E., S. Hollingshead, et al. U.S. Pat. No. 5,955,089 Sep. 21, 1999
Briles, D. E., L. S. McDaniel, et al. U.S. Pat. No. 6,500,613 Dec. 31, 2002
Briles, D. E., L. S. McDaniel, et al. U.S. Pat. No. 6,232,116 May 15, 2001
Briles, D. E., L. S. McDaniel, et al. U.S. Pat. No. 6,231,870 May 15, 2001
Briles, D. E., L. S. McDaniel, et al. U.S. Pat. No. 6,004,802 Dec. 21, 1999
Briles, D. E. and H.-Y. Wu. U.S. Pat. No. 6,042,838 Mar. 28, 2000
Briles, D. E. and H.-Y. Wu. U.S. Pat. No. 6,027,734 Feb. 22, 2000
Briles, D. E. and J. L. Yother. U.S. Pat. No. 5,965,400 Oct. 12, 1999
Briles, D. E. and J. L. Yother. U.S. Pat. No. 5,871,943 Feb. 16, 1999
Briles, D. E. and J. L. Yother. U.S. Pat. No. 5,856,170 Jan. 5, 1999
Briles, D. E. and J. L. Yother. U.S. Pat. No. 5,804,193 Sep. 8, 1998
Briles, D. E. and J. L. Yother. U.S. Pat. No. 5,753,463 May 19, 1998
Briles, D. E., J. L. Yother, et al. U.S. Pat. No. 5,997,882 Dec. 7, 1999
Briles, D. E., J. L. Yother, et al. U.S. Pat. No. 5,980,909 Nov. 9, 1999
Briles, D. E., J. L. Yother, et al. U.S. Pat. No. 5,476,929 Dec. 19, 1995
Briles, D. E., J. L. Yother, et al. U.S. Pat. No. 5,965,141 Oct. 12, 1999
Brown, E. G. and J. A. Tetro (2003). "Comparative analysis of the SARS coronavirus genome: a good start to a long journey." Lancet 361(9371): 1756-7.
Clark, S. C. and R. Kamen (1987). "The human hematopoietic colony-stimulating factors." Science 236(4806): 1229-37.
Corapi, W. V., R. J. Darteil, et al. (1995). "Localization of antigenic sites of the S glycoprotein of feline infectious peritonitis virus involved in neutralization and antibody-dependent enhancement." J Virol 69(5): 2858-62.
Dale, B., M. Yamanaka, et al. U.S. Pat. No. 5,811,104 Sep. 22, 1998
David, G. S. and H. E. Greene. U.S. Pat. No. 4,376,110 Mar. 8, 1983
Drosten, C., S. Gunther, et al. (2003). "Identification of a novel coronavirus in patients with severe acute respiratory syndrome." N Engl J Med 348(20): 1967-76.
Dunn, A. R., N. M. Gough, et al. U.S. Pat. No. 5,602,007 Feb. 11, 1997
Eldridge, J. H., J. K. Staas, et al. (1991). "Biodegradable microspheres as a vaccine delivery system." Mol Immunol 28(3): 287-94.
Engelhard, V. H. (1994). "Structure of peptides associated with class I and class II MHC molecules." Annu Rev Immunol 12: 181-207.
FDA, U. Good Laboratory Practice for Nonclinical Laboratory Studies. 21 C.F.R. section 58.
Fouchier, R. A., T. Kuiken, et al. (2003). "Aetiology: Koch's postulates fulfilled for SARS virus." Nature 423(6937): 240.
Garvin, R. T. and L. T. Malek. U.S. Pat. No. 5,641,663 Jun. 24, 1997
Gennaro, A. R., Ed. (1985). Remington's Pharmaceutical Science. Easton, Pa., Mack Publishing, Co.
Glenn, G. M. and C. R. Alving. U.S. Pat. No. 5,980,898 Nov. 9, 1999
Grant, S. M. and R. C. Heel (1992). "Recombinant granulocyte-macrophage colony-stimulating factor (rGM-CSF). A review of its pharmacological properties and prospective role in the management of myelosuppression." Drugs 43(4): 516-60.
Hammerling, e. a. (1981). Monoclonal Antibodies and T-Cell Hybridomas. NY, Elsevier: 563-681.
Hartig, P. C., M. C. Cardon, et al. (1991). "Generation of recombinant baculovirus via liposome-mediated transfection." Biotechniques 11(3): 310, 312-3.
Hartig, P. C., M. A. Chapman, et al. (1989). "Insect virus: assays for toxic effects and transformation potential in mammalian cells." Appl Environ Microbiol 55(8): 1916-20.
Holmes, K. V. (2003). "SARS-associated coronavirus." N Engl J Med 348(20): 1948-51.
Huebner, R. C., J. A. Norman, et al. U.S. Pat. No. 6,451,769 Sep. 17, 2002
Hunter. (1995). The Theory and Practical Application of Adjuvants. D. E. S. Stewart-Tull. NY, John Wiley and Sons: 51-94.
Jones, T., F. Allard, et al. (2003). "A nasal Proteosome influenza vaccine containing baculovirus-derived hemagglutinin induces protective mucosal and systemic immunity." Vaccine 21(25-26): 3706-12.
Klepfer, S., A. P. Reed, et al. (1995). "Cloning and expression of FECV spike gene in vaccinia virus. Immunization with FECV S causes early death after FIPV challenge." Adv Exp Med Biol 380: 235-41.
Knell, J., G. E. Smith, et al. WIPO Patent WO00/46354 2000-08-10
Kohler, G., S. C. Howe, et al. (1976). "Fusion between immunoglobulin-secreting and nonsecreting myeloma cell lines." Eur J Immunol 6(4): 292-5.

Kohler, G. and C. Milstein (1975). "Continuous cultures of fused cells secreting antibody of predefined specificity." Nature 256(5517): 495-7.

Kohler, G. and C. Milstein (1976). "Derivation of specific antibody-producing tissue culture and tumor lines by cell fusion." Eur J Immunol 6(7): 511-9.

Kontoyiannis, D. P., R. Pasqualini, et al. (2003). "Aminopeptidase N inhibitors and SARS." Lancet 361(9368): 1558.

Koprowski, H., W. U. Gerhard, et al. U.S. Pat. No. 4,196,265 Apr. 1, 1980

Ksiazek, T. G., D. Erdman, et al. (2003). "A novel coronavirus associated with severe acute respiratory syndrome." N Engl J Med 348(20): 1953-66.

Liu, S., R. Tobias, et al. (1997). "Removal of endotoxin from recombinant protein preparations." Clin Biochem 30(6): 455-63.

Loosmore, S. M. and J.-C. F. Audonnet. US Published Application 20030104008

Marra, M. A., S. J. Jones, et al. (2003). "The Genome sequence of the SARS-associated coronavirus." Science 300(5624): 1399-404.

Matsuo, K., Y. Chujo, et al. U.S. Pat. No. 5,858,369 Jan. 12, 1999

Miller, T. J., S. Klepfer, et al. U.S. Pat. No. 6,372,224 Apr. 16, 2002

Milstein, C. (1980). "Monoclonal antibodies." Sci Am 243 (4): 66-74.

Paoletti, E. and R. Gettig. U.S. Pat. No. 5,858,373 Jan. 12, 1999

Pharmeuropa (1996). Pharmeuropa 8(2).

Pillai, S. and R. Eby. U.S. Pat. No. 5,334,379 Aug. 2, 1994

Powell, M. F., M. J. Newman, et al. (1995). Vaccine design: the subunit and adjuvant approach. New York, Plenum Press.

Regelson, W., S. Kuhar, et al. (1960). "Synthetic polyelectrolytes as tumour inhibitors." Nature 186: 778-80.

Rosen (1968). Hemagglutination with Animal Viruses in Fundamental Techniques in Virology. New York, Academic Press.

Rota, P. A., M. S. Oberste, et al. (2003). "Characterization of a novel coronavirus associated with severe acute respiratory syndrome." Science 300(5624): 1394-9.

Rowe, R. C., P. J. Sheskey, et al., Eds. (2003). Handbook of Pharmaceutical Excipients. London and Washington D.C., Pharmaceutical Press and American Pharmaceutical Association.

Ruan, Y. J., C. L. Wei, et al. (2003). "Comparative full-length genome sequence analysis of 14 SARS coronavirus isolates and common mutations associated with putative origins of infection." Lancet 361(9371): 1779-85.

Saif, L. J. (1993). "Coronavirus immunogens." Vet Microbiol 37(3-4): 285-97.

Schultze, B., H. J. Gross, et al. (1991). "The S protein of bovine coronavirus is a hemagglutinin recognizing 9-O-acetylated sialic acid as a receptor determinant." J Virol 65(11): 6232-7.

Scott, F. W. (1987). "Immunization against feline coronaviruses." Adv Exp Med Biol 218: 569-76.

Smith, G. E., J. DeBartolomeis, et al. U.S. Pat. No. 6,224,882 May 1, 2001

Smith, G. E., H. G. Foellmer, et al. U.S. Pat. No. 6,103,526 Aug. 15, 2000

Smith, G. E., J. T. Matthews, et al. U.S. Pat. No. 6,485,729 Nov. 26, 2002

Smith, G. E. and M. D. Summers. U.S. Pat. No. 4,879,236 Nov. 7, 1989—The portion of the term of this patent subsequent to May 17, 2005 has been disclaimed.

Smith, G. E. and M. D. Summers. U.S. Pat. No. 4,745,051 May 17, 1988

Smith, G. E., F. Volvovitz, et al. U.S. Pat. No. 5,762,939 Jun. 9, 1998

Smith, G. E., F. Volvovitz, et al. U.S. Pat. No. 6,245,532 Jun. 12, 2001

Smith, G. E., F. Volvovitz, et al. U.S. Pat. No. 5,858,368 Jan. 12, 1999

Smith, G. E. e. a. (1983). "Molecular Engineering of the Autographa californica nuclear polyhedrosis virus genome: deletion mutaitions within the polyhedrin gene." J. Virol. 46: 584-593.

Souza, L. M. U.S. Pat. No. 4,999,291 Mar. 12, 1991—The portion of the term of this patent subsequent to Mar. 7, 2006 has been disclaimed.

Stohr, K. "Sars—Epidemiology" Presented at SARS: Developing a Research Response, May 30, 2003 (NIH, Bethesda, Md.) (slides available at the NIH website).

Sugioka, T., S. Miura, et al. U.S. Pat. No. 6,348,540 Feb. 19, 2002

Summers, M. D. and G: E. Smith (1987). "A manual of methods for baculovirus vectors and insect cell culture porcedures." Texas Agricultural Experiment Station Bulletin 1555.

Tang, D.-C. C., Z. Shi, et al. US Published Application 20030045492

Todd, C. W., L. A. Pozzi, et al. (1997). "Development of an adjuvant-active nonionic block copolymer for use in oil-free subunit vaccines formulations." Vaccine 15(5): 564-70.

Tuboly, T., E. Nagy, et al. (1994). "Immunogenicity of the S protein of transmissible gastroenteritis virus expressed in baculovirus." Arch Virol 137(1-2): 55-67.

Vennema, H., R. J. de Groot, et al. (1990). "Early death after feline infectious peritonitis virus challenge due to recombinant vaccinia virus immunization." J Virol 64(3): 1407-9.

Vennema, H., R. J. de Groot, et al. (1990). "Immunogenicity of recombinant feline infectious peritonitis virus spike protein in mice and kittens." Adv Exp Med Biol 276: 217-22.

Wands, J. R. and V. R. Zurawski, Jr. (1981). "High affinity monoclonal antibodies to hepatitis B surface antigen (HBsAg) produced by somatic cell hybrids." Gastroenterology 80(2): 225-32.

Warfield, R. B. and L. F. Stumpf. U.S. Pat. No. 2,909,462 Oct. 20, 1959

Wasmoen, T. and H.-J. Chu. U.S. Pat. No. 5,849,303 Dec. 15, 1998

Yu, X. J., C. Luo, et al. (2003). "Putative hAPN receptor binding sites in SARS_CoV spike protein." Acta Pharmacol Sin 24(6): 481-8.

Zelus, B. D., D. R. Wessner, et al. (1998). "Purified, soluble recombinant mouse hepatitis virus receptor, Bgp1(b), and Bgp2 murine coronavirus receptors differ in mouse hepatitis virus binding and neutralizing activities." J Virol 72(9): 7237-44.

What is claimed is:

1. A recombinant baculovirus vector that expresses:

(a) a baculovirus signal peptide; and (b) a SARS S protein, wherein expression of the SARS S protein is under control of a polyhedrin promoter.

2. The recombinant baculovirus vector of claim 1, wherein the baculovirus signal peptide comprises an amino acid sequence Met Pro Leu Tyr Lys Leu Leu Asn Val Leu Trp Leu Val Ala Val Ser Asn Ala Ile (SEQ ID NO: 28).

3. A recombinant baculovirus vector that comprises:

an isolated nucleic acid comprising a nucleotide sequence GCCCTTGTAC AAATTGTTAA ACGTTTTGTG GTTGGTCGCC GTTTCTAACG CGAT (SEQ ID NO: 29) encoding a baculovirus signal peptide, wherein the recombinant baculovirus vector also expresses a SARS S protein, wherein expression of the SARS S protein is under control of a polyhedrin promoter.

4. The recombinant baculovirus vector of claim 1 or 3, wherein the polyhedrin promoter is *Autographa californica* Nuclear Polyhedrosis Virus AcNPV.

5. The recombinant baculovirus vector of claim 1 or 3, wherein the SARS S protein is truncated.

6. An immunogenic composition comprising the recombinant baculovirus vector of claim 1 or 3.

7. An immunogenic composition comprising the recombinant baculovirus vector of claim 1 or 3, further comprising a carrier or diluent and/or adjuvant.

8. An immunogenic composition comprising the recombinant baculovirus vector of claim 1 or 3 in an aerosolizer or aerosol form, or a pump spray dispenser, thereby permitting intranasal administration of the immunogenic composition.

9. A method for producing a biologically active, highly pure, recombinant SARS S protein, comprising:

(a) infecting insect cells that grow in serum-free media with a recombinant baculovirus that comprises DNA coding for SARS S protein such that the SARS S protein is expressed recombinantly;

(b) culturing the infected insect cells in serum-free media; and (c) purifying the recombinant SARS S protein to 95% or greater purity, wherein:

the biologically active, highly pure, recombinant SARS S protein is produced; and is biologically active such that it agglutinates red blood cells.

10. The method of claim 9, wherein the SARS S protein consists essentially of an S1 protein.

11. The method of claim 9, wherein the SARS S protein consists essentially of an S2 protein.

12. The method of claim 9, wherein the baculovirus is *Autographa californica* Nuclear Polyhedrosis Virus (AcNPV).

13. The method of claim 12, wherein the DNA coding for the SARS S protein is under the control of a AcNPV polyhedrin promoter.

14. The method of claim 13, wherein the SARS S protein is expressed with a baculovirus signal peptide.

15. The method of claim 13 or 14, wherein the SARS S protein is expressed with a His tag.

16. The method of claim 14, wherein DNA coding for the baculovirus signal peptide is seamlessly joined to the DNA coding for the SARS S protein, without addition of a signal nucleotide.

17. The method of claim 16, wherein the recombinant baculovirus is prepared by a transfer vector, wherein the transfer vector is produced by a process comprising:

(a) cutting an initial vector having DNA coding for a leader sequence and a restriction site at a distance from the restriction site by an enzyme that so cuts, whereby the restriction site is excised from the initial vector, and the initial vector has a unique sticky end;

(b) performing in a separate reaction a nucleic acid amplification reaction of DNA coding for the SARS S protein to obtain an amplification product, whereby the restriction site is part of the amplification product;

(c) cutting the amplification product with the enzyme, whereby the amplification product has a unique sticky end; and (d) ligating the initial vector having the unique sticky end and the amplification product having the unique sticky end such that the transfer vector is obtained and intervening nucleic acid molecules between the DNA coding for the leader sequence and the DNA encoding the SARS S protein are avoided.

18. The method of claim 17, wherein the enzyme is Sapl.

19. The method of claim 17, wherein the amplification reaction is a polymerase chain reaction.

20. A method for preparing a baculovirus transfer vector for preparing a recombinant baculovirus that expresses a heterologous protein and a baculovirus signal peptide, wherein DNA coding for the heterologous protein is seamlessly joined to DNA coding for the baculovirus signal peptide, without addition of a single nucleotide, comprising:
  (a) cutting an initial vector having DNA coding for a leader sequence and a restriction site at a distance from the restriction site by an enzyme that so cuts, whereby the restriction site is excised from the initial vector, and the initial vector has a unique sticky end;
  (b) performing in a separate reaction a nucleic acid amplification reaction of DNA coding for the SARS S protein to obtain an amplification product, whereby the restriction site is part of the amplification product;
  (c) cutting the amplification product with the enzyme, whereby the amplification product has a unique sticky end; and
  (d) ligating the initial vector having the unique sticky end and the amplification product having the unique sticky end such that the transfer vector is obtained and intervening nucleic acid molecules between the DNA coding for the leader sequence and the DNA encoding the SARS S protein are avoided.

* * * * *

SEQUENCE LISTING

<160> NUMBER OF SEQ ID NOS: 29

<210> SEQ ID NO 1
<211> LENGTH: 3769
<212> TYPE: DNA
<213> ORGANISM: SARS coronavirus

<400> SEQUENCE: 1
catgtttatt ttcttattat ttcttactct cactagtggt agtgaccttg accggtgcac 60
cacttttgat gatgttcaag ctcctaatta cactcaacat acttcatcta tgaggggggt 120
ttactatcct gatgaaattt ttagatcaga cactctttat ttaactcagg atttatttct 180
tccattttat tctaatgtta cagggtttca tactattaat catacgtttg gcaaccctgt 240
catacctttt aaggatggta tttattttgc tgccacagag aaatcaaatg ttgtccgtgg 300
ttgggttttt ggttctacca tgaacaacaa gtcacagtcg gtgattatta ttaacaattc 360
tactaatgtt gttatacgag catgtaactt tgaattgtgt gacaaccctt tctttgctgt 420
ttctaaaccc atgggtacac agacacatac tatgatattc gataatgcat ttaattgcac 480
tttcgagtac atatctgatg ccttttcgct tgatgtttca gaaaagtcag gtaattttaa 540
acacttacga gagtttgtgt ttaaaaataa agatgggttt ctctatgttt ataagggcta 600
tcaacctata gatgtagttc gtgatctacc ttctggtttt aacactttga aacctatttt 660
taagttgcct cttggtatta acattacaaa ttttagagcc attcttacag ccttttcacc 720
tgctcaagac atttggggca cgtcagctgc agcctatttt gttggctatt taaagccaac 780
tacatttatg ctcaagtatg atgaaaatgg tacaatcaca gatgctgttg attgttctca 840
aaatccactt gctgaactca aatgctctgt taagagcttt gagattgaca aaggaattta 900
ccagacctct aatttcaggg ttgttccctc aggagatgtt gtgagattcc ctaatattac 960
aaacttgtgt ccttttggag aggtttttaa tgctactaaa ttcccttctg tctatgcatg 1020
ggagagaaaa aaaatttcta attgtgttgc tgattactct gtgctctaca actcaacatt 1080
tttttcaacc tttaagtgct atggcgtttc tgccactaag ttgaatgatc tttgcttctc 1140
caatgtctat gcagattctt ttgtagtcaa gggagatgat gtaagacaaa tagcgccagg 1200
acaaactggt gttattgctg attataatta taaattgcca gatgatttca tgggttgtgt 1260
ccttgcttgg aatactagga acattgatgc tacttcaact ggtaattata attataaata 1320
taggtatctt agacatggca agcttaggcc ctttgagaga gacatatcta atgtgccttt 1380
ctcccctgat ggcaaacctt gcaccccacc tgctcttaat tgttattggc cattaaatga 1440
ttatggtttt tacaccacta ctggcattgg ctaccaacct tacagagttg tagtactttc 1500
ttttgaactt ttaaatgcac cggccacggt ttgtggacca aaattatcca ctgaccttat 1560
taagaaccag tgtgtcaatt ttaattttaa tggactcact ggtactggtg tgttaactcc 1620
ttcttcaaag agatttcaac catttcaaca atttggccgt gatgtttctg atttcactga 1680
ttccgttcga gatcctaaaa catctgaaat attagacatt tcaccttgcg cttttggggg 1740
tgtaagtgta attacacctg gaacaaatgc ttcatctgaa gttgctgttc tatatcaaga 1800
tgttaactgc actgatgttt ctacagcaat tcatgcagat caactcacac cagcttggcg 1860
catatattct actggaaaca atgtattcca gactcaagca ggctgtctta taggagctga 1920
gcatgtcgac acttcttatg agtgcgacat tcctattgga gctggcattt gtgctagtta 1980
ccatacagtt tctttattac gtagtactag ccaaaaatct attgtggctt atactatgtc 2040

-continued

```
tttaggtgct gatagttcaa ttgcttactc taataacacc attgctatac ctactaactt   2100
ttcaattagc attactacag aagtaatgcc tgtttctatg gctaaaacct ccgtagattg   2160
taatatgtac atctgcggag attctactga atgtgctaat ttgcttctcc aatatggtag   2220
cttttgcaca caactaaatc gtgcactctc aggtattgct gctgaacagg atcgcaacac   2280
acgtgaagtg ttcgctcaag tcaaacaaat gtacaaaacc ccaactttga aatattttgg   2340
tggttttaat ttttcacaaa tattacctga ccctctaaag ccaactaaga ggtcttttat   2400
tgaggacttg ctctttaata aggtgacact cgctgatgct ggcttcatga agcaatatgg   2460
cgaatgccta ggtgatatta atgctagaga tctcatttgt gcgcagaagt tcaatggact   2520
tacagtgttg ccacctctgc tcactgatga tatgattgct gcctacactg ctgctctagt   2580
tagtggtact gccactgctg gatggacatt tggtgctggc gctgctcttc aaataccttt   2640
tgctatgcaa atggcatata ggttcaatgg cattggagtt acccaaaatg ttctctatga   2700
gaaccaaaaa caaatcgcca accaatttaa caaggcgatt agtcaaattc aagaatcact   2760
tacaacaaca tcaactgcat tgggcaagct gcaagacgtt gttaaccaga atgctcaagc   2820
attaaacaca cttgttaaac aacttagctc taattttggt gcaatttcaa gtgtgctaaa   2880
tgatatcctt tcgcgacttg ataaagtcga ggcggaggta caaattgaca ggttaattac   2940
aggcagactt caaagccttc aaacctatgt aacacaacaa ctaatcaggg ctgctgaaat   3000
cagggcttct gctaatcttg ctgctactaa aatgtctgag tgtgttcttg gacaatcaaa   3060
aagagttgac ttttgtggaa agggctacca ccttatgtcc ttcccacaag cagccccgca   3120
tggtgttgtc ttcctacatg tcacgtatgt gccatcccag gagaggaact tcaccacagc   3180
gccagcaatt tgtcatgaag gcaaagcata cttccctcgt gaaggtgttt ttgtgtttaa   3240
tggcacttct tggtttatta cacagaggaa cttcttttct ccacaaataa ttactacaga   3300
caatacattt gtctcaggaa attgtgatgt cgttattggc atcattaaca acacagttta   3360
tgatcctctg caacctgagc ttgactcatt caaagaagag ctggacaagt acttcaaaaa   3420
tcatacatca ccagatgttg atcttggcga catttcaggc attaacgctt ctgtcgtcaa   3480
cattcaaaaa gaaattgacc gcctcaatga ggtcgctaaa aatttaaatg aatcactcat   3540
tgaccttcaa gaattgggaa aatatgagca atatattaaa tggccttggt atgtttggct   3600
cggcttcatt gctggactaa ttgccatcgt catggttaca atcttgcttt gttgcatgac   3660
tagttgttgc agttgcctca agggtgcatg ctcttgtggt tcttgctgca agtttgatga   3720
ggatgactct gagccagttc tcaagggtgt caaattacat tacacataa               3769
```

<210> SEQ ID NO 2
<211> LENGTH: 1254
<212> TYPE: PRT
<213> ORGANISM: SARS coronavirus

<400> SEQUENCE: 2

```
Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80
```

```
Ile Pro Phe Lys Asp Gly Ile Tyr Phe Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Phe Lys Leu Pro Leu Gly
    210                 215                 220

Ile Asn Ile Thr Asn Phe Arg Ala Ile Leu Thr Ala Phe Ser Pro Ala
225                 230                 235                 240

Gln Asp Ile Trp Gly Thr Ser Ala Ala Ala Tyr Phe Val Gly Tyr Leu
                245                 250                 255

Lys Pro Thr Thr Phe Met Leu Lys Tyr Asp Glu Asn Gly Thr Ile Thr
            260                 265                 270

Asp Ala Val Asp Cys Ser Gln Asn Pro Leu Ala Glu Leu Lys Cys Ser
        275                 280                 285

Val Lys Ser Phe Glu Ile Asp Lys Gly Ile Tyr Gln Thr Ser Asn Phe
    290                 295                 300

Arg Val Val Pro Ser Gly Asp Val Val Arg Phe Pro Asn Ile Thr Asn
305                 310                 315                 320

Leu Cys Pro Phe Gly Glu Val Phe Asn Ala Thr Lys Phe Pro Ser Val
                325                 330                 335

Tyr Ala Trp Glu Arg Lys Lys Ile Ser Asn Cys Val Ala Asp Tyr Ser
            340                 345                 350

Val Leu Tyr Asn Ser Thr Phe Phe Ser Thr Phe Lys Cys Tyr Gly Val
        355                 360                 365

Ser Ala Thr Lys Leu Asn Asp Leu Cys Phe Ser Asn Val Tyr Ala Asp
    370                 375                 380

Ser Phe Val Val Lys Gly Asp Asp Val Arg Gln Ile Ala Pro Gly Gln
385                 390                 395                 400

Thr Gly Val Ile Ala Asp Tyr Asn Tyr Lys Leu Pro Asp Asp Phe Met
                405                 410                 415

Gly Cys Val Leu Ala Trp Asn Thr Arg Asn Ile Asp Ala Thr Ser Thr
            420                 425                 430

Gly Asn Tyr Asn Tyr Lys Tyr Arg Tyr Leu Arg His Gly Lys Leu Arg
        435                 440                 445

Pro Phe Glu Arg Asp Ile Ser Asn Val Pro Phe Ser Pro Asp Gly Lys
    450                 455                 460

Pro Cys Thr Pro Pro Ala Leu Asn Cys Tyr Trp Pro Leu Asn Asp Tyr
465                 470                 475                 480

Gly Phe Tyr Thr Thr Thr Gly Ile Gly Tyr Gln Pro Tyr Arg Val Val
                485                 490                 495

Val Leu Ser Phe Glu Leu Leu Asn Ala Pro Ala Thr Val Cys Gly Pro
```

```
                   500              505              510
Lys Leu Ser Thr Asp Leu Ile Lys Asn Gln Cys Val Asn Phe Asn Phe
            515              520              525

Asn Gly Leu Thr Gly Thr Gly Val Leu Thr Pro Ser Ser Lys Arg Phe
            530              535              540

Gln Pro Phe Gln Gln Phe Gly Arg Asp Val Ser Asp Phe Thr Asp Ser
545              550              555              560

Val Arg Asp Pro Lys Thr Ser Glu Ile Leu Asp Ile Ser Pro Cys Ala
                565              570              575

Phe Gly Gly Val Ser Val Ile Thr Pro Gly Thr Asn Ala Ser Ser Glu
            580              585              590

Val Ala Val Leu Tyr Gln Asp Val Asn Cys Thr Asp Val Ser Thr Ala
            595              600              605

Ile His Ala Asp Gln Leu Thr Pro Ala Trp Arg Ile Tyr Ser Thr Gly
        610              615              620

Asn Asn Val Phe Gln Thr Gln Ala Gly Cys Leu Ile Gly Ala Glu His
625              630              635              640

Val Asp Thr Ser Tyr Glu Cys Asp Ile Pro Ile Gly Ala Gly Ile Cys
            645              650              655

Ala Ser Tyr His Thr Val Ser Leu Leu Arg Ser Thr Ser Gln Lys Ser
            660              665              670

Ile Val Ala Tyr Thr Met Ser Leu Gly Ala Asp Ser Ser Ile Ala Tyr
            675              680              685

Ser Asn Asn Thr Ile Ala Ile Pro Thr Asn Phe Ser Ile Ser Ile Thr
            690              695              700

Thr Glu Val Met Pro Val Ser Met Ala Lys Thr Ser Val Asp Cys Asn
705              710              715              720

Met Tyr Ile Cys Gly Asp Ser Thr Glu Cys Ala Asn Leu Leu Leu Gln
                725              730              735

Tyr Gly Ser Phe Cys Thr Gln Leu Asn Arg Ala Leu Ser Gly Ile Ala
            740              745              750

Ala Glu Gln Asp Arg Asn Thr Arg Glu Val Phe Ala Gln Val Lys Gln
            755              760              765

Met Tyr Lys Thr Pro Thr Leu Lys Tyr Phe Gly Gly Phe Asn Phe Ser
770              775              780

Gln Ile Leu Pro Asp Pro Leu Lys Pro Thr Lys Arg Ser Phe Ile Glu
785              790              795              800

Asp Leu Leu Phe Asn Lys Val Thr Leu Ala Asp Ala Gly Phe Met Lys
                805              810              815

Gln Tyr Gly Glu Cys Leu Gly Asp Ile Asn Ala Arg Asp Leu Ile Cys
            820              825              830

Ala Gln Lys Phe Asn Gly Leu Thr Val Leu Pro Pro Leu Leu Thr Asp
            835              840              845

Asp Met Ile Ala Ala Tyr Thr Ala Ala Leu Val Ser Gly Thr Ala Thr
            850              855              860

Ala Gly Trp Thr Phe Gly Ala Gly Ala Ala Leu Gln Ile Pro Phe Ala
865              870              875              880

Met Gln Met Ala Tyr Arg Phe Asn Gly Ile Gly Val Thr Gln Asn Val
                885              890              895

Leu Tyr Glu Asn Gln Lys Gln Ile Ala Asn Gln Phe Asn Lys Ala Ile
                900              905              910

Ser Gln Ile Gln Glu Ser Leu Thr Thr Thr Ser Thr Ala Leu Gly Lys
            915              920              925
```

| Leu | Gln | Asp | Val | Val | Asn | Gln | Asn | Ala | Gln | Ala | Leu | Asn | Thr | Leu | Val |
| | | 930 | | | | | 935 | | | | | 940 | | | |

| Lys | Gln | Leu | Ser | Ser | Asn | Phe | Gly | Ala | Ile | Ser | Ser | Val | Leu | Asn | Asp |
| 945 | | | | | 950 | | | | | 955 | | | | | 960 |

| Ile | Leu | Ser | Arg | Leu | Asp | Lys | Val | Glu | Ala | Glu | Val | Gln | Ile | Asp | Arg |
| | | | | 965 | | | | | 970 | | | | | 975 | |

| Leu | Ile | Thr | Gly | Arg | Leu | Gln | Ser | Leu | Gln | Thr | Tyr | Val | Thr | Gln | Gln |
| | | | 980 | | | | | 985 | | | | | 990 | | |

| Leu | Ile | Arg | Ala | Ala | Glu | Ile | Arg | Ala | Ser | Ala | Asn | Leu | Ala | Ala | Thr |
| | | 995 | | | | | 1000 | | | | | 1005 | | | |

| Lys | Met | Ser | Glu | Cys | Val | Leu | Gly | Gln | Ser | Lys | Arg | Val | Asp | Phe |
| 1010 | | | | | 1015 | | | | | 1020 | | | | |

| Cys | Gly | Lys | Gly | Tyr | His | Leu | Met | Ser | Phe | Pro | Gln | Ala | Ala | Pro |
| 1025 | | | | | 1030 | | | | | 1035 | | | | |

| His | Gly | Val | Val | Phe | Leu | His | Val | Thr | Tyr | Val | Pro | Ser | Gln | Glu |
| 1040 | | | | | 1045 | | | | | 1050 | | | | |

| Arg | Asn | Phe | Thr | Thr | Ala | Pro | Ala | Ile | Cys | His | Glu | Gly | Lys | Ala |
| 1055 | | | | | 1060 | | | | | 1065 | | | | |

| Tyr | Phe | Pro | Arg | Glu | Gly | Val | Phe | Val | Phe | Asn | Gly | Thr | Ser | Trp |
| 1070 | | | | | 1075 | | | | | 1080 | | | | |

| Phe | Ile | Thr | Gln | Arg | Asn | Phe | Phe | Ser | Pro | Gln | Ile | Ile | Thr | Thr |
| 1085 | | | | | 1090 | | | | | 1095 | | | | |

| Asp | Asn | Thr | Phe | Val | Ser | Gly | Asn | Cys | Asp | Val | Val | Ile | Gly | Ile |
| 1100 | | | | | 1105 | | | | | 1110 | | | | |

| Ile | Asn | Asn | Thr | Val | Tyr | Asp | Pro | Leu | Gln | Pro | Glu | Leu | Asp | Ser |
| 1115 | | | | | 1120 | | | | | 1125 | | | | |

| Phe | Lys | Glu | Glu | Leu | Asp | Lys | Tyr | Phe | Lys | Asn | His | Thr | Ser | Pro |
| 1130 | | | | | 1135 | | | | | 1140 | | | | |

| Asp | Val | Asp | Leu | Gly | Asp | Ile | Ser | Gly | Ile | Asn | Ala | Ser | Val | Val |
| 1145 | | | | | 1150 | | | | | 1155 | | | | |

| Asn | Ile | Gln | Lys | Glu | Ile | Asp | Arg | Leu | Asn | Glu | Val | Ala | Lys | Asn |
| 1160 | | | | | 1165 | | | | | 1170 | | | | |

| Leu | Asn | Glu | Ser | Leu | Ile | Asp | Leu | Gln | Glu | Leu | Gly | Lys | Tyr | Glu |
| 1175 | | | | | 1180 | | | | | 1185 | | | | |

| Gln | Tyr | Ile | Lys | Trp | Pro | Trp | Tyr | Val | Trp | Leu | Gly | Phe | Ile | Ala |
| 1190 | | | | | 1195 | | | | | 1200 | | | | |

| Gly | Leu | Ile | Ala | Ile | Val | Met | Val | Thr | Ile | Leu | Leu | Cys | Cys | Met |
| 1205 | | | | | 1210 | | | | | 1215 | | | | |

| Thr | Ser | Cys | Cys | Ser | Cys | Leu | Lys | Gly | Ala | Cys | Ser | Cys | Gly | Ser |
| 1220 | | | | | 1225 | | | | | 1230 | | | | |

| Cys | Cys | Lys | Phe | Asp | Glu | Asp | Ser | Glu | Pro | Val | Leu | Lys | Gly |
| 1235 | | | | | 1240 | | | | | 1245 | | | |

| Val | Lys | Leu | His | Tyr | Thr |
| 1250 | | | | | |

<210> SEQ ID NO 3
<211> LENGTH: 3768
<212> TYPE: DNA
<213> ORGANISM: SARS coronavirus

<400> SEQUENCE: 3

```
atgtttattt tcttattatt tcttactctc actagtggta gtgaccttga ccggtgcacc     60
acttttgatg atgttcaagc tcctaattac actcaacata cttcatctat gaggggggtt    120
tactatcctg atgaaatttt tagatcagac actctttatt taactcagga tttatttctt    180
```

```
ccatttttatt ctaatgttac agggtttcat actattaatc atacgtttgg caaccctgtc    240
atacctttta aggatggtat ttattttgct gccacagaga aatcaaatgt tgtccgtggt    300 tgggttttg gttctaccat gaacaacaag tcacagtcgg tgattattat taacaattct    360
actaatgttg ttatacgagc atgtaacttt gaattgtgtg acaacccttt ctttgctgtt    420
tctaaaccca tgggtacaca gacacatact atgatattcg ataatgcatt taattgcact    480
ttcgagtaca tatctgatgc cttttcgctt gatgtttcag aaaagtcagg taattttaaa    540
cacttacgag agtttgtgtt taaaaataaa gatgggtttc tctatgttta agggctat     600 caacctatag atgtagttcg tgatctacct tctggtttta acactttgaa acctattttt    660
aagttgcctc ttggtattaa cattacaaat tttagagcca ttcttacagc cttttcacct    720
gctcaagaca tttggggcac gtcagctgca gcctattttg ttggctattt aaagccaact    780
acatttatgc tcaagtatga tgaaaatggt acaatcacag atgctgttga ttgttctcaa    840
aatccacttg ctgaactcaa atgctctgtt aagagctttg agattgacaa aggaatttac    900
cagacctcta atttcagggt tgttccctca ggagatgttg tgagattccc taatattaca    960
aacttgtgtc cttttggaga ggttttaat gctactaaat tcccttctgt ctatgcatgg   1020
gagagaaaaa aaatttctaa ttgtgttgct gattactctg tgctctacaa ctcaacattt   1080
ttttcaacct ttaagtgcta tggcgtttct gccactaagt tgaatgatct ttgcttctcc   1140
aatgtctatg cagattcttt tgtagtcaag ggagatgatg taagacaaat agcgccagga   1200
caaactggtg ttattgctga ttataattat aaattgccag atgatttcat gggttgtgtc   1260
cttgcttgga atactaggaa cattgatgct acttcaactg gtaattataa ttataaatat   1320
aggtatctta gacatggcaa gcttaggccc tttgagagag acatatctaa tgtgcctttc   1380 tccccctgatg gcaaaccttg caccccacct gctcttaatt gttattggcc attaaatgat   1440
tatggttttt acaccactac tggcattggc taccaacctt acagagttgt agtactttct   1500
tttgaacttt taaatgcacc ggccacggtt tgtggaccaa aattatccac tgaccttatt   1560
aagaaccagt gtgtcaattt taatttttaat ggactcactg gtactggtgt gttaactcct   1620
tcttcaaaga gatttcaacc atttcaacaa tttggccgtg atgtttctga tttcactgat   1680
tccgttcgag atcctaaaac atctgaaata ttagacattt caccttgcgc ttttgggggt   1740
gtaagtgtaa ttacacctgg aacaaatgct tcatctgaag ttgctgttct atatcaagat   1800
gttaactgca ctgatgtttc tacagcaatt catgcagatc aactcacacc agcttggcgc   1860
atatattcta ctgaaaacaa tgtattccag actcaagcag gctgtcttat aggagctgag   1920
catgtcgaca cttcttatga gtgcgacatt cctattggag ctggcatttg tgctagttac   1980
catacagttt cttttattcg tagtactagc caaaaatcta ttgtggctta tactatgtct   2040
ttaggtgctg atagttcaat tgcttactct aataacacca ttgctatacc tactaacttt   2100
tcaattagca ttactacaga agtaatgcct gtttctatgg ctaaaaacctc cgtagattgt   2160 aatatgtaca tctgcggaga ttctactgaa tgtgctaatt tgcttctcca atatggtagc   2220
ttttgcacac aactaaatcg tgcactctca ggtattgctg ctgaacagga tcgcaacaca   2280
cgtgaagtgt tcgctcaagt caaacaaatg tacaaaaccc caactttgaa atattttggt   2340
ggttttaatt tttcacaaat attacctgac cctctaaagc caactaagag gtctttttatt   2400 gaggacttgc tctttaataa ggtgacactc gctgatgctg gcttcatgaa gcaatatggc   2460
gaatgcctag gtgatattaa tgctagagat ctcatttgtg cgcagaagtt caatggactt   2520
acagtgttgc cacctctgct cactgatgat atgattgctg cctacactgc tgctctagtt   2580
```

-continued

```
agtggtactg ccactgctgg atggacattt ggtgctggcg ctgctcttca ataccttttt      2640
gctatgcaaa tggcatatag gttcaatggc attggagtta cccaaaatgt tctctatgag      2700
aaccaaaaac aaatcgccaa ccaatttaac aaggcgatta gtcaaattca agaatcactt      2760
acaacaacat caactgcatt gggcaagctg caagacgttg ttaaccagaa tgctcaagca      2820
ttaaacacac ttgttaaaca acttagctct aattttggtg caatttcaag tgtgctaaat      2880
gatatccttt cgcgacttga taaagtcgag gcggaggtac aaattgacag gttaattaca      2940
ggcagacttc aaagccttca aacctatgta acacaacaac taatcagggc tgctgaaatc      3000
agggcttctg ctaatcttgc tgctactaaa atgtctgagt gtgttcttgg acaatcaaaa      3060
agagttgact tttgtggaaa gggctaccac cttatgtcct tcccacaagc agccccgcat      3120
ggtgttgtct tcctacatgt cacgtatgtg ccatcccagg agaggaactt caccacagcg      3180
ccagcaattt gtcatgaagg caaagcatac ttccctcgtg aaggtgtttt tgtgtttaat      3240
ggcacttctt ggtttattac acagaggaac ttcttttctc cacaaataat tactacagac      3300
aatacatttg tctcaggaaa ttgtgatgtc gttattggca tcattaacaa cacagtttat      3360
gatcctctgc aacctgagct tgactcattc aaagaagagc tggacaagta cttcaaaaat      3420
catacatcac cagatgttga tcttggcgac atttcaggca ttaacgcttc tgtcgtcaac      3480
attcaaaaag aaattgaccg cctcaatgag gtcgctaaaa atttaaatga atcactcatt      3540
gaccttcaag aattgggaaa atatgagcaa tatattaaat ggccttggta tgtttggctc      3600
ggcttcattg ctggactaat tgccatcgtc atggttacaa tcttgctttg ttgcatgact      3660
agttgttgca gttgcctcaa gggtgcatgc tcttgtggtt cttgctgcaa gtttgatgag      3720
gatgactctg agccagttct caagggtgtc aaattacatt acacataa                  3768
```

<210> SEQ ID NO 4
<211> LENGTH: 231
<212> TYPE: DNA
<213> ORGANISM: SARS coronavirus

<400> SEQUENCE: 4

```
atgtactcat tcgtttcgga agaaacaggt acgttaatag ttaatagcgt acttcttttt      60
cttgctttcg tggtattctt gctagtcaca ctagccatcc ttactgcgct tcgattgtgt      120
gcgtactgct gcaatattgt taacgtgagt ttagtaaaac caacggttta cgtctactcg      180
cgtgttaaaa atctgaactc ttctgaagga gttcctgatc ttctggtcta a              231
```

<210> SEQ ID NO 5
<211> LENGTH: 76
<212> TYPE: PRT
<213> ORGANISM: SARS coronavirus

<400> SEQUENCE: 5

```
Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
                20                  25                  30

Ile Leu Thr Ala Leu Arg Leu Cys Ala Tyr Cys Cys Asn Ile Val Asn
                35                  40                  45

Val Ser Leu Val Lys Pro Thr Val Tyr Val Tyr Ser Arg Val Lys Asn
        50                  55                  60

Leu Asn Ser Ser Glu Gly Val Pro Asp Leu Leu Val
65                  70                  75
```

```
<210> SEQ ID NO 6
<211> LENGTH: 666
<212> TYPE: DNA
<213> ORGANISM: SARS coronavirus

<400> SEQUENCE: 6
atggcagaca acggtactat taccgttgag gagcttaaac aactcctgga acaatggaac      60
ctagtaatag gtttcctatt cctagcctgg attatgttac tacaatttgc ctattctaat     120
cggaacaggt ttttgtacat aataaagctt gttttcctct ggctcttgtg gccagtaaca     180
cttgcttgtt ttgtgcttgc tgctgtctac agaattaatt gggtgactgg cgggattgcg     240
attgcaatgg cttgtattgt aggcttgatg tggcttagct acttcgttgc ttccttcagg     300
ctgtttgctc gtaccgctc aatgtggtca ttcaacccag aaacaaacat tcttctcaat     360
gtgcctctcc gggggacaat tgtgaccaga ccgctcatgg aaagtgaact tgtcattggt     420
gctgtgatca ttcgtggtca cttgcgaatg gccggacact ccctagggcg ctgtgacatt     480
aaggacctgc caaaagagat cactgtggct acatcacgaa cgctttctta ttacaaatta     540
ggagcgtcgc agcgtgtagg cactgattca ggttttgctg catacaaccg ctaccgtatt     600
ggaaactata aattaaatac agaccacgcc ggtagcaacg acaatattgc tttgctagta     660
cagtaa                                                                 666

<210> SEQ ID NO 7
<211> LENGTH: 221
<212> TYPE: PRT
<213> ORGANISM: SARS coronavirus

<400> SEQUENCE: 7

Met Ala Asp Asn Gly Thr Ile Thr Val Glu Glu Leu Lys Gln Leu Leu
1               5                   10                  15

Glu Gln Trp Asn Leu Val Ile Gly Phe Leu Phe Leu Ala Trp Ile Met
            20                  25                  30

Leu Leu Gln Phe Ala Tyr Ser Asn Arg Asn Arg Phe Leu Tyr Ile Ile
        35                  40                  45

Lys Leu Val Phe Leu Trp Leu Leu Trp Pro Val Thr Leu Ala Cys Phe
    50                  55                  60

Val Leu Ala Ala Val Tyr Arg Ile Asn Trp Val Thr Gly Gly Ile Ala
65                  70                  75                  80

Ile Ala Met Ala Cys Ile Val Gly Leu Met Trp Leu Ser Tyr Phe Val
                85                  90                  95

Ala Ser Phe Arg Leu Phe Ala Arg Thr Arg Ser Met Trp Ser Phe Asn
            100                 105                 110

Pro Glu Thr Asn Ile Leu Leu Asn Val Pro Leu Arg Gly Thr Ile Val
        115                 120                 125

Thr Arg Pro Leu Met Glu Ser Glu Leu Val Ile Gly Ala Val Ile Ile
    130                 135                 140

Arg Gly His Leu Arg Met Ala Gly His Ser Leu Gly Arg Cys Asp Ile
145                 150                 155                 160

Lys Asp Leu Pro Lys Glu Ile Thr Val Ala Thr Ser Arg Thr Leu Ser
                165                 170                 175

Tyr Tyr Lys Leu Gly Ala Ser Gln Arg Val Gly Thr Asp Ser Gly Phe
            180                 185                 190

Ala Ala Tyr Asn Arg Tyr Arg Ile Gly Asn Tyr Lys Leu Asn Thr Asp
        195                 200                 205

His Ala Gly Ser Asn Asp Asn Ile Ala Leu Leu Val Gln
    210                 215                 220
```

<210> SEQ ID NO 8
<211> LENGTH: 1259
<212> TYPE: DNA
<213> ORGANISM: SARS coronavirus

<400> SEQUENCE: 8
atggacccca atcaaaccaa cgtagtgccc cccgcattac atttggtgga cccacagatt 60
caactgacaa taaccagaat ggaggacgca atggggcaag gccaaaacag cgccgacccc 120
aaggtttacc caataatact gcgtcttggt tcacagctct cactcagcat ggcaaggagg 180
aacttagatt ccctcgaggc cagggcgttc caatcaacac caatagtggt ccagatgacc 240
aaattggcta ctaccgaaga gctacccgac gagttcgtgg tggtgacggc aaaatgaaag 300
agctcagccc cagatggtac ttctattacc taggaactgg cccagaagct tcacttccct 360
acggcgctaa caaagaaggc atcgtatggg ttgcaactga gggagccttg aatacaccca 420
aagaccacat tggcacccgc aatcctaata acaatgctgc caccgtgcta caacttcctc 480
aaggaacaac attgccaaaa ggcttctacg cagagggaag cagaggcggc agtcaagcct 540
cttctcgctc ctcatcacgt agtcgcggta attcaagaaa ttcaactcct ggcagcagta 600
ggggaaattc tcctgctcga atggctagcg gaggtggtga aactgccctc gcgctattgc 660
tgctagacag attgaaccag cttgagagca aagtttctgg taaaggccaa caacaacaag 720
gccaaactgt cactaagaaa tctgctgctg aggcatctaa aaagcctcgc caaaaacgta 780
ctgccacaaa acagtacaac gtcactcaag catttgggag acgtggtcca gaacaaaccc 840
aaggaaattt cggggaccaa gacctaatca gacaaggaac tgattacaaa cattggccgc 900
aaattgcaca atttgctcca agtgcctctg cattctttgg aatgtcacgc attggcatgg 960
aagtcacacc ttcgggaaca tggctgactt atcatggagc cattaaattg gatgacaaag 1020
atccacaatt caaagacaac gtcatactgc tgaacaagca cattgacgca tacaaaacat 1080
tcccaccaac agagcctaaa aaggacaaaa agaaaaagac tgatgaagct cagcctttgc 1140
cgcagagaca aaagaagcag cccactgtga ctcttcttcc tgcggctgac atggatgatt 1200
tctccagaca acttcaaaat tccatgagtg gagcttctgc tgattcaact caggcataa 1259

<210> SEQ ID NO 9
<211> LENGTH: 422
<212> TYPE: PRT
<213> ORGANISM: SARS coronavirus

<400> SEQUENCE: 9

Met Ser Asp Asn Gly Pro Gln Ser Asn Gln Arg Ser Ala Pro Arg Ile
1               5                   10                  15

Thr Phe Gly Gly Pro Thr Asp Ser Thr Asp Asn Asn Gln Asn Gly Gly
            20                  25                  30

Arg Asn Gly Ala Arg Pro Lys Gln Arg Arg Pro Gln Gly Leu Pro Asn
        35                  40                  45

Asn Thr Ala Ser Trp Phe Thr Ala Leu Thr Gln His Gly Lys Glu Glu
    50                  55                  60

Leu Arg Phe Pro Arg Gly Gln Gly Val Pro Ile Asn Thr Asn Ser Gly
65                  70                  75                  80

Pro Asp Asp Gln Ile Gly Tyr Tyr Arg Arg Ala Thr Arg Arg Val Arg
                85                  90                  95

Gly Gly Asp Gly Lys Met Lys Glu Leu Ser Pro Arg Trp Tyr Phe Tyr
            100                 105                 110

```
Tyr Leu Gly Thr Gly Pro Glu Ala Ser Leu Pro Tyr Gly Ala Asn Lys
        115                 120                 125

Glu Gly Ile Val Trp Val Ala Thr Glu Gly Ala Leu Asn Thr Pro Lys
    130                 135                 140

Asp His Ile Gly Thr Arg Asn Pro Asn Asn Ala Ala Thr Val Leu
145                 150                 155                 160

Gln Leu Pro Gln Gly Thr Thr Leu Pro Lys Gly Phe Tyr Ala Glu Gly
                165                 170                 175

Ser Arg Gly Gly Ser Gln Ala Ser Ser Arg Ser Ser Arg Ser Arg
            180                 185                 190

Gly Asn Ser Arg Asn Ser Thr Pro Gly Ser Ser Arg Gly Asn Ser Pro
        195                 200                 205

Ala Arg Met Ala Ser Gly Gly Gly Glu Thr Ala Leu Ala Leu Leu Leu
    210                 215                 220

Leu Asp Arg Leu Asn Gln Leu Glu Ser Lys Val Ser Gly Lys Gly Gln
225                 230                 235                 240

Gln Gln Gln Gly Gln Thr Val Thr Lys Lys Ser Ala Ala Glu Ala Ser
                245                 250                 255

Lys Lys Pro Arg Gln Lys Arg Thr Ala Thr Lys Gln Tyr Asn Val Thr
            260                 265                 270

Gln Ala Phe Gly Arg Arg Gly Pro Glu Gln Thr Gln Gly Asn Phe Gly
        275                 280                 285

Asp Gln Asp Leu Ile Arg Gln Gly Thr Asp Tyr Lys His Trp Pro Gln
    290                 295                 300

Ile Ala Gln Phe Ala Pro Ser Ala Ser Ala Phe Phe Gly Met Ser Arg
305                 310                 315                 320

Ile Gly Met Glu Val Thr Pro Ser Gly Thr Trp Leu Thr Tyr His Gly
                325                 330                 335

Ala Ile Lys Leu Asp Asp Lys Asp Pro Gln Phe Lys Asp Asn Val Ile
            340                 345                 350

Leu Leu Asn Lys His Ile Asp Ala Tyr Lys Thr Phe Pro Pro Thr Glu
        355                 360                 365

Pro Lys Lys Asp Lys Lys Lys Thr Asp Glu Ala Gln Pro Leu Pro
    370                 375                 380

Gln Arg Gln Lys Lys Gln Pro Thr Val Thr Leu Leu Pro Ala Ala Asp
385                 390                 395                 400

Met Asp Asp Phe Ser Arg Gln Leu Gln Asn Ser Met Ser Gly Ala Ser
                405                 410                 415

Ala Asp Ser Thr Gln Ala
            420

<210> SEQ ID NO 10
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer 2165

<400> SEQUENCE: 10
aggttcgctc ttcaatgttt attttcttat tatttcttac tctc                    44

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: Synthetic
```

```
          primer 2166

<400> SEQUENCE: 11
aggttcgctc ttcagcgggt agtgaccttg accggtgc                              38

<210> SEQ ID NO 12
<211> LENGTH: 52
<212> TYPE: DNA
<213> ORGANISM: Artificial Sequence
<220> FEATURE:
<223> OTHER INFORMATION: Description of Artificial Sequence: Synthetic
      primer 2167

<400> SEQUENCE: 12
aggttcgctc ttcattaggt accaatagcc aacaaaatag gctgcagctg ac              52

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer 2168

<400> SEQUENCE: 13
cgtcagctgc agcctatttt gttggc                                           26

<210> SEQ ID NO 14
<211> LENGTH: 52
<212> TYPE: DNA
<213> ORGANISM: Artificial Sequence
<220> FEATURE:
<223> OTHER INFORMATION: Description of Artificial Sequence: Synthetic
      primer 2169

<400> SEQUENCE: 14
aggttcgctc ttcattaggt acccaaatga gatctctagc attaatatca cc              52

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      primer 2170

<400> SEQUENCE: 15
aggttcggat ccagatctca tttgtgcgca g                                     31

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      primer 2171

<400> SEQUENCE: 16
aggttcggta ccttatgtgt aatgtaattt gacacc                                36

<210> SEQ ID NO 17
<211> LENGTH: 1451
<212> TYPE: PRT
<213> ORGANISM: Canine enteric coronavirus

<400> SEQUENCE: 17

Met Ile Val Leu Thr Leu Cys Leu Phe Leu Phe Leu Tyr Ser Ser Val
```

-continued

```
1               5                   10                  15
Ser Cys Thr Ser Asn Asn Asp Cys Val Gln Val Asn Val Thr Gln Leu
                20                  25                  30

Pro Gly Asn Glu Asn Ile Ile Lys Asp Phe Leu Phe Gln Asn Phe Lys
                35                  40                  45

Glu Glu Gly Ser Leu Val Val Gly Gly Tyr Tyr Pro Thr Glu Val Trp
    50                  55                  60

Tyr Asn Cys Ser Thr Thr Gln Gln Thr Thr Ala Tyr Lys Tyr Phe Ser
65                  70                  75                  80

Asn Ile His Ala Phe Tyr Phe Asp Met Glu Ala Met Glu Asn Ser Thr
                85                  90                  95

Gly Asn Ala Arg Gly Lys Pro Leu Leu Val His Val His Gly Asn Pro
                100                 105                 110

Val Ser Ile Ile Val Tyr Ile Ser Ala Tyr Arg Asp Asp Val Gln Phe
                115                 120                 125

Arg Pro Leu Leu Lys His Gly Leu Leu Cys Ile Thr Lys Asn Asp Thr
                130                 135                 140

Val Asp Tyr Asn Ser Phe Thr Ile Asn Gln Trp Arg Asp Ile Cys Leu
145                 150                 155                 160

Gly Asp Asp Arg Lys Ile Pro Phe Ser Val Val Pro Thr Asp Asn Gly
                165                 170                 175

Thr Lys Leu Phe Gly Leu Glu Trp Asn Asp Asp Tyr Val Thr Ala Tyr
                180                 185                 190

Ile Ser Asp Glu Ser His Arg Leu Asn Ile Asn Asn Asn Trp Phe Asn
                195                 200                 205

Asn Val Thr Leu Leu Tyr Ser Arg Thr Ser Thr Ala Thr Trp Gln His
                210                 215                 220

Ser Ala Ala Tyr Val Tyr Gln Gly Val Ser Asn Phe Thr Tyr Tyr Lys
225                 230                 235                 240

Leu Asn Lys Thr Ala Gly Leu Lys Ser Tyr Glu Leu Cys Glu Asp Tyr
                245                 250                 255

Glu Tyr Cys Thr Gly Tyr Ala Thr Asn Val Phe Ala Pro Thr Ser Gly
                260                 265                 270

Gly Tyr Ile Pro Asp Gly Phe Ser Phe Asn Asn Trp Phe Met Leu Thr
                275                 280                 285

Asn Ser Ser Thr Phe Val Ser Gly Arg Phe Val Thr Asn Gln Pro Leu
                290                 295                 300

Leu Val Asn Cys Leu Trp Pro Val Pro Ser Phe Gly Val Ala Ala Gln
305                 310                 315                 320

Glu Phe Cys Phe Glu Gly Ala Gln Phe Ser Gln Cys Asn Gly Val Ser
                325                 330                 335

Leu Asn Asn Thr Val Asp Val Ile Arg Phe Asn Leu Asn Phe Thr Thr
                340                 345                 350

Asp Val Gln Ser Gly Met Gly Ala Thr Val Phe Ser Leu Asn Thr Thr
                355                 360                 365

Gly Gly Val Ile Leu Glu Ile Ser Cys Tyr Asn Asp Thr Val Ser Glu
                370                 375                 380

Ser Ser Phe Tyr Ser Tyr Gly Glu Ile Pro Phe Gly Val Thr Asp Gly
385                 390                 395                 400

Pro Arg Tyr Cys Tyr Val Leu Tyr Asn Gly Thr Ala Leu Lys Tyr Leu
                405                 410                 415

Gly Thr Leu Pro Pro Ser Val Lys Glu Ile Ala Ile Ser Lys Trp Gly
                420                 425                 430
```

His Phe Tyr Ile Asn Gly Tyr Asn Phe Phe Ser Thr Phe Pro Ile Asp
    435                 440                 445

Cys Ile Ala Phe Asn Leu Thr Thr Gly Ala Ser Gly Ala Phe Trp Thr
450                 455                 460

Ile Ala Tyr Thr Ser Tyr Thr Glu Ala Leu Val Gln Val Glu Asn Thr
465                 470                 475                 480

Ala Ile Lys Lys Val Thr Tyr Cys Asn Ser His Ile Asn Asn Ile Lys
            485                 490                 495

Cys Ser Gln Leu Thr Ala Asn Leu Gln Asn Gly Phe Tyr Pro Val Ala
                500                 505                 510

Ser Ser Glu Val Gly Leu Val Asn Lys Ser Val Val Leu Leu Pro Ser
                515                 520                 525

Phe Tyr Ser His Thr Ser Val Asn Ile Thr Ile Asp Leu Gly Met Lys
                530                 535                 540

Arg Ser Val Thr Val Thr Ile Ala Ser Pro Leu Ser Asn Ile Thr Leu
545                 550                 555                 560

Pro Met Gln Asp Asn Asn Ile Asp Val Tyr Cys Ile Arg Ser Asn Gln
                    565                 570                 575

Phe Ser Val Tyr Val His Ser Thr Cys Lys Ser Ser Leu Trp Asp Asn
                580                 585                 590

Asn Phe Asn Ser Ala Cys Thr Asp Val Leu Asp Ala Thr Ala Val Ile
            595                 600                 605

Lys Thr Gly Thr Cys Pro Phe Ser Phe Asp Lys Leu Asn Asn Tyr Leu
610                 615                 620

Thr Phe Asn Lys Phe Cys Leu Ser Leu Asn Pro Val Gly Ala Asn Cys
625                 630                 635                 640

Lys Leu Asp Val Ala Ala Arg Thr Arg Thr Asn Glu Gln Val Phe Gly
                    645                 650                 655

Ser Leu Tyr Val Ile Tyr Glu Glu Gly Asp Asn Ile Val Gly Val Pro
                660                 665                 670

Ser Asp Asn Ser Gly Leu His Asp Leu Ser Val Leu His Leu Asp Ser
            675                 680                 685

Cys Thr Asp Tyr Asn Ile Tyr Gly Arg Thr Gly Val Gly Ile Ile Arg
690                 695                 700

Lys Thr Asn Ser Thr Leu Leu Ser Gly Leu Tyr Tyr Thr Ser Leu Ser
705                 710                 715                 720

Gly Asp Leu Leu Gly Phe Lys Asn Val Ser Asp Gly Val Val Tyr Ser
                    725                 730                 735

Val Thr Pro Cys Asp Val Ser Ala Gln Ala Ala Val Ile Asp Gly Ala
                740                 745                 750

Ile Val Gly Ala Met Thr Ser Ile Asn Ser Glu Leu Leu Gly Leu Thr
            755                 760                 765

His Trp Thr Thr Thr Pro Asn Phe Tyr Tyr Tyr Ser Ile Tyr Asn Tyr
770                 775                 780

Thr Asn Val Met Asn Arg Gly Thr Ala Ile Asp Asn Asp Ile Asp Cys
785                 790                 795                 800

Glu Pro Ile Ile Thr Tyr Ser Asn Ile Gly Val Cys Lys Asn Gly Ala
                    805                 810                 815

Leu Val Phe Ile Asn Val Thr His Ser Asp Gly Asp Val Gln Pro Ile
                820                 825                 830

Ser Thr Gly Asn Val Thr Ile Pro Thr Asn Phe Thr Ile Ser Val Gln
            835                 840                 845

Val Glu Tyr Ile Gln Val Tyr Thr Thr Pro Val Ser Ile Asp Cys Ala
850                 855                 860

```
Arg Tyr Val Cys Asn Gly Asn Pro Arg Cys Asn Lys Leu Leu Thr Gln
865                 870                 875                 880

Tyr Val Ser Ala Cys Gln Thr Ile Glu Gln Ala Leu Ala Met Gly Ala
                885                 890                 895

Arg Leu Glu Asn Met Glu Ile Asp Ser Met Leu Phe Val Ser Glu Asn
            900                 905                 910

Ala Leu Lys Leu Ala Ser Val Glu Ala Phe Asn Ser Thr Glu Asn Leu
        915                 920                 925

Asp Pro Ile Tyr Lys Glu Trp Pro Asn Ile Gly Gly Ser Trp Leu Gly
    930                 935                 940

Gly Leu Lys Asp Ile Leu Pro Ser His Asn Ser Lys Arg Lys Tyr Arg
945                 950                 955                 960

Ser Ala Ile Glu Asp Leu Leu Phe Asp Lys Val Val Thr Ser Gly Leu
                965                 970                 975

Gly Thr Val Asp Glu Asp Tyr Lys Arg Ser Ala Gly Gly Tyr Asp Ile
            980                 985                 990

Ala Asp Leu Val Cys Ala Arg Tyr Tyr Asn Gly Ile Met Val Leu Pro
        995                 1000                1005

Gly Val Ala Asn Asp Asp Lys Met Thr Met Tyr Thr Ala Ser Leu
    1010                1015                1020

Thr Gly Gly Ile Thr Leu Gly Ala Leu Ser Gly Gly Ala Val Ala
    1025                1030                1035

Ile Pro Phe Ala Val Ala Val Gln Ala Arg Leu Asn Tyr Val Ala
    1040                1045                1050

Leu Gln Thr Asp Val Leu Asn Lys Asn Gln Gln Ile Leu Ala Asn
    1055                1060                1065

Ala Phe Asn Gln Ala Ile Gly Asn Ile Thr Gln Ala Phe Gly Lys
    1070                1075                1080

Val Asn Asp Ala Ile His Gln Thr Ser Lys Gly Leu Ala Thr Val
    1085                1090                1095

Ala Lys Ala Leu Ala Lys Val Gln Asp Val Val Asn Thr Gln Gly
    1100                1105                1110

Gln Ala Leu Ser His Leu Thr Val Gln Leu Gln Asn Asn Phe Gln
    1115                1120                1125

Ala Ile Ser Ser Ser Ile Ser Asp Ile Tyr Asn Arg Leu Asp Glu
    1130                1135                1140

Leu Ser Ala Asp Ala Gln Val Asp Arg Leu Ile Thr Gly Arg Leu
    1145                1150                1155

Thr Ala Leu Asn Ala Phe Val Ser Gln Thr Leu Thr Arg Gln Ala
    1160                1165                1170

Glu Val Arg Ala Ser Arg Gln Leu Ala Lys Asp Lys Val Asn Glu
    1175                1180                1185

Cys Val Arg Ser Gln Ser Gln Arg Phe Gly Phe Cys Gly Asn Gly
    1190                1195                1200

Thr His Leu Phe Ser Leu Ala Asn Ala Ala Pro Asn Gly Met Ile
    1205                1210                1215

Phe Phe His Thr Val Leu Leu Pro Thr Ala Tyr Glu Thr Val Thr
    1220                1225                1230

Ala Trp Ser Gly Ile Cys Ala Ser Asp Gly Ser Arg Thr Phe Gly
    1235                1240                1245

Leu Val Val Glu Asp Val Gln Leu Thr Leu Phe Arg Asn Leu Asp
    1250                1255                1260

Glu Lys Phe Tyr Leu Thr Pro Arg Thr Met Tyr Gln Pro Arg Val
```

```
                1265                1270                1275

Ala Thr Ser Ser Asp Phe Val Gln Ile Glu Gly Cys Asp Val Leu
        1280                1285                1290

Phe Val Asn Gly Thr Val Ile Glu Leu Pro Ser Ile Ile Pro Asp
        1295                1300                1305

Tyr Ile Asp Ile Asn Gln Thr Val Gln Asp Ile Leu Glu Asn Phe
        1310                1315                1320

Arg Pro Asn Trp Thr Val Pro Glu Leu Pro Leu Asp Ile Phe His
        1325                1330                1335

Ala Thr Tyr Leu Asn Leu Thr Gly Glu Ile Asn Asp Leu Glu Phe
        1340                1345                1350

Arg Ser Glu Lys Leu His Asn Thr Thr Val Glu Leu Ala Ile Leu
        1355                1360                1365

Ile Asp Asn Ile Asn Asn Thr Leu Val Asn Leu Glu Trp Leu Asn
        1370                1375                1380

Arg Ile Glu Thr Tyr Val Lys Trp Pro Trp Tyr Val Trp Leu Leu
        1385                1390                1395

Ile Gly Leu Val Val Ile Phe Cys Ile Pro Ile Leu Leu Phe Cys
        1400                1405                1410

Cys Cys Ser Thr Gly Cys Cys Gly Cys Ile Gly Cys Leu Gly Ser
        1415                1420                1425

Cys Cys His Ser Ile Cys Ser Arg Gly Gln Phe Glu Ser Tyr Glu
        1430                1435                1440

Pro Ile Glu Lys Val His Val His
        1445                1450

<210> SEQ ID NO 18
<211> LENGTH: 1453
<212> TYPE: PRT
<213> ORGANISM: Canine coronavirus

<400> SEQUENCE: 18

Met Ile Val Leu Ile Leu Cys Leu Leu Leu Phe Ser Tyr Asn Ser Val
1               5                   10                  15

Ile Cys Thr Ser Asn Asn Asp Cys Val Gln Gly Asn Val Thr Gln Leu
                    20                  25                  30

Pro Gly Asn Glu Asn Ile Ile Lys Asp Phe Leu Phe His Thr Phe Lys
                35                  40                  45

Glu Glu Pro Ser Val Val Gly Gly Tyr Tyr Pro Thr Glu Val Trp
    50                  55                  60

Tyr Asn Cys Ser Arg Ser Ala Thr Thr Thr Ala Tyr Lys Asp Phe Ser
65                  70                  75                  80

Asn Ile His Ala Phe Tyr Phe Asp Met Glu Ala Met Glu Asn Ser Thr
                    85                  90                  95

Gly Asn Ala Arg Gly Lys Pro Leu Leu Val His Val His Gly Asp Pro
                100                 105                 110

Val Ser Ile Ile Ile Tyr Ile Ser Ala Tyr Arg Asp Asp Val Gln Pro
            115                 120                 125

Arg Pro Leu Leu Lys His Gly Leu Leu Cys Ile Thr Lys Asn Lys Ile
        130                 135                 140

Ile Asp Tyr Asn Thr Phe Thr Ser Ala Gln Trp Ser Ala Ile Cys Leu
145                 150                 155                 160

Gly Asp Asp Arg Lys Ile Pro Phe Ser Val Ile Pro Thr Asp Asn Gly
                165                 170                 175

Thr Lys Ile Phe Gly Leu Glu Trp Asn Asp Asp Tyr Val Thr Ala Tyr
```

-continued

```
                180                 185                 190
Ile Ser Asp Arg Ser His His Leu Asn Ile Asn Asn Asn Trp Phe Asn
            195                 200                 205
Asn Val Thr Ile Leu Tyr Ser Arg Ser Ser Ser Ala Thr Trp Gln Lys
210                 215                 220
Ser Ala Ala Tyr Val Tyr Gln Gly Val Ser Asn Phe Thr Tyr Tyr Lys
225                 230                 235                 240
Leu Asn Asn Thr Asn Gly Leu Lys Ser Tyr Glu Leu Cys Glu Asp Tyr
            245                 250                 255
Glu Tyr Cys Thr Gly Tyr Ala Thr Asn Val Phe Ala Pro Thr Val Gly
            260                 265                 270
Gly Tyr Ile Pro His Gly Phe Ser Phe Asn Asn Trp Phe Met Arg Thr
            275                 280                 285
Asn Ser Ser Thr Phe Val Ser Gly Arg Phe Val Thr Asn Gln Pro Leu
            290                 295                 300
Leu Val Asn Cys Leu Trp Pro Val Pro Ser Phe Gly Val Ala Ala Gln
305                 310                 315                 320
Gln Phe Cys Phe Glu Gly Ala Gln Phe Ser Gln Cys Asn Gly Val Ser
            325                 330                 335
Leu Asn Asn Thr Val Asp Val Ile Arg Phe Asn Leu Asn Phe Thr Ala
            340                 345                 350
Leu Val Gln Ser Gly Met Gly Ala Thr Val Phe Ser Leu Asn Thr Thr
            355                 360                 365
Gly Gly Val Ile Leu Glu Ile Ser Cys Tyr Asn Asp Thr Val Ser Glu
            370                 375                 380
Ser Ser Phe Tyr Ser Tyr Gly Glu Ile Ser Phe Gly Val Thr Asp Gly
385                 390                 395                 400
Pro Arg Tyr Cys Phe Ala Leu Tyr Asn Gly Thr Ala Leu Lys Tyr Leu
            405                 410                 415
Gly Thr Leu Pro Pro Ser Val Lys Glu Ile Ala Ile Ser Lys Trp Gly
            420                 425                 430
His Phe Tyr Ile Asn Gly Tyr Asn Phe Phe Ser Thr Phe Pro Ile Asp
            435                 440                 445
Cys Ile Ser Phe Asn Leu Thr Thr Gly Asp Ser Gly Ala Phe Trp Thr
            450                 455                 460
Ile Ala Tyr Thr Ser Tyr Thr Asp Ala Leu Val Gln Val Glu Asn Thr
465                 470                 475                 480
Ala Ile Lys Lys Val Thr Tyr Cys Asn Ser His Ile Asn Asn Ile Lys
            485                 490                 495
Cys Ser Gln Leu Thr Ala Asn Leu Gln Asn Gly Phe Tyr Pro Val Ala
            500                 505                 510
Ser Ser Glu Val Gly Leu Val Asn Lys Ser Val Val Leu Leu Pro Ser
            515                 520                 525
Phe Tyr Ser His Thr Ser Val Asn Ile Thr Ile Asp Leu Gly Met Lys
            530                 535                 540
Arg Ser Gly Tyr Gly Gln Pro Ile Ala Ser Thr Leu Ser Asn Ile Thr
545                 550                 555                 560
Leu Pro Met Gln Asp Asn Asn Thr Asp Val Tyr Cys Ile Arg Ser Asn
            565                 570                 575
Arg Phe Ser Val Tyr Phe His Ser Thr Cys Lys Ser Ser Leu Trp Asp
            580                 585                 590
Asp Val Phe Asn Ser Asp Cys Thr Asp Val Leu Tyr Ala Thr Ala Val
            595                 600                 605
```

-continued

```
Ile Lys Thr Gly Thr Cys Pro Phe Ser Phe Asp Lys Leu Asn Asn Tyr
610                 615                 620
Leu Thr Phe Asn Lys Phe Cys Leu Ser Leu Asn Pro Val Gly Ala Asn
625                 630                 635                 640
Cys Lys Phe Asp Val Ala Ala Arg Thr Arg Thr Asn Glu Gln Val Val
                645                 650                 655
Arg Ser Leu Tyr Val Ile Tyr Glu Glu Gly Asp Asn Ile Val Gly Val
                660                 665                 670
Pro Ser Asp Asn Ser Gly Leu His Asp Leu Ser Val Leu His Leu Asp
                675                 680                 685
Ser Cys Thr Asp Tyr Asn Ile Tyr Gly Ile Thr Gly Val Gly Ile Ile
690                 695                 700
Arg Gln Thr Asn Ser Thr Leu Leu Ser Gly Leu Tyr Tyr Thr Ser Leu
705                 710                 715                 720
Ser Gly Asp Leu Leu Gly Phe Lys Asn Val Ser Asp Gly Val Ile Tyr
                725                 730                 735
Ser Val Thr Pro Cys Asp Val Ser Ala His Ala Ala Val Ile Asp Gly
                740                 745                 750
Ala Ile Val Gly Ala Met Thr Ser Ile Asn Ser Glu Leu Leu Gly Leu
                755                 760                 765
Thr His Trp Thr Thr Thr Pro Asn Phe Tyr Tyr Tyr Ser Ile Tyr Asn
770                 775                 780
Tyr Thr Asn Glu Arg Thr Arg Gly Thr Ala Ile Asp Ser Asn Asp Val
785                 790                 795                 800
Asp Cys Glu Pro Ile Ile Thr Tyr Ser Asn Ile Gly Val Cys Lys Asn
                805                 810                 815
Gly Ala Leu Val Phe Ile Asn Val Thr His Ser Asp Gly Asp Val Gln
                820                 825                 830
Pro Ile Ser Thr Gly Asn Val Thr Ile Pro Thr Asn Phe Thr Ile Ser
                835                 840                 845
Val Gln Val Glu Tyr Ile Gln Val Tyr Thr Thr Pro Val Ser Ile Asp
                850                 855                 860
Cys Ser Arg Tyr Val Cys Asn Gly Asn Pro Arg Cys Asn Lys Leu Leu
865                 870                 875                 880
Thr Gln Tyr Val Ser Ala Cys Gln Thr Ile Glu Gln Ala Leu Ala Met
                885                 890                 895
Gly Ala Arg Leu Glu Asn Met Glu Ile Asp Ser Met Leu Phe Val Ser
                900                 905                 910
Glu Asn Ala Leu Lys Leu Ala Ser Val Glu Ala Phe Asn Ser Thr Glu
                915                 920                 925
Thr Leu Asp Pro Ile Tyr Lys Glu Trp Pro Asn Ile Gly Gly Ser Trp
930                 935                 940
Leu Gly Gly Leu Lys Asp Ile Leu Pro Ser His Asn Ser Lys Arg Lys
945                 950                 955                 960
Tyr Arg Ser Ala Ile Glu Asp Leu Leu Phe Asp Lys Val Val Thr Ser
                965                 970                 975
Gly Leu Gly Thr Val Asp Glu Asp Tyr Lys Arg Cys Thr Gly Gly Tyr
                980                 985                 990
Asp Ile Ala Asp Leu Val Cys Ala  Gln Tyr Tyr Asn Gly  Ile Met Val
                995                 1000                1005
Leu Pro Gly Val Ala Asn Asp  Asp Lys Met Ala Met  Tyr Thr Ala
        1010                1015                1020
Ser Leu Ala Gly Gly Ile Thr  Leu Gly Ser Leu Gly  Gly Gly Ala
        1025                1030                1035
```

Val Ser Ile Pro Phe Ala Ile Ala Val Gln Ala Arg Leu Asn Tyr
    1040            1045            1050

Val Ala Leu Gln Thr Asp Val Leu Asn Lys Asn Gln Gln Ile Leu
    1055            1060            1065

Ala Asn Ala Phe Asn Gln Ala Ile Gly Asn Ile Thr Gln Ala Phe
    1070            1075            1080

Gly Lys Val Asn Asp Ala Ile His Gln Thr Ser Gln Gly Leu Ala
    1085            1090            1095

Thr Val Ala Lys Val Leu Ala Lys Val Gln Asp Val Val Asn Thr
    1100            1105            1110

Gln Gly Gln Ala Leu Ser His Leu Thr Leu Gln Leu Gln Asn Asn
    1115            1120            1125

Phe Gln Ala Ile Ser Ser Ser Ile Ser Asp Ile Tyr Asn Arg Leu
    1130            1135            1140

Asp Glu Leu Ser Ala Asp Ala Gln Val Asp Arg Leu Ile Thr Gly
    1145            1150            1155

Arg Leu Thr Ala Leu Asn Ala Phe Val Ser Gln Thr Leu Thr Arg
    1160            1165            1170

Gln Ala Glu Val Arg Ala Ser Arg Gln Leu Ala Lys Asp Lys Val
    1175            1180            1185

Asn Glu Cys Val Arg Ser Gln Ser Gln Arg Phe Gly Phe Cys Gly
    1190            1195            1200

Asn Gly Thr His Leu Phe Ser Leu Ala Asn Ala Ala Pro Asn Gly
    1205            1210            1215

Met Ile Phe Phe His Thr Val Leu Leu Pro Thr Ala Tyr Glu Thr
    1220            1225            1230

Val Thr Ala Trp Ser Gly Ile Cys Ala Ser Asp Gly Asp Arg Thr
    1235            1240            1245

Phe Gly Leu Val Val Lys Asp Val Gln Leu Thr Leu Phe Arg Asn
    1250            1255            1260

Leu Asp Asp Lys Phe Tyr Leu Thr Pro Arg Thr Met Tyr Gln Pro
    1265            1270            1275

Ile Val Ala Thr Ser Ser Asp Phe Val Gln Ile Glu Gly Cys Asp
    1280            1285            1290

Val Leu Phe Val Asn Ala Thr Val Ile Asp Leu Pro Ser Ile Ile
    1295            1300            1305

Pro Asp Tyr Ile Asp Ile Asn Gln Thr Val Gln Asp Ile Leu Glu
    1310            1315            1320

Asn Phe Arg Pro Asn Trp Thr Val Pro Glu Leu Pro Leu Asp Ile
    1325            1330            1335

Phe Asn Ala Thr Tyr Leu Asn Leu Thr Gly Glu Ile Asn Asp Leu
    1340            1345            1350

Glu Phe Arg Ser Glu Lys Leu His Asn Thr Thr Val Glu Leu Ala
    1355            1360            1365

Ile Leu Ile Asp Asn Ile Asn Asn Thr Leu Val Asn Leu Glu Trp
    1370            1375            1380

Leu Asn Arg Ile Glu Thr Tyr Val Lys Trp Pro Trp Tyr Val Trp
    1385            1390            1395

Leu Leu Ile Gly Leu Val Val Ile Phe Cys Ile Pro Ile Leu Leu
    1400            1405            1410

Phe Cys Cys Cys Ser Thr Gly Cys Cys Gly Cys Ile Gly Cys Leu
    1415            1420            1425

Gly Ser Cys Cys His Ser Ile Cys Ser Arg Arg Gln Phe Glu Ser

```
                 1430                1435                1440
Tyr Glu   Pro Ile Glu Lys Val   His Val His
    1445                1450

<210> SEQ ID NO 19
<211> LENGTH: 1454
<212> TYPE: PRT
<213> ORGANISM: Feline coronavirus

<400> SEQUENCE: 19

Met Ile Val Leu Val Thr Cys Ile Leu Leu Cys Ser Tyr His Thr
1               5                   10                  15

Val Ser Ser Thr Ser Asn Asn Asp Cys Arg Gln Val Asn Val Thr Gln
                20                  25                  30

Leu Ala Gly Asn Glu Asn Leu Ile Arg Asp Phe Leu Phe Gln Ser Phe
            35                  40                  45

Lys Glu Glu Gly Ile Val Val Val Gly Gly Tyr Tyr Pro Thr Glu Val
    50                  55                  60

Trp Tyr Asn Cys Ser Arg Thr Ala Thr Thr Thr Ala Tyr Glu Tyr Phe
65                  70                  75                  80

Asn Asn Ile His Ala Phe Tyr Phe Asp Met Glu Ala Met Glu Asn Ser
                85                  90                  95

Thr Gly Asn Ala Arg Gly Lys Pro Leu Leu Phe His Val His Gly Glu
            100                 105                 110

Pro Val Ser Ile Ile Ile Tyr Ile Ser Ala Tyr Gly Asp Asp Val Gln
    115                 120                 125

Gln Arg Pro Leu Leu Glu His Gly Leu Leu Cys Ile Thr Lys Asn Arg
130                 135                 140

Asn Ile Asp Tyr Asn Thr Phe Thr Ser Asn Gln Trp Asp Ser Ile Cys
145                 150                 155                 160

Thr Gly Asn Asp Arg Lys Ile Pro Phe Ser Val Ile Pro Arg Asp Asn
                165                 170                 175

Gly Thr Lys Ile Tyr Gly Leu Glu Trp Asn Asp Glu Phe Val Thr Ala
            180                 185                 190

Tyr Ile Ser Gly Arg Ser Tyr Asn Trp Asn Ile Asn Asn Asn Trp Phe
        195                 200                 205

Asn Asn Val Thr Leu Leu Tyr Ser Arg Ser Ser Thr Ala Thr Trp His
210                 215                 220

His Ser Ala Ala Tyr Val Tyr Gln Gly Val Ser Asn Phe Thr Tyr Tyr
225                 230                 235                 240

Lys Leu Asn Asn Thr Asn Gly Leu Lys Thr Tyr Glu Phe Cys Glu Asp
                245                 250                 255

Tyr Glu Tyr Cys Thr Gly Tyr Ala Thr Asn Val Phe Ala Pro Thr Val
            260                 265                 270

Gly Gly Tyr Ile Pro Asp Gly Phe Ser Phe Asn Asn Trp Phe Leu Leu
        275                 280                 285

Thr Asn Ser Ser Thr Phe Val Ser Gly Arg Phe Val Thr Asn Gln Pro
290                 295                 300

Leu Leu Val Asn Cys Leu Trp Pro Val Pro Ser Phe Gly Val Ala Ala
305                 310                 315                 320

Gln Glu Phe Cys Phe Glu Gly Ala Gln Phe Ser Gln Cys Ser Gly Val
                325                 330                 335

Ser Leu Asn Asn Thr Val Asp Val Ile Arg Phe Asn Leu Asn Phe Thr
            340                 345                 350

Ala Asp Val Gln Ser Gly Met Gly Ala Thr Val Phe Ser Leu Asn Thr
```

```
                355                 360                 365
Thr Gly Gly Val Ile Leu Glu Ile Ser Cys Tyr Asn Asp Thr Val Ser
370                 375                 380
Glu Ser Ser Phe Tyr Ser Tyr Gly Glu Ile Pro Phe Gly Ile Thr Asp
385                 390                 395                 400
Gly Pro Arg Tyr Cys Tyr Val Leu Tyr Asn Gly Thr Ala Leu Lys Tyr
                405                 410                 415
Leu Gly Thr Leu Pro Pro Ser Val Lys Glu Ile Ala Ile Ser Lys Trp
            420                 425                 430
Gly His Phe Tyr Ile Asn Gly Tyr Asn Phe Phe Ser Thr Phe Pro Ile
            435                 440                 445
Asp Cys Ile Ser Phe Asn Leu Thr Thr Gly Asp Ser Gly Ala Phe Trp
            450                 455                 460
Thr Ile Ala Tyr Thr Ser Tyr Thr Glu Ala Leu Val Gln Val Glu Asn
465                 470                 475                 480
Thr Ala Ile Lys Lys Val Thr Tyr Cys Asn Ser His Ile Asn Asn Ile
                485                 490                 495
Lys Cys Ser Gln Leu Thr Ala Asn Leu Asn Asn Gly Phe Tyr Pro Val
                500                 505                 510
Ala Ser Ser Glu Val Gly Leu Val Asn Lys Ser Val Val Leu Leu Pro
            515                 520                 525
Ile Phe Phe Ala His Thr Ala Ile Asn Ile Thr Ile Asp Leu Gly Met
            530                 535                 540
Lys Arg Ser Gly Tyr Gly Gln Pro Ile Ala Ser Thr Leu Ser Asn Ile
545                 550                 555                 560
Thr Leu Pro Met Gln Asp Asn Asn Thr Asp Val Tyr Cys Ile Arg Ser
                565                 570                 575
Asn Gln Phe Ser Val Tyr Val His Ser Ile Cys Lys Ser Ser Leu Trp
                580                 585                 590
Asp Asn Ile Phe Asn Gln Glu Cys Thr Asp Val Leu Asp Ala Thr Ala
            595                 600                 605
Val Ile Lys Thr Gly Thr Cys Pro Phe Ser Phe Asp Lys Leu Asn Asn
610                 615                 620
Tyr Leu Thr Phe Asn Lys Phe Cys Leu Ser Leu Ser Pro Val Gly Ala
625                 630                 635                 640
Asn Cys Lys Phe Asp Val Ala Ala Arg Thr Arg Thr Asn Glu Gln Val
                645                 650                 655
Val Arg Ser Leu Tyr Val Ile Tyr Glu Glu Gly Asp Asn Ile Val Gly
            660                 665                 670
Val Pro Ser Asp Asn Ser Gly Leu His Asp Leu Ser Val Leu His Leu
            675                 680                 685
Asp Ser Cys Thr Glu Tyr Asn Ile Tyr Gly Arg Thr Gly Val Gly Ile
            690                 695                 700
Ile Arg Gln Thr Asn Ser Thr Leu Leu Ser Gly Leu Tyr Tyr Thr Ser
705                 710                 715                 720
Leu Ser Gly Asp Leu Leu Gly Phe Lys Asn Val Ser Asp Gly Val Ile
                725                 730                 735
Tyr Ser Val Thr Pro Cys Asp Val Ser Ala Gln Ala Ala Val Ile Asp
                740                 745                 750
Gly Ala Ile Val Gly Ala Met Thr Ser Ile Asn Ser Glu Leu Leu Gly
            755                 760                 765
Leu Lys His Trp Thr Thr Thr Pro Asn Phe Tyr Tyr Tyr Ser Ile Tyr
            770                 775                 780
```

-continued

```
Asn Tyr Thr Asn Glu Arg Thr Arg Gly Thr Ala Ile Asp Ser Asn Asp
785                 790                 795                 800

Val Asp Cys Glu Pro Ile Ile Thr Tyr Ser Asn Ile Gly Val Cys Lys
            805                 810                 815

Asn Gly Ala Leu Val Phe Ile Asn Val Thr His Ser Asp Gly Asp Val
            820                 825                 830

Gln Pro Ile Ser Thr Gly Thr Val Thr Ile Pro Thr Asn Phe Thr Ile
            835                 840                 845

Ser Val Gln Val Glu Tyr Leu Gln Val Tyr Thr Thr Pro Val Ser Ile
850                 855                 860

Asp Cys Ala Arg Tyr Val Cys Asn Gly Asn Pro Arg Cys Asn Lys Leu
865                 870                 875                 880

Leu Thr Gln Tyr Val Ser Ala Cys Gln Thr Ile Glu Gln Ala Leu Ala
            885                 890                 895

Met Gly Ala Arg Leu Glu Asn Met Glu Val Asp Ser Met Leu Phe Val
            900                 905                 910

Ser Glu Asn Ala Leu Lys Leu Ala Ser Val Glu Ala Phe Asn Ser Thr
            915                 920                 925

Glu Asn Leu Asp Pro Ile Tyr Lys Glu Trp Pro Asn Ile Gly Gly Ser
930                 935                 940

Trp Leu Gly Gly Leu Lys Asp Ile Leu Pro Ser His Asn Ser Lys Arg
945                 950                 955                 960

Lys Tyr Arg Ser Ala Ile Glu Asp Leu Leu Phe Asp Lys Ala Val Thr
            965                 970                 975

Ser Gly Leu Gly Thr Val Asp Glu Asp Tyr Lys Arg Cys Thr Gly Gly
            980                 985                 990

Tyr Asp Ile Ala Asp Leu Val Cys Ala Gln Tyr Tyr Asn Gly Ile Met
            995                 1000                1005

Val Leu Pro Gly Val Ala Asn Asp Asp Lys Met Thr Met Tyr Thr
    1010                1015                1020

Ala Ser Leu Ala Gly Gly Ile Thr Leu Gly Ala Leu Gly Gly Gly
    1025                1030                1035

Ala Val Ala Ile Pro Phe Ala Val Ala Val Gln Ala Arg Leu Asn
    1040                1045                1050

Tyr Val Ala Leu Gln Thr Asp Val Leu Asn Lys Asn Gln Gln Ile
    1055                1060                1065

Leu Ala Asn Ala Phe Asn Gln Ala Ile Gly Asn Ile Thr Gln Ala
    1070                1075                1080

Phe Gly Lys Val Asn Asp Ala Ile His Gln Thr Ser Lys Gly Leu
    1085                1090                1095

Ala Thr Val Ala Lys Ala Leu Ala Lys Val Gln Asp Val Val Asn
    1100                1105                1110

Thr Gln Gly Gln Ala Leu Ser His Leu Thr Val Gln Leu Gln Asn
    1115                1120                1125

Asn Phe Gln Ala Ile Ser Ser Ser Ile Ser Asp Ile Tyr Asn Arg
    1130                1135                1140

Leu Asp Glu Leu Ser Ala Asp Ala Gln Val Asp Arg Leu Ile Thr
    1145                1150                1155

Gly Arg Leu Thr Ala Leu Asn Ala Phe Val Ser Gln Thr Leu Thr
    1160                1165                1170

Arg Gln Ala Glu Val Arg Ala Ser Arg Gln Leu Ala Lys Asp Lys
    1175                1180                1185

Val Asn Glu Cys Val Arg Ser Gln Ser Gln Arg Phe Gly Phe Cys
    1190                1195                1200
```

```
Gly Asn Gly Thr His Leu Phe Ser Leu Ala Asn Ala Ala Pro Asn
    1205                1210                1215

Gly Met Ile Phe Phe His Thr Val Leu Leu Pro Thr Ala Tyr Glu
    1220                1225                1230

Thr Val Thr Ala Trp Pro Gly Ile Cys Ala Ser Asp Gly Asp Arg
    1235                1240                1245

Thr Phe Gly Leu Val Val Lys Asp Val Gln Leu Thr Leu Phe Arg
    1250                1255                1260

Asn Leu Asp Asp Lys Phe Tyr Leu Thr Pro Arg Thr Met Tyr Gln
    1265                1270                1275

Pro Arg Ala Ala Thr Ser Ser Asp Phe Val Gln Ile Glu Gly Cys
    1280                1285                1290

Asp Val Leu Phe Val Asn Ala Thr Val Ile Asp Leu Pro Ser Ile
    1295                1300                1305

Ile Pro Asp Tyr Ile Asp Ile Asn Gln Thr Val Gln Asp Ile Leu
    1310                1315                1320

Glu Asn Tyr Arg Pro Asn Trp Thr Val Pro Glu Leu Thr Leu Asp
    1325                1330                1335

Ile Phe Asn Ala Thr Tyr Leu Asn Leu Thr Gly Glu Ile Asp Asp
    1340                1345                1350

Leu Glu Phe Arg Ser Glu Lys Leu His Asn Thr Thr Val Glu Leu
    1355                1360                1365

Ala Ile Leu Ile Asp Asn Ile Asn Asn Thr Leu Val Asn Leu Glu
    1370                1375                1380

Trp Leu Asn Arg Ile Glu Thr Tyr Val Lys Trp Pro Trp Tyr Val
    1385                1390                1395

Trp Leu Leu Ile Gly Leu Val Val Ile Phe Cys Ile Pro Leu Leu
    1400                1405                1410

Leu Phe Cys Cys Cys Ser Thr Gly Cys Cys Gly Cys Ile Gly Cys
    1415                1420                1425

Leu Gly Ser Cys Cys His Ser Met Cys Ser Arg Arg Gln Phe Glu
    1430                1435                1440

Asn Tyr Glu Pro Ile Glu Lys Val His Val His
    1445                1450

<210> SEQ ID NO 20
<211> LENGTH: 1452
<212> TYPE: PRT
<213> ORGANISM: Feline infectious peritonitis virus

<400> SEQUENCE: 20

Met Ile Val Leu Val Thr Cys Leu Leu Leu Cys Ser Tyr His Thr
1               5                   10                  15

Val Leu Ser Thr Thr Asn Asn Glu Cys Ile Gln Val Asn Val Thr Gln
                20                  25                  30

Leu Ala Gly Asn Glu Asn Leu Ile Arg Asp Phe Leu Phe Ser Asn Phe
                35                  40                  45

Lys Glu Glu Gly Ser Val Val Val Gly Gly Tyr Tyr Pro Thr Glu Val
    50                  55                  60

Trp Tyr Asn Cys Ser Arg Thr Ala Arg Thr Thr Ala Phe Gln Tyr Phe
65                  70                  75                  80

Asn Asn Ile His Ala Phe Tyr Phe Val Met Glu Ala Met Glu Asn Ser
                85                  90                  95

Thr Gly Asn Ala Arg Gly Lys Pro Leu Leu Phe His Val His Gly Glu
                100                 105                 110
```

```
Pro Val Ser Val Ile Ile Ser Ala Tyr Arg Asp Asp Val Gln Gln Arg
            115                 120                 125

Pro Leu Leu Lys His Gly Leu Val Cys Ile Thr Lys Asn Arg His Ile
        130                 135                 140

Asn Tyr Glu Gln Phe Thr Ser Asn Gln Trp Asn Ser Thr Cys Thr Gly
145                 150                 155                 160

Ala Asp Arg Lys Ile Pro Phe Ser Val Ile Pro Thr Asp Asn Gly Thr
                165                 170                 175

Lys Ile Tyr Gly Leu Glu Trp Asn Asp Asp Phe Val Thr Ala Tyr Ile
            180                 185                 190

Ser Gly Arg Ser Tyr His Leu Asn Ile Asn Thr Asn Trp Phe Asn Asn
        195                 200                 205

Val Thr Leu Leu Tyr Ser Arg Ser Ser Thr Ala Thr Trp Glu Tyr Ser
    210                 215                 220

Ala Ala Tyr Ala Tyr Gln Gly Val Ser Asn Phe Thr Tyr Tyr Lys Leu
225                 230                 235                 240

Asn Asn Thr Asn Gly Leu Lys Thr Tyr Glu Leu Cys Glu Asp Tyr Glu
                245                 250                 255

His Cys Thr Gly Tyr Ala Thr Asn Val Phe Ala Pro Thr Ser Gly Gly
            260                 265                 270

Tyr Ile Pro Asp Gly Phe Ser Phe Asn Asn Trp Phe Leu Leu Thr Asn
        275                 280                 285

Ser Ser Thr Phe Val Ser Gly Arg Phe Val Thr Asn Gln Pro Leu Leu
    290                 295                 300

Ile Asn Cys Leu Trp Pro Val Pro Ser Phe Gly Val Ala Ala Gln Glu
305                 310                 315                 320

Phe Cys Phe Glu Gly Ala Gln Phe Ser Gln Cys Asn Gly Val Ser Leu
                325                 330                 335

Asn Asn Thr Val Asp Val Ile Arg Phe Asn Leu Asn Phe Thr Ala Asp
            340                 345                 350

Val Gln Ser Gly Met Gly Ala Thr Val Phe Ser Leu Asn Thr Thr Gly
        355                 360                 365

Gly Val Ile Leu Glu Ile Ser Cys Tyr Ser Asp Thr Val Ser Glu Ser
    370                 375                 380

Ser Ser Tyr Ser Tyr Gly Glu Ile Pro Phe Gly Ile Thr Asp Gly Pro
385                 390                 395                 400

Arg Tyr Cys Tyr Val Leu Tyr Asn Gly Thr Ala Leu Lys Tyr Leu Gly
                405                 410                 415

Thr Leu Pro Pro Ser Val Lys Glu Ile Ala Ile Ser Lys Trp Gly His
            420                 425                 430

Phe Tyr Ile Asn Gly Tyr Asn Phe Phe Ser Thr Phe Pro Ile Gly Cys
        435                 440                 445

Ile Ser Phe Asn Leu Thr Thr Gly Val Ser Gly Ala Phe Trp Thr Ile
    450                 455                 460

Ala Tyr Thr Ser Tyr Thr Glu Ala Leu Val Gln Val Glu Asn Thr Ala
465                 470                 475                 480

Ile Lys Asn Val Thr Tyr Cys Asn Ser His Ile Asn Asn Ile Lys Cys
                485                 490                 495

Ser Gln Leu Thr Ala Asn Leu Asn Asn Gly Phe Tyr Pro Val Ala Ser
            500                 505                 510

Ser Glu Val Gly Phe Val Asn Lys Ser Val Val Leu Leu Pro Ser Phe
        515                 520                 525

Phe Thr Tyr Thr Ala Val Asn Ile Thr Ile Asp Leu Gly Met Lys Leu
```

-continued

```
                530                 535                 540
Ser Gly Tyr Gly Gln Pro Ile Ala Ser Thr Leu Ser Asn Ile Thr Leu
545                 550                 555                 560

Pro Met Gln Asp Asn Asn Thr Asp Val Tyr Cys Ile Arg Ser Asn Gln
                565                 570                 575

Phe Ser Val Tyr Val His Ser Thr Cys Lys Ser Ser Leu Trp Asp Asn
                580                 585                 590

Ile Phe Asn Gln Asp Cys Thr Asp Val Leu Glu Ala Thr Ala Val Ile
                595                 600                 605

Lys Thr Gly Thr Cys Pro Phe Ser Phe Asp Lys Leu Asn Asn Tyr Leu
610                 615                 620

Thr Phe Asn Lys Phe Cys Leu Ser Leu Ser Pro Val Gly Ala Asn Cys
625                 630                 635                 640

Lys Phe Asp Val Ala Ala Arg Thr Arg Thr Asn Glu Gln Val Val Arg
                645                 650                 655

Ser Leu Tyr Val Ile Tyr Glu Glu Gly Asp Asn Ile Val Gly Val Pro
                660                 665                 670

Ser Asp Asn Ser Gly Leu His Asp Leu Ser Val Leu His Leu Asp Ser
                675                 680                 685

Cys Thr Asp Tyr Asn Ile Tyr Gly Arg Thr Gly Val Gly Ile Ile Arg
690                 695                 700

Arg Thr Asn Ser Thr Leu Leu Ser Gly Leu Tyr Tyr Thr Ser Leu Ser
705                 710                 715                 720

Gly Asp Leu Leu Gly Phe Lys Asn Val Ser Asp Gly Val Ile Tyr Ser
                725                 730                 735

Val Thr Pro Cys Asp Val Ser Ala Gln Ala Ala Val Ile Asp Gly Ala
                740                 745                 750

Ile Val Gly Ala Met Thr Ser Ile Asn Ser Glu Leu Leu Gly Leu Thr
                755                 760                 765

His Trp Thr Thr Thr Pro Asn Phe Tyr Tyr Tyr Ser Ile Tyr Asn Tyr
                770                 775                 780

Thr Ser Glu Arg Thr Arg Gly Thr Ala Ile Asp Ser Asn Asp Val Asp
785                 790                 795                 800

Cys Glu Pro Val Ile Thr Tyr Ser Asn Ile Gly Val Cys Lys Asn Gly
                805                 810                 815

Ala Leu Val Phe Ile Asn Val Thr His Ser Asp Gly Asp Val Gln Pro
                820                 825                 830

Ile Ser Thr Gly Asn Val Thr Ile Pro Thr Asn Phe Thr Ile Ser Val
                835                 840                 845

Gln Val Glu Tyr Met Gln Val Tyr Thr Thr Pro Val Ser Ile Asp Cys
850                 855                 860

Ala Arg Tyr Val Cys Asn Gly Asn Pro Arg Cys Asn Lys Leu Leu Thr
865                 870                 875                 880

Gln Tyr Val Ser Ala Cys Gln Thr Ile Glu Gln Ala Leu Ala Met Gly
                885                 890                 895

Ala Arg Leu Glu Asn Met Glu Val Asp Ser Met Leu Phe Val Ser Glu
                900                 905                 910

Asn Ala Leu Lys Leu Ala Ser Val Glu Ala Phe Asn Ser Thr Glu Asn
                915                 920                 925

Leu Asp Pro Ile Tyr Lys Glu Trp Pro Ser Ile Gly Gly Ser Trp Leu
                930                 935                 940

Gly Gly Leu Lys Asp Ile Leu Pro Ser His Asn Ser Lys Arg Lys Tyr
945                 950                 955                 960
```

```
Gly Ser Ala Ile Glu Asp Leu Leu Phe Asp Lys Val Val Thr Ser Gly
            965                 970                 975

Leu Gly Thr Val Asp Glu Asp Tyr Lys Arg Cys Thr Gly Gly Tyr Asp
            980                 985                 990

Ile Ala Asp Leu Val Cys Ala Gln Tyr Tyr Asn Gly Ile Met Val Leu
            995                1000                1005

Pro Gly Val Ala Asn Ala Asp Lys Met Thr Met Tyr Thr Ala Ser
   1010                1015                1020

Leu Ala Gly Gly Ile Thr Leu Gly Ala Leu Gly Gly Gly Ala Val
   1025                1030                1035

Ala Ile Pro Phe Ala Val Ala Val Gln Ala Arg Leu Asn Tyr Val
   1040                1045                1050

Ala Leu Gln Thr Asp Val Leu Asn Lys Asn Gln Gln Ile Leu Ala
   1055                1060                1065

Asn Ala Phe Asn Gln Ala Ile Gly Asn Ile Thr Gln Ala Phe Gly
   1070                1075                1080

Lys Val Asn Asp Ala Ile His Gln Thr Ser Gln Gly Leu Ala Thr
   1085                1090                1095

Val Ala Lys Ala Leu Ala Lys Val Gln Asp Val Val Asn Thr Gln
   1100                1105                1110

Gly Gln Ala Leu Ser His Leu Thr Val Gln Leu Gln Asn Asn Phe
   1115                1120                1125

Gln Ala Ile Ser Ser Ser Ile Ser Asp Ile Tyr Asn Arg Leu Asp
   1130                1135                1140

Glu Leu Ser Ala Asp Ala Gln Val Asp Arg Leu Ile Thr Gly Arg
   1145                1150                1155

Leu Thr Ala Leu Asn Ala Phe Val Ser Gln Thr Leu Thr Arg Gln
   1160                1165                1170

Ala Glu Val Arg Ala Ser Arg Gln Leu Ala Lys Asp Lys Val Asn
   1175                1180                1185

Glu Cys Val Arg Ser Gln Ser Gln Arg Phe Gly Phe Cys Gly Asn
   1190                1195                1200

Gly Thr His Leu Phe Ser Leu Ala Asn Ala Ala Pro Asn Gly Met
   1205                1210                1215

Ile Phe Phe His Thr Val Leu Leu Pro Thr Ala Tyr Glu Thr Val
   1220                1225                1230

Thr Ala Trp Ser Gly Ile Cys Ala Ser Asp Gly Asp Arg Thr Phe
   1235                1240                1245

Gly Leu Val Val Lys Asp Val Gln Leu Thr Leu Phe Arg Asn Leu
   1250                1255                1260

Asp Asp Lys Phe Tyr Leu Thr Pro Arg Thr Met Tyr Gln Pro Arg
   1265                1270                1275

Val Ala Thr Ser Ser Asp Phe Val Gln Ile Glu Gly Cys Asp Val
   1280                1285                1290

Leu Phe Val Asn Ala Thr Val Ile Asp Leu Pro Ser Ile Ile Pro
   1295                1300                1305

Asp Tyr Ile Asp Ile Asn Gln Thr Val Gln Asp Ile Leu Glu Asn
   1310                1315                1320

Tyr Arg Pro Asn Trp Thr Val Pro Glu Phe Thr Leu Asp Ile Phe
   1325                1330                1335

Asn Ala Thr Tyr Leu Asn Leu Thr Gly Glu Ile Asp Asp Leu Glu
   1340                1345                1350

Phe Arg Ser Glu Lys Leu His Asn Thr Thr Val Glu Leu Ala Ile
   1355                1360                1365
```

```
Leu Ile Asp Asn Ile Asn Asn Thr Leu Val Asn Leu Glu Trp Leu
        1370            1375                1380

Asn Arg Ile Glu Thr Tyr Val Lys Trp Pro Trp Tyr Val Trp Leu
1385                1390                1395

Leu Ile Gly Leu Val Val Val Phe Cys Ile Pro Leu Leu Leu Phe
    1400                1405                1410

Cys Cys Phe Ser Thr Gly Cys Cys Gly Cys Ile Gly Cys Leu Gly
        1415                1420                1425

Ser Cys Cys His Ser Ile Cys Ser Arg Arg Gln Phe Glu Asn Tyr
    1430                1435                1440

Glu Pro Ile Glu Lys Val His Val His
        1445                1450

<210> SEQ ID NO 21
<211> LENGTH: 1449
<212> TYPE: PRT
<213> ORGANISM: Porcine transmissible gastro coronavirus

<400> SEQUENCE: 21

Met Lys Lys Leu Phe Val Val Leu Val Val Met Pro Leu Ile Tyr Gly
1               5                   10                  15

Asp Asn Phe Pro Cys Ser Lys Leu Thr Asn Arg Thr Ile Gly Asn His
                20                  25                  30

Trp Asn Leu Ile Glu Thr Phe Leu Leu Asn Tyr Ser Ser Arg Leu Ser
            35                  40                  45

Pro Asn Ser Asp Val Val Leu Gly Asp Tyr Phe Pro Thr Val Gln Pro
        50                  55                  60

Trp Phe Asn Cys Ile His Asn Asn Ser Asn Asp Leu Tyr Val Thr Leu
65                  70                  75                  80

Glu Asn Leu Lys Ala Leu Tyr Trp Asp Tyr Ala Thr Glu Asn Ser Thr
                85                  90                  95

Trp Asn His Lys Gln Arg Leu Asn Val Val Asn Gly Tyr Pro Tyr
                100                 105                 110

Ser Ile Thr Val Thr Thr Thr Arg Asn Phe Asn Ser Ala Glu Gly Ala
            115                 120                 125

Ile Ile Cys Ile Cys Lys Gly Ser Pro Pro Thr Thr Thr Thr Glu Ser
        130                 135                 140

Ser Leu Thr Cys Asn Trp Gly Ser Glu Cys Arg Leu Asn His Lys Phe
145                 150                 155                 160

Pro Ile Cys Pro Ser Asn Ser Glu Ala Asn Cys Gly Asn Met Leu Tyr
                165                 170                 175

Gly Leu Gln Trp Phe Ala Asp Ala Val Val Ala Tyr Leu His Gly Ala
            180                 185                 190

Ser Tyr Arg Ile Ser Phe Glu Asn Gln Trp Ser Gly Thr Val Thr Leu
        195                 200                 205

Gly Asp Met Arg Ala Thr Thr Leu Glu Thr Ala Gly Thr Leu Val Asp
    210                 215                 220

Leu Trp Trp Phe Asn Pro Val Tyr Asp Val Ser Tyr Tyr Arg Val Asn
225                 230                 235                 240

Asn Lys Asn Gly Thr Thr Val Val Ser Asn Cys Thr Asp Gln Cys Ala
                245                 250                 255

Ser Tyr Val Ala Asn Val Phe Thr Thr Gln Pro Gly Gly Phe Ile Pro
            260                 265                 270

Ser Asp Phe Ser Phe Asn Asn Trp Phe Leu Leu Thr Asn Ser Ser Thr
        275                 280                 285
```

-continued

```
Leu Val Ser Gly Lys Leu Val Thr Lys Gln Pro Leu Val Asn Cys
    290                 295                 300
Leu Trp Pro Val Pro Ser Phe Glu Glu Ala Ser Thr Phe Cys Phe
305                 310                 315                 320
Glu Gly Ala Gly Phe Asp Gln Cys Asn Gly Ala Val Leu Asn Asn Thr
                325                 330                 335
Val Asp Val Ile Arg Phe Asn Leu Asn Phe Thr Thr Asn Val Gln Ser
                340                 345                 350
Gly Lys Gly Ala Thr Val Phe Ser Leu Asn Thr Thr Gly Gly Val Thr
                355                 360                 365
Leu Glu Ile Ser Cys Tyr Asn Asp Thr Val Ser Asp Ser Ser Phe Ser
    370                 375                 380
Ser Tyr Gly Glu Ile Pro Phe Gly Val Thr Asp Gly Pro Arg Tyr Cys
385                 390                 395                 400
Tyr Val Leu Tyr Asn Gly Thr Ala Leu Lys Tyr Leu Gly Thr Leu Pro
                405                 410                 415
Pro Ser Val Lys Glu Ile Ala Ile Ser Lys Trp Gly His Phe Tyr Ile
                420                 425                 430
Asn Gly Tyr Asn Phe Phe Ser Thr Phe Pro Ile Asp Cys Ile Ser Phe
                435                 440                 445
Asn Leu Thr Thr Gly Asp Ser Asp Val Phe Trp Thr Ile Ala Tyr Thr
    450                 455                 460
Ser Tyr Thr Glu Ala Leu Val Gln Val Glu Asn Thr Ala Ile Thr Lys
465                 470                 475                 480
Val Thr Tyr Cys Asn Ser Tyr Val Asn Asn Ile Lys Cys Ser Gln Leu
                485                 490                 495
Thr Ala Asn Leu Asn Asn Gly Phe Tyr Pro Val Ser Ser Ser Glu Val
                500                 505                 510
Gly Phe Val Asn Lys Ser Val Val Leu Leu Pro Thr Phe Tyr Thr His
                515                 520                 525
Thr Ile Val Asn Ile Thr Ile Gly Leu Gly Met Lys Arg Ser Gly Tyr
    530                 535                 540
Gly Gln Pro Ile Ala Ser Thr Leu Ser Asn Ile Thr Leu Pro Met Gln
545                 550                 555                 560
Asp Asn Asn Ile Asp Val Tyr Cys Ile Arg Ser Asp Gln Phe Ser Val
                565                 570                 575
Tyr Val His Ser Thr Cys Lys Ser Ala Leu Trp Asp Asn Val Phe Lys
                580                 585                 590
Arg Asn Cys Thr Asp Val Leu Asp Ala Thr Ala Val Ile Lys Thr Gly
                595                 600                 605
Thr Cys Pro Phe Ser Phe Asp Lys Leu Asn Asn Tyr Leu Thr Phe Asn
    610                 615                 620
Lys Phe Cys Leu Ser Leu Ser Pro Val Gly Ala Asn Cys Lys Phe Asp
625                 630                 635                 640
Val Ala Ala Arg Thr Arg Ala Asn Asp Gln Val Val Arg Ser Leu Tyr
                645                 650                 655
Val Ile Tyr Glu Glu Gly Asp Asn Ile Val Gly Val Pro Ser Asp Asn
                660                 665                 670
Ser Gly Leu His Asp Leu Ser Val Leu His Leu Asp Ser Cys Thr Asp
                675                 680                 685
Tyr Asn Ile Tyr Gly Arg Ser Gly Val Gly Ile Ile Arg Gln Thr Asn
    690                 695                 700
Arg Thr Leu Leu Ser Gly Leu Tyr Tyr Thr Ser Leu Ser Gly Asp Leu
```

```
                705                 710                 715                 720
Leu Gly Phe Lys Asn Val Ser Asp Gly Val Ile Tyr Ser Val Thr Pro
                    725                 730                 735

Cys Asp Val Ser Ala Gln Ala Val Ile Asp Gly Thr Ile Val Gly
                740                 745                 750

Ala Ile Thr Ser Ile Asn Ser Glu Leu Leu Gly Leu Thr His Trp Thr
                755                 760                 765

Thr Thr Pro Asn Phe Tyr Tyr Tyr Ser Ile Tyr Asn Tyr Thr Asn Asp
                770                 775                 780

Met Thr Arg Gly Thr Ala Ile Asp Ser Asn Asp Val Asp Cys Glu Pro
785                 790                 795                 800

Val Ile Thr Tyr Ser Asn Ile Gly Val Cys Lys Asn Gly Ala Leu Val
                805                 810                 815

Phe Ile Asn Val Thr His Ser Asp Gly Asp Val Gln Pro Ile Ser Thr
                820                 825                 830

Gly Asn Val Thr Ile Pro Thr Asn Phe Thr Ile Ser Val Gln Val Glu
                835                 840                 845

Tyr Ile Gln Val Tyr Thr Thr Pro Val Ser Ile Asp Cys Ser Arg Tyr
                850                 855                 860

Val Cys Asn Gly Asn Pro Arg Cys Asn Lys Leu Leu Thr Gln Tyr Val
865                 870                 875                 880

Ser Ala Cys Gln Thr Ile Glu Gln Ala Leu Ala Val Gly Ala Arg Leu
                885                 890                 895

Glu Asn Met Glu Val Asp Ser Met Leu Phe Val Ser Glu Asn Ala Leu
                900                 905                 910

Lys Leu Ala Ser Val Glu Ala Phe Asn Ser Ser Glu Thr Leu Asp Pro
                915                 920                 925

Ile Tyr Lys Glu Trp Pro Asn Ile Gly Gly Ser Trp Leu Glu Gly Leu
                930                 935                 940

Lys Tyr Ile Leu Pro Ser Asp Asn Ser Lys Arg Lys Tyr Arg Ser Ala
945                 950                 955                 960

Ile Glu Asp Leu Leu Phe Ser Lys Val Val Thr Ser Gly Leu Gly Thr
                965                 970                 975

Val Asp Glu Asp Tyr Lys Arg Cys Thr Gly Gly Tyr Asp Ile Ala Asp
                980                 985                 990

Leu Val Cys Ala Gln Tyr Tyr Asn Gly Ile Met Val Leu Pro Gly Val
                995                 1000                1005

Ala Asn Ala Asp Lys Met Thr Met Tyr Thr Ala Ser Leu Ala Gly
                1010                1015                1020

Gly Ile Thr Leu Gly Ala Leu Gly Gly Gly Ala Val Ala Ile Pro
                1025                1030                1035

Phe Ala Val Ala Val Gln Ala Arg Leu Asn Tyr Val Ala Leu Gln
                1040                1045                1050

Thr Asp Val Leu Asn Lys Asn Gln Gln Ile Leu Ala Ser Ala Phe
                1055                1060                1065

Asn Gln Ala Ile Gly Asn Ile Thr Gln Ser Phe Gly Lys Val Asn
                1070                1075                1080

Asp Ala Ile His Gln Thr Ser Arg Gly Leu Ala Thr Val Ala Lys
                1085                1090                1095

Ala Leu Ala Lys Val Gln Asp Val Val Asn Thr Gln Gly Gln Ala
                1100                1105                1110

Leu Ser His Leu Thr Val Gln Leu Gln Asn Asn Phe Gln Ala Ile
                1115                1120                1125
```

Ser Ser Ser Ile Ser Asp Ile Tyr Asn Arg Leu Asp Glu Leu Ser
1130               1135                    1140

Ala Asp Ala His Val Asp Arg Leu Ile Thr Gly Arg Leu Thr Ala
1145               1150                    1155

Leu Asn Ala Phe Val Ser Gln Thr Leu Thr Arg Gln Ala Glu Val
1160               1165                    1170

Arg Ala Ser Arg Gln Leu Ala Lys Asp Lys Val Asn Glu Cys Val
1175               1180                    1185

Arg Ser Gln Ser Gln Arg Phe Gly Phe Cys Gly Asn Gly Thr His
1190               1195                    1200

Leu Phe Ser Leu Ala Asn Ala Ala Pro Asn Gly Met Ile Phe Phe
1205               1210                    1215

His Ala Val Leu Leu Pro Thr Ala Tyr Glu Thr Val Thr Ala Trp
1220               1225                    1230

Ala Gly Ile Cys Ala Leu Asp Gly Asp Arg Thr Phe Gly Leu Val
1235               1240                    1245

Val Lys Asp Val Gln Leu Thr Leu Phe Arg Asn Leu Asp Asp Lys
1250               1255                    1260

Phe Tyr Leu Thr Pro Arg Thr Met Tyr Gln Pro Arg Val Ala Thr
1265               1270                    1275

Ser Ser Asp Phe Val Gln Ile Glu Gly Cys Asp Val Leu Phe Val
1280               1285                    1290

Asn Ala Thr Leu Ser Asp Leu Pro Ser Ile Ile Pro Asp Tyr Ile
1295               1300                    1305

Asp Ile Asn Gln Thr Val Gln Asp Ile Leu Glu Asn Phe Arg Pro
1310               1315                    1320

Asn Trp Thr Val Pro Glu Leu Thr Phe Asp Ile Phe Asn Ala Thr
1325               1330                    1335

Tyr Leu Asn Leu Thr Gly Glu Ile Asp Asp Leu Glu Phe Arg Ser
1340               1345                    1350

Glu Lys Leu His Asn Thr Thr Val Glu Leu Ala Ile Leu Ile Asp
1355               1360                    1365

Asn Ile Asn Asn Thr Leu Val Asn Leu Glu Trp Leu Asn Arg Ile
1370               1375                    1380

Glu Thr Tyr Val Lys Trp Pro Trp Tyr Val Trp Leu Leu Ile Gly
1385               1390                    1395

Leu Val Val Ile Phe Cys Ile Pro Leu Leu Leu Phe Cys Cys Cys
1400               1405                    1410

Ser Thr Gly Cys Cys Gly Cys Ile Gly Cys Leu Gly Ser Cys Cys
1415               1420                    1425

His Ser Ile Cys Ser Arg Arg Gln Phe Glu Asn Tyr Glu Pro Ile
1430               1435                    1440

Glu Lys Val His Ile His
1445

<210> SEQ ID NO 22
<211> LENGTH: 1225
<212> TYPE: PRT
<213> ORGANISM: Porcine respiratory coronavirus

<400> SEQUENCE: 22

Met Lys Lys Leu Phe Val Val Leu Val Val Met Pro Leu Ile Tyr Gly
1               5                   10                  15

Asp Lys Phe Pro Thr Ser Val Val Ser Asn Cys Thr Asp Gln Cys Ala
            20                  25                  30

-continued

```
Ser Tyr Val Ala Asn Val Phe Thr Ile Leu Pro Gly Gly Phe Ile Pro
        35                  40                  45

Ser Asp Phe Ser Phe Asn Asn Trp Phe Leu Leu Thr Asn Ser Ser Thr
    50                  55                  60

Leu Val Asn Gly Lys Leu Val Thr Lys Gln Pro Leu Leu Val Asn Cys
65                  70                  75                  80

Leu Trp Pro Val Pro Ser Phe Glu Glu Val Ala Ser Thr Phe Cys Phe
                85                  90                  95

Glu Gly Ala Asp Phe Asp Gln Cys Asn Gly Ala Val Leu Asn Asn Thr
            100                 105                 110

Val Asp Val Ile Arg Phe Asn Leu Asn Phe Thr Thr Asn Val Gln Ser
        115                 120                 125

Gly Lys Gly Ala Thr Val Phe Ser Leu Asn Thr Thr Gly Gly Val Thr
    130                 135                 140

Leu Glu Ile Ser Cys Tyr Asn Asp Thr Val Ser Asp Ser Ser Phe Ser
145                 150                 155                 160

Ser Tyr Gly Glu Ile Pro Phe Gly Val Thr Asn Gly Pro Arg Tyr Cys
                165                 170                 175

Tyr Val Leu Tyr Asn Gly Thr Ala Leu Lys Tyr Leu Gly Thr Leu Pro
            180                 185                 190

Pro Ser Val Lys Glu Ile Ala Ile Ser Lys Trp Gly His Phe Tyr Ile
        195                 200                 205

Asn Gly Tyr Asn Phe Phe Ser Thr Phe Pro Ile Asp Cys Ile Ser Phe
    210                 215                 220

Asn Leu Thr Thr Gly Asp Ser Asp Val Phe Trp Thr Ile Ala Tyr Thr
225                 230                 235                 240

Ser Tyr Thr Glu Ala Leu Val Gln Val Glu Asn Thr Ala Ile Thr Asn
                245                 250                 255

Val Thr Tyr Cys Asn Ser Tyr Val Asn Asn Ile Lys Cys Ser Gln Leu
            260                 265                 270

Thr Ala Asn Leu Asn Asn Gly Phe Tyr Pro Val Ser Ser Ser Glu Val
        275                 280                 285

Gly Ser Val Asn Lys Ser Val Val Leu Leu Pro Ser Phe Leu Thr His
    290                 295                 300

Thr Ile Val Asn Ile Thr Ile Gly Leu Gly Met Lys Arg Ser Gly Tyr
305                 310                 315                 320

Gly Gln Pro Ile Ala Ser Thr Leu Ser Asn Ile Thr Leu Pro Met Gln
                325                 330                 335

Asp Asn Asn Asn Asp Val Tyr Cys Val Arg Ser Asp Gln Phe Ser Val
            340                 345                 350

Tyr Val His Ser Thr Cys Lys Ser Val Leu Trp Asp Asn Val Phe Lys
        355                 360                 365

Arg Asn Cys Thr Asp Val Leu Asp Ala Thr Ala Val Ile Lys Thr Gly
    370                 375                 380

Thr Cys Pro Phe Ser Phe Asp Lys Leu Asn Asn Tyr Leu Thr Phe Asn
385                 390                 395                 400

Lys Phe Cys Leu Ser Leu Ser Pro Val Gly Ala Asn Cys Lys Phe Asp
                405                 410                 415

Val Ala Ala Arg Thr Arg Thr Asn Asp Gln Val Val Arg Ser Leu Tyr
            420                 425                 430

Val Ile Tyr Glu Glu Gly Asp Ser Ile Val Gly Val Pro Ser Asp Asn
        435                 440                 445

Ser Gly Leu His Asp Leu Ser Val Leu His Leu Asp Ser Cys Thr Asp
    450                 455                 460
```

```
Tyr Asn Ile Tyr Gly Arg Thr Gly Val Gly Ile Ile Arg Gln Thr Asn
465                 470                 475                 480

Arg Thr Ile Leu Ser Gly Leu Tyr Tyr Thr Ser Leu Ser Gly Asp Leu
            485                 490                 495

Leu Gly Phe Thr Asn Val Ser Asp Gly Val Ile Tyr Ser Val Thr Pro
                500                 505                 510

Cys Asp Val Ser Ala Gln Ala Ala Ile Ile Asp Gly Thr Ile Val Gly
            515                 520                 525

Ala Ile Thr Ser Ile Asn Ser Glu Leu Leu Gly Leu Thr His Trp Thr
            530                 535                 540

Thr Thr Pro Asn Phe Tyr Tyr Ser Ile Tyr Asn Tyr Thr Asn Asp
545                 550                 555                 560

Lys Thr Arg Gly Thr Pro Ile Gly Ser Asn Asp Val Asp Cys Glu Pro
                565                 570                 575

Val Ile Thr Tyr Ser Asn Ile Gly Val Cys Lys Asn Gly Ala Leu Val
            580                 585                 590

Phe Ile Asn Val Thr His Ser Asp Gly Asp Val Gln Pro Ile Ser Thr
            595                 600                 605

Gly Asn Val Thr Ile Pro Thr Asn Phe Thr Ile Ser Val Gln Val Glu
610                 615                 620

Tyr Ile Gln Val Tyr Thr Thr Pro Val Ser Ile Asp Cys Ser Arg Tyr
625                 630                 635                 640

Val Cys Asn Gly Asn Pro Arg Cys Asn Lys Leu Leu Thr Gln Tyr Val
                645                 650                 655

Ser Ala Cys Gln Thr Ile Glu Gln Ala Leu Ala Met Gly Ala Arg Leu
                660                 665                 670

Glu Asn Met Glu Val Asp Ser Met Leu Phe Val Ser Glu Asn Ala Leu
            675                 680                 685

Lys Leu Ala Ser Val Glu Ala Phe Asn Ser Ser Glu Thr Leu Asp Pro
690                 695                 700

Ile Tyr Lys Glu Trp Pro Asn Ile Gly Gly Phe Trp Leu Glu Gly Leu
705                 710                 715                 720

Lys Tyr Ile Leu Pro Ser Asp Asn Ser Lys Arg Lys Tyr Arg Ser Ala
                725                 730                 735

Ile Glu Asp Leu Leu Phe Ser Lys Val Val Thr Ser Gly Leu Gly Thr
                740                 745                 750

Val Asp Glu Asp Tyr Lys Arg Cys Thr Gly Gly Tyr Asp Ile Ala Asp
            755                 760                 765

Leu Val Cys Ala Gln Tyr Tyr Asn Gly Ile Met Val Leu Pro Gly Val
            770                 775                 780

Ala Asn Ala Asp Lys Met Thr Met Tyr Thr Ala Ser Leu Ala Gly Gly
785                 790                 795                 800

Ile Thr Leu Gly Ala Leu Gly Gly Gly Ala Val Ala Ile Pro Phe Ala
                805                 810                 815

Val Ala Val Gln Ala Arg Leu Asn Tyr Val Ala Leu Gln Thr Asp Val
            820                 825                 830

Leu Asn Lys Asn Gln Gln Ile Leu Ala Ser Ala Phe Asn Gln Ala Ile
            835                 840                 845

Gly Asn Ile Thr Gln Ser Phe Gly Lys Val Asn Asp Ala Ile His Gln
            850                 855                 860

Thr Ser Arg Gly Leu Thr Thr Val Ala Lys Ala Leu Ala Lys Val Gln
865                 870                 875                 880

Asp Val Val Asn Thr Gln Gly Gln Ala Leu Arg His Leu Thr Val Gln
```

```
                    885                 890                 895
Leu Gln Asn Asn Phe Gln Ala Ile Ser Ser Ile Ser Asp Ile Tyr
            900                 905                 910
Asn Arg Leu Asp Glu Leu Ser Ala Asp Ala Gln Val Asp Arg Leu Ile
            915                 920                 925
Thr Gly Arg Leu Thr Ala Leu Asn Ala Phe Val Ser Gln Thr Leu Thr
            930                 935                 940
Arg Gln Ala Glu Val Arg Ala Ser Arg Gln Leu Ala Lys Asp Lys Val
945                 950                 955                 960
Asn Glu Cys Val Arg Ser Gln Ser Gln Arg Phe Gly Phe Cys Gly Asn
            965                 970                 975
Gly Thr His Leu Phe Ser Leu Ala Asn Ala Ala Pro Asn Gly Met Ile
            980                 985                 990
Phe Phe His Thr Val Leu Leu Pro Thr Ala Tyr Glu Thr Val Thr Ala
            995                 1000                1005
Trp Ser Gly Ile Cys Ala Leu Asp Val Asp Arg Thr Phe Gly Leu
        1010                1015                1020
Val Val Lys Asp Val Gln Leu Thr Leu Phe Arg Asn Leu Asp Asp
        1025                1030                1035
Lys Phe Tyr Leu Thr Pro Arg Thr Met Tyr Gln Pro Arg Val Ala
        1040                1045                1050
Thr Ser Ser Asp Phe Val Gln Ile Glu Gly Cys Asp Val Leu Phe
        1055                1060                1065
Val Asn Thr Thr Val Ser Asp Leu Pro Ser Ile Ile Pro Asp Tyr
        1070                1075                1080
Ile Asp Ile Asn Gln Thr Val Gln Asp Ile Leu Glu Asn Phe Arg
        1085                1090                1095
Pro Asn Trp Thr Val Pro Glu Leu Thr Leu Asp Val Phe Asn Ala
        1100                1105                1110
Thr Tyr Leu Asn Leu Thr Gly Glu Ile Asp Asp Leu Glu Phe Arg
        1115                1120                1125
Ser Glu Lys Leu His Asn Thr Thr Val Glu Leu Ala Ile Leu Ile
        1130                1135                1140
Asp Asn Ile Asn Asn Thr Val Val Asn Leu Glu Trp Leu Asn Arg
        1145                1150                1155
Ile Glu Thr Tyr Val Lys Trp Pro Trp Tyr Val Trp Leu Leu Ile
        1160                1165                1170
Gly Leu Val Val Ile Phe Cys Ile Pro Leu Leu Leu Phe Cys Cys
        1175                1180                1185
Cys Ser Thr Gly Cys Cys Gly Cys Ile Gly Cys Leu Gly Ser Cys
        1190                1195                1200
Cys His Ser Ile Phe Ser Arg Arg Gln Phe Glu Asn Tyr Glu Pro
        1205                1210                1215
Ile Glu Lys Val His Val His
        1220                1225

<210> SEQ ID NO 23
<211> LENGTH: 1173
<212> TYPE: PRT
<213> ORGANISM: Human coronavirus

<400> SEQUENCE: 23

Met Phe Val Leu Leu Val Ala Tyr Ala Leu Leu His Ile Ala Gly Cys
1               5                   10                  15

Gln Thr Thr Asn Gly Leu Asn Thr Ser Tyr Ser Val Cys Asn Gly Cys
```

```
                    20                  25                  30
Val Gly Tyr Ser Glu Asn Val Phe Ala Val Glu Ser Gly Tyr Ile
            35                  40                  45

Pro Ser Asp Phe Ala Phe Asn Asn Trp Phe Leu Leu Thr Asn Thr Ser
        50                  55                  60

Ser Val Val Asp Gly Val Val Arg Ser Phe Gln Pro Leu Leu Leu Asn
65                  70                  75                  80

Cys Leu Trp Ser Val Ser Gly Leu Arg Phe Thr Thr Gly Phe Val Tyr
                85                  90                  95

Phe Asn Gly Thr Gly Arg Gly Asp Cys Lys Gly Phe Ser Ser Asp Val
            100                 105                 110

Leu Ser Asp Val Ile Arg Tyr Asn Leu Asn Phe Glu Glu Asn Leu Arg
        115                 120                 125

Arg Gly Thr Ile Leu Phe Lys Thr Ser Tyr Gly Val Val Val Phe Tyr
    130                 135                 140

Cys Thr Asn Asn Thr Leu Val Ser Gly Asp Ala His Ile Pro Phe Gly
145                 150                 155                 160

Thr Val Leu Gly Asn Phe Tyr Cys Phe Val Asn Thr Thr Ile Gly Asn
                165                 170                 175

Glu Thr Thr Ser Ala Phe Val Gly Ala Leu Pro Lys Thr Val Arg Glu
            180                 185                 190

Phe Val Ile Ser Arg Thr Gly His Phe Tyr Ile Asn Gly Tyr Arg Tyr
        195                 200                 205

Phe Thr Leu Gly Asn Val Glu Ala Val Asn Phe Asn Val Thr Thr Ala
    210                 215                 220

Glu Thr Thr Asp Phe Cys Thr Val Ala Leu Ala Ser Tyr Ala Asp Val
225                 230                 235                 240

Leu Val Asn Val Ser Gln Thr Ser Ile Ala Asn Ile Ile Tyr Cys Asn
                245                 250                 255

Ser Val Ile Asn Arg Leu Arg Cys Asp Gln Leu Ser Phe Asp Val Pro
            260                 265                 270

Asp Gly Phe Tyr Ser Thr Ser Pro Ile Gln Ser Val Glu Leu Pro Val
        275                 280                 285

Ser Ile Val Ser Leu Pro Val Tyr His Lys His Thr Phe Ile Val Leu
    290                 295                 300

Tyr Val Asp Phe Lys Pro Gln Ser Gly Gly Gly Lys Cys Phe Asn Cys
305                 310                 315                 320

Tyr Pro Ala Gly Val Asn Ile Thr Leu Ala Asn Phe Asn Glu Thr Lys
                325                 330                 335

Gly Pro Leu Cys Val Asp Thr Ser His Phe Thr Thr Lys Tyr Val Ala
            340                 345                 350

Val Tyr Ala Asn Val Gly Arg Trp Ser Ala Ser Ile Asn Thr Gly Asn
        355                 360                 365

Cys Pro Phe Ser Phe Gly Lys Val Asn Asn Phe Val Lys Phe Gly Ser
    370                 375                 380

Val Cys Phe Ser Leu Lys Asp Ile Pro Gly Gly Cys Ala Met Pro Ile
385                 390                 395                 400

Val Ala Asn Trp Ala Tyr Ser Lys Tyr Tyr Thr Ile Gly Ser Leu Tyr
                405                 410                 415

Val Ser Trp Ser Asp Gly Asp Gly Ile Thr Gly Val Pro Gln Pro Val
            420                 425                 430

Glu Gly Val Ser Ser Phe Met Asn Val Thr Leu Asp Lys Cys Thr Lys
        435                 440                 445
```

-continued

Tyr Asn Ile Tyr Asp Val Ser Gly Val Gly Val Ile Arg Val Ser Asn
    450                 455                 460

Asp Thr Phe Leu Asn Gly Ile Thr Tyr Thr Ser Ser Gly Asn Leu
465                 470                 475                 480

Leu Gly Phe Lys Asp Val Thr Lys Gly Thr Ile Tyr Ser Ile Thr Pro
                485                 490                 495

Cys Asn Pro Pro Asp Gln Leu Val Val Tyr Gln Gln Ala Val Val Gly
                500                 505                 510

Ala Met Leu Ser Glu Asn Phe Thr Ser Tyr Gly Phe Ser Asn Val Val
            515                 520                 525

Glu Leu Pro Lys Phe Phe Tyr Ala Ser Asn Gly Thr Tyr Asn Cys Thr
    530                 535                 540

Asp Ala Val Leu Thr Tyr Ser Ser Phe Gly Val Cys Ala Asp Gly Ser
545                 550                 555                 560

Ile Ile Ala Val Gln Pro Arg Asn Val Ser Tyr Asp Ser Val Ser Ala
                565                 570                 575

Ile Val Thr Ala Asn Leu Ser Ile Pro Ser Asn Trp Thr Thr Ser Val
            580                 585                 590

Gln Val Glu Tyr Leu Gln Ile Thr Ser Thr Pro Ile Val Val Asp Cys
    595                 600                 605

Ser Thr Tyr Val Cys Asn Gly Asn Val Arg Cys Val Glu Leu Leu Lys
610                 615                 620

Gln Tyr Thr Ser Ala Cys Lys Thr Ile Glu Asp Ala Leu Arg Asn Ser
625                 630                 635                 640

Ala Arg Leu Glu Ser Ala Asp Val Ser Glu Met Leu Thr Phe Asp Lys
                645                 650                 655

Lys Ala Phe Thr Leu Ala Asn Val Ser Ser Phe Gly Asp Tyr Asn Leu
            660                 665                 670

Ser Ser Val Ile Pro Ser Leu Pro Thr Ser Gly Ser Arg Val Ala Gly
    675                 680                 685

Arg Ser Ala Ile Glu Asp Ile Leu Phe Ser Lys Leu Val Thr Ser Gly
690                 695                 700

Leu Gly Thr Val Asp Ala Asp Tyr Lys Lys Cys Thr Lys Gly Leu Ser
705                 710                 715                 720

Ile Ala Asp Leu Ala Cys Ala Gln Tyr Tyr Asn Gly Ile Met Val Leu
                725                 730                 735

Pro Gly Val Ala Asp Ala Glu Arg Met Ala Met Tyr Thr Gly Ser Leu
            740                 745                 750

Ile Gly Gly Ile Ala Leu Gly Gly Leu Thr Ser Ala Val Ser Ile Pro
    755                 760                 765

Phe Ser Leu Ala Ile Gln Ala Arg Leu Asn Tyr Val Ala Leu Gln Thr
770                 775                 780

Asp Val Leu Gln Glu Asn Gln Lys Ile Leu Ala Ala Ser Phe Asn Lys
785                 790                 795                 800

Ala Met Thr Asn Ile Val Asp Ala Phe Thr Gly Val Asn Asp Ala Ile
                805                 810                 815

Thr Gln Thr Ser Gln Ala Leu Gln Thr Val Ala Thr Ala Leu Asn Lys
            820                 825                 830

Ile Gln Asp Val Val Asn Gln Gln Gly Asn Ser Leu Asn His Leu Thr
    835                 840                 845

Ser Gln Leu Arg Gln Asn Phe Gln Ala Ile Ser Ser Ser Ile Gln Ala
850                 855                 860

Ile Tyr Asp Arg Leu Asp Thr Ile Gln Ala Asp Gln Gln Val Asp Arg
865                 870                 875                 880

```
Leu Ile Thr Gly Arg Leu Ala Ala Leu Asn Val Phe Val Ser His Thr
                885                 890                 895

Leu Thr Lys Tyr Thr Glu Val Arg Ala Ser Arg Gln Leu Ala Gln Gln
            900                 905                 910

Lys Val Asn Glu Cys Val Lys Ser Gln Ser Lys Arg Tyr Gly Phe Cys
        915                 920                 925

Gly Asn Gly Thr His Ile Phe Ser Ile Val Asn Ala Ala Pro Glu Gly
    930                 935                 940

Leu Val Phe Leu His Thr Val Leu Leu Pro Thr Gln Tyr Lys Asp Val
945                 950                 955                 960

Glu Ala Trp Ser Gly Leu Cys Val Asp Gly Thr Asn Gly Tyr Val Leu
                965                 970                 975

Arg Gln Pro Asn Leu Ala Leu Tyr Lys Glu Gly Asn Tyr Tyr Arg Ile
            980                 985                 990

Thr Ser Arg Ile Met Phe Glu Pro Arg Ile Pro Thr Met Ala Asp Phe
        995                 1000                1005

Val Gln Ile Glu Asn Cys Asn Val Thr Phe Val Asn Ile Ser Arg
        1010                1015                1020

Ser Glu Leu Gln Thr Ile Val Pro Glu Tyr Ile Asp Val Asn Lys
        1025                1030                1035

Thr Leu Gln Glu Leu Ser Tyr Lys Leu Pro Asn Tyr Thr Val Pro
        1040                1045                1050

Asp Leu Val Val Glu Gln Tyr Asn Gln Thr Ile Leu Asn Leu Thr
        1055                1060                1065

Ser Glu Ile Ser Thr Leu Glu Asn Lys Ser Ala Glu Leu Asn Tyr
        1070                1075                1080

Thr Val Gln Lys Leu Gln Thr Leu Ile Asp Asn Ile Asn Ser Thr
        1085                1090                1095

Leu Val Asp Leu Lys Trp Leu Asn Arg Val Glu Thr Tyr Ile Lys
        1100                1105                1110

Trp Pro Trp Trp Val Trp Leu Cys Ile Ser Val Val Leu Ile Phe
        1115                1120                1125

Val Val Ser Met Leu Leu Leu Cys Cys Cys Ser Thr Gly Cys Cys
        1130                1135                1140

Gly Phe Phe Ser Cys Phe Ala Ser Ser Ile Arg Gly Cys Cys Glu
        1145                1150                1155

Ser Thr Lys Leu Pro Tyr Tyr Asp Val Glu Lys Ile His Ile Gln
        1160                1165                1170

<210> SEQ ID NO 24
<211> LENGTH: 1383
<212> TYPE: PRT
<213> ORGANISM: Porcine epidemic diarrhea virus

<400> SEQUENCE: 24

Met Arg Ser Leu Ile Tyr Phe Trp Leu Leu Leu Pro Val Leu Pro Thr
1               5                   10                  15

Leu Ser Leu Pro Gln Asp Val Thr Arg Cys Gln Ser Thr Thr Asn Phe
                20                  25                  30

Arg Arg Phe Phe Ser Lys Phe Asn Val Gln Ala Pro Ala Val Val Val
            35                  40                  45

Leu Gly Gly Tyr Leu Pro Ser Met Asn Ser Ser Trp Tyr Cys Gly
        50                  55                  60

Thr Gly Ile Glu Thr Ala Ser Gly Val His Gly Ile Phe Leu Ser Tyr
65                  70                  75                  80
```

```
Ile Asp Ser Gly Gln Gly Phe Glu Ile Gly Ile Ser Gln Glu Pro Phe
            85                  90                  95

Asp Pro Ser Gly Tyr Gln Leu Tyr Leu His Lys Ala Thr Asn Gly Asn
            100                 105                 110

Thr Asn Ala Thr Ala Arg Leu Arg Ile Cys Gln Phe Pro Asp Asn Lys
            115                 120                 125

Thr Leu Gly Pro Thr Val Asn Asp Val Thr Thr Gly Arg Asn Cys Leu
130                 135                 140

Phe Asn Lys Ala Ile Pro Ala Tyr Met Arg Asp Gly Lys Asp Ile Val
145                 150                 155                 160

Val Gly Ile Thr Trp Asp Asn Asp Arg Val Thr Val Phe Ala Asp Lys
                165                 170                 175

Ile Tyr His Phe Tyr Leu Lys Asn Asp Trp Ser Arg Val Ala Thr Arg
                180                 185                 190

Cys Tyr Asn Arg Arg Ser Cys Ala Met Gln Tyr Val Tyr Thr Pro Thr
                195                 200                 205

Tyr Tyr Met Leu Asn Val Thr Ser Ala Gly Glu Asp Gly Ile Tyr Tyr
            210                 215                 220

Glu Pro Cys Thr Ala Asn Cys Thr Gly Tyr Ala Ala Asn Val Phe Ala
225                 230                 235                 240

Thr Asp Ser Asn Gly His Ile Pro Glu Gly Phe Ser Phe Asn Asn Trp
                245                 250                 255

Phe Leu Leu Ser Asn Asp Ser Thr Leu Leu His Gly Lys Val Val Ser
                260                 265                 270

Asn Gln Pro Leu Leu Val Asn Cys Leu Leu Ala Ile Pro Lys Ile Tyr
            275                 280                 285

Gly Leu Gly Gln Phe Phe Ser Phe Asn His Thr Met Asp Gly Val Cys
            290                 295                 300

Asn Gly Ala Ala Val Asp Arg Ala Pro Glu Ala Leu Arg Phe Asn Ile
305                 310                 315                 320

Asn Asp Thr Ser Val Ile Leu Ala Glu Gly Ser Ile Val Leu His Thr
                325                 330                 335

Ala Leu Gly Thr Asn Leu Ser Phe Val Cys Ser Asn Ser Ser Asp Pro
                340                 345                 350

His Leu Ala Ile Phe Ala Ile Pro Leu Gly Ala Thr Glu Val Pro Tyr
            355                 360                 365

Tyr Cys Phe Leu Lys Val Asp Thr Tyr Asn Ser Thr Val Tyr Lys Phe
370                 375                 380

Leu Ala Val Leu Pro Ser Thr Val Arg Glu Ile Val Ile Thr Lys Tyr
385                 390                 395                 400

Gly Asp Val Tyr Val Asn Gly Phe Gly Tyr Leu His Leu Gly Leu Leu
                405                 410                 415

Asp Ala Val Thr Ile Tyr Phe Thr Gly His Gly Thr Asp Asp Asp Val
            420                 425                 430

Ser Gly Phe Trp Thr Ile Ala Ser Thr Asn Phe Val Asp Ala Leu Ile
            435                 440                 445

Glu Val Gln Gly Thr Ser Ile Gln Arg Ile Leu Tyr Cys Asp Asp Pro
            450                 455                 460

Val Ser Gln Leu Lys Cys Ser Gln Val Ala Phe Asp Leu Asp Asp Gly
465                 470                 475                 480

Phe Tyr Pro Ile Ser Ser Arg Asn Leu Leu Ser His Glu Gln Pro Ile
            485                 490                 495

Ser Phe Val Thr Leu Pro Ser Phe Asn Asp His Ser Phe Val Asn Ile
```

```
                500             505             510
Thr Val Ser Ala Ala Phe Gly Gly Leu Ser Ser Ala Asn Leu Val Ala
            515                 520                 525
Ser Asp Thr Thr Ile Asn Gly Phe Ser Ser Phe Cys Val Asp Thr Arg
            530                 535                 540
Gln Phe Thr Ile Thr Leu Phe Tyr Asn Val Thr Asn Ser Tyr Gly Tyr
545                 550                 555                 560
Val Ser Lys Ser Gln Asp Ser Asn Cys Pro Phe Thr Leu Gln Ser Val
                565                 570                 575
Asn Asp Tyr Leu Ser Phe Ser Lys Phe Cys Val Ser Thr Ser Leu Leu
                580                 585                 590
Ala Gly Ala Cys Thr Ile Asp Leu Phe Gly Tyr Pro Ala Phe Gly Ser
                595                 600                 605
Gly Val Lys Leu Thr Ser Leu Tyr Phe Gln Phe Thr Lys Gly Glu Leu
            610                 615                 620
Ile Thr Gly Thr Pro Lys Pro Leu Glu Gly Ile Thr Asp Val Ser Phe
625                 630                 635                 640
Met Thr Leu Asp Val Cys Thr Lys Tyr Thr Ile Tyr Gly Phe Lys Gly
                645                 650                 655
Glu Gly Ile Ile Thr Leu Thr Asn Ser Ser Ile Leu Ala Gly Val Tyr
                660                 665                 670
Tyr Thr Ser Asp Ser Gly Gln Leu Leu Ala Phe Lys Asn Val Thr Ser
                675                 680                 685
Gly Ala Val Tyr Ser Val Thr Pro Cys Ser Phe Ser Glu Gln Ala Ala
                690                 695                 700
Tyr Val Asn Asp Asp Ile Val Gly Val Ile Ser Ser Leu Ser Asn Ser
705                 710                 715                 720
Thr Phe Asn Asn Thr Arg Glu Leu Pro Gly Phe Phe Tyr His Ser Asn
                725                 730                 735
Asp Gly Ser Asn Cys Thr Glu Pro Val Leu Val Tyr Ser Asn Ile Gly
                740                 745                 750
Val Cys Lys Ser Gly Ser Ile Gly Tyr Val Pro Ser Gln Tyr Gly Gln
                755                 760                 765
Val Lys Ile Ala Pro Thr Val Thr Gly Asn Ile Ser Ile Pro Thr Asn
                770                 775                 780
Phe Ser Met Ser Ile Arg Thr Glu Tyr Leu Gln Leu Tyr Asn Thr Pro
785                 790                 795                 800
Val Ser Val Asp Cys Ala Thr Tyr Val Cys Asn Gly Asn Ser Arg Cys
                805                 810                 815
Lys Gln Leu Leu Thr Gln Tyr Thr Ala Ala Cys Lys Thr Ile Glu Ser
                820                 825                 830
Ala Leu Gln Leu Ser Ala Arg Leu Glu Ser Val Glu Val Asn Ser Met
                835                 840                 845
Leu Thr Ile Ser Glu Glu Ala Leu Gln Leu Ala Thr Ile Ser Ser Phe
                850                 855                 860
Asn Gly Asp Gly Tyr Asn Phe Thr Asn Val Leu Gly Ala Ser Val Tyr
865                 870                 875                 880
Asp Pro Ala Ser Gly Arg Val Val Gln Lys Arg Ser Val Ile Glu Asp
                885                 890                 895
Leu Leu Phe Asn Lys Val Val Thr Asn Gly Leu Gly Thr Val Asp Glu
                900                 905                 910
Asp Tyr Lys Arg Cys Ser Asn Gly Arg Ser Val Ala Asp Leu Val Cys
                915                 920                 925
```

-continued

```
Ala Gln Tyr Tyr Ser Gly Val Met Val Leu Pro Gly Val Val Asp Ala
930                 935                 940
Glu Lys Leu His Met Tyr Ser Ala Ser Leu Ile Gly Met Ala Leu
945                 950                 955                 960
Gly Gly Ile Thr Ala Ala Ala Leu Pro Phe Ser Tyr Ala Val Gln
            965                 970                 975
Ala Arg Leu Asn Tyr Leu Ala Leu Gln Thr Asp Val Leu Gln Arg Asn
            980                 985                 990
Gln Gln Leu Leu Ala Glu Ser Phe Asn Ser Ala Ile Gly Asn Ile Thr
        995                 1000                1005
Ser Ala Phe Glu Ser Val Lys Glu Ala Ile Ser Gln Thr Ser Lys
        1010                1015                1020
Gly Leu Asn Thr Val Ala His Ala Leu Thr Lys Val Gln Glu Val
        1025                1030                1035
Val Asn Ser Gln Gly Ser Ala Leu Asn Gln Leu Thr Val Gln Leu
        1040                1045                1050
Gln His Asn Phe Gln Ala Ile Ser Ser Ser Ile Asp Asp Ile Tyr
        1055                1060                1065
Ser Arg Leu Asp Ile Leu Leu Ala Asp Val Gln Val Asp Arg Leu
        1070                1075                1080
Ile Thr Gly Arg Leu Ser Ala Leu Asn Ala Phe Val Ala Gln Thr
        1085                1090                1095
Leu Thr Lys Tyr Thr Glu Val Gln Ala Ser Arg Lys Leu Ala Gln
        1100                1105                1110
Gln Lys Val Asn Glu Cys Val Lys Ser Gln Ser Gln Arg Tyr Gly
        1115                1120                1125
Phe Cys Gly Gly Asp Gly Glu His Ile Phe Ser Leu Val Gln Ala
        1130                1135                1140
Ala Pro Gln Gly Leu Leu Phe Leu His Thr Val Leu Val Pro Gly
        1145                1150                1155
Asp Phe Val Asn Val Leu Ala Ile Ala Gly Leu Cys Val Asn Gly
        1160                1165                1170
Glu Ile Ala Leu Thr Leu Arg Glu Pro Gly Leu Val Leu Phe Thr
        1175                1180                1185
His Glu Leu Gln Thr Tyr Thr Ala Thr Glu Tyr Phe Val Ser Ser
        1190                1195                1200
Arg Arg Met Phe Glu Pro Arg Lys Pro Thr Val Ser Asp Phe Val
        1205                1210                1215
Gln Ile Glu Ser Cys Val Val Thr Tyr Val Asn Leu Thr Ser Asp
        1220                1225                1230
Gln Leu Pro Asp Val Ile Pro Asp Tyr Ile Asp Val Asn Lys Thr
        1235                1240                1245
Leu Asp Glu Ile Leu Ala Ser Leu Pro Asn Arg Thr Gly Pro Ser
        1250                1255                1260
Leu Pro Leu Asp Val Phe Asn Ala Thr Tyr Leu Asn Leu Thr Gly
        1265                1270                1275
Glu Ile Ala Asp Leu Glu Gln Arg Ser Glu Ser Leu Arg Asn Thr
        1280                1285                1290
Thr Glu Glu Leu Arg Ser Leu Ile Asn Asn Ile Asn Asn Thr Leu
        1295                1300                1305
Val Asp Leu Glu Trp Leu Asn Arg Val Glu Thr Tyr Ile Lys Trp
        1310                1315                1320
Pro Trp Trp Val Trp Leu Ile Ile Val Ile Val Leu Ile Phe Val
        1325                1330                1335
```

```
Val Ser Leu Leu Val Phe Cys Cys Ile Ser Thr Gly Cys Cys Gly
    1340                1345                1350

Cys Cys Gly Cys Cys Gly Ala Cys Phe Ser Gly Cys Cys Arg Gly
    1355                1360                1365

Pro Arg Leu Gln Pro Tyr Glu Ala Phe Glu Lys Val His Val Gln
    1370                1375                1380

<210> SEQ ID NO 25
<211> LENGTH: 1363
<212> TYPE: PRT
<213> ORGANISM: Bovine coronavirus

<400> SEQUENCE: 25

Met Phe Leu Ile Leu Leu Ile Ser Leu Pro Met Ala Leu Ala Val Ile
1               5                   10                  15

Gly Asp Leu Lys Cys Thr Thr Val Ser Ile Asn Asp Val Asp Thr Gly
            20                  25                  30

Val Pro Ser Val Ser Thr Asp Thr Val Asp Val Thr Asn Gly Leu Gly
        35                  40                  45

Thr Tyr Tyr Val Leu Asp Arg Val Tyr Leu Asn Thr Thr Leu Leu Leu
50                  55                  60

Asn Gly Tyr Tyr Pro Thr Ser Gly Ser Thr Tyr Arg Asn Met Ala Leu
65                  70                  75                  80

Lys Gly Thr Leu Leu Leu Ser Thr Leu Trp Phe Lys Pro Pro Phe Leu
                85                  90                  95

Ser Asp Phe Ile Asn Gly Ile Phe Ala Lys Val Lys Asn Thr Lys Val
            100                 105                 110

Ile Lys Asn Gly Val Met Tyr Ser Glu Phe Pro Ala Ile Thr Ile Gly
        115                 120                 125

Ser Thr Phe Val Asn Thr Ser Tyr Ser Val Val Val Gln Pro His Thr
130                 135                 140

Thr Asn Leu Asp Asn Lys Leu Gln Gly Leu Leu Glu Ile Ser Val Cys
145                 150                 155                 160

Gln Tyr Thr Met Cys Glu Tyr Pro His Thr Ile Cys His Pro Asn Leu
                165                 170                 175

Gly Asn Arg Arg Ile Glu Leu Trp His Trp Asp Thr Gly Val Val Ser
            180                 185                 190

Cys Leu Tyr Lys Arg Asn Phe Thr Tyr Asp Val Asn Ala Asp Tyr Leu
        195                 200                 205

Tyr Phe His Phe Tyr Gln Glu Gly Gly Thr Phe Tyr Ala Tyr Phe Thr
210                 215                 220

Asp Thr Gly Val Val Thr Lys Phe Leu Phe Asn Val Tyr Leu Gly Thr
225                 230                 235                 240

Val Leu Ser His Tyr Tyr Val Met Pro Leu Thr Cys Asn Ser Ala Met
                245                 250                 255

Thr Leu Glu Tyr Trp Val Thr Pro Leu Thr Ser Lys Gln Tyr Leu Leu
            260                 265                 270

Ala Phe Asn Gln Asp Gly Val Ile Phe Asn Ala Val Asp Cys Lys Ser
        275                 280                 285

Asp Phe Met Ser Glu Ile Lys Cys Lys Thr Leu Ser Ile Ala Pro Ser
290                 295                 300

Thr Gly Val Tyr Glu Leu Asn Gly Tyr Thr Val Gln Pro Ile Ala Asp
305                 310                 315                 320

Val Tyr Arg Arg Ile Pro Asn Leu Pro Asp Cys Asn Ile Glu Ala Trp
                325                 330                 335
```

```
Leu Asn Asp Lys Ser Val Pro Ser Pro Leu Asn Trp Glu Arg Lys Thr
            340                 345                 350

Phe Ser Asn Cys Asn Phe Asn Met Ser Ser Leu Met Ser Phe Ile Gln
        355                 360                 365

Ala Asp Ser Phe Thr Cys Asn Asn Ile Asp Ala Ala Lys Ile Tyr Gly
370                 375                 380

Met Cys Phe Ser Ser Ile Thr Ile Asp Lys Phe Ala Ile Pro Asn Gly
385                 390                 395                 400

Arg Lys Val Asp Leu Gln Leu Gly Asn Leu Gly Tyr Leu Gln Ser Phe
                405                 410                 415

Asn Tyr Arg Ile Asp Thr Thr Ala Thr Ser Cys Gln Leu Tyr Tyr Asn
                420                 425                 430

Leu Pro Ala Ala Asn Val Ser Val Ser Arg Phe Asn Pro Ser Thr Trp
            435                 440                 445

Asn Arg Arg Phe Gly Phe Thr Glu Gln Ser Val Phe Lys Pro Gln Pro
        450                 455                 460

Val Gly Val Phe Thr Asp His Asp Val Val Tyr Ala Gln His Cys Phe
465                 470                 475                 480

Lys Ala Pro Thr Asn Phe Cys Pro Cys Lys Leu Asp Gly Ser Leu Cys
                485                 490                 495

Val Gly Ser Gly Ser Gly Ile Asp Ala Gly Tyr Lys Asn Ser Gly Ile
            500                 505                 510

Gly Thr Cys Pro Ala Gly Thr Asn Tyr Leu Thr Cys His Asn Ala Ala
        515                 520                 525

Gln Cys Asp Cys Leu Cys Thr Pro Asp Pro Ile Thr Ser Lys Ser Thr
    530                 535                 540

Gly Pro Tyr Lys Cys Pro Gln Thr Lys Tyr Leu Val Gly Ile Gly Glu
545                 550                 555                 560

His Cys Ser Gly Leu Ala Ile Lys Ser Asp Tyr Cys Gly Gly Asn Pro
                565                 570                 575

Cys Thr Cys Gln Pro Gln Ala Phe Leu Gly Trp Ser Val Asp Ser Cys
            580                 585                 590

Leu Gln Gly Asp Arg Cys Asn Ile Phe Ala Asn Phe Ile Leu His Asp
        595                 600                 605

Val Asn Ser Gly Thr Thr Cys Ser Thr Asp Leu Gln Lys Ser Asn Thr
610                 615                 620

Asp Ile Ile Leu Gly Val Cys Val Asn Tyr Asp Leu Tyr Gly Ile Thr
625                 630                 635                 640

Gly Gln Gly Ile Phe Val Glu Val Asn Ala Thr Tyr Tyr Asn Ser Trp
                645                 650                 655

Gln Asn Leu Leu Tyr Asp Ser Asn Gly Asn Leu Tyr Gly Phe Arg Asp
        660                 665                 670

Tyr Leu Thr Asn Arg Thr Phe Met Ile Arg Ser Cys Tyr Ser Gly Arg
            675                 680                 685

Val Ser Ala Ala Phe His Ala Asn Ser Ser Glu Pro Ala Leu Leu Phe
690                 695                 700

Arg Asn Ile Lys Cys Asn Tyr Val Phe Asn Asn Thr Leu Ser Arg Gln
705                 710                 715                 720

Leu Gln Pro Ile Asn Tyr Phe Asp Ser Tyr Leu Gly Cys Val Val Asn
                725                 730                 735

Ala Asp Asn Ser Thr Ser Ser Ala Val Gln Thr Cys Asp Leu Thr Val
            740                 745                 750

Gly Ser Gly Tyr Cys Val Asp Tyr Ser Thr Lys Arg Arg Ser Arg Arg
```

```
                      755                 760                 765
Ala Ile Thr Thr Gly Tyr Arg Phe Thr Asn Phe Glu Pro Phe Thr Val
        770                 775                 780

Asn Ser Val Asn Asp Ser Leu Glu Pro Val Gly Gly Leu Tyr Glu Ile
785                 790                 795                 800

Gln Ile Pro Ser Glu Phe Thr Ile Gly Asn Met Glu Glu Phe Ile Gln
                805                 810                 815

Ile Ser Ser Pro Lys Val Thr Ile Asp Cys Ser Ala Phe Val Cys Gly
            820                 825                 830

Asp Tyr Ala Ala Cys Lys Ser Gln Leu Val Glu Tyr Gly Ser Phe Cys
            835                 840                 845

Asp Asn Ile Asn Ala Ile Leu Thr Glu Val Asn Glu Leu Leu Asp Thr
        850                 855                 860

Thr Gln Leu Gln Val Ala Asn Ser Leu Met Asn Gly Val Thr Leu Ser
865                 870                 875                 880

Thr Lys Leu Lys Asp Gly Val Asn Phe Asn Val Asp Asp Ile Asn Phe
                885                 890                 895

Ser Pro Val Leu Gly Cys Leu Gly Ser Asp Cys Asn Lys Val Ser Ser
            900                 905                 910

Arg Ser Ala Ile Glu Asp Leu Leu Phe Ser Lys Val Lys Leu Ser Asp
        915                 920                 925

Val Gly Phe Val Glu Ala Tyr Asn Asn Cys Thr Gly Gly Ala Glu Ile
930                 935                 940

Arg Asp Leu Ile Cys Val Gln Ser Tyr Asn Gly Ile Lys Val Leu Pro
945                 950                 955                 960

Pro Leu Leu Ser Glu Asn Gln Ile Ser Gly Tyr Thr Leu Ala Ala Thr
                965                 970                 975

Ser Ala Ser Leu Phe Pro Pro Trp Ser Ala Ala Gly Val Pro Phe
            980                 985                 990

Tyr Leu Asn Val Gln Tyr Arg Ile Asn Gly Ile Gly Val Thr Met Asp
        995                 1000                1005

Val Leu Ser Gln Asn Gln Lys Leu Ile Ala Asn Ala Phe Asn Asn
    1010                1015                1020

Ala Leu Asp Ala Ile Gln Glu Gly Phe Asp Ala Thr Asn Ser Ala
    1025                1030                1035

Leu Val Lys Ile Gln Ala Val Val Asn Ala Asn Ala Glu Ala Leu
    1040                1045                1050

Asn Asn Leu Leu Gln Gln Leu Ser Asn Arg Phe Gly Ala Ile Ser
    1055                1060                1065

Ser Ser Leu Gln Glu Ile Leu Ser Arg Leu Asp Ala Leu Glu Ala
    1070                1075                1080

Gln Ala Gln Ile Asp Arg Leu Ile Asn Gly Arg Leu Thr Ala Leu
    1085                1090                1095

Asn Ala Tyr Val Ser Gln Gln Leu Ser Asp Ser Thr Leu Val Lys
    1100                1105                1110

Phe Ser Ala Ala Gln Ala Met Glu Lys Val Asn Glu Cys Val Lys
    1115                1120                1125

Ser Gln Ser Ser Arg Ile Asn Phe Cys Gly Asn Gly Asn His Ile
    1130                1135                1140

Ile Ser Leu Val Gln Asn Ala Pro Tyr Gly Leu Tyr Phe Ile His
    1145                1150                1155

Phe Ser Tyr Val Pro Thr Lys Tyr Val Thr Ala Lys Val Ser Pro
    1160                1165                1170
```

-continued

Gly Leu Cys Ile Ala Gly Asp Arg Gly Ile Ala Pro Lys Ser Gly
    1175                1180                1185

Tyr Phe Val Asn Val Asn Asn Thr Trp Met Phe Thr Gly Ser Gly
    1190                1195                1200

Tyr Tyr Tyr Pro Glu Pro Ile Thr Gly Asn Asn Val Val Val Met
    1205                1210                1215

Ser Thr Cys Ala Val Asn Tyr Thr Lys Ala Pro Asp Val Met Leu
    1220                1225                1230

Asn Ile Ser Thr Pro Asn Leu Pro Asp Phe Lys Glu Glu Leu Asp
    1235                1240                1245

Gln Trp Phe Lys Asn Gln Thr Ser Val Ala Pro Asp Leu Ser Leu
    1250                1255                1260

Asp Tyr Ile Asn Val Thr Phe Leu Asp Leu Gln Asp Glu Met Asn
    1265                1270                1275

Arg Leu Gln Glu Ala Ile Lys Val Leu Asn Gln Ser Tyr Ile Asn
    1280                1285                1290

Leu Lys Asp Ile Gly Thr Tyr Glu Tyr Tyr Val Lys Trp Pro Trp
    1295                1300                1305

Tyr Val Trp Leu Leu Ile Gly Leu Ala Gly Val Ala Met Leu Val
    1310                1315                1320

Leu Leu Phe Phe Ile Cys Cys Cys Thr Gly Cys Gly Thr Ser Cys
    1325                1330                1335

Phe Lys Lys Cys Gly Gly Cys Cys Asp Asp Tyr Thr Gly His Gln
    1340                1345                1350

Glu Leu Val Ile Lys Thr Ser His Asp Asp
    1355                1360

<210> SEQ ID NO 26
<211> LENGTH: 1255
<212> TYPE: PRT
<213> ORGANISM: SARS coronavirus

<400> SEQUENCE: 26

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
                20                  25                  30

His Thr Ser Ser Met Arg Gly Val Tyr Tyr Pro Asp Glu Ile Phe Arg
            35                  40                  45

Ser Asp Thr Leu Tyr Leu Thr Gln Asp Leu Phe Leu Pro Phe Tyr Ser
        50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

```
Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Arg Asp
        195                 200                 205

Leu Pro Ser Gly Phe Asn Thr Leu Lys Pro Ile Phe Lys Leu Pro Leu
210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Tyr Phe Val Gly Tyr
                245                 250                 255

Leu Lys Pro Thr Thr Phe Met Leu Lys Tyr Asp Glu Asn Gly Thr Ile
        260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
        290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
        530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ala Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605
```

-continued

Ala Ile His Ala Asp Gln Leu Thr Pro Ala Trp Arg Ile Tyr Ser Thr
610             615                 620
Gly Asn Asn Val Phe Gln Thr Gln Ala Gly Cys Leu Ile Gly Ala Glu
625             630                 635                 640
His Val Asp Thr Ser Tyr Glu Cys Asp Ile Pro Ile Gly Ala Gly Ile
            645                 650                 655
Cys Ala Ser Tyr His Thr Val Ser Leu Leu Arg Ser Thr Ser Gln Lys
            660                 665                 670
Ser Ile Val Ala Tyr Thr Met Ser Leu Gly Ala Asp Ser Ser Ile Ala
            675                 680                 685
Tyr Ser Asn Asn Thr Ile Ala Ile Pro Thr Asn Phe Ser Ile Ser Ile
            690                 695                 700
Thr Thr Glu Val Met Pro Val Ser Met Ala Lys Thr Ser Val Asp Cys
705             710                 715                 720
Asn Met Tyr Ile Cys Gly Asp Ser Thr Glu Cys Ala Asn Leu Leu Leu
            725                 730                 735
Gln Tyr Gly Ser Phe Cys Thr Gln Leu Asn Arg Ala Leu Ser Gly Ile
            740                 745                 750
Ala Ala Glu Gln Asp Arg Asn Thr Arg Glu Val Phe Ala Gln Val Lys
            755                 760                 765
Gln Met Tyr Lys Thr Pro Thr Leu Lys Tyr Phe Gly Gly Phe Asn Phe
770             775                 780
Ser Gln Ile Leu Pro Asp Pro Leu Lys Pro Thr Lys Arg Ser Phe Ile
785             790                 795                 800
Glu Asp Leu Leu Phe Asn Lys Val Thr Leu Ala Asp Ala Gly Phe Met
            805                 810                 815
Lys Gln Tyr Gly Glu Cys Leu Gly Asp Ile Asn Ala Arg Asp Leu Ile
            820                 825                 830
Cys Ala Gln Lys Phe Asn Gly Leu Thr Val Leu Pro Pro Leu Leu Thr
            835                 840                 845
Asp Asp Met Ile Ala Ala Tyr Thr Ala Ala Leu Val Ser Gly Thr Ala
850             855                 860
Thr Ala Gly Trp Thr Phe Gly Ala Gly Ala Ala Leu Gln Ile Pro Phe
865             870                 875                 880
Ala Met Gln Met Ala Tyr Arg Phe Asn Gly Ile Gly Val Thr Gln Asn
            885                 890                 895
Val Leu Tyr Glu Asn Gln Lys Gln Ile Ala Asn Gln Phe Asn Lys Ala
            900                 905                 910
Ile Ser Gln Ile Gln Glu Ser Leu Thr Thr Thr Ser Thr Ala Leu Gly
            915                 920                 925
Lys Leu Gln Asp Val Val Asn Gln Asn Ala Gln Ala Leu Asn Thr Leu
930             935                 940
Val Lys Gln Leu Ser Ser Asn Phe Gly Ala Ile Ser Ser Val Leu Asn
945             950                 955                 960
Asp Ile Leu Ser Arg Leu Asp Lys Val Glu Ala Glu Val Gln Ile Asp
            965                 970                 975
Arg Leu Ile Thr Gly Arg Leu Gln Ser Leu Gln Thr Tyr Val Thr Gln
            980                 985                 990
Gln Leu Ile Arg Ala Ala Glu Ile Arg Ala Ser Ala Asn Leu Ala Ala
            995                 1000                1005
Thr Lys Met Ser Glu Cys Val Leu Gly Gln Ser Lys Arg Val Asp
    1010            1015               1020
Phe Cys Gly Lys Gly Tyr His Leu Met Ser Phe Pro Gln Ala Ala
    1025            1030               1035

Pro His Gly Val Val Phe Leu His Val Thr Tyr Val Pro Ser Gln
    1040                1045                1050

Glu Arg Asn Phe Thr Thr Ala Pro Ala Ile Cys His Glu Gly Lys
    1055                1060                1065

Ala Tyr Phe Pro Arg Glu Gly Val Phe Val Phe Asn Gly Thr Ser
    1070                1075                1080

Trp Phe Ile Thr Gln Arg Asn Phe Phe Ser Pro Gln Ile Ile Thr
    1085                1090                1095

Thr Asp Asn Thr Phe Val Ser Gly Asn Cys Asp Val Val Ile Gly
    1100                1105                1110

Ile Ile Asn Asn Thr Val Tyr Asp Pro Leu Gln Pro Glu Leu Asp
    1115                1120                1125

Ser Phe Lys Glu Glu Leu Asp Lys Tyr Phe Lys Asn His Thr Ser
    1130                1135                1140

Pro Asp Val Asp Leu Gly Asp Ile Ser Gly Ile Asn Ala Ser Val
    1145                1150                1155

Val Asn Ile Gln Lys Glu Ile Asp Arg Leu Asn Glu Val Ala Lys
    1160                1165                1170

Asn Leu Asn Glu Ser Leu Ile Asp Leu Gln Glu Leu Gly Lys Tyr
    1175                1180                1185

Glu Gln Tyr Ile Lys Trp Pro Trp Tyr Val Trp Leu Gly Phe Ile
    1190                1195                1200

Ala Gly Leu Ile Ala Ile Val Met Val Thr Ile Leu Leu Cys Cys
    1205                1210                1215

Met Thr Ser Cys Cys Ser Cys Leu Lys Gly Ala Cys Ser Cys Gly
    1220                1225                1230

Ser Cys Cys Lys Phe Asp Glu Asp Asp Ser Glu Pro Val Leu Lys
    1235                1240                1245

Gly Val Lys Leu His Tyr Thr
    1250                1255

<210> SEQ ID NO 27
<211> LENGTH: 544
<212> TYPE: PRT
<213> ORGANISM: Avian infectious bronchitis virus

<400> SEQUENCE: 27

Met Leu Val Lys Ser Leu Phe Leu Val Thr Ile Leu Phe Ala Leu Cys
1               5                   10                  15

Ser Ala Asn Leu Tyr Asp Asn Glu Ser Phe Val Tyr Tyr Tyr Gln Ser
                20                  25                  30

Ala Phe Arg Pro Gly His Gly Trp His Leu His Gly Gly Ala Tyr Ala
            35                  40                  45

Val Val Asn Val Ser Ser Glu Asn Asn Asn Ala Gly Thr Ala Pro Ser
        50                  55                  60

Cys Thr Ala Gly Ala Ile Gly Tyr Ser Lys Asn Leu Ser Ala Ala Ser
65                  70                  75                  80

Val Ala Met Thr Ala Pro Leu Ser Gly Met Ser Trp Ser Ala Asn Ser
                85                  90                  95

Phe Cys Thr Ala His Cys Asn Phe Thr Ser Tyr Ile Val Phe Val Thr
            100                 105                 110

His Cys Tyr Lys Ser Gly Ser Asn Ser Cys Pro Leu Thr Gly Leu Ile
        115                 120                 125

Pro Ser Gly Tyr Ile Arg Ile Ala Ala Met Lys His Gly Ser Ala Met
    130                 135                 140

-continued

```
Pro Gly His Leu Phe Tyr Asn Leu Thr Val Ser Val Thr Lys Tyr Pro
145                 150                 155                 160

Lys Phe Arg Ser Leu Gln Cys Val Asn Asn Tyr Thr Ser Val Tyr Leu
            165                 170                 175

Asn Gly Asp Leu Val Phe Thr Ser Asn Tyr Thr Glu Asp Val Val Ala
        180                 185                 190

Ala Gly Val His Phe Lys Ser Gly Pro Ile Thr Tyr Lys Val Met
    195                 200                 205

Arg Glu Val Lys Ala Leu Ala Tyr Phe Val Asn Gly Thr Ala His Asp
210                 215                 220

Val Ile Leu Cys Asp Asp Thr Pro Arg Gly Leu Leu Ala Cys Gln Tyr
225                 230                 235                 240

Asn Thr Gly Asn Phe Ser Asp Gly Phe Tyr Pro Phe Thr Asn Thr Ser
                245                 250                 255

Ile Val Lys Asp Lys Phe Ile Val Tyr Arg Glu Ser Ser Val Asn Thr
            260                 265                 270

Thr Leu Thr Leu Thr Asn Phe Thr Phe Ser Asn Glu Ser Gly Ala Pro
        275                 280                 285

Pro Asn Thr Gly Gly Val Asp Ser Phe Ile Leu Tyr Gln Thr Gln Thr
    290                 295                 300

Ala Gln Ser Gly Tyr Tyr Asn Phe Asn Phe Ser Phe Leu Ser Ser Phe
305                 310                 315                 320

Val Tyr Arg Glu Ser Asn Tyr Met Tyr Gly Ser Tyr His Pro Arg Cys
                325                 330                 335

Ser Phe Arg Pro Glu Thr Leu Asn Gly Leu Trp Phe Asn Ser Leu Ser
            340                 345                 350

Val Ser Leu Thr Tyr Gly Pro Ile Gln Gly Gly Cys Lys Gln Ser Val
        355                 360                 365

Phe Asn Gly Lys Ala Thr Cys Cys Tyr Ala Tyr Ser Tyr Gly Gly Pro
    370                 375                 380

Arg Gly Cys Lys Gly Val Tyr Arg Gly Glu Leu Thr Gln His Phe Glu
385                 390                 395                 400

Cys Gly Leu Leu Val Tyr Val Thr Lys Ser Asp Gly Ser Arg Ile Gln
                405                 410                 415

Thr Ala Thr Gln Pro Pro Val Leu Thr Gln Asn Phe Tyr Asn Asn Ile
            420                 425                 430

Asn Leu Gly Lys Cys Val Asp Tyr Asn Ile Tyr Gly Arg Ile Gly Gln
        435                 440                 445

Gly Leu Ile Thr Asn Val Thr Asp Leu Ala Val Ser Tyr Asn Tyr Leu
    450                 455                 460

Ser Asp Ala Gly Leu Ala Ile Leu Asp Thr Ser Gly Ala Ile Asp Ile
465                 470                 475                 480

Phe Val Val Gln Gly Glu Tyr Gly Pro Asn Tyr Tyr Lys Val Asn Pro
                485                 490                 495

Gly Glu Asp Val Asn Gln Gln Phe Val Val Ser Gly Gly Lys Leu Val
            500                 505                 510

Gly Ile Leu Thr Ser Arg Asn Glu Thr Gly Ser Gln Leu Leu Glu Asn
        515                 520                 525

Gln Phe Tyr Ile Lys Ile Thr Asn Gly Thr Arg Arg Ser Arg Arg Ser
    530                 535                 540
```

<210> SEQ ID NO 28
<211> LENGTH: 19
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 28

Met Pro Leu Tyr Lys Leu Leu Asn Val Leu Trp Leu Val Ala Val Ser
1               5                   10                  15

Asn Ala Ile

<210> SEQ ID NO 29
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gcccttgtac aaattgttaa acgttttgtg gttggtcgcc gtttctaacg cgat          54
```